(12) United States Patent
Kuroda et al.

(10) Patent No.: US 9,932,331 B2
(45) Date of Patent: Apr. 3, 2018

(54) PHENYL TETRAHYDROISOQUINOLINE COMPOUND SUBSTITUTED WITH HETEROARYL

(71) Applicant: TAISHO PHARMACEUTICAL CO., LTD, Tokyo (JP)

(72) Inventors: Shoichi Kuroda, Tokyo (JP); Kenichi Kawabe, Tokyo (JP); Yasunobu Ushiki, Tokyo (JP); Hiroshi Ohta, Tokyo (JP); Fumito Uneuchi, Tokyo (JP); Tsuyoshi Shibata, Tokyo (JP); Hideaki Tabuse, Tokyo (JP); Eiji Munetomo, Tokyo (JP); Sumi Chonan, Tokyo (JP)

(73) Assignee: TAISHO PHARMACEUTICAL CO., LTD. (JP)

( * ) Notice: Subject to any disclaimer, the term of this patent is extended or adjusted under 35 U.S.C. 154(b) by 0 days.

(21) Appl. No.: 15/328,223

(22) PCT Filed: Jul. 24, 2015

(86) PCT No.: PCT/JP2015/071111
§ 371 (c)(1),
(2) Date: Jan. 23, 2017

(87) PCT Pub. No.: WO2016/013657
PCT Pub. Date: Jan. 28, 2016

(65) Prior Publication Data
US 2017/0210736 A1    Jul. 27, 2017

(30) Foreign Application Priority Data

Jul. 25, 2014 (JP) ................. 2014-151726
Mar. 13, 2015 (JP) ................. 2015-051289

(51) Int. Cl.
*C07D 417/10* (2006.01)
*C07D 401/10* (2006.01)
(Continued)

(52) U.S. Cl.
CPC ......... *C07D 417/10* (2013.01); *C07D 401/10* (2013.01); *C07D 401/14* (2013.01);
(Continued)

(58) Field of Classification Search
None
See application file for complete search history.

(56) References Cited

U.S. PATENT DOCUMENTS

2003/0171580 A1   9/2003   Hofmeister et al.
2003/0187045 A1   10/2003   Heinelt et al.
(Continued)

FOREIGN PATENT DOCUMENTS

CA   2241531 A1   7/1997
CA   2 387 529 A1   3/2001
(Continued)

OTHER PUBLICATIONS

S. Müller-Lissner et al., "Levels of satisfaction with current chronic constipation treatment options in Europe—an internet survey", Alimentary Pharmacology Therapeutics, 2013, pp. 137-145, 37.
(Continued)

*Primary Examiner* — Alexander R Pagano
*Assistant Examiner* — Ebenezer O. Sackey
(74) *Attorney, Agent, or Firm* — Finnegan, Henderson, Farabow, Garrett & Dunner, LLP

(57) ABSTRACT

The present invention provides a compound represented by the following formula [1] or a pharmaceutically acceptable salt thereof which has an excellent NHE3 inhibitory effect:

A-Y        [1]

wherein
A represents a structure represented by the following formula [2]:

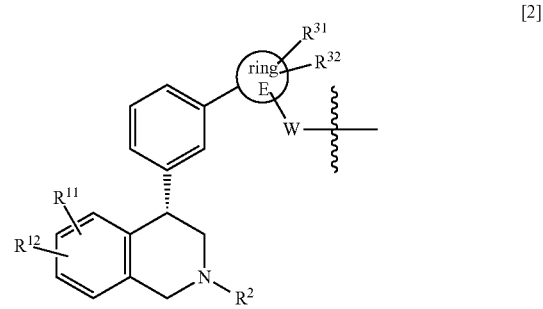

wherein
$R^{11}$ and $R^{12}$ each represent a halogen atom or others as described herein,
$R^2$ represents $C_{1-6}$ alkyl or others as described herein,
ring E represents triazole, tetrazole, pyrimidine, or others as described herein,
$R^{31}$ and $R^{32}$ each represent a hydrogen atom, $C_{1-6}$ alkyl, $C_{1-6}$ alkoxy, or others as described herein, and
W represents a single bond, the formula —NH—, the formula —O—, or the formula —CONH—, and
Y represents a hydrogen atom or a structure selected from

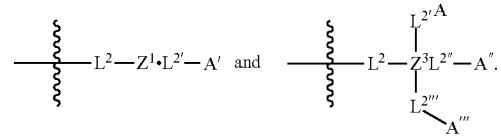

21 Claims, No Drawings

(51) Int. Cl.
  *C07D 413/10*  (2006.01)
  *C07D 405/10*  (2006.01)
  *C07D 401/14*  (2006.01)
  *C07D 413/14*  (2006.01)

(52) U.S. Cl.
  CPC ......... *C07D 405/10* (2013.01); *C07D 413/10* (2013.01); *C07D 413/14* (2013.01)

(56) References Cited

U.S. PATENT DOCUMENTS

| | | |
|---|---|---|
| 2004/0006119 A1 | 1/2004 | Lang et al. |
| 2004/0044211 A1 | 3/2004 | Hofmeister et al. |
| 2004/0224965 A1 | 11/2004 | Gericke et al. |
| 2004/0259927 A1 | 12/2004 | Heinelt et al. |
| 2005/0009863 A1 | 1/2005 | Hofmeister et al. |
| 2005/0009864 A1 | 1/2005 | Hofmeister et al. |
| 2005/0020612 A1 | 1/2005 | Gericke |
| 2005/0054705 A1 | 3/2005 | Heinelt et al. |
| 2005/0075385 A1 | 4/2005 | Lang et al. |
| 2005/0113396 A1 | 5/2005 | Gericke et al. |
| 2007/0225323 A1 | 9/2007 | Lang et al. |
| 2008/0058328 A1 | 3/2008 | Heinelt et al. |
| 2008/0194621 A1 | 8/2008 | Lang |
| 2009/0118327 A1 | 5/2009 | Lang et al. |

FOREIGN PATENT DOCUMENTS

| | | |
|---|---|---|
| JP | 2005-515205 A | 5/2005 |
| JP | 2005-524616 A | 8/2005 |
| JP | 2006-521306 A | 9/2006 |
| JP | 2008-513525 A | 5/2008 |
| JP | 2008-526906 A | 7/2008 |
| JP | 2009-508889 A | 3/2009 |
| JP | 2012-514009 A | 6/2012 |
| WO | 97/24113 A1 | 7/1997 |
| WO | 01/21582 A1 | 3/2001 |
| WO | 01/72742 A1 | 10/2001 |
| WO | 01/79186 A1 | 10/2001 |
| WO | 03/048129 A1 | 6/2003 |
| WO | 03/051866 A | 6/2003 |
| WO | 03/053434 A1 | 7/2003 |
| WO | 03/055490 A1 | 7/2003 |
| WO | 03/055880 A2 | 7/2003 |
| WO | 03/101984 A1 | 12/2003 |
| WO | 2004/069806 A2 | 8/2004 |
| WO | 2004/069811 A1 | 8/2004 |
| WO | 2004/085404 A1 | 10/2004 |
| WO | 2004/107246 A1 | 12/2004 |
| WO | 2005/026173 A1 | 3/2005 |
| WO | 2006/032372 A1 | 3/2006 |
| WO | 2006/074813 A1 | 7/2006 |
| WO | 2007/033773 A1 | 3/2007 |
| WO | 2007/107245 A1 | 9/2007 |
| WO | 2010/025856 A1 | 3/2010 |
| WO | 2010/078449 A2 | 7/2010 |
| WO | 2014/029983 A1 | 2/2014 |
| WO | 2014/029984 A1 | 2/2014 |
| WO | 2014/169094 A2 | 10/2014 |

OTHER PUBLICATIONS

J. F. Johanson et al., "Chronic constipation: a survey of the patient perspective", Alimentary Pharmacology & Therapeutics, 2007, pp. 599-608, 25.

Nicolas C. Zachos et al., "Molecular Physiology of Intestinal Na+/H+ EXCAHNGE", Annual Review of Physiology, 2005, pp. 411, 67.

P.R. Kiela et al., "Apical Na+/H+ Exchangers in the Mammalian Gastrointestinal Tract", Journal of Physiology and Pharmacology, 2006, pp. 51-79, 57, Suppl 7.

Lara R. Gawenis et al., "Intestinal NaCl transport in NHE2 and NHE3 knockout mice", American Journal of Physiology Gastrointestinal and Liver Physiology, 2002, G776-G784, 282.

Dominik Linz et al., "Antihypertensive and Laxative Effects by Pharmacological Inhibition of Sodium-Proton-Exchanger Subtype 3-Mediated Sodium Absorption in the Gut", Hypertension, 2012, pp. 1560-1567, 60.

Andrew G. Spencer et al., "Intestinal Inhibition of the Na+/H+ Exchanger 3 Prevents Cardiorenal Damage in Rats and Inhibits Na + Uptake in Humans", Science Translational Medicine, 2014, pp. 1-6, 6, 227ra36.

Eric D. Labonté et al., "Gastrointestinal Inhibition of Sodium-Hydrogen Exchanger 3 Reduces Phosphorus Absorption and Protects against Vascular Calcification in CKD", Journal of the American Society of Nephrology, 2015, pp. 1138-1149, 26, 5.

Hruska Ka e al., Toseki Ryoho, 2012, Next VIII, 3 pages provided.

International Search Report for PCT/JP2015/071111, dated Oct. 20, 2015.

Fukagawa et al., "Clinical Practice Guideline for CKD-MBD", Journal of Japanese Society for Dialysis Therapy, 45, 4, 301-356, 2012.

PHENYL TETRAHYDROISOQUINOLINE COMPOUND SUBSTITUTED WITH HETEROARYL

CROSS REFERENCE TO RELATED APPLICATIONS

This is a National Stage of International Application No. PCT/JP2015/071111 filed Jul. 24, 2015, claiming priority based on Japanese Patent Application No. 2014-151726 filed Jul. 25, 2014 and Japanese Patent Application No. 2015-051289 filed Mar. 13, 2015, the contents of all of which are incorporated herein by reference in their entirety.

TECHNICAL FIELD

The present invention relates to a novel compound having a $Na^+/H^+$ exchanger 3 (natrium hydrogen exchanger 3; hereinafter, also referred to as "NHE3") inhibitory effect and a medicament comprising the same as an active ingredient.

BACKGROUND ART

Constipation refers to a condition having decrease in stool frequency and stool output and involving pain or difficulty in fecal excretion. The frequency of constipation is presumably increasing due to change in diet, inadequate exercise, stressful social life due to many time restrictions, and aging society.

Ingested food is digested in the stomach and the small intestine, and the nutrients are mainly absorbed in the small intestine. Then, undigested bowel contents are sent from the small intestine to the large intestine. In the large intestine, the contents are solidified while water is absorbed, and the resultant is moved toward the anus by peristalsis to reach the sigmoid colon so that feces are retained. Upon entrance of the retained feces into the rectum by a contraction motion called mass peristalsis, the rectal walls expand. This stimulus is transferred to the spinal defecation center, resulting in defecation reflex to cause anal sphincter laxity and rectal contraction. At the same time therewith, the urge to defecate is recognized by the cerebrum, and the abdominal pressure is voluntarily increased to defecate. However, constipation occurs when the autonomic function, motor function, or defecation reflex function of the lower gastrointestinal tract is decreased due to aging, change in diet, or inadequate exercise, etc., or when excessive water absorption, reduced bowel fluid secretion, etc., in the intestinal tract is induced.

A large number of constipation patients often perform self-care treatment with OTC drugs, folk medicine, or the like, because constipation, albeit with discomfort, does not cause serious problems to daily life. However, constipation incurs reduction in QOL as well as generalized illness. In the case where constipation arises as a partial symptom of a systemic disease, the importance of the treatment thereof is pointed out.

Constipation is divided into organic constipation and functional constipation according to a cause thereof. The organic constipation is constipation that occurs due to the obstruction of the gastrointestinal tract attributed to colonic polyps, colorectal cancer, or the like. On the other hand, the functional constipation is classified into drug-induced constipation, symptomatic constipation, and chronic idiopathic constipation. The drug-induced constipation is constipation that is caused by a drug, such as opioid, which decreases bowel motility. The symptomatic constipation is constipation that occurs secondary due to a disease other than gastrointestinal disease. The chronic idiopathic constipation is constipation that occurs most frequently among the functional constipation cases. The chronic idiopathic constipation occurs due to stress or change in eating environment.

Irritable bowel syndrome with constipation (IBS-C) is constipation having persistent digestive symptoms composed mainly of abdominal pain or abdominal discomfort and abnormal bowel movements without organic change in gastrointestinal tract. Some of functional constipation patients are also diagnosed with IBS-C.

Examples of drugs for constipation include: osmotic laxatives classified into saline laxatives such as magnesium oxide or sugar laxatives such as lactulose; bulk-forming laxatives such as calcium polycarbophil; stimulant laxatives such as sennoside and sodium picosulfate; and emollient laxatives such as dioctyl sodium sulfosuccinate. A serotonin 4 (5-HT4) receptor agonist such as prucalopride, a type-2 chloride channel (ClC-2) agonist such as lubiprostone, or the like is also used.

For the medication of constipation, a saline laxative or a bulk-forming laxative is first used. The saline laxative magnesium oxide requires attention to hypermagnesemia in aged people or renal damage or the like. The bulk-forming laxative calcium polycarbophil acts mildly and requires time for exerting its effects. If these drugs are insufficient, a stimulant laxative is used. However, the stimulant laxative becomes addictive by long-term usage and causes atrophy of the enteric plexus and deterioration in the laxity of the large intestine, although this laxative acts on the enteric plexus and enhances peristalsis. Its use is limited to the minimum amount for the minimum period.

Lubiprostone, which has been approved in recent years, manifests nausea or vomiting as an adverse effect. This drug also requires careful administration for patients with severe renal dysfunction.

Thus, the existing therapeutic drugs for constipation are not yet perfect in terms of safety and efficacy, and all of the drugs are not highly satisfactory according to the reports (Non Patent Literatures 1 and 2). There is a demand for the development of a safer and more effective therapeutic drug for constipation. Such a drug is considered to be beneficial for many patients with chronic constipation.

Digestive juice secreted into the gastrointestinal tract is rich in sodium. This sodium is reabsorbed by the gastrointestinal tract so that the homeostasis of sodium in the body is maintained. Specifically, the gastrointestinal tract absorbs 9 L of body fluids and approximately 800 mmol of sodium in which 7.5 L of body fluids and 650 mmol of sodium are derived from the digestive juice, and the remaining 1.5 L of body fluids and 150 mmol of sodium are orally derived (Non Patent Literature 3). The gastrointestinal tract absorbs almost the whole amount of sodium, and the amount of sodium excreted into feces is approximately 5 mmol.

A principal mechanism for this sodium reabsorption is electroneutral transport and electrogenic transport (Non Patent Literature 4). The electroneutral transport is mainly mediated by NHE3 expressed in the small intestine and the proximal colon. For example, about half of the sodium absorption in the jejunum is reportedly derived from NHE3 (Non Patent Literature 5). The electrogenic transport is mediated by the epithelial sodium channel ENac in the distal colon.

A substance inhibiting the NHE3 activity in the intestinal tract (hereinafter, referred to as a NHE3-inhibiting substance) allows sodium to be retained in the intestinal tract by suppressing intestinal sodium absorption. The retained sodium draws out water by osmotic pressure and therefore softens intestinal contents. Therefore, the NHE3-inhibiting substance is considered to be useful as a therapeutic drug for chronic constipation, IBS-C, or drug-induced constipation (Non Patent Literatures 6 and 7).

The NHE3-inhibiting substance also allows sodium to be excreted into feces by suppressing intestinal sodium absorption. Therefore, the NHE3-inhibiting substance is considered to be also useful as a drug that mimics salt restriction.

An antihypertensive drug such as an angiotensin receptor antagonist or an angiotensin-converting enzyme inhibitor is used as an existing therapeutic drug for hypertension or therapeutic drug for nephropathy. However, the effects of these drugs are not sufficient. Although dietary salt restriction is known to be beneficial for the prevention and treatment of these diseases, it is difficult to continuously comply with salt restriction in modern life. Meanwhile, the NHE3-inhibiting substance that mimics salt restriction has been reported to decrease blood pressure in rats and further to decrease blood pressure more strongly by combined use with an angiotensin-converting enzyme inhibitor (Non Patent Literature 6). Therefore, the NHE3-inhibiting substance is considered to exert therapeutic effects in monotherapy and combination therapy with an existing antihypertensive drug.

Here, renal failure patients with severe renal dysfunctions cannot sufficiently excrete redundant sodium and body fluids into urine. Furthermore, the efficacy of a diuretic also disappears. Therefore, the patients must receive hemodialysis several times a week. Body weight gain and blood pressure elevation occur due to body fluid retention between dialysis sessions, and blood pressure reduction occurs through amelioration in body fluid retention by dialysis operation. Such blood pressure elevation and reduction caused by repeated body fluid retention and dialytic water removal adversely affect the cardiac functions of the renal failure patients and cause the risk of developing heart disease and poorer prognosis. Therefore, strict salt restriction and water deprivation are demanded on the renal failure patients in order to reduce variations in blood pressure. However, it is difficult to comply with this regimen due to its stringency. The NHE3-inhibiting substance has been reported to enhance sodium excretion into feces in rats, to inhibit body fluid retention, and to prevent cardiomegaly (Non Patent Literature 7).

Therefore, the NHE3-inhibiting substance is considered to be also useful as a drug for reducing the risk of developing heart disease in renal failure patients.

Meanwhile, a certain kind of NHE3-inhibiting substance has been reported not only to inhibit intestinal sodium absorption but to inhibit phosphorus absorption and to enhance phosphorus excretion into feces (Patent Literature 24 and Non Patent Literature 8). A certain kind of NHE3-inhibiting substance has been further reported to lower phosphorus concentration in blood by administration to renal failure rats.

Phosphorus metabolism is maintained by two main effects, absorption and excretion in the small intestine and the kidney. Approximately 1.2 g/day of phosphorus is ingested, ⅓ (approximately 0.4 g) of which is excreted into feces and the remaining ⅔ (approximately 0.8 g) of which is absorbed (Non Patent Literature 9). Further, approximately 0.8 g/day of phosphorus is excreted into urine. Digestive juice also contains phosphorus, which is excreted into feces. In the body as well, phosphorus is held in equilibrium between the bone and blood.

Here, renal failure patients with severe renal dysfunctions cannot excrete approximately 0.8 g/day of phosphorus. Therefore, their phosphorus concentrations in blood are elevated to cause hyperphosphatemia. In the hyperphosphatemia, abnormal functions of the bone or the parathyroid gland occur, causing osteoporosis or hyperparathyroidism. Furthermore, phosphorus deposits in a blood vessel, together with calcium, to calcify the blood vessel. Therefore, the risk of developing cardiovascular disease is increased.

The guideline of the Japanese Society for Dialysis Therapy, "Clinical Practice Guideline for the Management of Chronic Kidney Disease-Mineral and Bone Disorder", has reported that deranged mineral metabolism in chronic kidney disease largely influences not only abnormalities in the bone or the parathyroid gland but life prognosis via vascular calcification or the like, and has proposed such a combined disorder as chronic kidney disease-mineral and bone disorder (hereinafter, also referred to as CKD-MBD) (Non Patent Literature 10). The CKD-MBD guideline points out that, particularly, hyperphosphatemia causes abnormal functions of the bone or the parathyroid gland, aggravates vascular calcification, increases the risk of developing osteoporosis or cardiovascular disease, and largely influences life prognosis. The guideline further recommends managing hyperphosphatemia by remedy as a priority.

For renal failure patients, phosphorus in blood is removed by dialysis. However, it is impossible to keep phosphorus concentration in blood in a normal range by dialysis alone. Therefore, a phosphate binder serving as a therapeutic drug for hyperphosphatemia is used as the second-best approach. The phosphate binder is a drug that enhances phosphorus excretion by binding to phosphorus in the intestinal tract and moving in this bound state into feces. Such a drug, albeit having a reliable effect of lowering phosphorus concentration in blood, has large medication burdens with a daily dose of several grams. The medication burdens significantly impair adherence for dialysis patients who are originally forced to restrict water intake and need to take a large number of tablets. The phosphate binder is classified into metal-containing type and polymeric phosphate binders, each of which presents problems. The metal-containing phosphate binder presents concerns about long-term safety due to metal loading. Also, the polymeric phosphate binder swells in the intestinal tract and therefore frequently causes gastrointestinal symptoms such as constipation or abdominal distention.

Therefore, a drug improved in terms of safety and convenience and having good adherence is desired as a novel therapeutic drug for hyperphosphatemia.

The NHE3-inhibiting substance neither contains a metal nor is a polymer and is therefore free from the adverse reactions specific for the phosphate binder described above. Also, the NHE3-inhibiting substance can probably reduce a dose as compared with the phosphate binder. Therefore, the NHE3-inhibiting substance is considered to be useful as a therapeutic drug for hyperphosphatemia improved in terms of safety and convenience and having good adherence. Furthermore, the NHE3-inhibiting substance that can be used for a long period is considered to be useful as a drug ameliorating CKD-MBD.

Water restriction is demanded on renal failure patients so as not to aggravate body fluid retention. Therefore, the water content in the intestinal tract is decreased. The renal failure patients also have the risk of hyperkalemia. Thus, restriction of vegetable intake is imposed thereon in order to restrict potassium intake. Due to the restriction of the water and vegetable intake, the renal failure patients develop constipation with high frequency. The NHE3-inhibiting substance is considered to also have an ameliorating effect on constipation specific for renal failure patients.

Thus, the NHE3-inhibiting substance serves as a drug capable of treating hyperphosphatemia and CKD-MBD in renal failure patients, a drug capable of mitigating body fluid retention, and a drug capable of ameliorating even constipation in renal failure patients, and is expected as a very useful drug that comprehensively improves QOL of renal failure patients.

Body fluid retention also occurs in heart failure patients. This body fluid retention further aggravates cardiac functions. In general, a diuretic is used in the treatment of heart failure. However, the diuretic may exhibit attenuated efficacy for patients with reduced renal functions and cause potassium abnormalities. The NHE3-inhibiting substance can allow body fluids to be excreted into feces, regardless of renal functions. Therefore, the NHE3-inhibiting substance is considered to be useful as a novel therapeutic drug for heart failure.

In addition, body fluid retention also occurs in liver cirrhosis patients. Furthermore, for example, a PPAR agonist, which is useful in the treatment of type 2 diabetes mellitus, also causes drug-induced body fluid retention. The NHE3-inhibiting substance is considered to be also able to mitigate such body fluid retention.

Acylguanidine derivatives (Patent Literature 1), amidine derivatives (Patent Literatures 2 and 3), guanidine derivatives (Patent Literatures 4 to 6), tetrahydroisoquinoline derivatives (Patent Literatures 7 to 14), 2-aminoimidazolidine or 2-aminoimidazole derivatives (Patent Literatures 15 to 19), aminodihydroisoquinoline derivatives (Patent Literatures 20 and 21), aminoindane derivatives (Patent Literatures 22 and 23), and the like have been reported as compounds inhibiting NHE3. Nonetheless, no compound having the structure of the present invention has been disclosed.

A certain kind of NHE3-inhibiting compound has been reported to have a phosphorus absorption inhibitory effect. Nonetheless, this effect has not been reported as to a compound having the structure of the present invention (Patent Literature 24 and Non Patent Literature 8).

PRIOR ART LITERATURE

Patent Literatures

[Patent Literature 1] WO97/24113
[Patent Literature 2] WO2001/021582
[Patent Literature 3] WO2001/072742
[Patent Literature 4] WO2001/0791866
[Patent Literature 5] WO2003/051866
[Patent Literature 6] WO2003/055490
[Patent Literature 7] WO2003/048129
[Patent Literature 8] WO2003/055880
[Patent Literature 9] WO2004/085404
[Patent Literature 10] WO2006/032372
[Patent Literature 11] WO2006/074813
[Patent Literature 12] WO2007/033773
[Patent Literature 13] WO2010/078449
[Patent Literature 14] WO2014/029984
[Patent Literature 15] WO2003/053434
[Patent Literature 16] WO2003/101984
[Patent Literature 17] WO2004/069806
[Patent Literature 18] WO2004/069811
[Patent Literature 19] WO2005/026173
[Patent Literature 20] WO2007/107245
[Patent Literature 21] WO2007/107246
[Patent Literature 22] WO2010/025856
[Patent Literature 23] WO2014/029983
[Patent Literature 24] WO2014/169094

NON PATENT LITERATURES

[Non Patent Literature 1] Alimentary Pharmacology and Therapeutics, 37, 137-145, 2013
[Non Patent Literature 2] Alimentary Pharmacology and Therapeutics, 25, 599-608, 2007
[Non Patent Literature 3] Annual Review of Physiology, 67, 411-443, 2005
[Non Patent Literature 4] Journal of physiology and pharmacology, 57, 7, 51-79, 2006
[Non Patent Literature 5] American Journal of Physiology-Gastrointestinal and Liver Physiology, 282, G776-G784, 2002
[Non Patent Literature 6] Hypertension, 60, 1560-1567, 2012
[Non Patent Literature 7] Science Translational Medicine, 6, 227ra36, 1-6, 2014
[Non Patent Literature 8] Journal of the American Society of Nephrology, 26, 5, 1138-1149, 2015
[Non Patent Literature 9] Toseki Ryoho (dialysis therapy in English) Next VIII, 2012
[Non Patent Literature 10] Journal of Japanese Society for Dialysis Therapy, 45, 4, 301-356, 2012

SUMMARY OF THE INVENTION

Problems to be Solved by the Invention

An object of the present invention is to provide a compound having an excellent NHE3 inhibitory effect.

Means for Solving the Problems

The present inventors have conducted diligent studies to attain the object and consequently found that a compound represented by the formula [1] given below has an excellent NHE3 inhibitory effect.

Specifically, the present invention provides
(1) a compound represented by the following formula [1] or a pharmaceutically acceptable salt thereof:

[Formula 1]

$$A\text{-}Y \qquad [1]$$

wherein
A represents a structure represented by the following formula [2]:

[Formua 2]

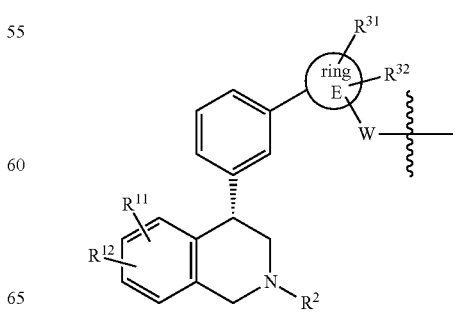

wherein

R[11] and R[12] are the same or different and each represent a hydrogen atom or a halogen atom, R[2] represents a hydrogen atom or $C_{1-6}$ alkyl, ring E represents pyrrole, furan, pyrazole, imidazole, isoxazole, oxazole, isothiazole, triazole, oxadiazole, tetrazole, pyridine, pyridazine, pyrimidine, or pyrazine, R[31] and R[32] are the same or different and each represent a hydrogen atom, cyano, $C_{1-6}$ alkyl, $C_{1-6}$ alkoxy, or mono-$C_{1-6}$ alkylamino, and W represents a single bond, the formula —NH—, the formula —O—, or the formula —CONH—, and Y represents a hydrogen atom or any structure of the following formulas [3']:

[Formula 3]

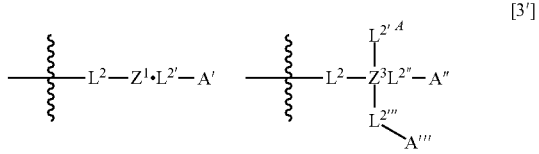

wherein $Z^1$ represents any structure of the following formula group [4']:

[Formula 4]

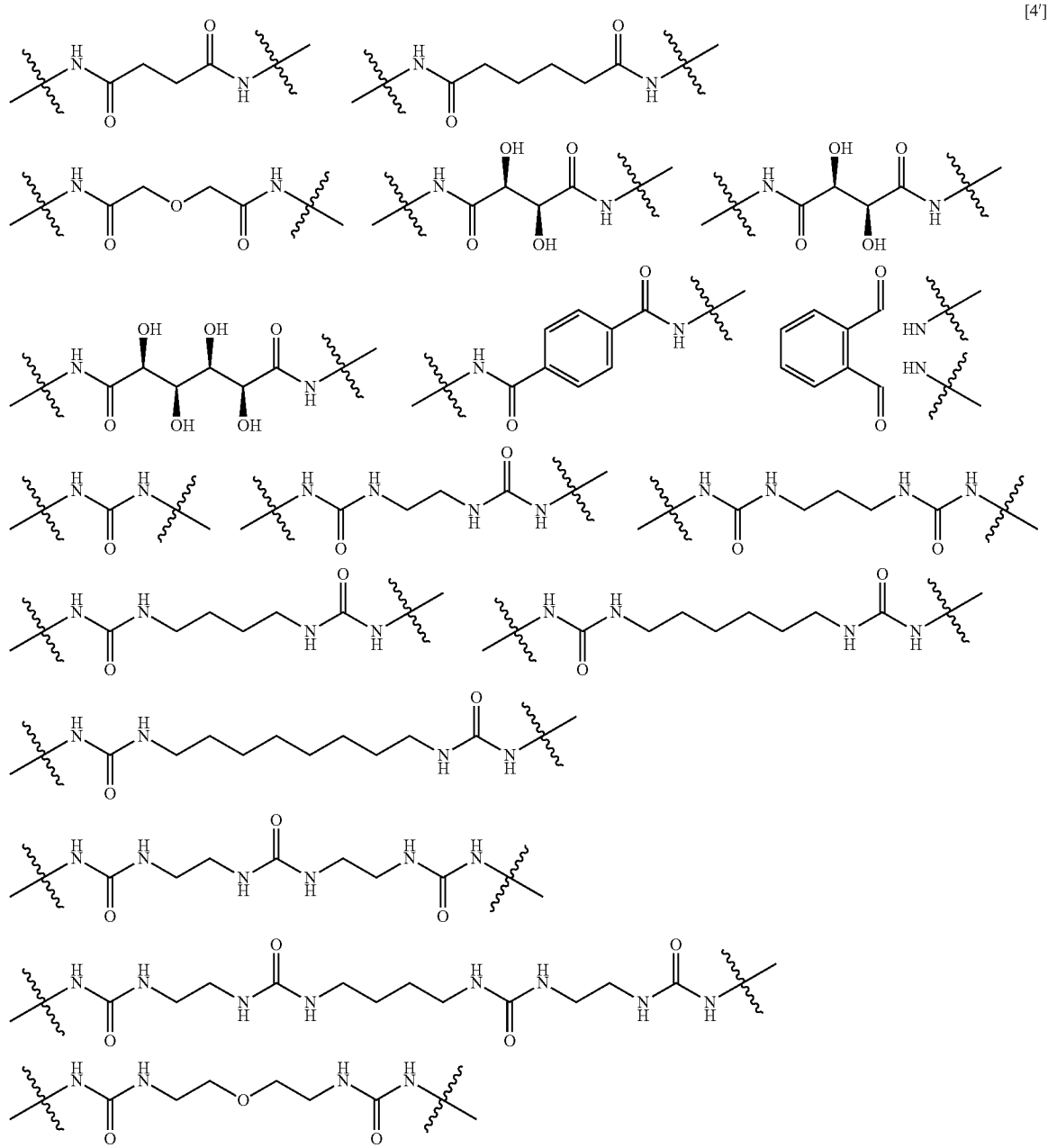

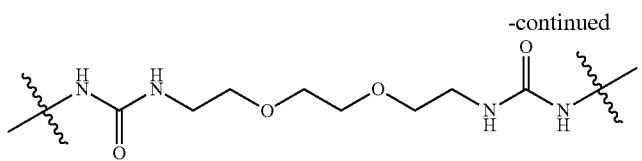
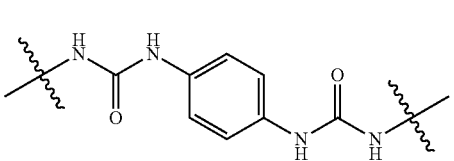

$Z^3$ represents a structure of the following formula [4-a]:

[Formula 5]

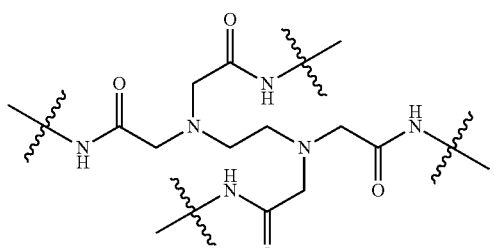

[4-a]

$L^2$, $L^{2\prime}$, $L^{2\prime\prime}$, and $L^{2\prime\prime\prime}$ are the same or different and each represent any structure of the following formula group [5]:

[Formula 6]

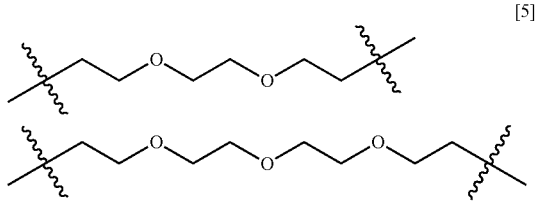

[5]

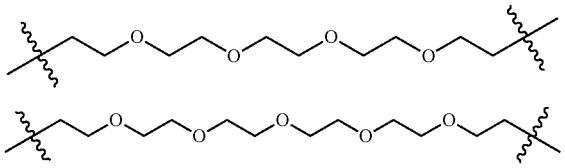

and

A', A", and A'" each represent the same structure as the structure represented by A.

An alternative aspect of the present invention provides (2) the compound according to (1) or a pharmaceutically acceptable salt thereof, wherein Y is a hydrogen atom or a structure represented by the following formula [3]:

[Formula 7]

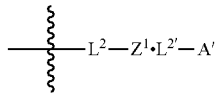

[3]

wherein $Z^1$ is any structure of the following formula group [4]:

[Formula 8]

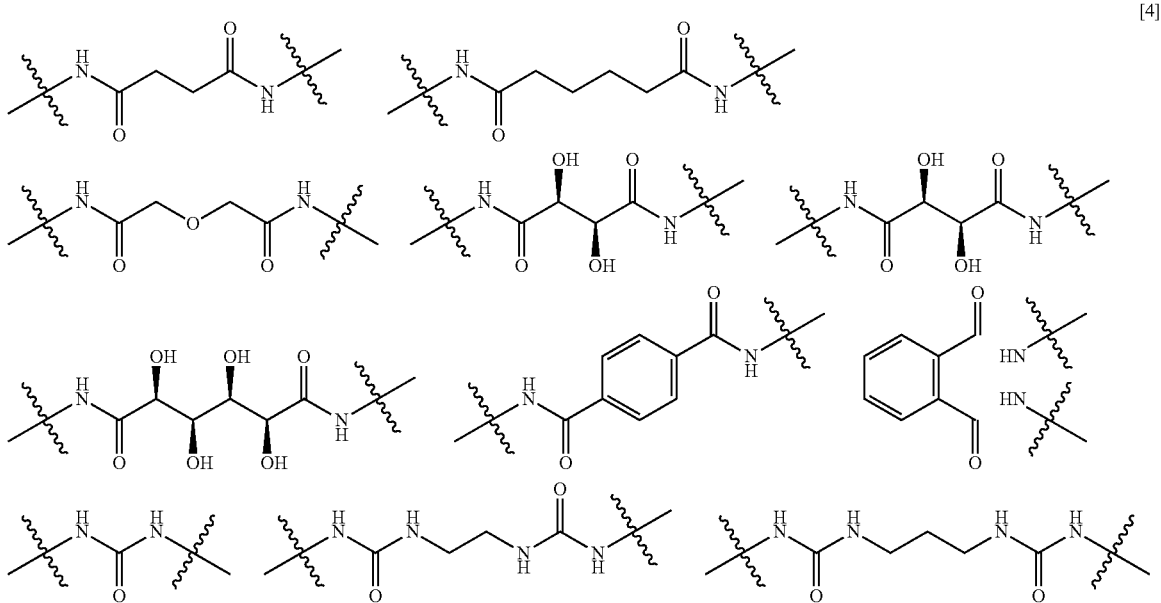

[4]

and

L² and L²' are the same and are any structure of the following formula group [5]:

[Formula 9]

[5]

and

A' is the same structure as the structure represented by A.

An alternative aspect of the present invention provides (3) the compound according to (1) or (2) or a pharmaceutically acceptable salt thereof, wherein Y is a structure represented by the following formula [3]:

[Formula 10]

$$-L^2-Z^1\cdot L^{2\prime}-A'$$

[3]

wherein

L², L²', Z¹, and A' are as defined above.

An alternative aspect of the present invention provides (4) the compound according to any of (1) to (3) or a pharmaceutically acceptable salt thereof, wherein Z¹ is any structure of the following formula group [6]:

[Formula 11]

[6]

An alternative aspect of the present invention provides (5) the compound according to (4) or a pharmaceutically acceptable salt thereof, wherein the structure represented by the formula [2] is a structure of the following formula [7]:

[Formula 12]

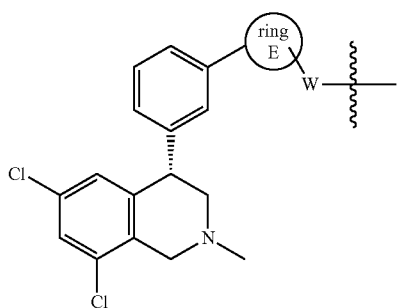

wherein
ring E and W are as defined above.

An alternative aspect of the present invention provides (6) the compound according to (5) or a pharmaceutically acceptable salt thereof, wherein
in the formula [7], the structure represented by the following formula [8] is any structure of the following formula group [9]:

[Formula 13]

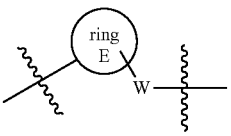

[8]

[Formula 14]

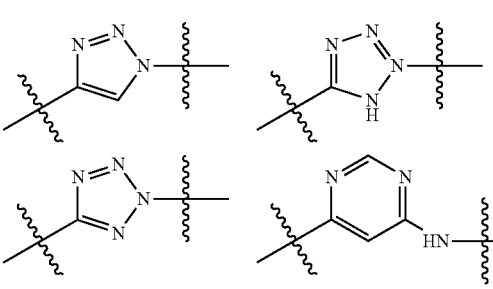

[9]

An alternative aspect of the present invention provides (7) the compound according to (1) or a pharmaceutically acceptable salt thereof, wherein
the compound is represented by the following formula [16]:

[Formula 15]

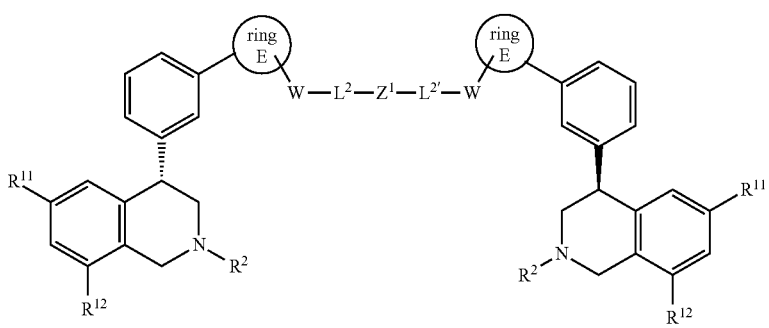

[16]

wherein
each of $R^{11}$ and $R^{12}$ is a halogen atom,
$R^2$ is $C_{1-6}$ alkyl,
ring E is pyrazole, imidazole, triazole, tetrazole, pyridine, pyridazine, or pyrimidine,
W is a single bond, the formula —NH—, the formula —O—, or the formula —CONH—,
$Z^1$ is any structure of the following formula group [17]:

[Formula 16]

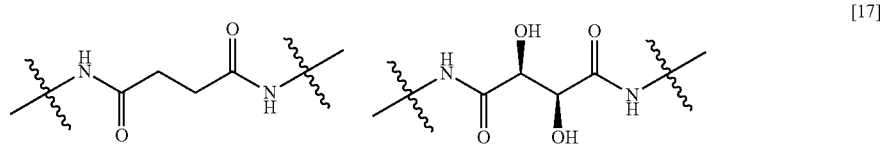

[17]

-continued

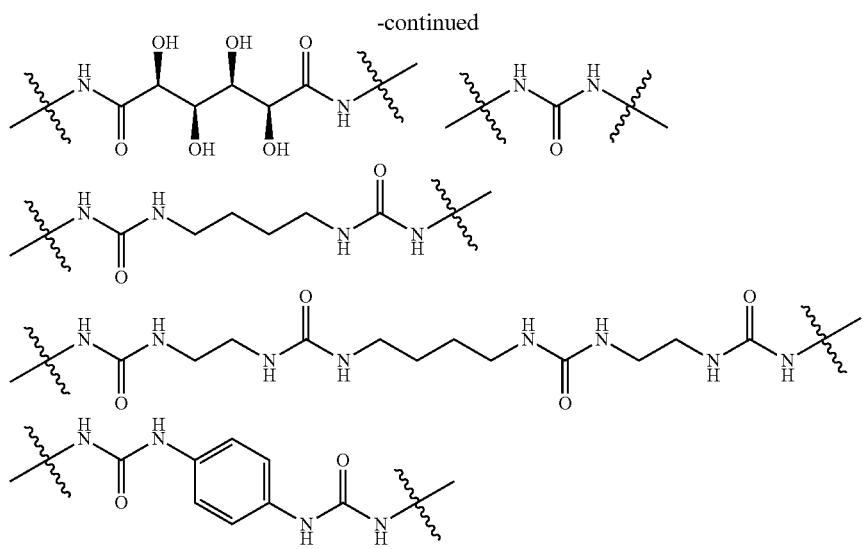

and each of $L^2$ and $L^{2\prime}$ is any structure of the following formula group [5]:

[Formula 17]

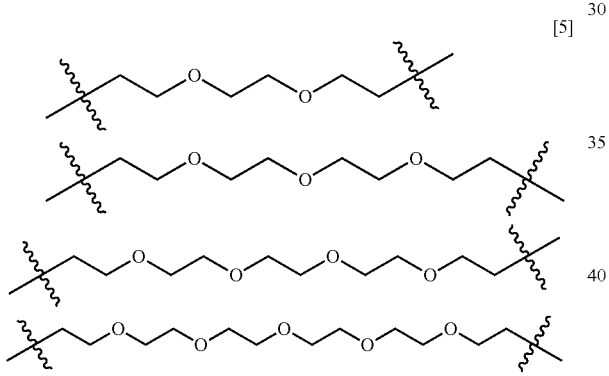

[5]

An alternative aspect of the present invention provides (8) the compound according to (7) or a pharmaceutically acceptable salt thereof, wherein each of $R^{11}$ and $R^{12}$ is a chlorine atom, $R^2$ is methyl, ring E is triazole, tetrazole, pyridine, pyridazine, or pyrimidine, W is a single bond, the formula —NH—, or the formula —CONH—, and $Z^1$ is any structure of the following formula group [17']:

[Formula 18]

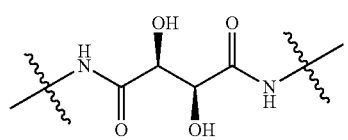

[17']

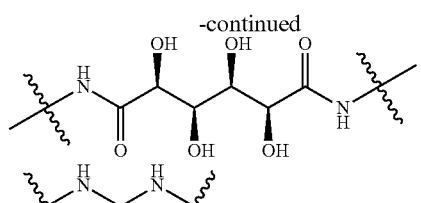

An alternative aspect of the present invention provides (9) the compound according to (8) or a pharmaceutically acceptable salt thereof, wherein in the formula [16], the structure represented by the following formula [8] is any structure of the following formula group [18]:

[Formula 19]

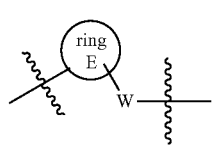

[8]

[Formula 20]

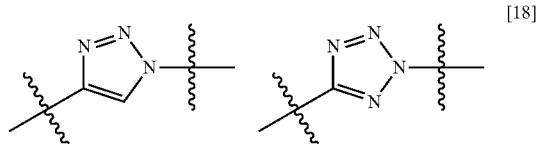

[18]

17
-continued
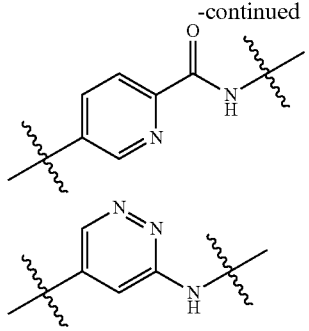
18
-continued
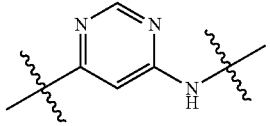
An alternative aspect of the present invention provides
(10) the compound according to (1) or (7) or a pharmaceutically acceptable salt thereof which is shown in the following:
[Formula 21]
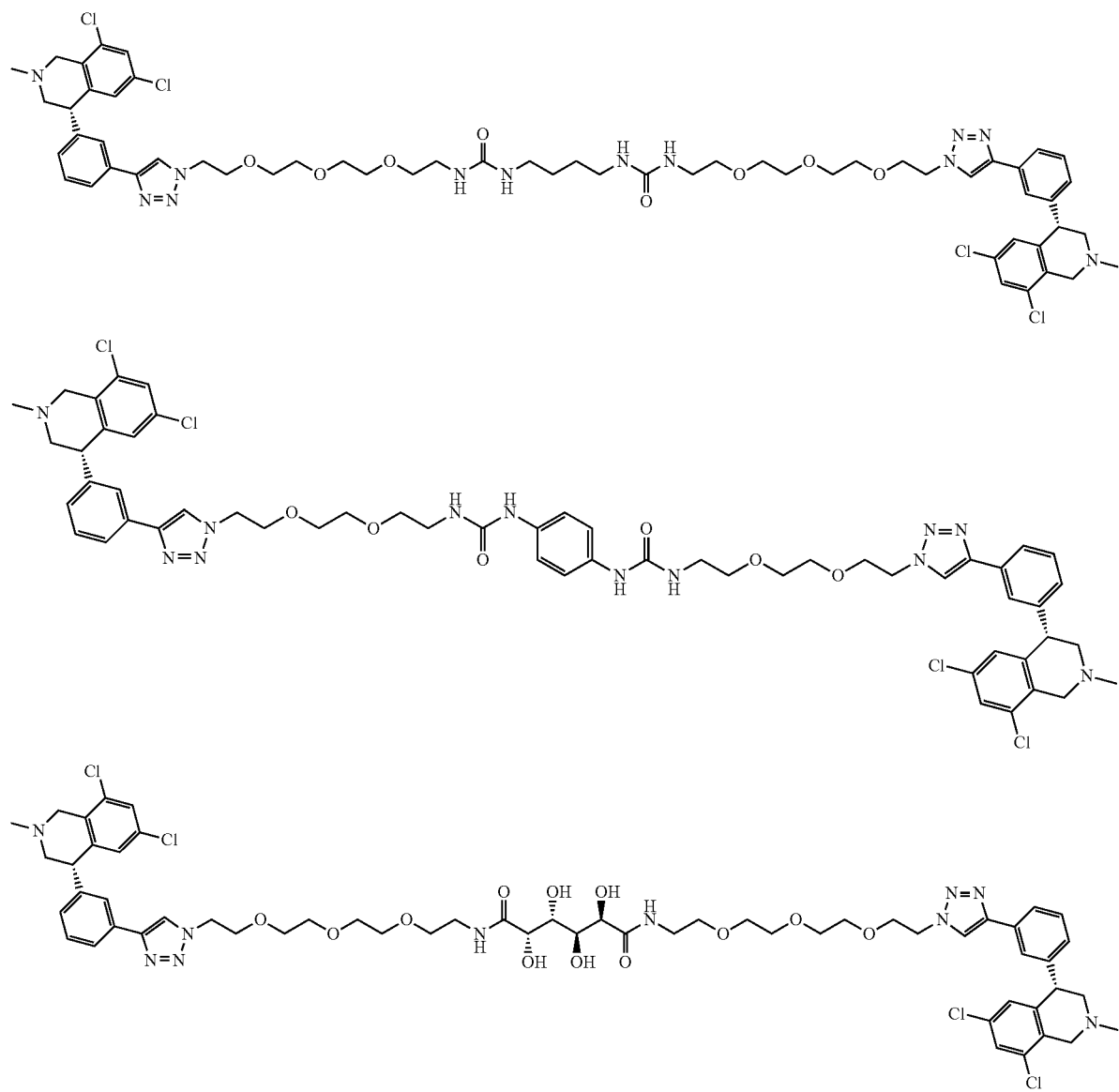

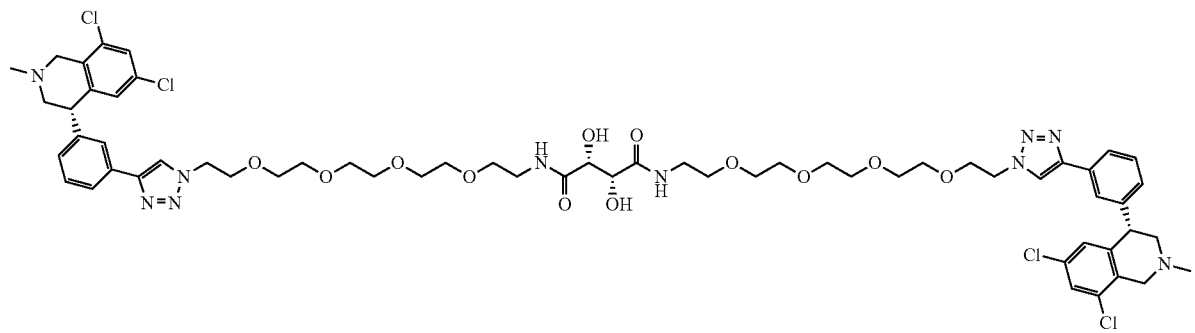
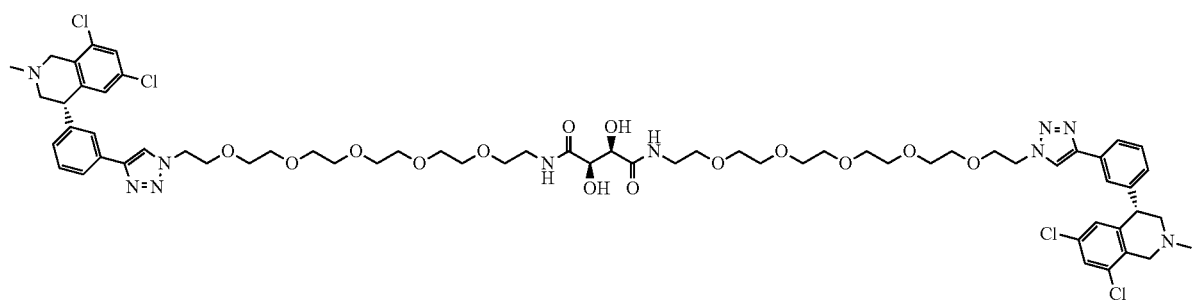
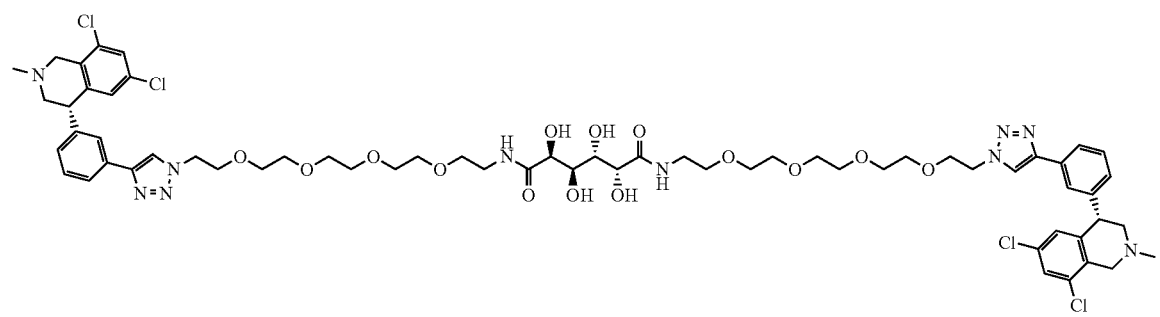
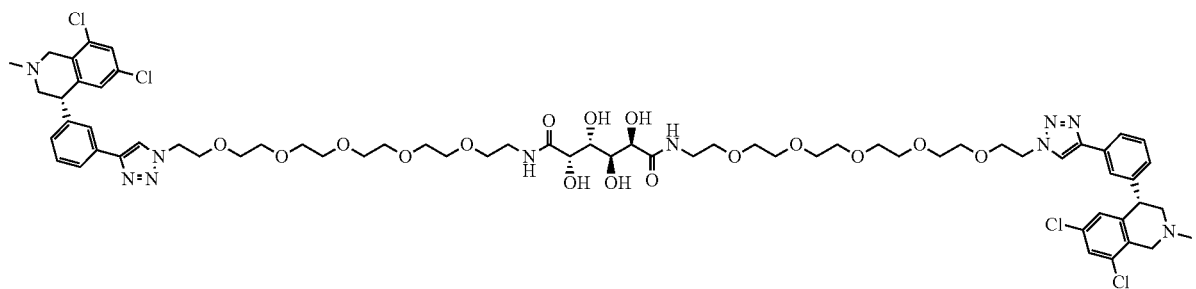

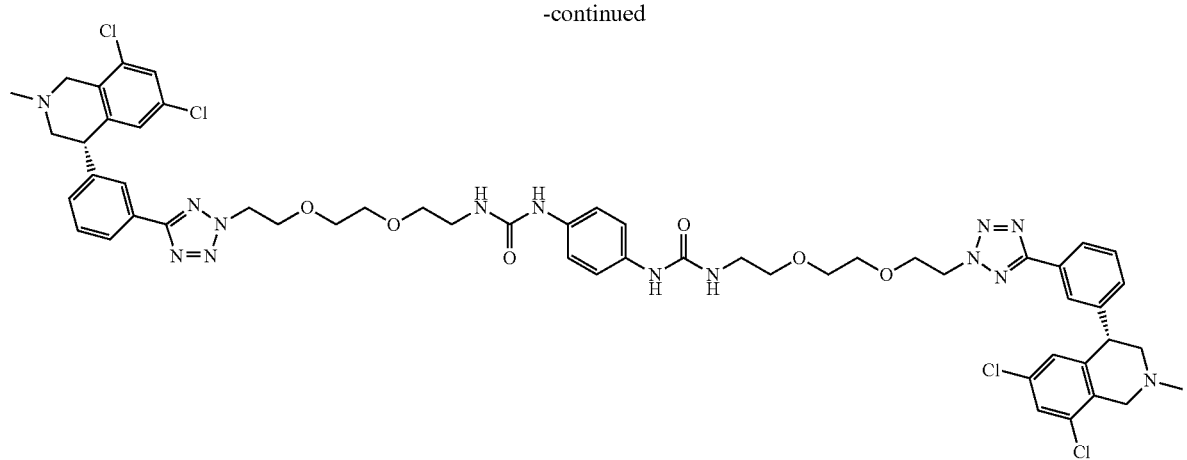
[Formula 22]
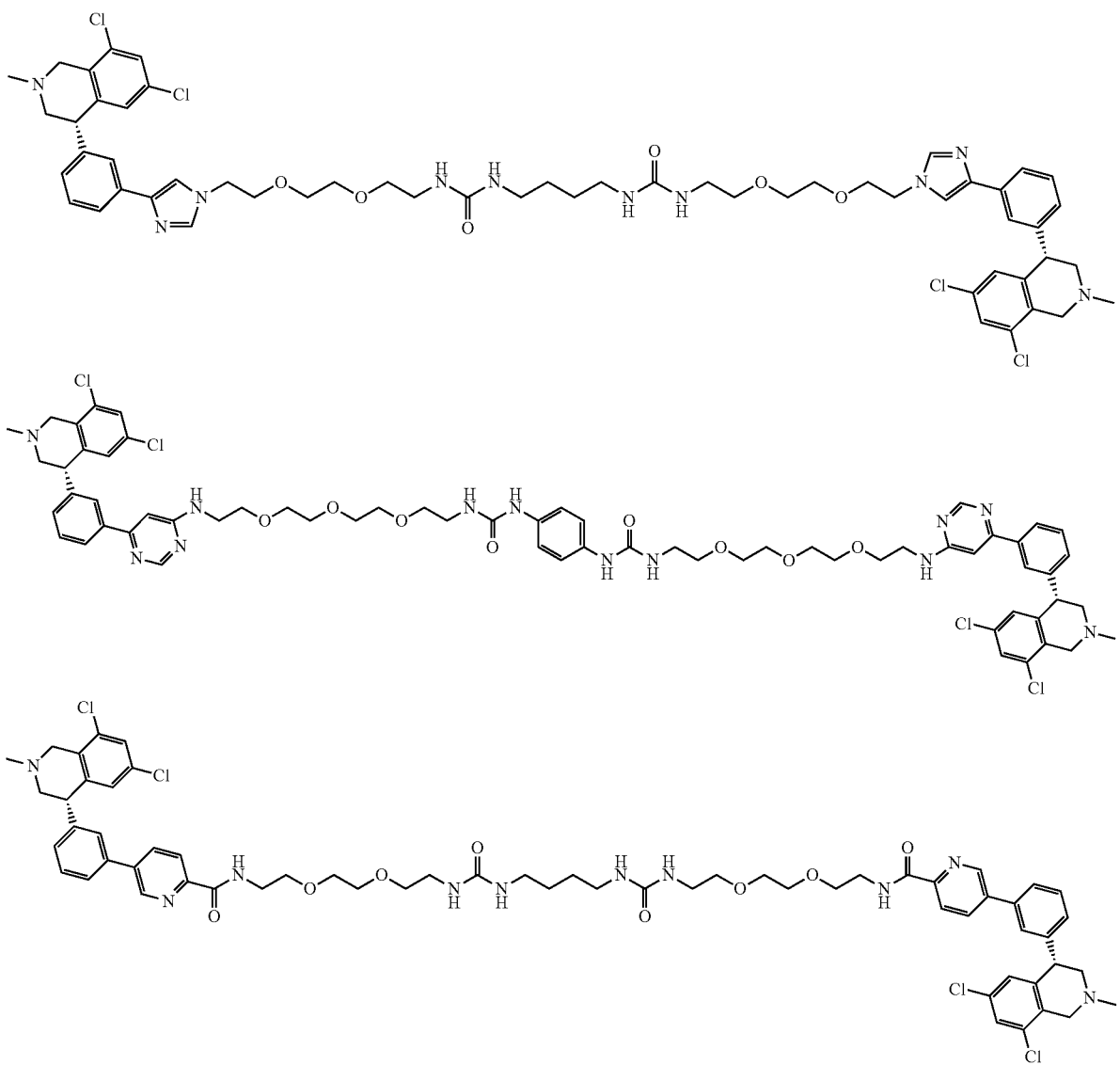

-continued

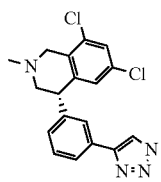
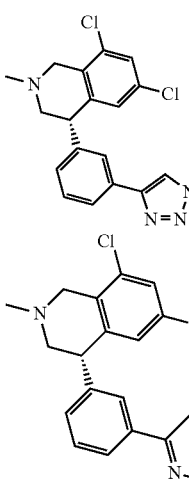
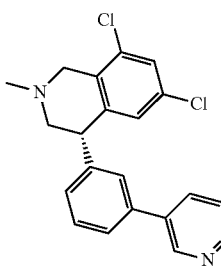
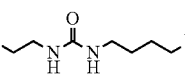
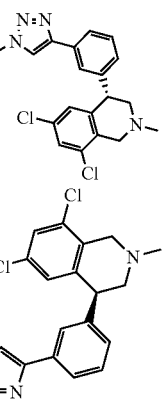
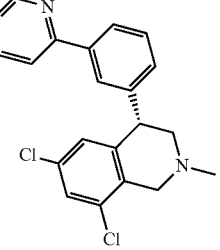
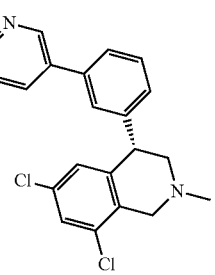

An alternative aspect of the present invention provides
(11) a medicament comprising a compound according to any of (1) to (10) or a pharmaceutically acceptable salt thereof as an active ingredient.

An alternative aspect of the present invention provides
(12) a NHE3 inhibitor comprising a compound according to any of (1) to (10) or a pharmaceutically acceptable salt thereof as an active ingredient.

An alternative aspect of the present invention provides
(13) an intestinal water secretion promoter comprising a compound according to any of (1) to (10) or a pharmaceutically acceptable salt thereof as an active ingredient.

An alternative aspect of the present invention provides
(14) a prophylactic or therapeutic drug for constipation comprising a compound according to any of (1) to (10) or a pharmaceutically acceptable salt thereof as an active ingredient.

An alternative aspect of the present invention provides
(15) a sodium absorption inhibitor comprising a compound according to any of (1) to (10) or a pharmaceutically acceptable salt thereof as an active ingredient.

An alternative aspect of the present invention provides
(16) a prophylactic or therapeutic drug for hypertension comprising a compound according to any of (1) to (10) or a pharmaceutically acceptable salt thereof as an active ingredient.

An alternative aspect of the present invention provides
(17) a prophylactic or therapeutic drug for nephropathy comprising a compound according to any of (1) to (10) or a pharmaceutically acceptable salt thereof as an active ingredient.

An alternative aspect of the present invention provides (18) a prophylactic or therapeutic drug for body fluid retention comprising a compound according to any of (1) to (10) or a pharmaceutically acceptable salt thereof as an active ingredient.

An alternative aspect of the present invention provides (19) a phosphorus absorption inhibitor comprising a compound according to any of (1) to (10) or a pharmaceutically acceptable salt thereof as an active ingredient.

An alternative aspect of the present invention provides (20) a prophylactic or therapeutic drug for hyperphosphatemia comprising a compound according to any of (1) to (10) or a pharmaceutically acceptable salt thereof as an active ingredient.

An alternative aspect of the present invention provides (21) a prophylactic or therapeutic drug for CKD-MBD comprising a compound according to any of (1) to (10) or a pharmaceutically acceptable salt thereof as an active ingredient.

Advantageous Effect of the Invention

The present invention can provide a compound having an excellent NHE3 inhibitory effect.

The compound of the present invention has a NHE3 inhibitory effect. A medicament comprising the compound of the present invention as an active ingredient can serve as a medicament effective for the prevention or treatment of constipation, hypertension, nephropathy, body fluid retention derived from renal failure, and body fluid retention caused by heart failure, liver cirrhosis, or drugs.

Some compounds of the present invention have a phosphorus absorption inhibitory effect. A medicament comprising any of these compounds as an active ingredient can serve as a medicament effective for the prevention or treatment of hyperphosphatemia and CKD-MBD.

EMBODIMENTS FOR CARRYING OUT THE INVENTION

The present invention provides a compound represented by the formula [1] or a pharmaceutically acceptable salt thereof which has an excellent NHE3 inhibitory effect.

Hereinafter, the compound of the present invention will be described in more detail. However, the present invention is not particularly limited by the embodiments.

The "halogen atom" refers to a fluorine atom, a chlorine atom, a bromine atom, or an iodine atom.

The "$C_{1-6}$ alkyl" refers to linear or branched alkyl having 1 to 6 carbon atoms. Examples thereof include methyl, ethyl, n-propyl, isopropyl, n-butyl, isobutyl, sec-butyl, tert-butyl, n-pentyl, isopentyl, neopentyl, 2-methylbutyl, n-hexyl, and isohexyl.

The "$C_{1-6}$ alkoxy" refers to linear or branched alkoxy having 1 to 6 carbon atoms. Examples thereof include methoxy, ethoxy, n-propoxy, isopropoxy, n-butoxy, isobutoxy, sec-butoxy, tert-butoxy, n-pentyloxy, isopentyloxy, neopentyloxy, 2-methylbutoxy, n-hexyloxy, and isohexyloxy.

The "mono-$C_{1-6}$ alkylamino" refers to amino having one "$C_{1-6}$ alkyl" described above as a substituent. Examples thereof include methylamino, ethylamino, n-propylamino, isopropylamino, n-butylamino, isobutylamino, sec-butylamino, tert-butylamino, n-pentylamino, isopentylamino, neopentylamino, 2-methylbutylamino, n-hexylamino, and isohexylamino.

One preferred form of the compound of the present invention is as follows.

$R^{11}$ is preferably a halogen atom, more preferably a chlorine atom.

$R^{12}$ is preferably a halogen atom, more preferably a chlorine atom.

$R^2$ is preferably $C_{1-6}$ alkyl, more preferably methyl.

Ring E is preferably pyrazole, imidazole, triazole, tetrazole, pyridine, pyridazine, pyrimidine, or pyrazine.

In this respect, $R^{31}$ is preferably a hydrogen atom, and $R^{32}$ is preferably a hydrogen atom.

In this respect, W is preferably a single bond or the formula —NH—.

Ring E is more preferably triazole, tetrazole, or pyrimidine.

In this respect, $R^{31}$ is preferably a hydrogen atom, and $R^{32}$ is preferably a hydrogen atom.

In this respect, W is preferably a single bond or the formula —NH—.

Ring E is further preferably triazole or tetrazole.

In this respect, $R^{31}$ is preferably a hydrogen atom, and $R^{32}$ is preferably a hydrogen atom.

In this respect, W is preferably a single bond.

In this respect, ring E and W (structure represented by the following formula [8] in the formula [7]) particularly preferably constitute any structure of the following formula group [10]:

[Formula 23]

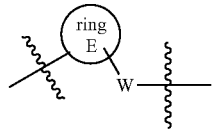

[8]

[Formula 24]

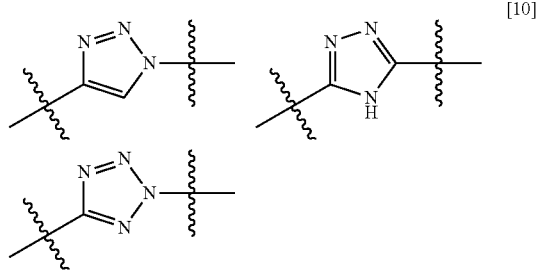

[10]

Alternatively, ring E is further preferably pyrimidine.

In this respect, $R^{31}$ is preferably a hydrogen atom, and $R^{32}$ is preferably a hydrogen atom.

In this respect, W is preferably the formula —NH—.

In this respect, ring E and W (structure represented by the following formula [8] in the formula [7]) particularly preferably constitute a structure of the following formula [11]:

[Formula 25]

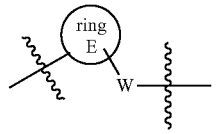

[8]

[Formula 26]

[11]

*structure with pyrimidine ring and HN group*

Y is preferably a structure represented by the following formula [3]:

[Formula 27]

$$\text{---}L^2\text{---}Z^1\text{·}L^{2'}\text{---}A'$$ [3]

In this formula, $Z^1$ is preferably any structure of the following formula group [6]:

[Formula 28]

[6]

*structures showing various linkers including diol diamides, triol diamides, tetraol diamides, urea-containing linkers with alkyl, PEG, and phenyl spacers*

Each of $L^2$ and $L^{2'}$ is preferably any structure of the following formula group [5]:

[Formula 29]

[5]

*PEG linker structures of varying lengths (2, 3, 4, and 5 ethylene glycol units)*

Another preferred form of the compound of the present invention is as follows.

$R^{11}$ is preferably a halogen atom, more preferably a chlorine atom.

$R^{12}$ is preferably a halogen atom, more preferably a chlorine atom.

$R^2$ is preferably $C_{1-6}$ alkyl, more preferably methyl.

Ring E is preferably pyrazole, imidazole, triazole, tetrazole, pyridine, pyridazine, or pyrimidine.

In this respect, $R^{31}$ is preferably a hydrogen atom, and $R^{32}$ is preferably a hydrogen atom.

In this respect, W is preferably a single bond, the formula —NH—, or the formula —CONH—.

Ring E is more preferably triazole, tetrazole, pyridine, pyridazine, or pyrimidine.

In this respect, $R^{31}$ is preferably a hydrogen atom, and $R^{32}$ is preferably a hydrogen atom.

In this respect, W is preferably a single bond, the formula —NH—, or the formula —CONH—.

Ring E is further preferably triazole or tetrazole.

In this respect, $R^{31}$ is preferably a hydrogen atom, and $R^{32}$ is preferably a hydrogen atom.

In this respect, W is preferably a single bond.

In this respect, ring E and W (structure represented by the following formula [8] in the formula [7]) particularly preferably constitute any structure of the following formula group [19]:

[Formula 30]

[8]

*structure showing ring E connected to W*

[Formula 31]

[19]

*triazole and tetrazole ring structures*

Alternatively, ring E is further preferably pyridine, pyridazine, or pyrimidine.

In this respect, $R^{31}$ is preferably a hydrogen atom, and $R^{32}$ is preferably a hydrogen atom.

In this respect, W is preferably the formula —NH— or the formula —CONH—.

In this respect, ring E and W (structure represented by the following formula [8] in the formula [7]) particularly preferably constitute a structure of the following formula [20]:

[Formula 32]

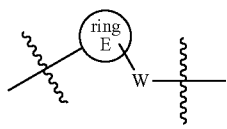
[8]

[Formula 33]

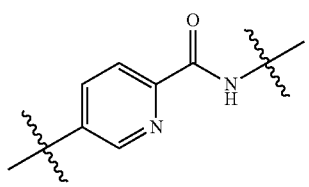
[20]

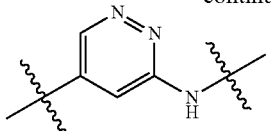

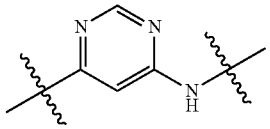

Y is preferably a structure represented by the following formula [3]:

[Formula 34]

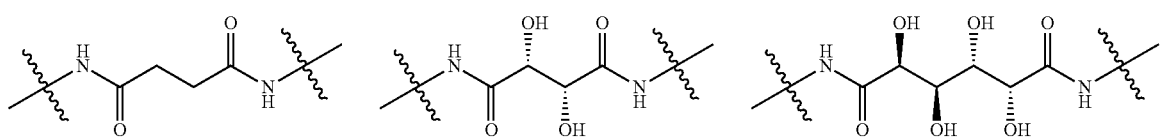
[3]

In this formula, $Z^1$ is preferably any structure of the following formula group [17]:

[Formula 35]

[17]

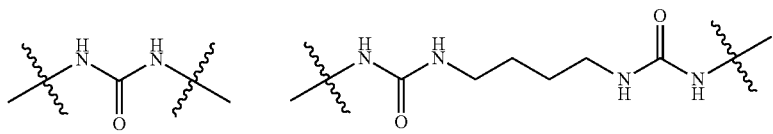

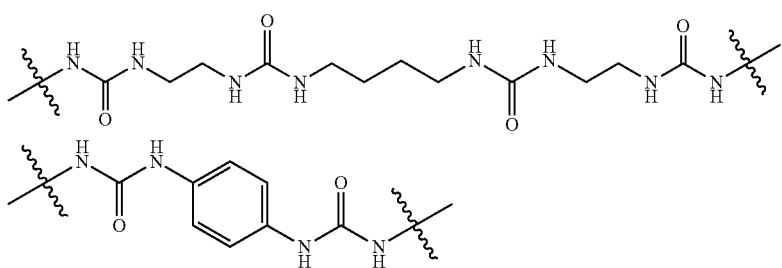

$Z^1$ is more preferably any structure of the following formula group [17']:
[Formula 36]
[17']
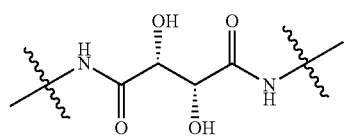
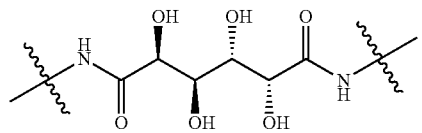
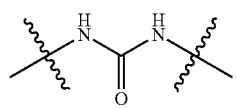
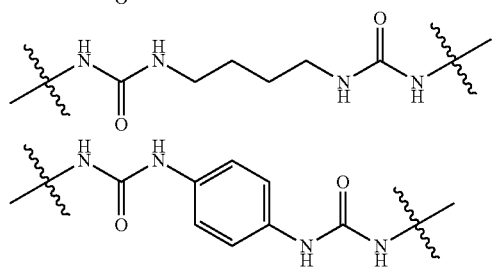
Each of $L^2$ and $L^{2'}$ is preferably any structure of the following formula group [5]:
[Formula 37]
[5]
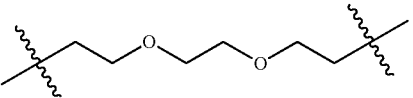
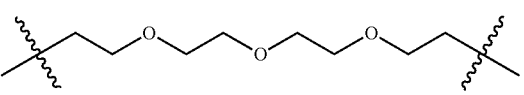
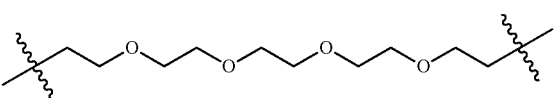
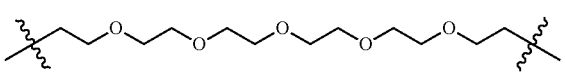
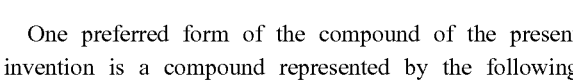
One preferred form of the compound of the present invention is a compound represented by the following formula [1-a] or a pharmaceutically acceptable salt thereof:
[Formula 38]
[1-a]
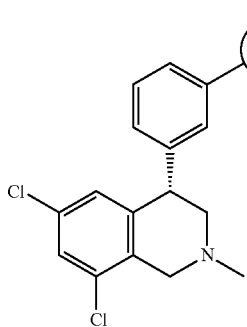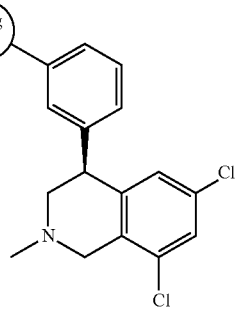

In this formula, preferred forms of ring E, W, $Z^1$, $L^2$, and $L^{2'}$ are as described above.

In a more preferred aspect, ring E is triazole, tetrazole, or pyrimidine.

In this respect, W is preferably a single bond or the formula —NH—.

In a further preferred aspect, ring E is triazole or tetrazole.

In this respect, W is preferably a single bond.

In a particularly preferred aspect, the structure represented by the following formula [8] in the formula [1-a] is any structure of the following formula group [10]:

[Formula 39]

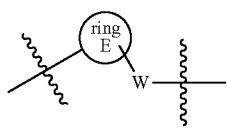

[8]

[Formula 40]

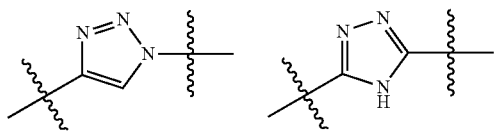

[10]

In an alternative further preferred aspect, ring E is pyrimidine.

In this respect, W is preferably the formula —NH—.

$Z^1$ is a structure of the following formula [12]:

[Formula 41]

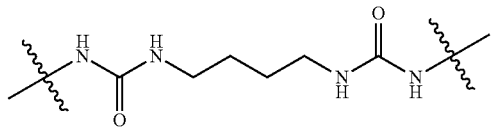

[12]

$L^2$ and $L^{2'}$ are the same and are any structure of the following formula group [13]:

[Formula 42]

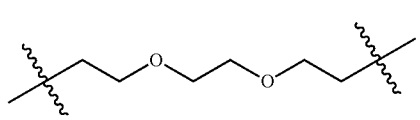

[13]

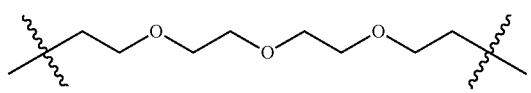

In a particularly preferred aspect, the structure represented by the following formula [8] in the formula [1-a] is a structure of the following formula [11]:

[Formula 43]

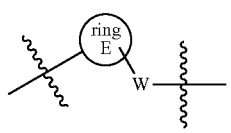

[8]

[Formula 44]

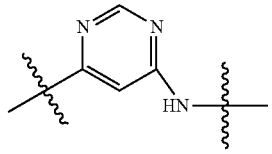

[11]

An alternative preferred form of the compound of the present invention is a compound represented by the following formula [1-a] or a pharmaceutically acceptable salt thereof:

[Formula 45]

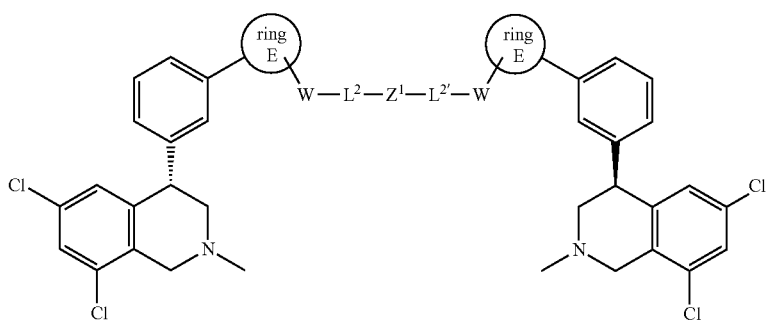

[1-a]

In this formula, preferred forms of ring E, W, $Z^1$, $L^2$, and $L^{2'}$ are as described above.

In a more preferred aspect, ring E is triazole, tetrazole, pyridine, pyridazine, or pyrimidine.

In this respect, W is preferably a single bond, the formula —NH—, or the formula —CONH—.

In a further preferred aspect, ring E is triazole or tetrazole.

In this respect, W is preferably a single bond.

$Z^1$ is preferably a structure of the following formula [17']:

[Formula 46]

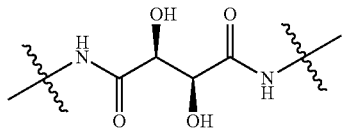
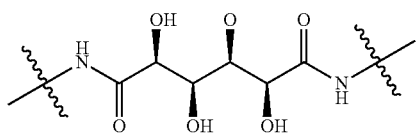
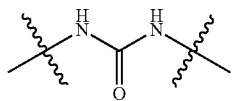
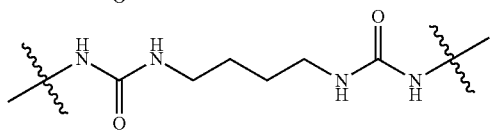
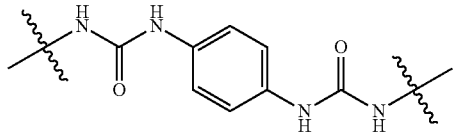

[17']

Preferably, $L^2$ and $L^{2'}$ are the same and are any structure of the following formula group [5]:

[Formula 47]

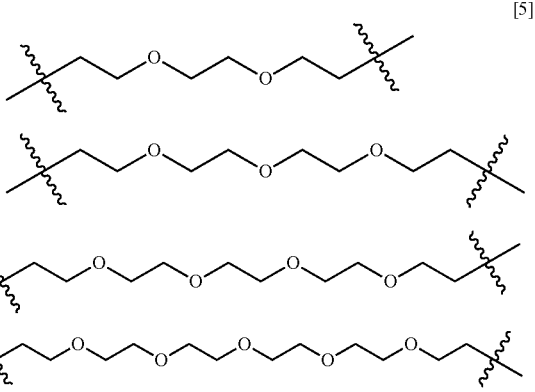

[5]

In a particularly preferred aspect, the structure represented by the following formula [8] in the formula [1-a] is any structure of the following formula group [19]:

[Formula 48]

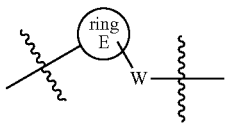

[8]

[Formula 49]

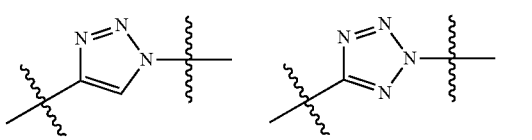

[19]

In an alternative further preferred aspect, ring E is pyridine, pyridazine, or pyrimidine.

In this respect, W is preferably the formula —NH— or the formula —CONH—.

Z¹ is preferably a structure of the following formula [21]:

[Formula 50]

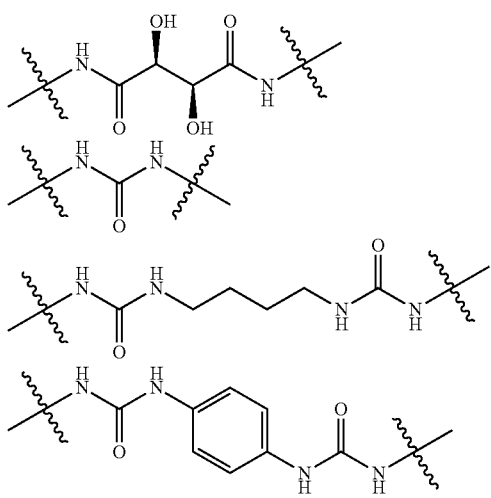
[21]

L² and L²' are the same and are any structure of the following formula group [22]:

[Formula 51]

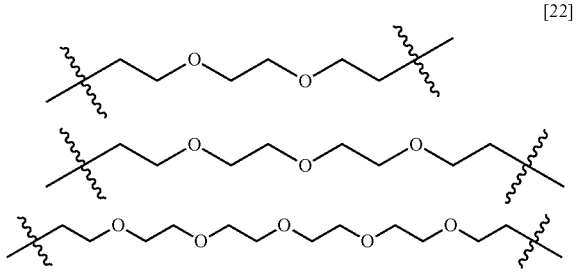
[22]

In a particularly preferred aspect, the structure represented by the following formula [8] in the formula [1-a] is a structure of the following formula [23]:

[Formula 52]

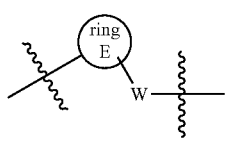
[8]

[Formula 53]

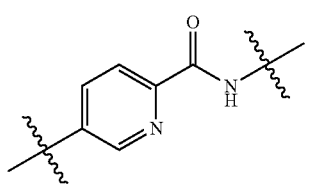
[23]

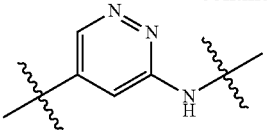

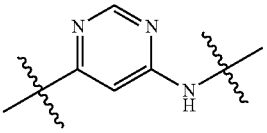

The compound of the present invention is a heteroaryl-substituted phenyltetrahydroisoquinoline compound. The compound of the present invention may be a pharmaceutically acceptable salt thereof (hereinafter, appropriately referred to as the "compound of the present invention").

Examples of the pharmaceutically acceptable salt include: acid addition salts including mineral acid salts such as hydrochloride, hydrobromide, hydroiodide, phosphate, sulfate, and nitrate, sulfonates such as methanesulfonate, ethanesulfonate, benzenesulfonate, p-toluenesulfonate, and trifluoromethanesulfonate, and organic acid salts such as oxalate, tartrate, citrate, maleate, succinate, acetate, trifluoroacetate, benzoate, mandelate, ascorbate, lactate, gluconate, and malate; amino acid salts such as glycine salt, lysine salt, arginine salt, ornithine salt, glutarate, and aspartate; inorganic salts such as lithium salt, sodium salt, potassium salt, calcium salt, and magnesium salt: and salts with organic bases, such as ammonium salt, triethylamine salt, diisopropylamine salt, and cyclohexylamine salt. The salt includes hydrate salts.

The compound of the present invention may have a chiral center. In this case, various optical isomers exist. Thus, the compound of the present invention may exist as separate optically active forms (R) and (S) and as a racemate or a (RS) mixture. Also, a compound having two or more chiral centers may further exist as diastereomers based on each optical isomerism. The compound of the present invention also includes mixtures containing all of these forms at arbitrary ratios. For examples, the diastereomers can be resolved by a method well known to those skilled in the art, for example, a fractional crystallization method. Also, the optically active forms can be obtained by an organic chemical approach well known for this purpose. The compound of the present invention may have geometric isomers such as cis and trans forms. The compound of the present invention further has tautomerism, and various tautomers exist. The compound of the present invention also includes these isomers and mixtures containing these isomers at arbitrary ratios.

When the compound of the present invention or the salt thereof forms a hydrate or a solvate, this hydrate or solvate is also included in the scope of the compound of the present invention or the salt thereof.

The compound of the present invention has a NHE3 inhibitory effect. The compound of the present invention allows sodium to be retained in the intestinal tract and draws out water. The compound of the present invention can solve constipation by softening intestinal contents. In this context, the constipation encompasses organic constipation, medicinal constipation, symptomatic constipation, and other constipation cases.

The compound of the present invention can also be used in combination with an existing therapeutic drug for constipation having a mechanism of action other than the NHE3 inhibitory effect, or a drug under development. The combined use of the compound of the present invention with an additional drug can be expected to exert stronger pharmacological effects than effects obtained with each drug alone.

Examples of the existing therapeutic drug for constipation that can be used in combination therewith can include: osmotic laxatives classified into saline laxatives such as magnesium oxide or sugar laxatives such as lactulose; bulk-forming laxatives such as calcium polycarbophil; stimulant laxatives such as sennoside and sodium picosulfate; emollient laxatives such as dioctyl sodium sulfosuccinate; serotonin 4 (5-HT4) receptor agonists such as mosapride; and type-2 chloride channel (ClC-2) agonists such as lubiprostone.

Examples of the drug under development that can be used in combination therewith can include: guanylate cyclase receptor agonists such as linaclotide:opioid receptor antagonists such as methylnaltrexone; IBAT-inhibiting substances such as elobixibat; SGLT1-inhibiting substances such as KWA-0711; serotonin 4 (5-HT4) receptor agonists such as DSP-6952; and GPR38 agonists such as DS-3801.

The compound of the present invention is capable of preventing or treating hypertension by inhibiting intestinal sodium absorption and allowing sodium to be excreted into feces. In this context, the hypertension encompasses essential hypertension, secondary hypertension, and salt-sensitive hypertension. The compound of the present invention is considered to be also useful as a drug that mimics salt restriction.

The compound of the present invention is capable of preventing or treating nephropathy by inhibiting intestinal sodium absorption. In this context, the nephropathy encompasses diabetic nephropathy, glomerulonephritis, nephrosclerosis, and polycystic kidney disease.

The compound of the present invention is capable of preventing or treating body fluid retention because the compound inhibits intestinal sodium absorption and enhances sodium excretion and body fluid excretion into feces. In this context, the body fluid retention encompasses body fluid retention caused by renal failure, body fluid retention caused by heart failure, body fluid retention caused by liver cirrhosis, and body fluid retention caused by drugs.

Therefore, the compound of the present invention can also be used in combination with an existing therapeutic drug for hypertension, nephropathy or ameliorating body fluid retention, or a drug under development, which have a mechanism of action other than the NHE3 inhibitory effect. The combined use of the compound of the present invention with an additional drug can be expected to exert stronger pharmacological effects than effects obtained with each drug alone.

Examples of the existing therapeutic drug for hypertension, therapeutic drug for nephropathy, therapeutic drug for heart failure, or drug ameliorating body fluid retention that can be used in combination therewith can include: angiotensin II receptor antagonists such as candesartan; angiotensin-converting enzyme inhibitors such as lisinopril; aldosterone receptor antagonists such as eplerenone; renin inhibitors such as aliskiren; calcium channel antagonists such as amlodipine; diuretics such as thiazide diuretics and loop diuretics; α and β blockers such as carvedilol; and K channel blockers such as amiodarone.

Examples of the drug under development that can be used in combination therewith can include: endothelin receptor antagonists such as atrasentan; PKC inhibitors such as ruboxistaurin; CCR2 receptor antagonists such as BMS-741672; aldosterone receptor antagonists such as BAY-94-8862; urotensin receptor antagonists such as ACT-058362; phosphodiesterase inhibitors such as PF-489791; NEP/ECE inhibitors such as daglutril; TGF beta antibodies such as LY-2382770; glycation reaction inhibitors such as aminoguanidine; Keap1-Nrf2 activators such as bardoxolone methyl; VAP-1 inhibitors such as ASP-8232; aldosterone synthase inhibitors; intestinal trypsin inhibitors; LPA receptor antagonists; epoxide hydrolase inhibitors; and EP4 receptor antagonists.

The compound of the present invention is further expected to inhibit the progression of diabetic nephropathy by combination with a therapeutic drug for diabetes mellitus or a drug under development.

Examples of the therapeutic drug for diabetes mellitus that can be used in combination therewith can include: insulin preparations: α-glucosidase inhibitors such as acarbose; SGLT2 inhibitors such as luseogliflozin; biguanide drugs such as metformin; insulin secretagogues such as mitiglinide; dipeptidyl peptidase IV inhibitors such as sitagliptin; GLP-1 receptor agonists such as liraglutide; PPARγ agonists such as pioglitazone; and aldose reductase inhibitors such as epalrestat.

Examples of the drug under development that can be used in combination therewith can include: glucokinase activators such as PF-04937319; glucagon receptor antagonists such as MK-0893; GLP-1 receptor agonists such as TTP054; amylin agonists such as pramlintide; 11 beta HSD1 inhibitors such as INCB-13739; GPR40 receptor agonists such as TAK-875; ACC inhibitors such as PSN-821; GPR119 receptor agonists such as PSN-821; GPR120 receptor agonists such as LC-540449; TGR5 receptor agonists such as SB-756050; aldose reductase inhibitors such as ranirestat; SGLT1-inhibiting substances such as KWA-0711; and adiponectin receptor agonists.

In addition, the compound of the present invention inhibits intestinal phosphorus absorption and allows phosphorus to be excreted into feces. Therefore, the compound of the present invention is considered to be also useful as a therapeutic drug for hyperphosphatemia.

The compound of the present invention is capable of preventing or treating CKD-MBD by inhibiting intestinal phosphorus absorption. In this context, the CKD-MBD encompasses hyperphosphatemia, hypercalcemia, hyperparathyroidism, vascular calcification, and osteoporosis caused by abnormal bone metabolism.

Therefore, the compound of the present invention can also be used in combination with an existing therapeutic drug or a drug under development for CKD-MBD having a mechanism of action other than the NHE3 inhibitory effect. The combined use of the compound of the present invention with an additional drug can be expected to exert stronger pharmacological effects than effects obtained with each drug alone.

Examples of the existing therapeutic drug for CKD-MBD that can be used in combination therewith can include: phosphate binders such as calcium carbonate, sevelamer hydrochloride, bixalomer, lanthanum carbonate, and ferric citrate; therapeutic drugs for hyperparathyroidism such as cinacalcet and falecalcitriol; and therapeutic drugs for osteoporosis including bisphosphonate preparations such as sodium ibandronate.

Examples of the therapeutic drug for CKD-MBD under development that can be used in combination therewith can include: phosphate binders such as PA21; and therapeutic drugs for hyperparathyroidism such as ONO-5163 and KHK7580.

The compound of the present invention can be administered alone or together with a pharmaceutically acceptable additive.

In order to use the compound of the present invention as a medicament, the medicament can be in any form of a solid composition, a liquid composition, and other compositions, and the optimum one is selected according to the need. The medicament of the present invention can be produced by mixing the compound of the present invention with a pharmaceutically acceptable additive. Specifically, the compound of the present invention can be prepared into tablets, pills, capsules, granules, dusts, powders, solutions, emulsions, suspensions, injections, or the like according to a formulation technique commonly used by adding an excipient or a diluent commonly used and, if necessary, a binder, a disintegrant, a lubricant, a coating agent, a sugar coating agent, a pH adjuster, a solubilizer, or an aqueous or non-aqueous solvent, etc., generally used. Examples of the additive can include water, lactose, dextrose, fructose, sucrose, sorbitol, mannitol, polyethylene glycol, propylene glycol, starch, corn starch, gum, gelatin, alginate, calcium silicate, calcium phosphate, cellulose, water syrup, methylcellulose, polyvinylpyrrolidone, alkyl p-hydroxybenzoate, talc, stearic acid, magnesium stearate, agar, pectin, gum arabic, glycerin, sesame oil, olive oil, soybean oil, cacao butter, ethylene glycol, low-viscosity hydroxypropylcellulose (HPC-L), microcrystalline cellulose, carboxymethylcellulose (CMC), carboxymethylcellulose sodium (CMC-Na), and other additives commonly used.

Also, the compound of the present invention can form, for a preparation, a clathrate compound with α, β, or γ-cyclodextrin or methylated cyclodextrin, etc.

The medicament according to the present invention can be in the form of a single preparation (combination drug) of the compound of the present invention and the aforementioned compound that can be used in combination therewith, or two or more preparations separately formulated from these compounds. In the case of the two or more preparations separately formulated from these compounds, the individual preparations can be administered at the same time or at a given interval of time. The two or more preparations can also be administered at their respective different numbers of doses per day. Also, the two or more preparations can also be administered through different routes.

When the medicament according to the present invention is produced in the form of two different preparations, these preparations are highly likely to be administered at the same time or at a very short interval. Therefore, it is preferred that a document such as a package insert of a commercially available medicament or a sales brochure should state that these preparations are used in combination.

Production examples of the preparations of the compound of the present invention will be shown below.

FORMULATION EXAMPLE 1

Granules containing the following components are produced.

Components: the compound represented by the formula [1] or the pharmaceutically acceptable salt thereof, lactose, corn starch, and HPC-L.

The compound represented by the formula [1] or the pharmaceutically acceptable salt thereof and lactose are sifted. Corn starch is sifted. These components are mixed in a mixer. An aqueous solution of HPC-L is added to the mixed powder, and the mixture is kneaded, granulated (extrusion granulation), and then dried. The obtained dried granules are sifted through a vibrating screen to obtain granules.

FORMULATION EXAMPLE 2

Powders for encapsulation containing the following components are produced.

Components: the compound represented by the formula [1] or the pharmaceutically acceptable salt thereof, lactose, corn starch, and magnesium stearate.

The compound represented by the formula [1] or the pharmaceutically acceptable salt thereof and lactose are sifted. Corn starch is sifted. These components are mixed with magnesium stearate in a mixer to obtain powders. The obtained powders can be encapsulated.

FORMULATION EXAMPLE 3

Granules for encapsulation containing the following components are produced.

Components: the compound represented by the formula [1] or the pharmaceutically acceptable salt thereof, lactose, corn starch, and HPC-L.

The compound represented by the formula [1] or the pharmaceutically acceptable salt thereof and lactose are sifted. Corn starch is sifted. These components are mixed in a mixer. An aqueous solution of HPC-L is added to the mixed powder, and the mixture is kneaded, granulated, and then dried. The obtained dried granules are sifted through a vibrating screen and size-regulated to obtain granules. The obtained granules can be encapsulated.

FORMULATION EXAMPLE 4

Tablets containing the following components are produced.

Components: the compound represented by the formula [1] or the pharmaceutically acceptable salt thereof, lactose, microcrystalline cellulose, magnesium stearate, and CMC-Na.

The compound represented by the formula [1] or the pharmaceutically acceptable salt thereof, lactose, microcrystalline cellulose, and CMC-Na are sifted and mixed. Magnesium stearate is added to the mixed powder to obtain a mixed powder for preparations. This mixed powder is directly compressed to obtain tablets.

When the compound of the present invention is used as a NHE3 inhibitor or the like, the compound of the present invention may be orally administered as it is. Alternatively, an agent comprising the compound of the present invention as an active ingredient may be orally administered.

When the compound of the present invention is used as a phosphorus absorption inhibitor or the like, the compound of the present invention may be orally administered as it is. Alternatively, an agent comprising the compound of the present invention as an active ingredient may be orally administered.

The dose of the compound of the present invention differs depending on a recipient, an administration route, a target disease, symptoms, etc. For example, one dose for oral administration to an adult patient having anemia is usually 0.1 mg to 1000 mg, preferably 1 mg to 200 mg, and this amount is desirably administered once to three times a day, or once every two or three days.

The compound of the present invention can be synthesized by methods shown below. The production methods described below are given as examples of general production methods and do not limit the methods for producing the compound of the present invention.

The compound of the present invention may be synthesized by use of a method known per se in the chemical field, or a method similar thereto involving one or two or more processes. Examples of such a method include methods described in ORGANIC FUNCTIONAL GROUP PREPARATIONS, 2nd edition, ACADEMIC PRESS, INC., 1986, Comprehensive Organic Transformations, VCH Publishers Inc., 1989, and Basics and Experiments of Peptide Synthesis, Maruzen Publishing Co., Ltd., 1985.

For the synthesis of the compound of the present invention, appropriate methods for protecting and deprotecting a functional group contained in a starting material or an intermediate, etc., can be carried out according to methods well known to those skilled in the art, for example, methods described in Greene's Protective Groups in Organic Synthesis, John Wiley and Sons, Inc., 2006.

General methods for producing the compound of the present invention are shown in schemes 1 to 18. The production methods described below are given as examples of general methods for producing compounds that occupy the great majority of Examples, and do not limit the methods for producing the compound of the present invention. The compound of the present invention can also be produced by use of a method well known to those skilled in the art, such as changing the orders of steps, carrying out a reaction with a hydroxy group or an amino group provided with a protective group and carrying out deprotection in a later step, or changing $R^2$, $R^{11}$, $R^{12}$, ring E, $G^2$, $G^3$, $G^4$, $Z^A$, $Z^B$, $X^1$, $Z^1$ and W without departing from the present invention by adding a new step during the course of each step.

In these general production methods, the "Sonogashira coupling reaction" means a reaction through, for example, which an aryl halide compound or a heteroaryl halide compound and an acetylene compound are coupled using a palladium catalyst and a copper catalyst in the presence of a base such as triethylamine or N,N-diisopropylethylamine at a temperature of 20° C. to 200° C. in an inert solvent.

Examples of the palladium catalyst for use in the "Sonogashira coupling reaction" include palladium catalysts generally known to those skilled in the art, such as tetrakis (triphenylphosphine)palladium(0), tris (dibenzylideneacetone)dipalladium(0), and bis (triphenylphosphine)palladium(II) dichloride. Examples of the copper catalyst include copper catalysts generally known to those skilled in the art, such as copper(I) iodide, copper(I) bromide, and copper(I) chloride.

In these general production methods, the "Huisgen cycloaddition" means a reaction through which, for example, an azide compound and an alkyne compound are subjected to [3+2] dipolar cycloaddition in the presence of a copper catalyst, in the presence or absence of a base, and in the presence or absence of sodium ascorbate at a temperature of 20° C. to 160° C. in an inert solvent.

Examples of the copper catalyst for use in the "Huisgen cycloaddition" include copper catalysts generally known to those skilled in the art, such as copper(I) iodide, copper(I) bromide, and copper(II) sulfate.

In these general production methods, the "Suzuki coupling reaction" means a reaction through which, for example, a vinyl halide compound, an aryl halide compound, or a heteroaryl halide compound and an aryl boron compound or a heteroaryl boron compound are coupled in the presence of a palladium catalyst and a base such as potassium carbonate or sodium carbonate at a temperature of 20° C. to 160° C. in an inert solvent.

Examples of the palladium catalyst for use in the "Suzuki coupling reaction" include palladium catalysts generally known to those skilled in the art, such as tetrakis(triphenylphosphine)palladium(0), bis(dibenzylideneacetone)palladium(0), tris(dibenzylideneacetone)dipalladium(0), bis(triphenylphosphine)palladium(II) dichloride, bis (triphenylphosphine)palladium(II) diacetate, and a [1,1'-bis (diphenylphosphino)ferrocene]palladium(II) dichloride-dichloromethane complex (1:1). Alternatively, a palladium (0) catalyst may be generated in a system using palladium (II) acetate or palladium-active carbon and triphenylphosphine in the presence of a base and used in the reaction.

Compounds (1-a), (2-a), (3-a), (3-b), (3-c), (3-e), (5-b), (6-a), (7-a), (7-b), (8-a), (8-b), (8-c), (10-a), (10-b), (10-d), (10-j), (11-a), (11-g), (12-a), (12-b), (13-b), (14-a), (16-c), and (18-a) serving as starting materials for use in general synthesis methods given below can be obtained as commercially available compounds, compounds known in the art, or compounds synthesized from compounds readily available by use of various organic synthesis approaches generally known to those skilled in the art.

Scheme 1: Method for Synthesizing Compound (1-b) or (1-c) from Compound (1-a)

[Formula 54]

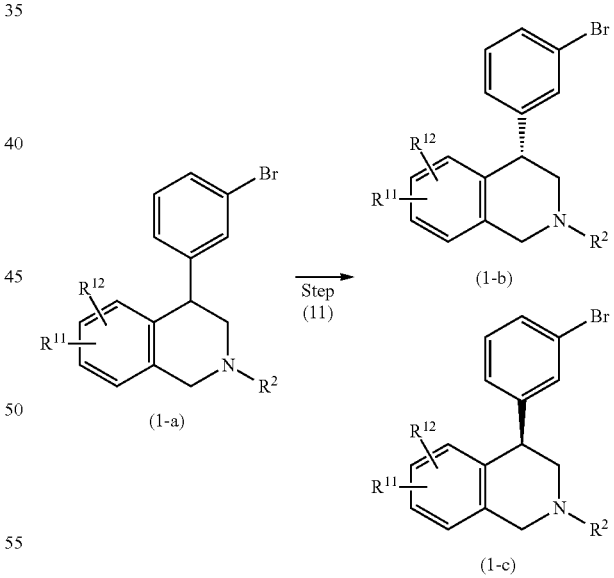

In the scheme, $R^2$, $R^{11}$, and $R^{12}$ are as defined above.

Step (1-1):

Method for producing compound (1-b) or compound (1-c): Compound (1-b) or compound (1-c) can be obtained with high optical purity by optical resolution of compound (1-a) using chiral preparative HPLC or the like.

Scheme 2: Method for Synthesizing Compound (2-c) from Compound (1-b)

[Formula 55]

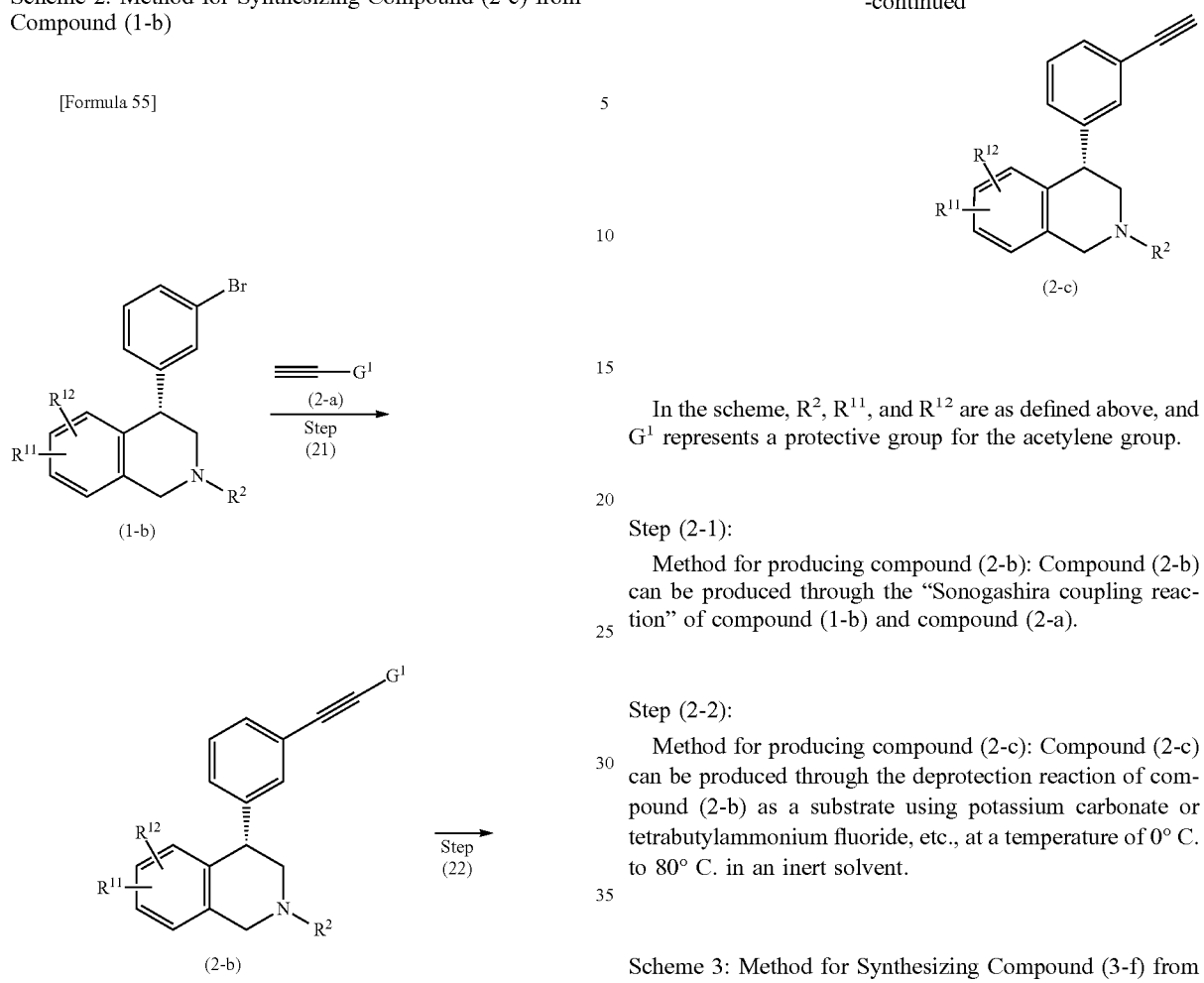

In the scheme, $R^2$, $R^{11}$, and $R^{12}$ are as defined above, and $G^1$ represents a protective group for the acetylene group.

Step (2-1):

Method for producing compound (2-b): Compound (2-b) can be produced through the "Sonogashira coupling reaction" of compound (1-b) and compound (2-a).

Step (2-2):

Method for producing compound (2-c): Compound (2-c) can be produced through the deprotection reaction of compound (2-b) as a substrate using potassium carbonate or tetrabutylammonium fluoride, etc., at a temperature of 0° C. to 80° C. in an inert solvent.

Scheme 3: Method for Synthesizing Compound (3-f) from Compound (1-b) or (3-d)

[Formula 56]

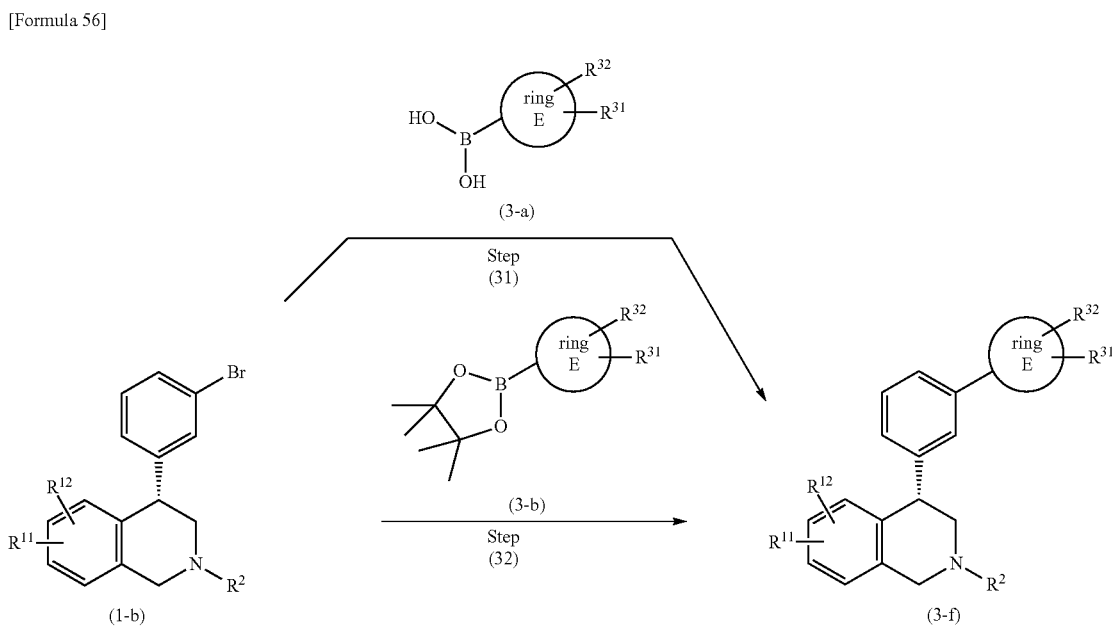

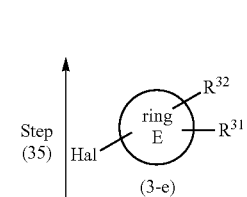
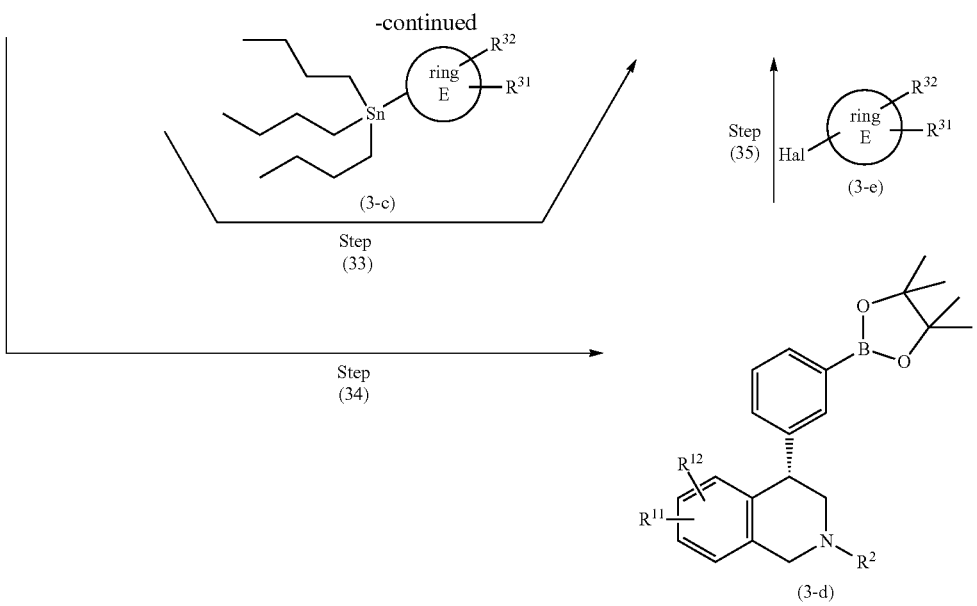

In the scheme, $R^2$, $R^{11}$, $R^{12}$, $R^{31}$, $R^{32}$, and ring E are as defined above, and Hal represents a halogen atom.

Step (3-1):

Method for producing compound (3-f): Compound (3-f) can be produced through the "Suzuki coupling reaction" of compound (1-b) and compound (3-a).

Step (3-2):

Different method for producing compound (3-f): Compound (3-f) can be produced through the "Suzuki coupling reaction" of compound (1-b) and compound (3-b).

Step (3-3):

Different method for producing compound (3-f): Compound (3-f) can be produced through the coupling reaction of compound (1-b) and compound (3-c) using a palladium (0) catalyst such as tetrakis(triphenylphosphine)palladium (0) at a temperature of 20° C. to 160° C. in an inert solvent.

Step (3-4):

Method for producing compound (3-d): Compound (3-d) can be produced through the reaction of compound (1-b) as a substrate with bis(pinacolato)diboron in the presence of a palladium catalyst such as a [1,1'-bis(diphenylphosphino)ferrocene]palladium(II) dichloride-dichloromethane complex (1:1) and a base such as potassium acetate at a temperature of 20° C. to 160° C. in an inert solvent.

Step (3-5):

Different method for producing compound (3-f): Compound (3-f) can be produced through the "Suzuki coupling reaction" of compound (3-d) and compound (3-e).

Scheme 4: Method for synthesizing compound (4-b) from compound (1-b)

[Formula 57]

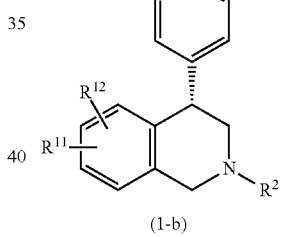

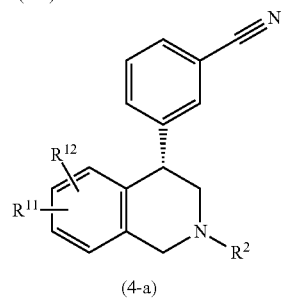

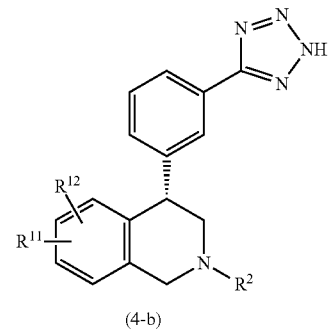

In the scheme, $R^2$, $R^{11}$, and $R^{12}$ are as defined above.

Step (4-1):

Method for producing compound (4-a): Compound (4-a) can be produced through the reaction of compound (1-b) as a substrate with zinc dicyanide in the presence of a palladium(0) catalyst such as tetrakis(triphenylphosphine)palladium(0) at a temperature of 20° C. to 160° C. in an inert solvent.

Step (4-2):

Method for producing compound (4-b): Compound (4-b) can be produced through the reaction of compound (4-a) as a substrate with an azide such as sodium azide in the presence of an inorganic acid salt of amine such as ammonium chloride or triethylamine hydrochloride at a temperature of 20° C. to 150° C. in an inert solvent.

Scheme 5: Method for Synthesizing Compound (5-c) from Compound (4-a)

[Formula 58]

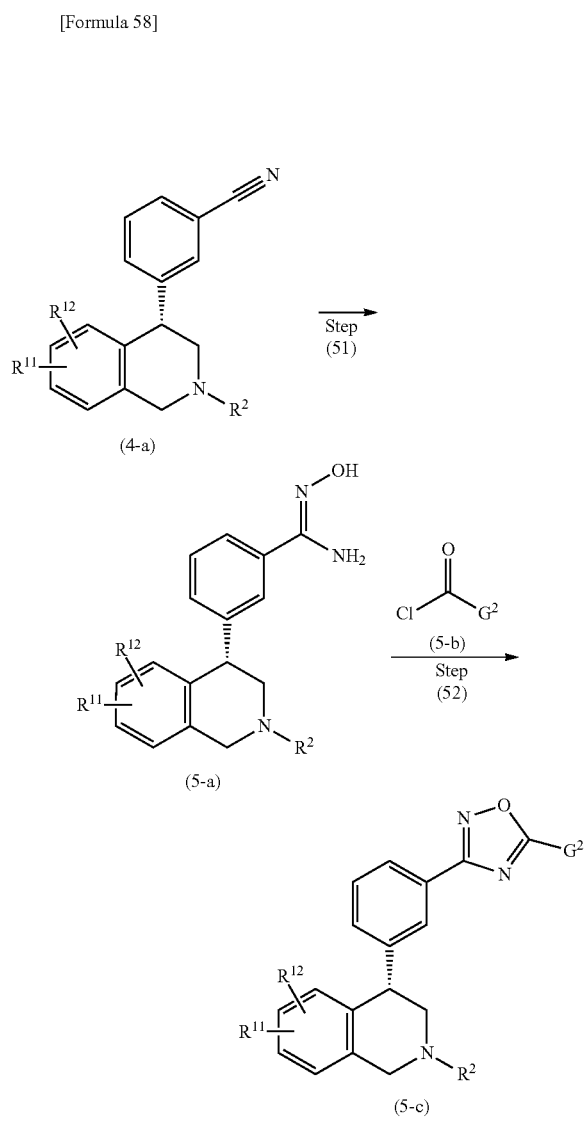

In the scheme, $R^2$, $R^{11}$, and $R^{12}$ are as defined above, and $G^2$ represents a $C_{1-6}$ alkyl group.

Step (5-1):

Method for producing compound (5-a): Compound (5-a) can be produced through the reaction of compound (4-a) as a substrate with hydroxylamine at a temperature of 20° C. to 80° C. in an inert solvent.

Step (5-2):

Method for producing compound (5-c): Compound (5-c) can be produced through the reaction of compound (5-a) as a substrate with compound (5-b) in the presence of a base such as triethylamine or N,N-diisopropylethylamine at a temperature of 0° C. to 160° C. in an inert solvent.

Scheme 6: Method for Synthesizing Compound (6-b) from Compound (2-c)

[Formula 59]

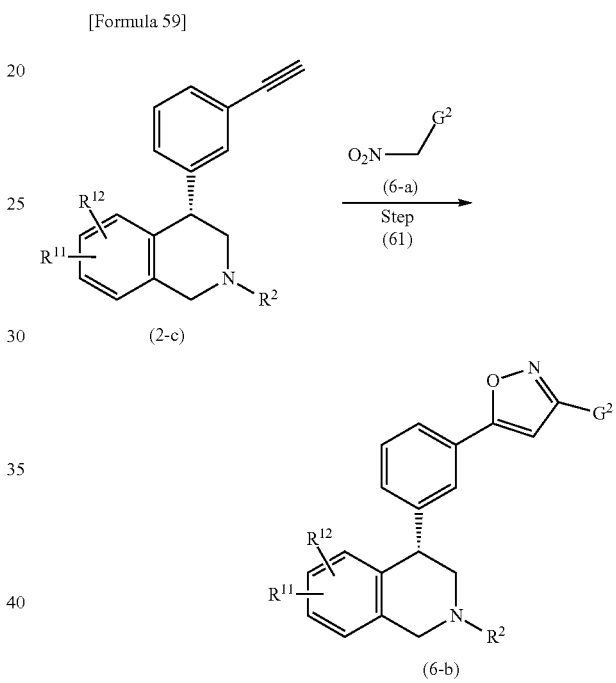

In the scheme, $R^2$, $R^{11}$, and $R^{12}$ are as defined above, and $G^2$ represents a $C_{1-6}$ alkyl group.

Step (6-1):

Method for producing compound (6-b): Compound (6-b) can be produced through the reaction of compound (2-c) as a substrate with compound (6-a) in the presence of phenyl isocyanate and a base such as triethylamine or N,N-diisopropylethylamine at a temperature of 20° C. to 100° C. in an inert solvent.

Scheme 7: Method for Synthesizing Compound (7-d) from Compound (7-a)

[Formula 60]

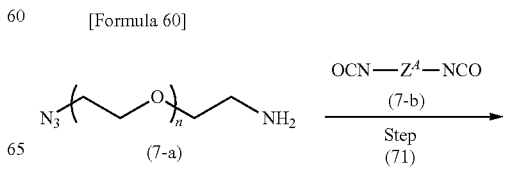

51

-continued

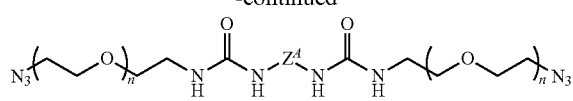

(7-c)

Step
(72) ↓

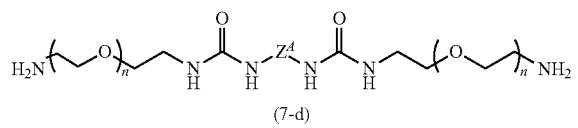

(7-d)

In the scheme, n represents an integer of 2 to 5, and $Z^A$ represents any structure represented by the following formula group [14]:

[Formula 61]

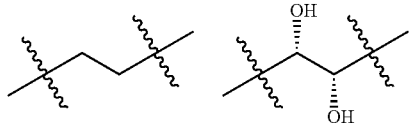

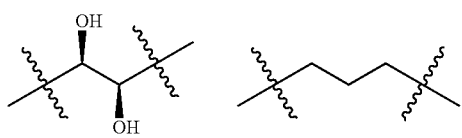

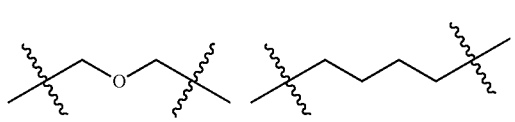

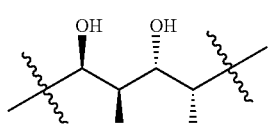

[14]

52

-continued

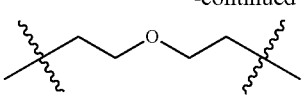

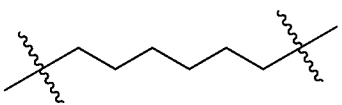

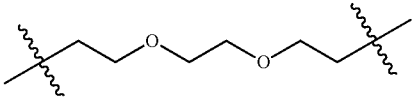

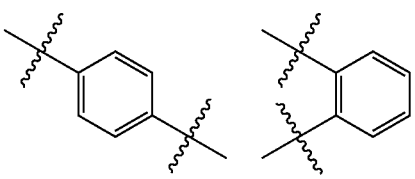

Step (7-1):
Method for producing compound (7-c): Compound (7-c) can be produced through the reaction of compound (7-a) as a substrate with compound (7-b) in the presence or absence of a base such as triethylamine or N,N-diisopropylethylamine at a temperature of 0° C. to 100° C. in an inert solvent.

Step (7-2):
Method for producing compound (7-d): Compound (7-d) can be produced by the action of triphenylphosphine and water on compound (7-b) as a substrate at a temperature of 0° C. to 80° C. in an inert solvent, or by the action of palladium-active carbon or the like thereon in the presence or absence of an acid in a hydrogen atmosphere or under pressurized hydrogen.

Scheme 8: Method for Synthesizing Compound (8-d) from Compound (7-a)

[Formula 62]

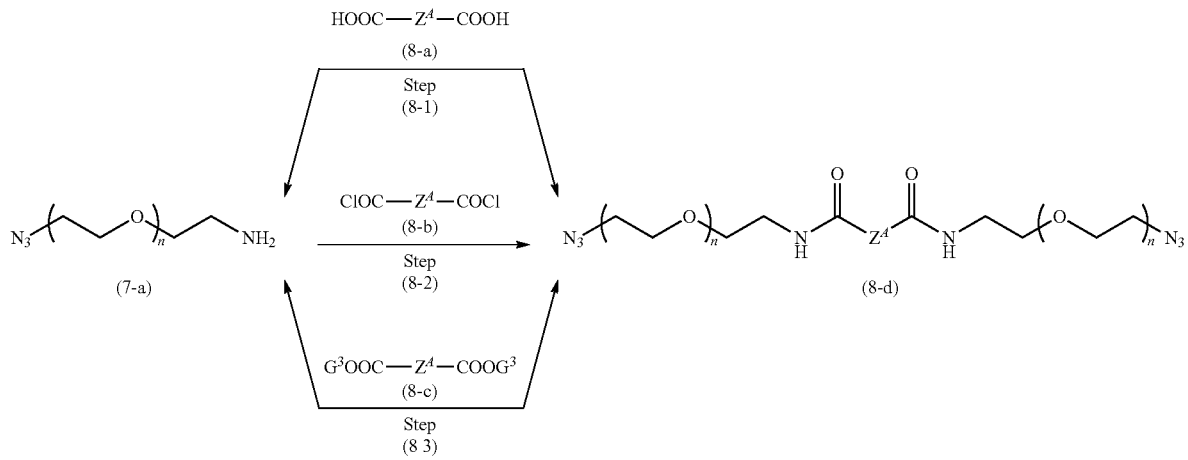

In the scheme, $G^3$ represents a protective group for the carboxy group, and n and $Z^A$ are as defined above.

Step (8-1):

Method for producing compound (8-d): Compound (8-d) can be produced through the reaction of compound (7-a) as a substrate with compound (8-a) in the presence of a dehydrative condensing agent such as various carbodiimides, diphenylphosphoric acid azide, benzotriazol-1-yloxy-trisdimethylaminophosphonium salt, or 4-(4,6-dimethoxy-1,3,5-triazin-2-yl)-4-methylmorpholine hydrochloride and in the presence or absence of a base such as triethylamine or N,N-diisopropylethylamine at a temperature of 0° C. to 80° C. in an inert solvent.

Step (8-2):

Different method for producing compound (8-d): Compound (8-d) can be produced through the reaction of compound (7-a) as a substrate with compound (8-b) in the presence of a base such as triethylamine or N,N-diisopropylethylamine at a temperature of 0° C. to 80° C. in an inert solvent.

Step (8-3):

Different method for producing compound (8-d): Compound (8-d) can be produced through the reaction of compound (7-a) as a substrate with compound (8-c) in the presence or absence of a base such as triethylamine or N,N-diisopropylethylamine at a temperature of 0° C. to 80° C. in an inert solvent.

Scheme 9: Method for Synthesizing Compound (9-a) from Compound (2-c)

[Formula 63]

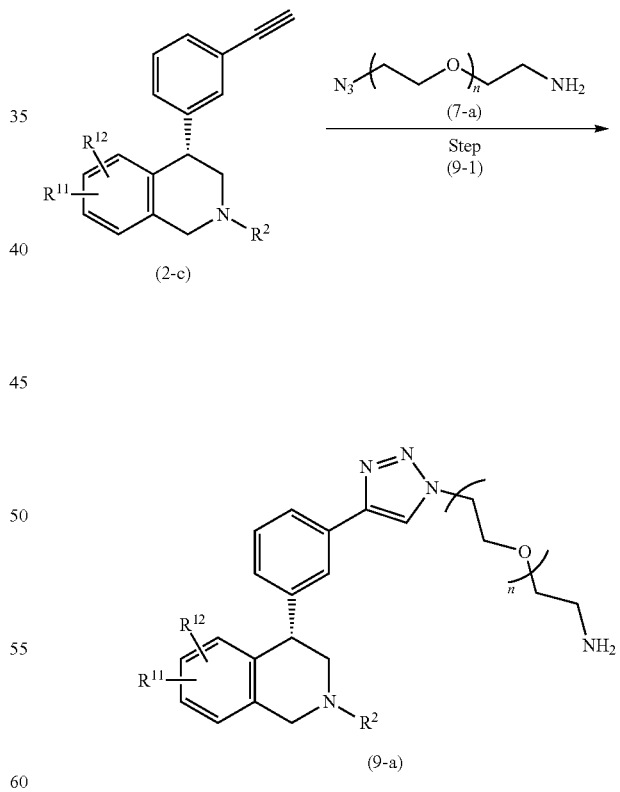

In the scheme, $R^2$, $R^{11}$, $R^{12}$, and n are as defined above.

Step (9-1):

Method for producing compound (9-a): Compound (9-a) can be produced through the "Huisgen cycloaddition" of compound (2-c) and compound (7-a).

Scheme 10: Method for synthesizing compound (10-i) from compound (10-a)

[Formula 64]

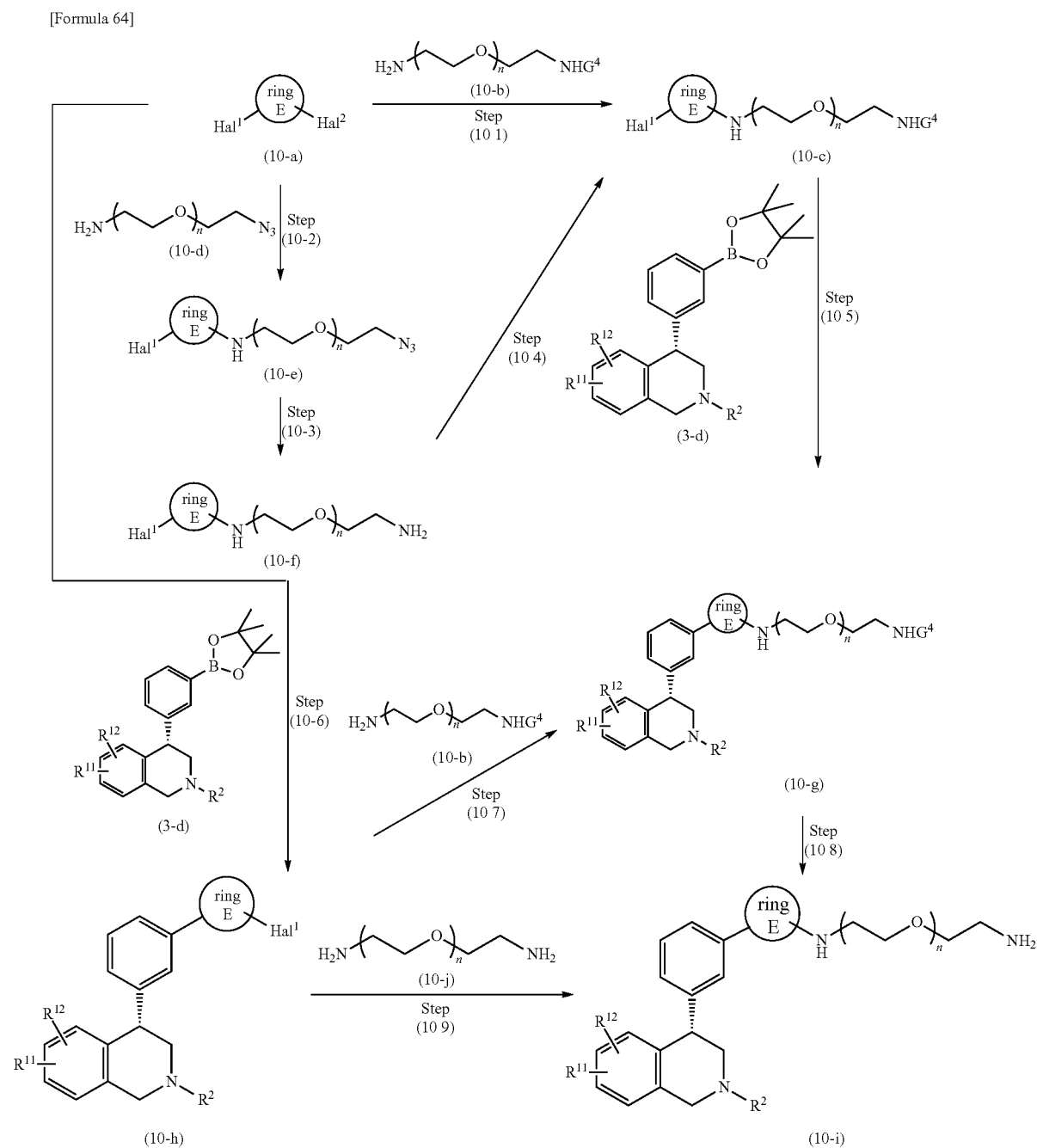

In the scheme, $R^2$, $R^{11}$, $R^{12}$, ring E, and n are as defined above, $Hal^1$ and $Hal^2$ are the same or different and each represent a halogen atom, and $G^4$ represents a protective group for the amino group.

Step (10-1):

Method for producing compound (10-c): Compound (10-c) can be produced through the reaction of compound (10-a) as a substrate with compound (10-b) in the presence or absence of a base such as triethylamine, N,N-diisopropylethylamine, or potassium carbonate at a temperature of 20° C. to 180° C. in an inert solvent.

Step (10-2):

Method for producing compound (10-e): Compound (10-e) can be produced through the reaction of compound (10-a) as a substrate with compound (10-d) by the same operation as in step (10-1).

Step (10-3):

Method for producing compound (10-f): Compound (10-f) can be produced by the action of triphenylphosphine and water on compound (10-e) as a substrate at a temperature of 0° C. to 80° C. in an inert solvent.

Step (10-4):

Different method for producing compound (10-c): Compound (10-c) can be produced by the protection of an amino group in compound (10-f) as a substrate using di-tert-butyl dicarbonate or the like at a temperature of 0° C. to 80° C. in an inert solvent.

Step (10-5):

Method for producing compound (10-g): Compound (10-g) can be produced through the "Suzuki coupling reaction" of compound (10-c) and compound (3-d).

Step (10-6):

Method for producing compound (10-h): Compound (10-h) can be produced through the "Suzuki coupling reaction" of compound (10-a) and compound (3-d).

Step (10-7):

Different method for producing compound (10-g): Compound (10-g) can be produced through the reaction of compound (10-h) as a substrate with compound (10-b) by the same operation as in step (10-1).

Step (10-8):

Method for producing compound (10-i): Compound (10-i) can be produced through the deprotection reaction of compound (10-g) as a substrate using an acid such as hydrochloric acid, hydrobromic acid, or trifluoroacetic acid at a temperature of 20° C. to 100° C. in an inert solvent, or through the deprotection reaction thereof using palladium-active carbon or the like in the presence or absence of an acid in a hydrogen atmosphere or under pressurized hydrogen.

Step (10-9):

Different method for producing compound (10-i): Compound (10-i) can be produced through the reaction of compound (10-h) as a substrate with compound (10-j) by the same operation as in step (10-1).

Scheme 11: Method for Synthesizing Compound (1-f) from Compound (10-a)

[Formula 65]

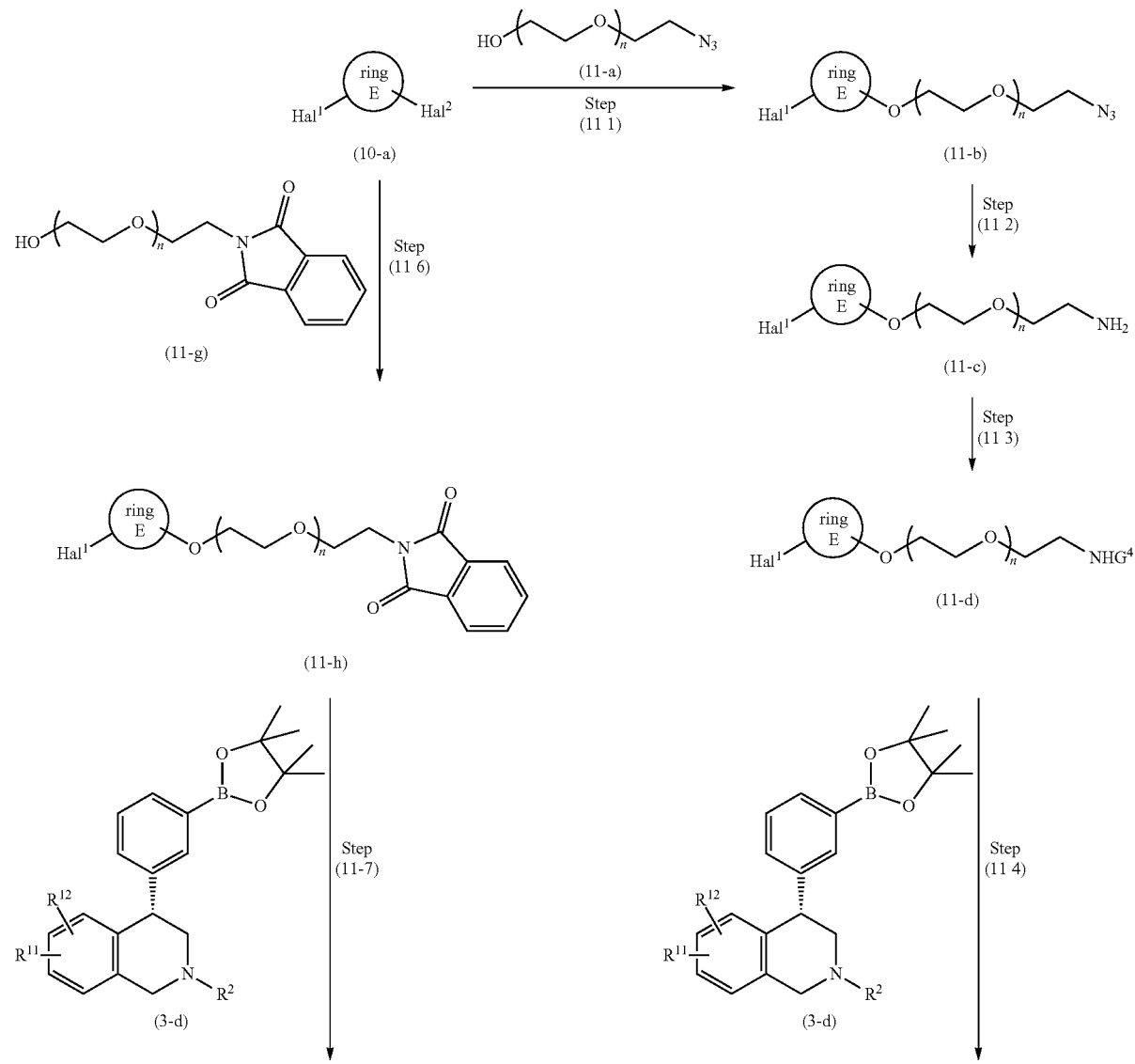

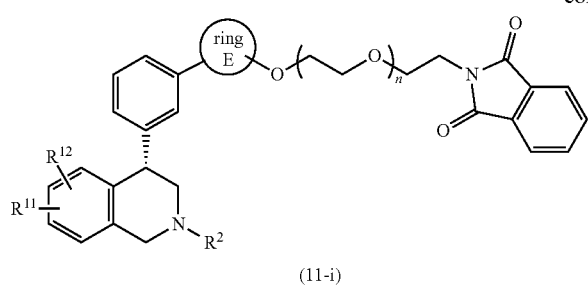

(11-i)

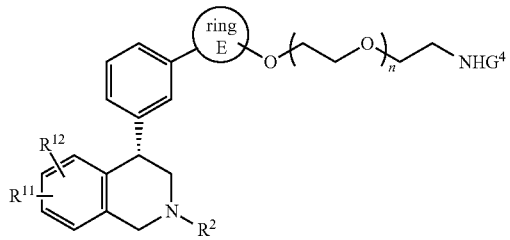

(11-e)

Step (11-5)

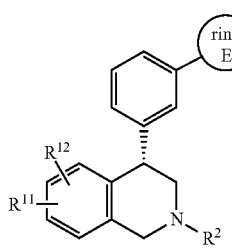

(11-f)

Step (11-8)

In the scheme, $R^2$, $R^{11}$, $R^{12}$, ring E, $Hal^1$, $Hal^2$, n, and $G^4$ are as defined above.

Step (11-1):

Method for producing compound (11-b): Compound (11-b) can be produced through the reaction of compound (10-a) as a substrate with compound (11-a) in the presence of a base such as potassium tert-butoxide at a temperature of 0° C. to 60° C. in an inert solvent.

Step (11-2):

Method for producing compound (11-c): Compound (11-c) can be produced with compound (11-b) as a substrate by the same operation as in step (10-3).

Step (11-3):

Method for producing compound (11-d): Compound (11-d) can be produced by the protection of an amino group in compound (11-c) as a substrate using di-tert-butyl dicarbonate or the like at a temperature of 0° C. to 80° C. in an inert solvent.

Step (11-4):

Method for producing compound (11-e): Compound (11-e) can be produced through the "Suzuki coupling reaction" of compound (11-d) and compound (3-d).

Step (11-5):

Method for producing compound (11-f): Compound (11-f) can be produced with compound (11-e) as a substrate by the same operation as in step (10-8).

Step (11-6):

Method for producing compound (11-h): Compound (11-h) can be produced through the reaction of compound (10-a) as a substrate with compound (11-g) in the presence of a base such as sodium hydride at a temperature of 0° C. to 100° C. in an inert solvent.

Step (11-7):

Method for producing compound (11-i): Compound (11-i) can be produced through the "Suzuki coupling reaction" of compound (11-h) and compound (3-d).

Step (11-8):

Different method for producing compound (11-f): Compound (11-f) can be produced through the deprotection reaction of compound (11-i) as a substrate using hydrazine or the like at a temperature of 20° C. to 100° C. in an inert solvent.

Scheme 12: Method for Synthesizing Compound (12-f) from Compound (12-a)

[Formula 66]

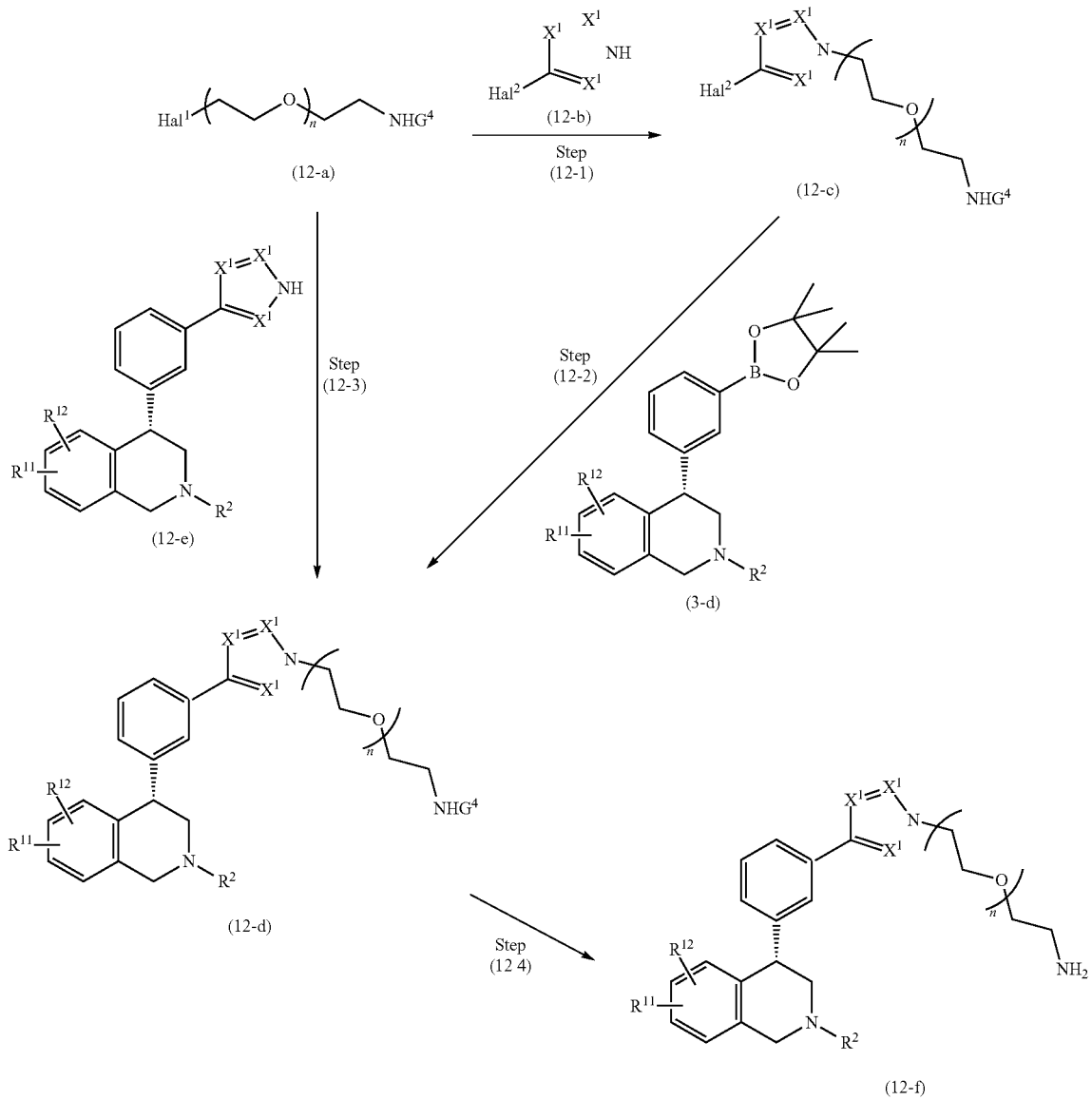

In the scheme, $R^2$, $R^{11}$, $R^{12}$, n, $Hal^1$, $Hal^2$, and $G^4$ are as defined above, and $X^1$ are the same or different and each represent the formula —CH— or a nitrogen atom.

Step (12-1):

Method for producing compound (12-c): Compound (12-c) can be produced through the reaction of compound (12-a) as a substrate with compound (12-b) in the presence of a base such as potassium carbonate and in the presence or absence of tetrabutylammonium iodide at a temperature of 0° C. to 160° C. in an inert solvent.

Step (12-2):

Method for producing compound (12-d): Compound (12-d) can be produced through the "Suzuki coupling reaction" of compound (12-c) and compound (3-d).

Step (12-3):

Different method for producing compound (12-d): Compound (12-d) can be produced through the reaction of compound (12-a) as a substrate with compound (12-e) in the presence of a base such as potassium carbonate and in the presence or absence of tetrabutylammonium iodide at a temperature of 0° C. to 160° C. in an inert solvent.

Step (12-4):

Method for producing compound (12-f): Compound (12-f) can be produced with compound (12-d) as a substrate by the same operation as in step (10-8).

Scheme 13: Method for Synthesizing Compound (13-e) or (13-f) from Compound (4-a)
[Formula 67]
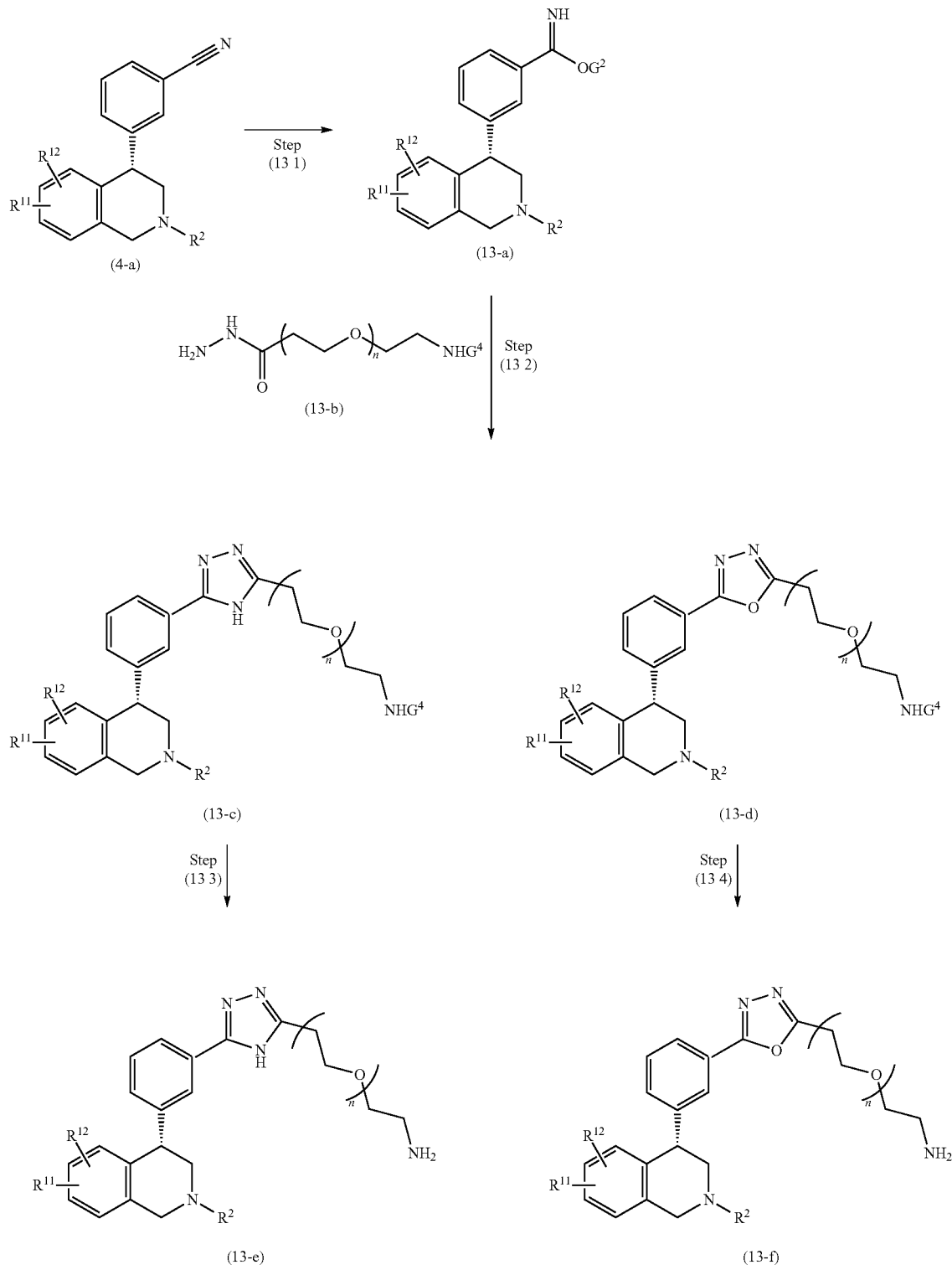

In the scheme, $R^2$, $R^{11}$, $R^{12}$, n, $G^2$ and $G^4$ are as defined above.

Step (13-1):

Method for producing compound (13-a): Compound (13-a) can be produced by the action of an alkali metal alkoxide such as sodium methoxide, an acid such as hydrochloric acid, or acetyl chloride, etc., on compound (4-a) as a substrate at a temperature of 0° C. to 80° C. in an alcohol solvent such as methanol or ethanol.

Step (13-2):

Method for producing compound (13-c) or compound (13-d): Compound (13-c) or compound (13-d) can be produced through the reaction of compound (13-a) as a substrate with compound (13-b) at a temperature of 20° C. to 160° C. in an inert solvent. Each obtained compound can be isolated by resolution using silica gel column chromatography, HPLC, or the like.

Step (13-3):

Method for producing compound (13-e): Compound (12-f) can be produced with compound (13-c) as a substrate by the same operation as in step (10-8).

Step (13-4):

Method for producing compound (13-f): Compound (13-f) can be produced with compound (13-d) as a substrate by the same operation as in step (10-8).

Scheme 14: Method for Synthesizing Compound (14-e) from Compound (14-a)

[Formula 68]

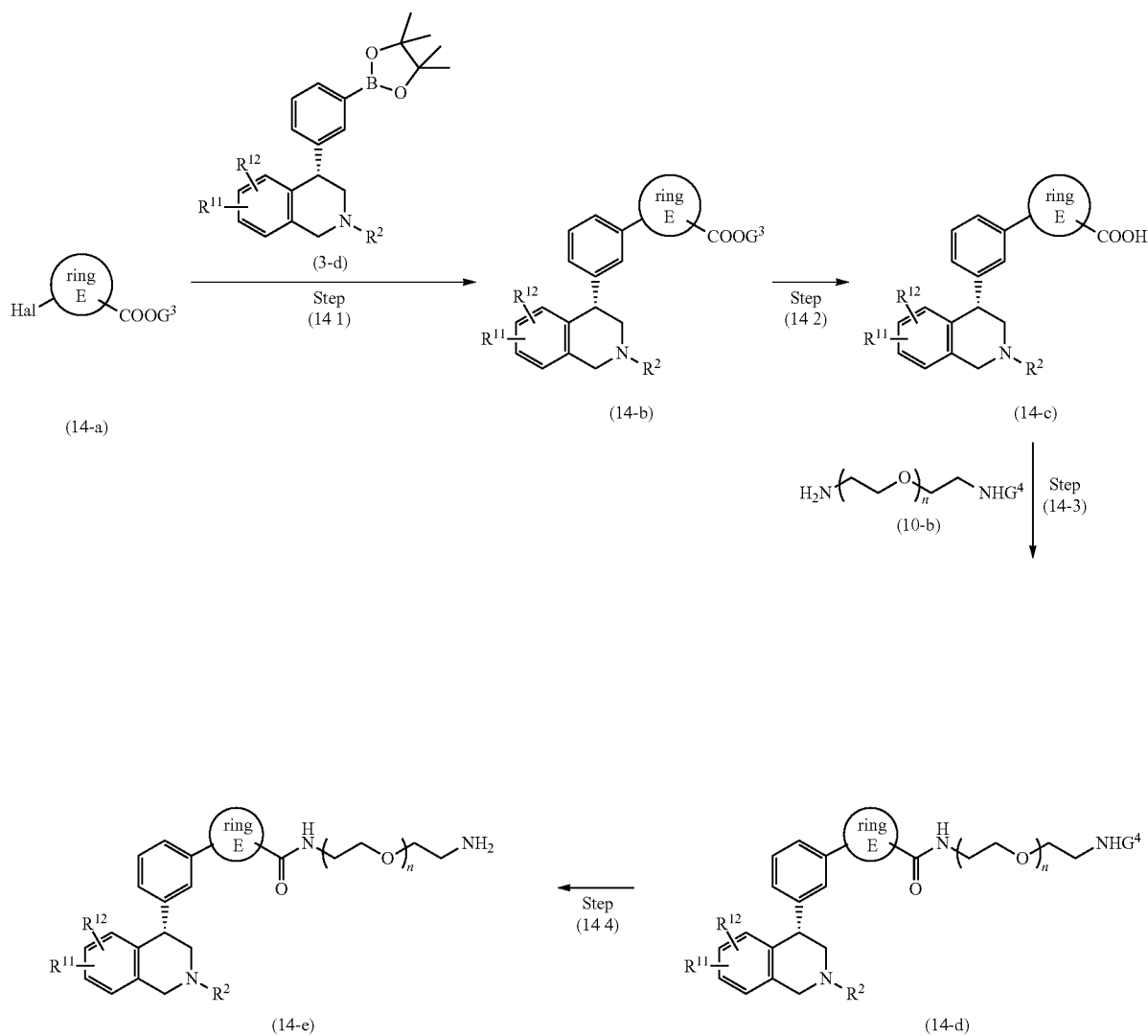

In the scheme, $R^2$, $R^{11}$, $R^{12}$, ring E, Hal, $G^3$, $G^4$, and n are as defined above.

Step (14-1):
Method for producing compound (14-b): Compound (14-b) can be produced through the "Suzuki coupling reaction" of compound (14-a) and compound (3-d).

Step (14-2):
Method for producing compound (14-c): Compound (14-c) can be produced by the action of lithium hydroxide or sodium hydroxide, etc., on compound (14-b) as a substrate at a temperature of 0° C. to 100° C. in an inert solvent.

Step (14-3):
Different method for producing compound (14-d): Compound (14-d) can be produced through the reaction of compound (14-c) as a substrate with compound (10-b) by the same operation as in step (8-1).

Step (14-4):
Compound (14-e) can be produced with compound (14-d) as a substrate by the same operation as in step (10-8).

Scheme 15: Method for Synthesizing Compound (15-b) from Compound (15-a)

[Formula 69]

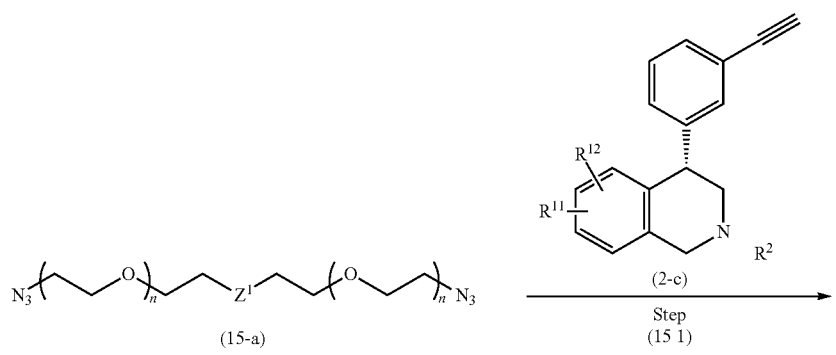

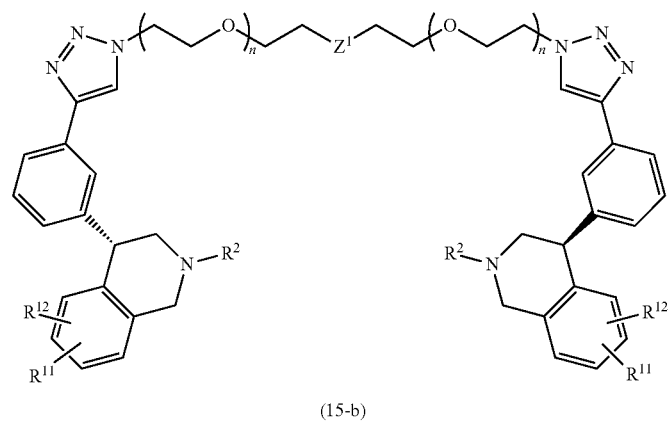

In the scheme, $Z^1$, $R^2$, $R^{11}$, $R^{12}$, and n are as defined above.

Step (15-1):

Method for producing compound (15-b): Compound (15-b) can be produced through the "Huisgen cycloaddition" of compound (15-a) and compound (2-c).

Scheme 16: Method for Synthesizing Compound (16-b) from Compound (16-a)

[Formula 70]

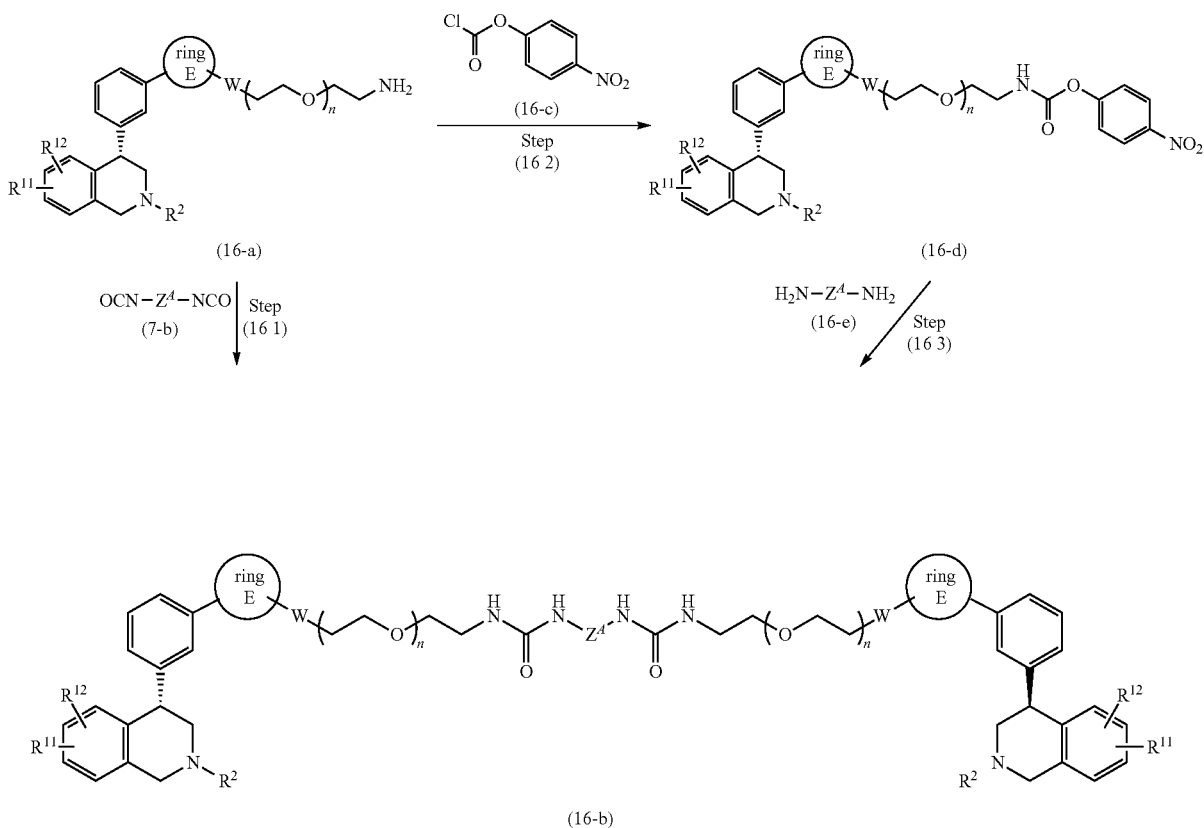

(16-b)

In the scheme, $R^2$, $R^{11}$, $R^{12}$, ring E, W, n, and $Z^A$ are as defined above.

Step (16-1):

Method for producing compound (16-b): Compound (16-b) can be produced through the reaction of compound (16-a) as a substrate with compound (7-b) by the same operation as in step (7-1).

Method for producing compound (16-d): Compound (16-d) can be produced through the reaction of compound (16-a) as a substrate with compound (16-c) in the presence or absence of a base such as triethylamine or N,N-diisopropylethylamine at a temperature of 0° C. to 160° C. in an inert solvent.

Different method for producing compound (16-b): Compound (16-b) can be produced through the reaction of compound (16-d) as a substrate with compound (16-e) in the presence or absence of a base such as triethylamine or N,N-diisopropylethylamine at a temperature of 0° C. to 160° C. in an inert solvent.

Scheme 17: Method for Synthesizing Compound (17-a) from Compound (16-a)

[Formula 71]

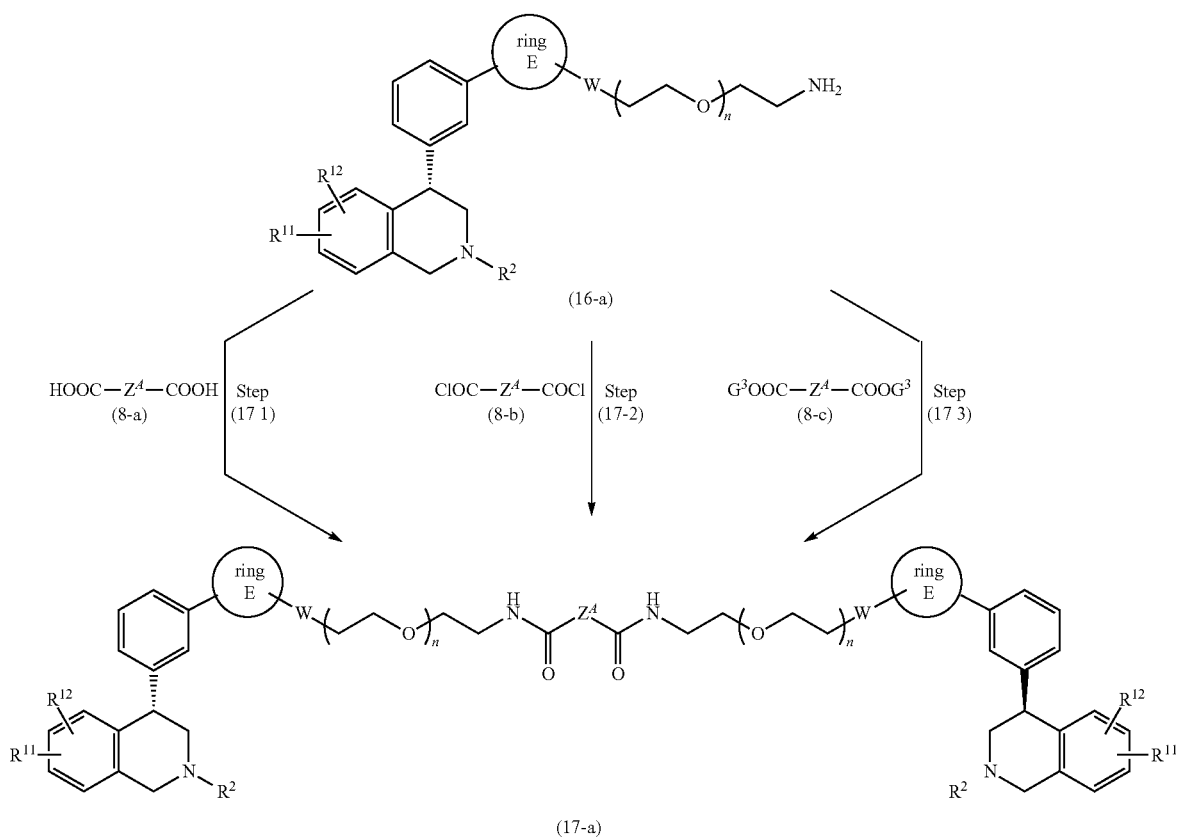

In the scheme, $R^2$, $R^{11}$, $R^{12}$, ring E, W, n, $Z^A$, and $G^3$ are as defined above.

Step (17-1):
Method for producing compound (17-a): Compound (17-a) can be produced through the reaction of compound (16-a) as a substrate with compound (8-a) by the same operation as in step (8-1).

Step (17-2):
Different method for producing compound (17-a): Compound (17-a) can be produced through the reaction of compound (16-a) as a substrate with compound (8-b) by the same operation as in step (8-2).

Step (17-3):
Different method for producing compound (17-a): Compound (17-a) can be produced through the reaction of compound (16-a) as a substrate with compound (8-c) by the same operation as in step (8-3).

Scheme 18: Method for Synthesizing Compound (18-c) from Compound (18-a)
[Formula 72]
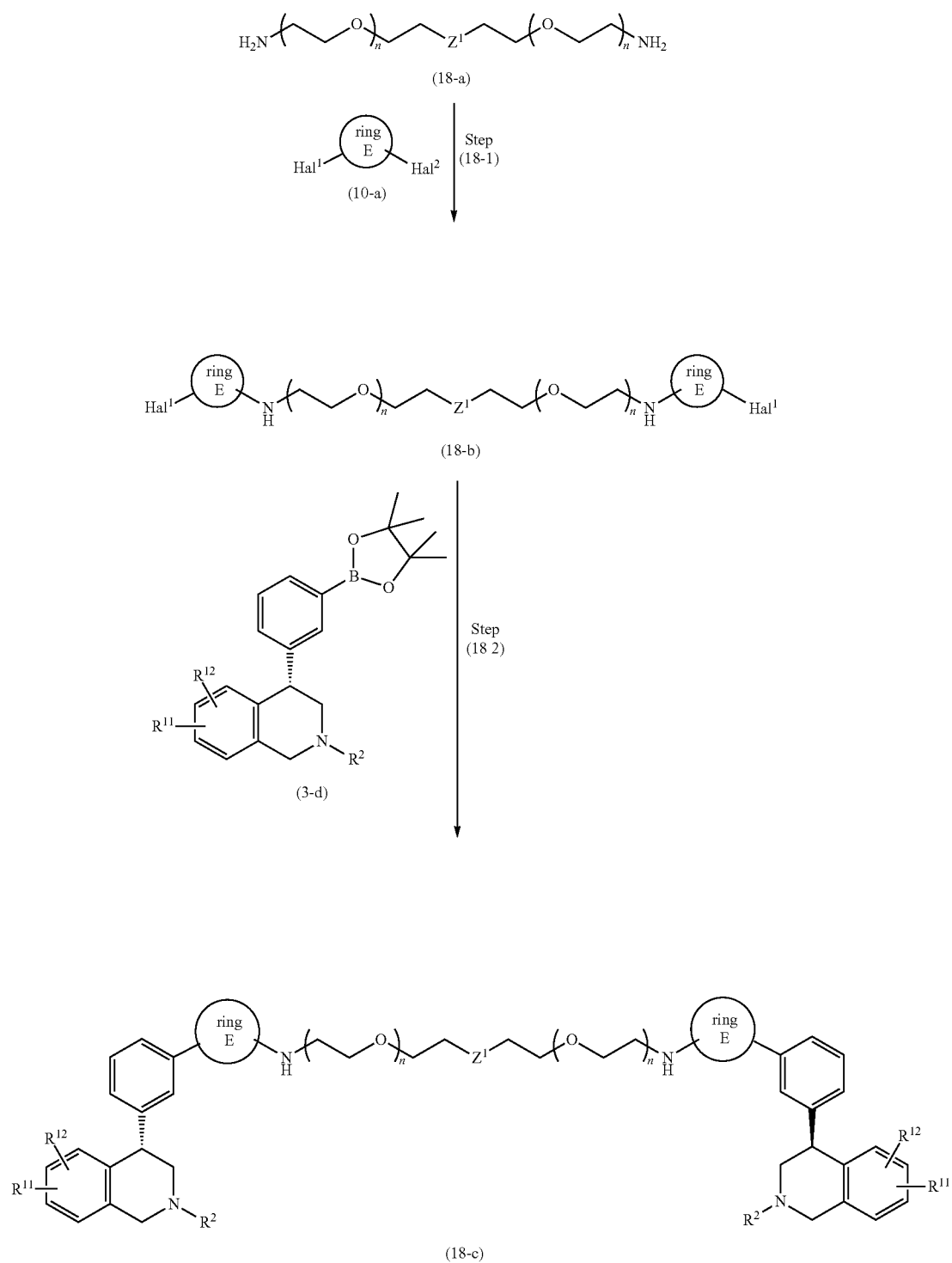

In the scheme, n, $Z^1$, $Hal^1$, $Hal^2$, ring E. $R^2$, $R^{11}$, and $R^{12}$ are as defined above.

Step (18-1):

Method for producing compound (18-b): Compound (18-b) can be produced through the reaction of compound (18-a) as a substrate with compound (10-a) by the same operation as in step (10-1).

Step (18-2):

Method for producing compound (18-c): Compound (18-c) can be produced through the "Suzuki coupling reaction" of compound (18-b) and compound (3-d).

Scheme 19: Method for Synthesizing Compound (19-c) from Compound (7-a)

[Formula 73]

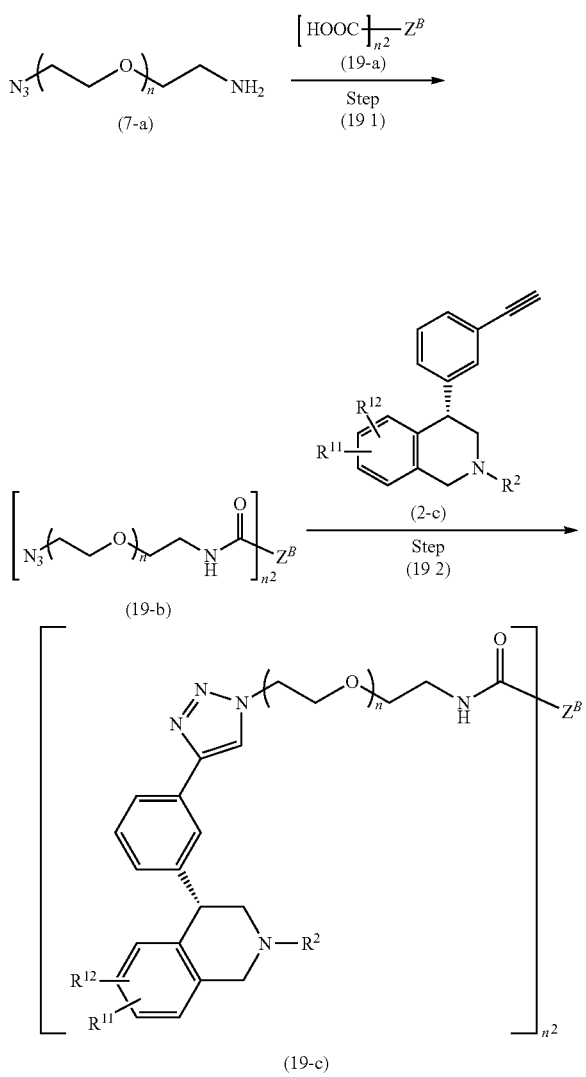

In the scheme, n, $R^2$, $R^{11}$, and $R^{12}$ are as defined above, $n^2$ represents 4, and $Z^B$ represents a structure represented by the following formula [15]:

[Formula 74]

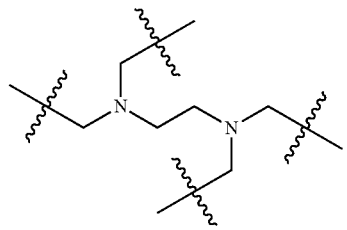

[15]

Step (19-1):

Method for producing compound (19-b): Compound (19-b) can be produced through the reaction of compound (7-a) as a substrate with compound (19-a) by the same operation as in step (8-1).

Step (19-2):

Method for producing compound (19-c): Compound (19-c) can be produced through the "Huisgen cycloaddition" of compound (19-b) and compound (2-c).

The reaction temperature in the general methods for producing the compound of the present invention is −78° C. to 250° C., preferably −20° C. to 80° C. The reaction time is 5 minutes to 3 days, preferably 30 minutes to 18 hours. These production methods can be carried out under normal pressure, under increased pressure, under microwave irradiation, etc.

The base, the acid, and the inert solvent described in the general methods for producing the compound of the present invention will be described more specifically, but are not limited to examples below. Also, an isolation approach that can be used will be specifically described, but is not limited to examples below.

Examples of the "base" include: inorganic bases such as alkali metal or alkaline earth metal hydrides (lithium hydride, sodium hydride, potassium hydride, calcium hydride, etc.), alkali metal or alkaline earth metal amides (lithium amide, sodium amide, lithium diisopropylamide, lithium dicyclohexylamide, lithium hexamethyldisilazide, potassium hexamethyldisilazide, etc.), alkali metal or alkaline earth metal hydroxides (sodium hydroxide, potassium hydroxide, lithium hydroxide, barium hydroxide, etc.), alkali metal or alkaline earth metal carbonates (sodium carbonate, potassium carbonate, calcium carbonate, cesium carbonate, etc.), alkali metal bicarbonates (sodium bicarbonate, potassium bicarbonate, etc.), and alkali metal or alkaline earth metal phosphates (tripotassium phosphate, etc.); alkali metal or alkaline earth metal $C_{1-15}$ alkoxides (sodium methoxide, sodium ethoxide, potassium tert-butoxide, etc.): amines (triethylamine, N,N-diisopropylethylamine, N-methylmorpholine, etc.); and basic heterocyclic compounds (pyridine, 4-dimethylaminopyridine, DBU (1,8-diazabicyclo[5.4.0]undec-7-ene), DBN (1,5-diazabicyclo[4.3.0]non-5-ene), imidazole, 2,6-lutidine, etc.).

Examples of the "acid" include inorganic acids (hydrochloric acid, hydrobromic acid, sulfuric acid, nitric acid, phosphoric acid, etc.), organic acids (p-toluenesulfonic acid, methanesulfonic acid, trifluoroacetic acid, formic acid, acetic acid, camphorsulfonic acid, etc.), and Lewis acids (boron trifluoride, boron tribromide, aluminum chloride, scandium triflate, ytterbium triflate, etc.).

The "inert solvent" is not particularly limited as long as the solvent does not inhibit the reaction and dissolves a starting material to some extent. Examples thereof include nitrile solvents, amide solvents, halocarbon solvents, ether solvents, aromatic solvents, hydrocarbon solvents, ester solvents, alcohol solvents, sulfoxide solvents, and water. Two or more of these solvents may be used as a mixture at an arbitrary ratio.

Examples of the nitrile solvents include acetonitrile and propionitrile. Examples of the amide solvents include N,N-dimethylformamide (hereinafter, also abbreviated to DMF), N,N-dimethylacetamide, and N-methylpyrrolidone. Examples of the halocarbon solvents include dichloromethane, chloroform, 1,2-dichloroethane, and carbon tetrachloride. Examples of the ether solvents include diethyl ether (hereinafter, also abbreviated to "ether"), tetrahydrofuran (hereinafter, also abbreviated to THF), 1,4-dioxane, and 1,2-dimethoxyethane. Examples of the aromatic solvents include benzene, toluene, xylene, and pyridine. Examples of the hydrocarbon solvents include pentane, hexane, heptane, and cyclohexane. Examples of the ester solvents include ethyl acetate and ethyl formate. Examples of the alcohol solvents include methanol, ethanol, isopropyl alcohol, tert-butyl alcohol, and ethylene glycol. Examples of the sulfoxide solvents include dimethyl sulfoxide (hereinafter, also abbreviated to DMSO).

The compounds obtained by the production methods described above can each be isolated and purified by an approach known in the art, for example, solvent extraction, liquid conversion, dissolution, crystallization, recrystallization, or various chromatography techniques.

Protective groups that can be used for compounds in the general production of the compound of the present invention will be described below but are not limited to examples below. Any of other appropriate protective groups can be selected.

Examples of the protective group for amino include $C_{1-6}$ acyl (formyl, acetyl, propionyl, etc.), $C_{2-15}$ alkoxycarbonyl (methoxycarbonyl, ethoxycarbonyl, tert-butoxycarbonyl, benzyloxycarbonyl, 9-fluorenylmethyloxycarbonyl, etc.), arylcarbonyl (benzoyl, etc.), trityl, phthaloyl, N,N-dimethylaminomethylene, substituted silyl (trimethylsilyl, triethylsilyl, dimethylphenylsilyl, tert-butyldimethylsilyl, tert-butyldiethylsilyl, tert-butyldiphenylsilyl, etc.), and $C_{2-6}$ alkenyl (1-allyl, etc.), which are generally used in peptide synthesis. These groups may each be substituted by one or more substituents selected from a halogen atom, $C_{1-6}$ alkoxy (methoxy, ethoxy, propoxy, etc.), and nitro.

Examples of the protective group for carboxy include $C_{1-6}$ alkyl (methyl, ethyl, tert-butyl, etc.), $C_{7-20}$ aralkyl (benzyl, trityl, etc.), phenyl, substituted silyl (trimethylsilyl, triethylsilyl, diinethylphenylsilyl, tert-butyldimethylsilyl, tert-butyldiethylsilyl, tert-butyldiphenylsilyl, etc.), and $C_{2-6}$ alkenyl (1-allyl, etc.). These groups may each be substituted by one or more substituents selected from a halogen atom, $C_{1-6}$ alkoxy (methoxy, ethoxy, propoxy, etc.), and nitro.

Examples of the protective group for hydroxy include $C_{1-6}$ alkyl (methyl, ethyl, tert-butyl, etc.), $C_{7-20}$ aralkyl (benzyl, trityl, etc.), phenyl, substituted silyl (trimethylsilyl, triethylsilyl, dimethylphenylsilyl, tert-butyldimethylsilyl, tert-butyldiethylsilyl, tert-butyldiphenylsilyl, etc.), $C_{2-6}$ alkenyl (1-allyl, etc.), $C_{1-6}$ acyl (formyl, acetyl, propionyl, etc.), $C_{2-15}$ alkoxycarbonyl (methoxycarbonyl, ethoxycarbonyl, tert-butoxycarbonyl, benzyloxycarbonyl, 9-fluorenylmethyloxycarbonyl, etc.), arylcarbonyl (benzoyl, etc.), 2-tetrahydropyranyl, and 2-tetrahydrofuryl. These groups may each be substituted by one or more substituents selected from a halogen atom, $C_{1-6}$ alkoxy (methoxy, ethoxy, propoxy, etc.), and nitro.

Carbonyl can be protected, for example, by forming cyclic acetal (1,3-dioxane, 1,3-dioxolane, etc.) or noncyclic acetal (di-$C_{1-6}$ alkylacetal (dimethylacetal, diethylacetal, etc.)).

The present invention will be described in more detail with reference to Reference Examples, Examples, Test Examples, and Formulation Examples below. However, the present invention is not intended to be limited by these examples, and various changes or modifications may be made without departing from the scope of the present invention.

The present invention will be described in more detail with reference to Reference Examples, Examples, and Test Examples, below. However, the present invention is not intended to be limited by these examples, and various changes or modifications may be made without departing from the scope of the present invention.

NMR (nuclear magnetic resonance) spectra were measured at room temperature at 200 MHz (GEMINI 2000/200, Varian Instruments) 300 MHz (INOVA 300, Varian Instruments, JEOL JNM-ECP300, JEOL Ltd., or JEOL JNM-ECX 300, JEOL Ltd.), 500 MHz (JEOL ECA 500 or JEOL JNM-ECP 500, JEOL Ltd.), or 600 MHz (JEOL JNM-ECA 600, JEOL Ltd.). Chemical shift values in the present specification were indicated by parts per million (δ) values with respect to an internal standard (tetramethylsilane).

Mass spectra were measured with Waters Micromass ZQ (ESI: electrospray ionization), Waters Acquity SQ Detector (ESI: electrospray ionization), Thermo SCIENTIFIC LTQ XL (ESI: electrospray ionization), Micromass GCT mass spectrometer (EI: electronic ionization), Shimadzu LCMS-2010EV mass spectrometer (ESI: electrospray ionization/APCI: atmospheric pressure chemical ionization Dual), Shimadzu LCMS-IT-TOF mass spectrometer (ESI: electrospray ionization/APCI: atmospheric pressure chemical ionization Dual), Thermo Fisher Scientific LCQ Deca XP (ESI: electrospray ionization), or Agilent Technologies Quadrupole LC/MS 6130 (ESI: electrospray ionization/APCI: atmospheric pressure chemical ionization Dual).

The degree of progression of each reaction was measured by use of TLC (Merck KGaA "Silica gel 60, F254" or Fuji Silysia Chemical Ltd. "CHROMATOREX TLC Plates NH"), revers-phase HPLC, or LC-MS.

Merck KGaA "Silica gel 60", Fuji Silysia Chemical Ltd. "Silica gel PSQ60", Kanto Chemical Co., Inc. "Silica gel 60" or "Silica gel 60N", Fuji Silysia Chemical Ltd. "CHROMATOREX NH", or a packed colunm (YAMAZEN Hi-Flash™ Column, MORITEX Purif Pack, MORITEX Purif Pack-NH, Biotage (registered trademark) SNAP Cartridge KP-Sil, Biotage (registered trademark) SNAP Cartridge KP-NH, Biotage (registered trademark) SNAP Cartridge HP-Sphere, or Biotage (registered trademark) ZIP™ Cartridge) was used in silica gel column chromatography.

SunFire™ Prep C18OBD™ 5 µm (I.D. 30 mm, length 50 mm), YMC-Actus Triart C18 5 µm (50×30 mm), Daicel Corporation CHIRALCEL OD-H 5 µm (I.D. 20 mm, length 250 mm), GL Science Inc. Inertsil ODS-3 5 µm (I.D. 20 mm, length 250 mm), Daicel Corporation CHIRALPAK IA 5 µm (I.D. 20 mm, length 250 mm), Daicel Corporation CHIRALPAK IB 5 µm (I.D. 20 mm, length 250 mm), or Daicel Corporation CHIRALPAK IE 5 µm (I.D. 20 mm, length 250 mm) was used as a preparative HPLC column.

Agilent Technologies Quadrupole LC/MS 6130 (Waters XBridge™ Prep C18 5 µm OBD™ (I.D. 19 mm, length 100 mm), or YMC-Actus Triart C18 5 µm (50×30 mm)) was used in preparative LC-MS.

REFERENCE EXAMPLE 1-1

(4S)-4-(3-Bromophenyl)-6,8-dichloro-2-methyl-1,2,3,4-tetrahydroisoquinoline

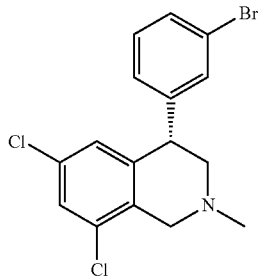

[Formula 75]

4-(3-Bromophenyl)-6,8-dichloro-2-methyl-1,2,3,4-tetrahydroisoquinoline (20 mg, described in the pamphlet of WO2003/048129) was divided into four portions (5 mg each) and resolved by chiral preparative HPLC (CHIRALPAK IA 5 μm (I.D. 20 mm, length 250 mm), hexane:2-propanol=10:90, 5.0 mL/min, 254 nm). A fraction eluted at a later retention time (retention time: approximately 22 min) was concentrated to obtain the title compound (6.0 mg, 100% ee) as a colorless oil substance.

LC-MS Retention Time 0.647 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 372 [M+H]$^+$.
Chiral HPLC Retention Time 2.780 min
Column: CHIRALPAK IA 3 um, 4.6×150 mm
Solvent: Hexane:2-propanol=10:90, 1 ml/min.

REFERENCE EXAMPLE 1-2

(4S)-4-(3-Bromophenyl)-6,8-dichloro-2-methyl-1,2,3,4-tetrahydroisoquinoline (2S,3S)-(+)-dibenzoyl-D-tartrate monoethanol monohydrate A solution of 4-(3-bromophenyl)-6,8-dichloro-2-methyl-1,2,3,4-tetrahydroisoquinoline (68 g, described in the pamphlet of WO2003/048129) in ethanol (1.4 L) was heated to 40° C. (2S,3S)-(+)-Dibenzoyl-D-tartaric acid (65 g) and water (68 mL) were added thereto, and the mixture was heated to 72° C., then allowed to cool, and stirred. At the point in time when the mixture was allowed to cool to 40 to 50° C., seed crystals were added thereto. The reaction system was ice-cooled, and the insoluble matter was filtered and washed with ice-cooled ethanol to obtain the title compound (55 g, 38%, 99.5% ee) as a colorless solid.

$^1$H NMR (300 MHz, CD$_3$OD) δ ppm 1.17 (t, J=7.0 Hz, 3H), 2.87 (s, 3H), 3.13-3.26 (m, 1H), 3.46-3.54 (m, 1H), 3.55-3.65 (m, 2H), 4.05-4.17 (m, 1H), 4.37-4.54 (m, 2H), 4.83-4.91 (m, 2H), 5.87-5.93 (m, 2H), 6.64-6.70 (m, 1H), 7.10-7.18 (m, 1H), 7.28 (t, J=7.8 Hz, 1H), 7.37-7.43 (m, 2H), 7.45-7.53 (m, 5H), 7.57-7.67 (m, 2H), 8.06-8.15 (m, 4H).
MS (+): 372 [M+H]$^+$.

REFERENCE EXAMPLE 2-1

(4S)-6,8-Dichloro-4-(3-ethynylphenyl)-2-methyl-1,2,3,4-tetrahydroisoquinoline

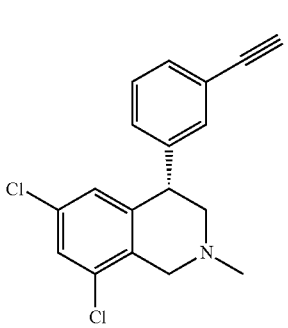

[Formula 76]

(1) To a solution of (4S)-4-(3-bromophenyl)-6,8-dichloro-2-methyl-1,2,3,4-tetrahydroisoquinoline (0.20 g) obtained in Reference Example 1-1 in acetonitrile (2.0 mL) and triethylamine (2.3 mL), copper(I) iodide (5.1 mg), bis(triphenylphosphine)palladium(II) dichloride (19 mg), and trimethylsilylacetylene (0.12 mL) were added, and the mixture was stirred for 1 hour under microwave irradiation (Biotage 60, 100° C.). The reaction solution was filtered through Celite (registered trademark), and then, the filtrate was concentrated under reduced pressure. The obtained residue was purified by silica gel column chromatography (Biotage(registered trademark) SNAP Cartridge HP-Sphere, hexane:ethyl acetate=100:0→70:30) to obtain (4S)-6,8-dichloro-2-methyl-4-{3-[(trimethylsilyl)ethynyl]phenyl}-1,2,3,4-tetrahydroisoquinoline (0.13 g, 59%) as a brown oil substance.

LC-MS Retention Time 0.935 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20) 1.2-1.4 min(1:99)
MS (+): 388 [M+H]$^+$.

(2) To a solution of (4S)-6,8-dichloro-2-methyl-4-{3-[(trimethylsilyl)ethynyl]phenyl}-1,2,3,4-tetrahydroisoquinoline (0.13 g) in methanol (3.8 mL), potassium carbonate (0.18 g) was added under ice cooling, and the mixture was stirred at room temperature for 1 hour. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge KP-NH, hexane:ethyl acetate=100:0→80:20) to obtain the title compound (83 mg, 82%) as a brown oil substance.

LC-MS Retention Time 0.635 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 316 [M+H]$^+$.

REFERENCE EXAMPLE 2-2

(4S)-6,8-Dichloro-4-(3-ethynylphenyl)-2-methyl-1,2,3,4-tetrahydroisoquinoline hydrochloride (4S)-6,8-Dichloro-4-(3-ethynylphenyl)-2-methyl-1,2,3,4-tetrahydroisoquinoline obtained in Reference Example 2-1 was dissolved in ethanol. To the solution, 4 mol/L hydrogen chloride in 1,4-dioxane was then added, and the solvent was distilled off under reduced pressure to obtain the title compound (0.17 g) as a colorless solid.

LC-MS Retention Time 0.635 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 316 [M+H]$^+$.

REFERENCE EXAMPLE 3-1

6,8-Dichloro-2-methyl-4-[3-(4,4,5,5-tetramethyl-1,3,2-dioxaborolan-2-yl)phenyl]-1,2,3,4-tetrahydroisoquinoline

[Formula 77]

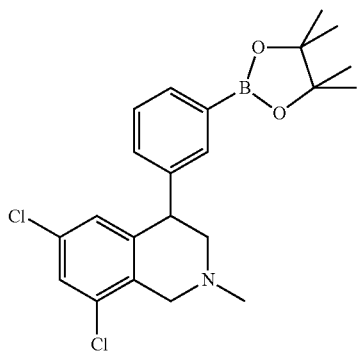

To a solution of 4-(3-bromophenyl)-6,8-dichloro-2-methyl-1,2,3,4-tetrahydroisoquinoline (0.50 g, described in the pamphlet of WO2003/048129) (0.50 g) in 1,4-dioxane (5.0 mL), bis(pinacolato)diboron (0.51 g), a [1,1'-bis(diphenylphosphino)ferrocene]palladium(II) dichloride-dichloromethane complex (1:1) (0.11 g), and potassium acetate (0.26 g) were added at room temperature in a nitrogen gas atmosphere, and the mixture was stirred at 90° C. for 6 hours. The reaction solution was allowed to cool, and then, water was added thereto, followed by extraction with ethyl acetate. The organic layer was dried over anhydrous magnesium sulfate and filtered through Celite (registered trademark), and then, the filtrate was concentrated under reduced pressure. The obtained residue was purified by silica gel column chromatography (Biotage(registered trademark) SNAP Cartridge HP-Sphere, hexane:ethyl acetate=100:0→50:50) to obtain the title compound (0.35 g, 53%) as a brown oil substance.

$^1$H NMR (300 MHz, CDCl$_3$) δ ppm 1.36 (s, 12H), 2.49 (s, 3H), 2.59 (dd, J=11.5, 9.5 Hz, 1H), 3.02-3.09 (m, 1H), 3.44-3.52 (m, 1H), 3.94 (d, J=16.0 Hz, 1H), 4.25-4.33 (m, 1H), 6.72-6.77 (m, 1H), 7.15-7.23 (m, 2H), 7.28-7.35 (m, 1H), 7.63 (s, 1H), 7.73 (dt, J=7.3, 1.2 Hz, 1H).
MS (+): 418 [M+H]$^+$.

REFERENCE EXAMPLE 3-2

(4S)-6,8-Dichloro-2-methyl-4-[3-(4,4,5,5-tetramethyl-1,3,2-dioxaborolan-2-yl)phenyl]-1,2,3,4-tetrahydroisoquinoline

[Formula 78]

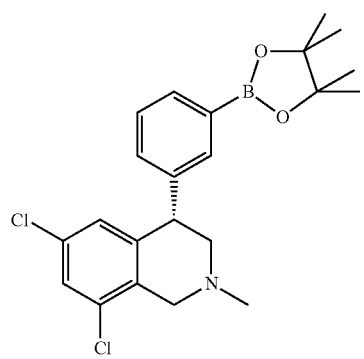

A suspension of (4S)-4-(3-bromophenyl)-6,8-dichloro-2-methyl-1,2,3,4-tetrahydroisoquinoline (0.66 g) obtained in Reference Example 1-1, bis(pinacolato)diboron (0.67 g), potassium acetate (0.35 g), and a [1,1'-bis(diphenylphosphino)ferrocene]palladium(II) dichloride-dichloromethane complex (1:1) (0.14 g) in 1,4-dioxane (8.8 mL) was stirred at 80° C. for 12 hours in an argon gas atmosphere. Water was added to the reaction solution. Then, the reaction mixture was dried over anhydrous magnesium sulfate and filtered, and then, the solvent was distilled off under reduced pressure. The obtained residue was purified by silica gel column chromatography (Biotage(registered trademark) SNAP Cartridge HP-Sphere, hexane:ethyl acetate=100:0→70:30) and further purified by silica gel column chromatography (Biotage(registered trademark) SNAP Cartridge HP-Sphere, hexane:ethyl acetate=99:1→50:50) to obtain the title compound (0.15 g, 20%) as a colorless amorphous substance.

$^1$H NMR (300 MHz, CDCl$_3$) δ ppm 1.36 (s, 12H), 2.48 (s, 3H), 2.52-2.63 (m, 1H), 2.96-3.06 (m, 1H), 3.42-3.53 (m, 1H), 3.82-3.94 (m, 1H), 4.22-4.33 (m, 1H), 6.73-6.78 (m, 1H), 7.15-7.23 (m, 2H), 7.28-7.35 (m, 1H), 7.62-7.66 (m, 1H), 7.69-7.75 (m, 1H).
MS (+): 418 [M+H]$^+$.

REFERENCE EXAMPLE 3-3

(4S)-6,8-Dichloro-2-methyl-4-[3-(4,4,5,5-tetramethyl-1,3,2-dioxaborolan-2-yl)phenyl]-1,2,3,4-tetrahydroisoquinoline hydrochloride To ((4S)-6,8-dichloro-2-methyl-4-[3-(4,4,5,5-tetramethyl-1,3,2-dioxaborolan-2-yl)phenyl]-1,2,3,4-tetrahydroisoquinoline (25 mg) obtained in Reference Example 3-2, 4 mol/L hydrogen chloride in ethyl acetate (0.20 mL) was added, and the mixture was stirred at room temperature for 13 hours. The insoluble matter was collected by filtration to obtain the title compound (22 mg) as a colorless solid.

$^1$H NMR (300 MHz, DMSO-d$_6$) δ ppm 1.29 (s, 12H), 2.96 (s, 3H), 3.46-3.64 (m, 1H), 3.65-3.86 (m, 1H), 4.25-

4.51 (m, 1H), 4.51-4.63 (m, 1H), 4.63-4.83 (m, 1H), 6.71 (br. s., 1H), 7.35-7.51 (m, 2H), 7.55 (br. s., 1H), 7.61-7.76 (m, 2H), 11.32 (br. s., 1H).

MS (+):418 [M+H]$^+$.

REFERENCE EXAMPLE 4-1 3-[(4S)-6,8-Dichloro-2-methyl-1,2,3,4-tetrahydroisoquinolin-4-yl]benzonitrile

[Formula 79]

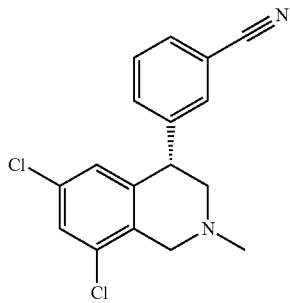

To a solution of (4S)-4-(3-bromophenyl)-6,8-dichloro-2-methyl-1,2,3,4-tetrahydroisoquinoline (0.50 g) obtained in Reference Example 1-1 in N,N-dimethylformamide (5.0 mL), zinc dicyanide (0.40 g) and tetrakis(triphenylphosphine)palladium(0) (0.31 g) were added at room temperature in a nitrogen gas atmosphere, and the mixture was stirred at 100° C. for 5 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→30:70) to obtain the title compound (0.40 g, 94%) as a pale yellow oil substance.

LC-MS Retention Time 0.553 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(80:20)→1.2-1.4 min(1:99)
MS (+): 317 [M+H]$^+$.

REFERENCE EXAMPLE 5-1 1,1'-Butane-1,4-diyl-bis(3-{2-[2-(2-azidoethoxy)ethoxy]ethyl}urea)

[Formula 80]

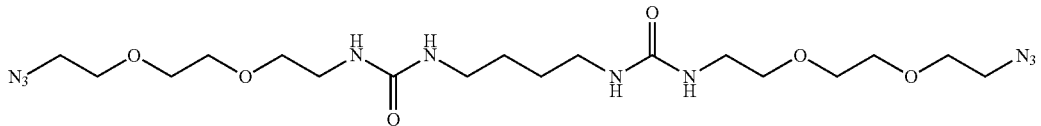

To a solution of 2-[2-(2-azidoethoxy)ethoxy]ethanamine (0.50 g) in 1,2-dichloroethane (10 mL), triethylamine (0.60 g) and 1,4-diisocyanatobutane (0.20 g) were added, and the mixture was stirred overnight at room temperature. The reaction solution was concentrated under reduced pressure, and then, the obtained residue was purified by silica gel column chromatography (Biotage (registered trademark) SNAP Cartridge HP-Sphere, chloroform:methanol=100:0→80:20) to obtain the title compound (0.52 g, 37%) as a colorless solid.

LC-MS Retention Time 0.588 min

LC:Agilent 1290

ESI/APCI MS:Agilent 6130

Column: Waters Acquity CSH C18 1.7 um, 2.1×50 mm
Solvent: H$_2$O:CH$_3$CN(0.1% Formic acid)

Gradient: 0.8 mL/min, 0 min(80:20)→1.2-1.4 min(1:99)
MS (+): 489 [M+H]$^+$.

REFERENCE EXAMPLE 5-2 1,1'-Butane-1,4-diyl-bis[3-(2-{2-[2-(2-azidoethoxy)ethoxy]ethoxy}ethyl)urea]

[Formula 81]

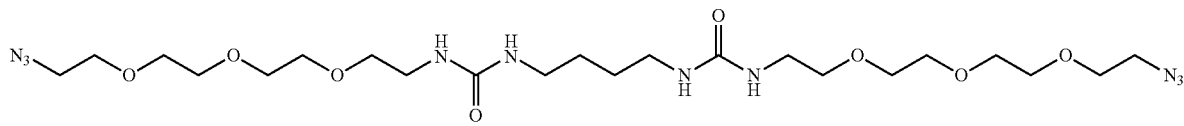

To a solution of 2-(2-(2-(2-azidoethoxy)ethoxy)ethoxy) ethanamine (0.50 g) in chloroform (7.5 mL), triethylamine (0.79 mL) was added under ice cooling, then a solution of 1,4-diisocyanatobutane (0.15 mL) in chloroform (7.5 mL) was added dropwise at room temperature, and the mixture was stirred at room temperature for 10 minutes. The reaction solution was concentrated under reduced pressure, and then, the obtained residue was purified by silica gel column chromatography (Biotage(registered trademark) SNAP Cartridge HP-Sphere, chloroform:methanol=100:0→90:10) to obtain the title compound (0.50 g, 76%) as a colorless solid.

$^1$H NMR (300 MHz, CDCl$_3$) δ ppm 1.43-1.58 (m, 4H), 3.15-3.23 (m, 4H), 3.32-3.45 (m, 8H), 3.52-3.58 (m, 4H), 3.62-3.72 (m, 20H), 5.10-5.25 (m, 4H).

MS (+): 577 [M+H]$^+$.

REFERENCE EXAMPLE 5-3

1,1'-Benzene-1,4-diylbis(3-{2-[2-(2-azidoethoxy)ethoxy]ethyl}urea)

[Formula 82]

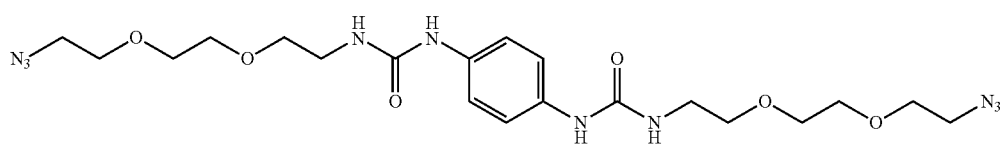

The title compound (0.16 g, 55%) was obtained as a colorless solid through substantially the same reaction as in Reference Example 5-1 except that 1,4-diisocyanatobenzene was used instead of 1,4-diisocyanatobutane.

LC-MS Retention Time 0.679 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(80:20)→1.2-1.4 min(1:99)
MS (+): 509 [M+H]$^+$.

REFERENCE EXAMPLE 5-4

1,1'-[Carbonylbis(iminoethane-2,1-diyl)]bis[3-(2-{2-[2-(2-azidoethoxy)ethoxy]ethoxy}ethyl)urea]

[Formula 83]

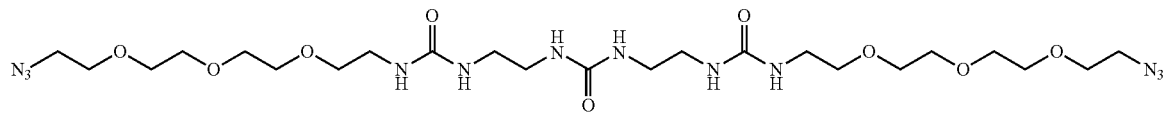

(1) To a solution of 1,1'-carbonyldiimidazole (1.6 g) in tetrahydrofuran (10 mL), tert-butyl (2-aminoethyl)carbamate (3.2 g) was added, and the mixture was stirred at room temperature for 3 hours. Water was added to the reaction solution, followed by extraction with chloroform. The organic layer was dried over sodium sulfate and filtered, and then, the filtrate was concentrated under reduced pressure. To the obtained residue, a small amount of chloroform was added, then ethyl acetate was added, and the insoluble matter was collected by filtration to obtain di-tert-butyl [carbonylbis(iminoethane-2,1-diyl)]biscarbamate (1.6 g) as a colorless amorphous substance.

LC-MS Retention Time 0.728 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(80:20)→1.2-1.4 min(1:99)
MS (+): 347 [M+H]$^+$.

(2) To di-tert-butyl [carbonylbis(iminoethane-2,1-diyl)] biscarbamate (1.4 g), a 4 mol/L solution of hydrogen chloride in 1,4-dioxane (5.0 mL) was added, and the mixture was stirred at room temperature for 1 hour. Then, 1,4-dioxane (5.0 mL) was added thereto, and the mixture was stirred at room temperature for 16 hours. The insoluble matter was collected by filtration and washed with chloroform to obtain 1,3-bis(2-aminoethyl)urea hydrochloride (0.70 g, 80%) as a colorless amorphous substance.

LC-MS Retention Time 0.230 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 147 $[M+H]^+$.

(3) To a solution of 2-{2-[2-(2-azidoethoxy)ethoxy]ethoxy}ethanamine (0.93 g) in chloroform (10 mL), triethylamine (0.85 mL) and 4-nitrophenyl carbonochloridate (0.82 g) were added, and the mixture was stirred at 0° C. for 30 minutes. Water was added to the reaction solution, followed by extraction with chloroform. The organic layer was dried over sodium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=95:5→0:100) to obtain 4-nitrophenyl (2-{2-[2-(2-azidoethoxy)ethoxy]ethoxy}ethyl)carbamate (0.90 g, 55%) as a colorless oil substance.

LC-MS Retention Time 0.868 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 384 $[M+H]^+$.

(4) To a solution of 4-nitrophenyl (2-{2-[2-(2-azidoethoxy)ethoxy]ethoxy}ethyl)carbamate (0.89 g) in chloroform (4.0 mL), triethylamine (0.32 mL) and 1,3-bis(2-aminoethyl)urea hydrochloride (0.25 g) were added, and the mixture was stirred at room temperature for 30 minutes. Then, N,N-dimethylformamide (4.0 mL) was added thereto, and the mixture was stirred at 60° C. for 2 hours. Ethyl acetate (20 mL) was added to the reaction solution, and the mixture was stirred for 30 minutes under ice cooling. Then, the insoluble matter was collected by filtration to obtain the title compound (0.55 g, 75%) as a colorless amorphous substance.

LC-MS Retention Time 0.580 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 635 $[M+H]^+$.

REFERENCE EXAMPLE 6-1

N,N'-Bis{2-[2-(2-azidoethoxy)ethoxy]ethyl}butanediamide

[Formula 84]

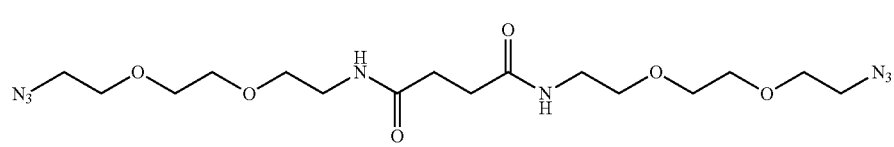

To a solution of 2-[2-(2-azidoethoxy)ethoxy]ethanamine (0.20 g) in N,N-dimethylformamide (10 mL), butanedioic acid (68 mg), O-(7-azabenzotriazol-1-yl)-N,N,N',N'-tetramethyluronium hexafluorophosphate (0.87 g), and triethylamine (0.12 g) were added, and the mixture was stirred overnight at room temperature. The reaction solution was purified by preparative LC-MS (LC (Agilent 1260), ESIMS (6130 Quadrupole, ESI), column (YMC-Actus Triart 5 μm C18 50×30 mm), mobile phase (0.1% formic acid in $H_2O$: 0.1% formic acid in $CH_3CN$=90:10→20:80→5:95), 50 mL/min.) to obtain the title compound (0.16 g, 65%) as a colorless oil substance.

LC-MS Retention Time 0.583 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 431 $[M+H]^+$.

REFERENCE EXAMPLE 6-2

1-Azido-N-{2-[2-(2-azidoethoxy)ethoxy]ethyl}-10-oxo-3,6,12-trioxa-9-azatetradecan-14-amide

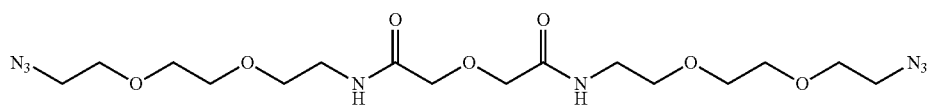

[Formula 85]

The title compound (0.15 g, 61%) was obtained as a colorless oil substance through substantially the same reaction as in Reference Example 6-1 except that 2,2'-oxydiacetic acid was used instead of butanedioic acid.
LC-MS Retention Time 0.601 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 447 $[M+H]^+$.

REFERENCE EXAMPLE 6-3

(2R,3R)—N,N'-Bis{2-[2-(2-azidoethoxy)ethoxy]ethyl}-2,3-dihydroxybutanediamide

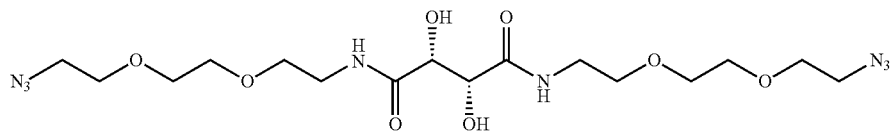

[Formula 86]

The title compound (0.15 g, 56%) was obtained as a colorless oil substance through substantially the same reaction as in Reference Example 6-1 except that L-(+)-tartaric acid was used instead of butanedioic acid.
LC-MS Retention Time 0.512 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 463 $[M+H]^+$.

REFERENCE EXAMPLE 6-4

(2R,3S,4R,5S)—N,N'-Bis{2-[2-(2-azidoethoxy)ethoxy]ethyl}-2,3,4,5-tetrahydroxyhexanediamide

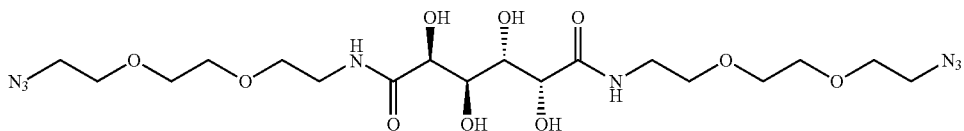

[Formula 87]

To a solution of 1,6-dimethyl D-galactarate (0.25 g, described in the pamphlet of WO2014/002039) in methanol (5.0 mL), 2-[2-(2-azidoethoxy)ethoxy]ethanamine (0.46 g) and N,N-diisopropylethylamine (0.46 g) were added, and the mixture was stirred for 6 hours under heating to reflux. The reaction solution was concentrated under reduced pressure, and the obtained residue was purified by preparative LC-MS (LC (Agilent 1260), ESIMS (6130 Quadrupole, ESI), column (YMC-Actus Triart 5 μm C18 50×30 mm), mobile phase (0.1% formic acid in H$_2$O:0.1% formic acid in CH$_3$CN=95:5→50:50→5:95), 50 mL/min.) to obtain the title compound (0.25 g, 46%) as a colorless solid.

LC-MS Retention Time 0.823 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 523 [M+H]$^+$.

REFERENCE EXAMPLE 6-5

(2R,3S,4R,5S)—N,N'-Bis(2-{2-[2-(2-azidoethoxy)ethoxy]ethoxy}ethyl)-2,3,4,5-tetrahydroxyhexanediamide To a solution of 1,6-dimethyl D-galactarate (0.50 g, described in the pamphlet of WO2014/002039) in methanol (5.0 mL), 2-{2-[2-(2-azidoethoxy)ethoxy]ethoxy}ethanamine (1.1 g) and N,N-diisopropylethylamine (0.92 g) were added, and the mixture was stirred for 6 hours under heating to reflux. The reaction solution was concentrated under reduced pressure, and the obtained residue was purified by preparative LC-MS (LC (Agilent 1260), ESIMS (6130 Quadrupole, ESI), column (YMC-Actus Triart 5 μm C18 50×30 mm), mobile phase (0.1% formic acid in H$_2$O: 0.1% formic acid in CH$_3$CN=95:5→50:50→5:95), 50 mL/min.) to obtain the title compound (0.85 g, 66%) as a colorless solid.

LC-MS Retention Time 0.934 min

LC:Agilent 1290

ESI/APCI MS:Agilent 6130

Column: Waters Acquity CSH C18 1.7 um, 2.1×50 mm

Solvent: H$_2$O:CH$_3$CN(0.1% Formic acid)

Gradient: 0.8 mL/min, 0 min(95:5)→1.2 min(50:50)

1.0 mL/min, →1.38 min(3:97)
MS (+): 611 [M+H]$^+$.

[Formula 88]

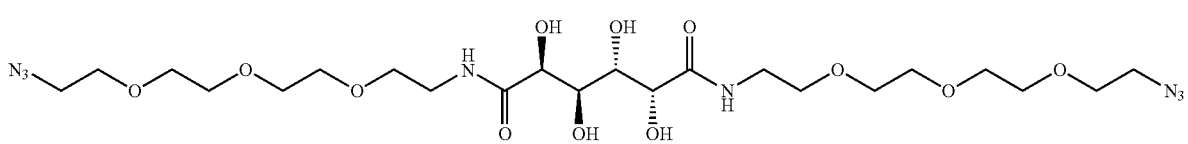

REFERENCE EXAMPLE 6-6

1-Azido-N-(2-{2-[2-(2-azidoethoxy)ethoxy]ethoxy}ethyl)-15,18-bis(1-azido-13-oxo-3,6,9-trioxa-12-azatetradecan-14-yl)-13-oxo-3,6,9-trioxa-12,15,18-triazaicosan-20-amide

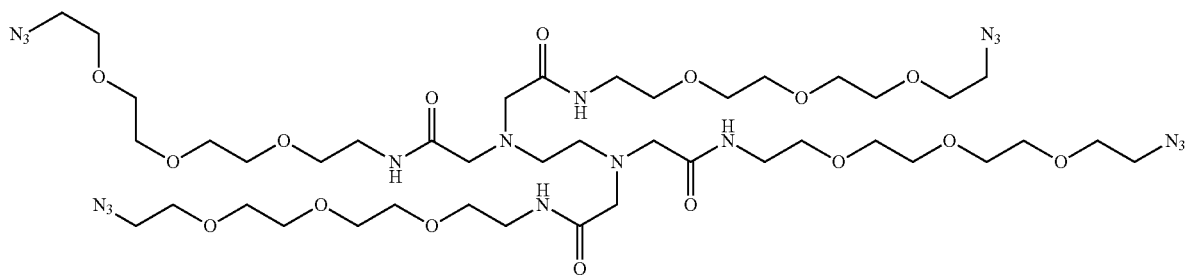

[Formula 89]

To a solution of 2,2',2'',2'''-(ethane-1,2-diyldinitrilo)tetraacetic acid (0.17 g) and 2-{2-[2-(2-azidoethoxy)ethoxy]ethoxy}ethanamine (0.17 g) in N,N-dimethylformamide (5.0 mL), 2-{2-[2-(2-azidoethoxy)ethoxy]ethoxy}ethanamine (0.50 g), O-(7-azabenzotriazol-1-yl)-N,N,N',N'-tetramethyluronium hexafluorophosphate (1.1 g), and N,N-diisopropylethylamine (0.50 mL) were added, and the mixture was stirred overnight at room temperature. The reaction solution was purified by reverse-phase preparative HPLC (column (YMC-Actus Triart 5 μm C18 50×30 mm), mobile phase (0.1% trifluoroacetic acid in H$_2$O:0.1% trifluoroacetic acid in MeCN=90:10→20:80→5:95, 40 mL/min.) to obtain the title compound (0.38 g, 61%) as a colorless oil substance.

LC-MS Retention Time 1.200 min

LC:Agilent 1290

ESI/APCI MS:Agilent 6130

Column: Waters Acquity CSH C18 1.7 um, 2.1×50 mm

Solvent: H$_2$O:CH$_3$CN(0.1% Formic acid)

Gradient: 0.8 mL/min, 0 min(95:5)→1.2 min(50:50)

1.0 mL/min, →1.38 min(3:97)

MS (+): 1094 [M+H]$^+$.

REFERENCE EXAMPLE 7-1

2-(2-{2-[2-(4-{3-[(4S)-6,8-Dichloro-2-methyl-1,2,3,4-tetrahydroisoquinolin-4-yl]phenyl}-1H-1,2,3-triazol-1-yl)ethoxy]ethoxy}ethoxy)ethanamine

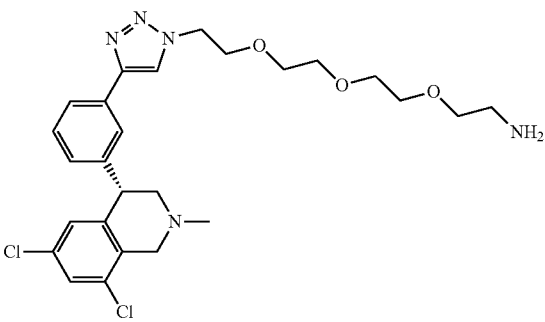

[Formula 90]

A solution of (4S)-6,8-dichloro-4-(3-ethynylphenyl)-2-methyl-1,2,3,4-tetrahydroisoquinoline hydrochloride (50 mg) obtained in Reference Example 2-2, 2-(2-(2-(2-azidoethoxy)ethoxy)ethoxy)ethanamine (31 mg), copper sulfate (2.0 mg), and sodium ascorbate (6.0 mg) in an ethanol (2.0 mL)-water (0.5 mL) mixed solvent was stirred overnight at room temperature. The reaction solution was purified by reverse-phase preparative HPLC (column (YMC-Actus Triart 5 m C18 50×30 mm), mobile phase (0.1% trifluoroacetic acid in H$_2$O:0.1% trifluoroacetic acid in MeCN=90:10→20:80→5:95, 40 mL/min.) and further purified by silica gel column chromatography (Biotage(registered trademark) SNAP Cartridge KP-NH, chloroform:methanol=100:0→90:10) to obtain the title compound (40 mg, 53%) as a colorless oil substance.

LC-MS Retention Time 0.769 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 534 $[M+H]^+$.

REFERENCE EXAMPLE 7-2

14-(4-{3-[(4S)-6,8-Dichloro-2-methyl-1,2,3,4-tetrahydroisoquinolin-4-yl]phenyl}-1H-1,2,3-triazol-1-yl)-3,6,9,12-tetraoxatetradecan-1-amine

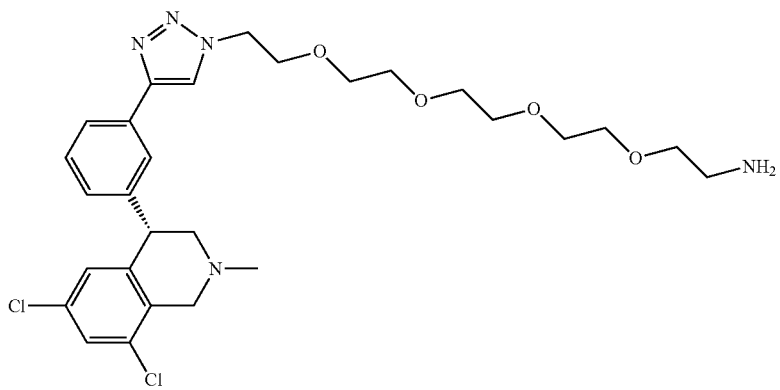

[Formula 91]

(1) To a solution of 3,6,9,12-tetraoxatetradecane-1,14-diol (2.0 g) in chloroform (20 mL), p-toluenesulfonyl chloride (3.2 g) was added, and then, potassium hydroxide (3.8 g) was slowly added under ice cooling. The mixture was stirred for 3 hours under ice cooling, and then, water was added to the reaction solution, followed by extraction with chloroform. The organic layer was dried over anhydrous magnesium sulfate and filtered, and then, the filtrate was concentrated under reduced pressure to obtain 3,6,9,12-tetraoxatetradecane-1,14-diylbis(4-methylbenzenesulfonate) (4.7 g) as a pale yellow oil substance.

$^1$H NMR (300 MHz, $CDCl_3$) δ ppm 2.45 (s, 6H), 3.50-3.65 (m, 12H), 3.66-3.72 (m, 4H), 4.11-4.19 (m, 4H), 7.30-7.38 (m, 4H), 7.74-7.84 (m, 4H).
MS (+): 547 $[M+H]^+$.

(2) To a solution of 3,6,9,12-tetraoxatetradecane-1,14-diylbis(4-methylbenzenesulfonate) (4.7 g) in N,N-dimethylformamide (40 mL), tetrabutylammonium iodide (0.31 g) and sodium azide (2.2 g) were added, and the mixture was stirred at 80° C. for 3 hours. The reaction solution was allowed to cool, and then, the solvent was distilled off under reduced pressure. Diethyl ether was added to the obtained residue, and the mixture was stirred at room temperature for 15 minutes. The insoluble matter was filtered off, and the filtrate was concentrated under reduced pressure. The obtained residue was purified by silica gel column chromatography (Biotage(registered trademark) SNAP Cartridge HP-Sphere, hexane:ethyl acetate=75:25→10:90) to obtain 1,14-diazido-3,6,9,12-tetraoxatetradecane (1.7 g, 71% (2 steps)) as a pale yellow oil substance.

$^1$H NMR (300 MHz, $CDCl_3$) δ ppm 3.39 (t, J=5.1 Hz, 4H), 3.64-3.71 (m, 16H).
MS (+): 311 $[M+Na]^+$.

(3) To a solution of 1,14-diazido-3,6,9,12-tetraoxatetradecane (1.7 g) in diethyl ether (10 mL), tetrahydrofuran (1 mL) and 1 mol/L hydrochloric acid (15 mL) were added under ice cooling. Then, a solution of triphenylphosphine (1.6 g) in diethyl ether (5.0 mL) was added thereto, and the mixture was stirred at room temperature for 30 hours. The organic layer was removed, and the aqueous layer was washed with diethyl ether. The pH of the aqueous layer was adjusted to 14 by the addition of sodium hydroxide, followed by extraction with chloroform. The organic layer was dried over anhydrous magnesium sulfate and filtered, and then, the filtrate was concentrated under reduced pressure to obtain 14-azido-3,6,9,12-tetraoxatetradecan-1-amine (1.3 g, 85%) as a colorless oil substance.

$^1$H NMR (300 MHz, $CDCl_3$) δ ppm 2.87 (t, J=5.2 Hz, 2H), 3.39 (t, J=5.2 Hz, 2H), 3.48-3.54 (m, 2H), 3.58-3.72 (m, 14H).
MS (+): 263 $[M+H]^+$.

(4) The title compound (98 mg, 30%) was obtained as a colorless oil substance through substantially the same reaction as in Reference Example 7-1 except that 14-azido-3,6,9,12-tetraoxatetradecan-1-amine was used instead of 2-(2-(2-azidoethoxy)ethoxy)ethanamine.

$^1$H NMR (300 MHz, $CDCl_3$) δ ppm 2.48 (s, 3H), 2.63 (dd, J=11.5, 8.5 Hz, 1H), 2.84 (t, J=5.3 Hz, 2H), 3.02 (dd, J=11.5, 5.3 Hz, 1H), 3.42-3.69 (m, 15H), 3.84 (d, J=15.7 Hz, 1H), 3.88-3.96 (m, 2H), 4.21-4.32 (m, 1H), 4.55-4.63 (m, 2H), 6.81 (dd, J=2.0, 0.9 Hz, 1H), 7.10 (dt, J=7.7, 1.4 Hz, 1H), 7.22 (dd, J=2.0, 0.9 Hz, 1H), 7.36 (t, J=7.7 Hz, 1H), 7.68 (dt, J=7.7, 1.4 Hz, 1H), 7.74 (t, J=1.4 Hz, 1H), 7.99 (s, 1H).

MS (+): 578 [M+H]$^+$.

REFERENCE EXAMPLE 7-3

17-(4-{3-[(4S)-6,8-Dichloro-2-methyl-1,2,3,4-tetra-hydroisoquinolin-4-yl]phenyl}-1H-1,2,3-triazol-1-yl)-3,6,9,12,15-pentaoxaheptadecan-1-amine

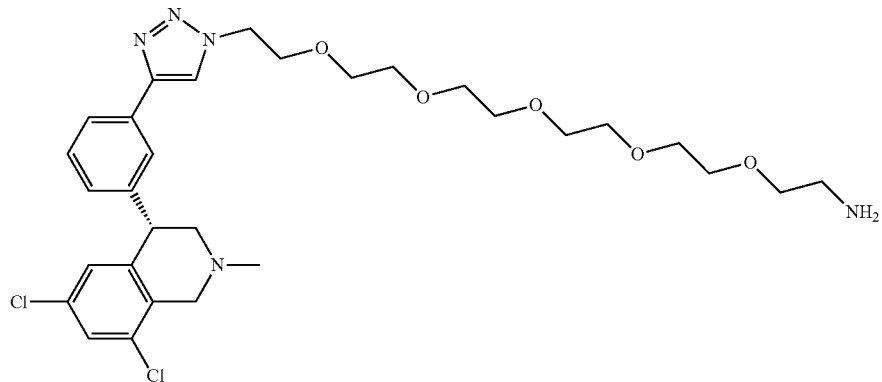

[Formula 92]

The title compound (0.13 g, 28% (4 steps)) was obtained as a colorless oil substance through substantially the same reaction as in Reference Example 7-2(1)(2)(3)(4) except that 3,6,9,12,15-pentaoxaheptadecane-1,17-diol was used instead of 3,6,9,12-tetraoxatetradecane-1.14-diol.

$^1$H NMR (300 MHz, CDCl$_3$) δ ppm 2.48 (s, 3H), 2.63 (dd, J=11.7, 8.5 Hz, 1H), 2.84 (t, J=5.3 Hz, 2H), 3.03 (dd, J=11.7, 4.7 Hz, 1H), 3.43-3.70 (m, 19H), 3.84 (d, J=16.0 Hz, 1H), 3.88-3.95 (m, 2H), 4.21-4.33 (m, 1H), 4.54-4.63 (m, 2H), 6.81 (d, J=1.1 Hz, 1H), 7.10 (d, J=7.7 Hz, 1H), 7.19-7.25 (m, 1H), 7.36 (t, J=7.7 Hz, 1H), 7.68 (dt, J=7.7, 1.4 Hz, 1H), 7.72-7.76 (m, 1H), 7.99 (s, 1H).

MS (+): 622 [M+H]$^+$.

REFERENCE EXAMPLE 7-4

(2R,3R)—N,N'-Bis(14-azido-3,6,9,12-tetraoxatetradec-1-yl)-2,3-dihydroxybutanediamide

[Formula 93]

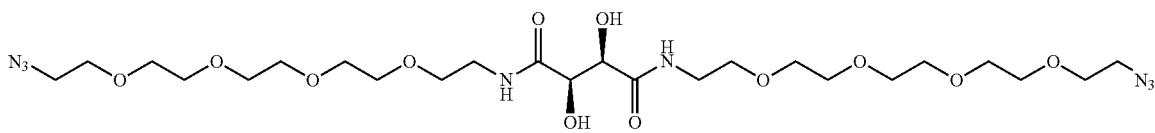

To 14-azido-3,6,9,12-tetraoxatetradecan-1-amine (0.30 g) obtained in Reference Example 7-2(3) and N,N-diisopropylethylamine (0.20 mL) in methanol (6.0 mL), (+)-dimethyl L-tartrate (82 mg) was added, and the mixture was stirred at 60° C. for 48 hours. The reaction solution was allowed to cool to room temperature and then concentrated under reduced pressure. 1 mol/L hydrochloric acid was added to the obtained residue, followed by extraction with chloroform. The organic layer was passed through Biotage (registered trademark) Phase Separator, and then, the filtrate was concentrated under reduced pressure to obtain the title compound (0.12 g) as a yellow oil substance.

LC-MS Retention Time 1.097 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 639 $[M+H]^+$.

REFERENCE EXAMPLE 7-5

(2R,3R)—N,N'-Bis(17-azido-3,6,9,12,15-pentaoxaheptadec-1-yl)-2,3-dihydroxybutanediamide

[Formula 94]

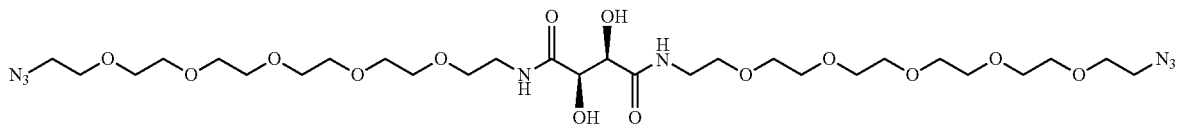

The title compound (0.19 g, 51%) was obtained as a pale yellow oil substance through substantially the same reaction as in Reference Example 7-4 except that 17-azido-3,6,9,12,15-pentaoxaheptadecan-1-amine obtained in Reference Example 7-3(3) was used instead of 14-azido-3,6,9,12-tetraoxatetradecan-1-amine obtained in Reference Example 7-2(3).

LC-MS Retention Time 1.144 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 727 $[M+H]^+$.

REFERENCE EXAMPLE 7-6

(2R,3S,4R,5S)—N,N'-Bis(14-azido-3,6,9,12-tetraoxatetradec-1-yl)-2,3,4,5-tetrahydroxyhexanediamide

[Formula 95]

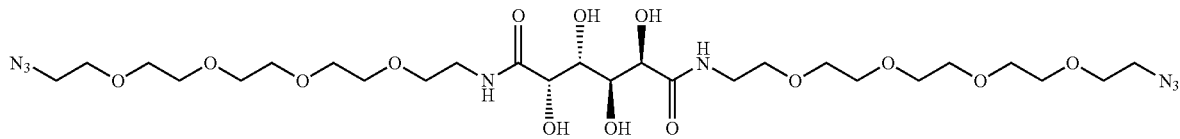

The title compound (0.20 g, 63%) was obtained as a colorless solid through substantially the same reaction as in Reference Example 6-4 except that 14-azido-3,6,9,12-tetraoxatetradecan-1-amine obtained in Reference Example 7-2(3) was used instead of 2-[2-(2-azidoethoxy)ethoxy]ethanamine.

LC-MS Retention Time 1.012 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 699 [M+H]$^+$.

REFERENCE EXAMPLE 7-7

(2R,3S,4R,5S)—N,N'-Bis(17-azido-3,6,9,12,15-pentaoxaheptadec-1-yl)-2,3,4,5-tetrahydroxyhexanediamide

[Formula 96]

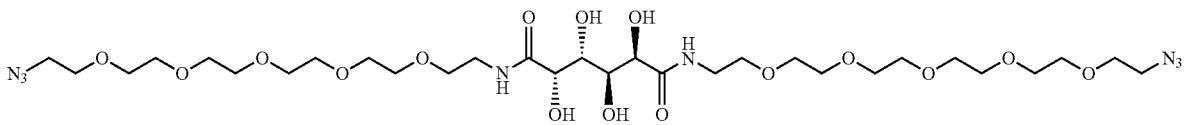

The title compound (0.25 g, 61%) was obtained as a colorless solid through substantially the same reaction as in Reference Example 6-4 except that 17-azido-3,6,9,12,15-pentaoxaheptadecan-1-amine obtained in Reference Example 7-3(3) was used instead of 2-[2-(2-azidoethoxy)ethoxy]ethanamine.

LC-MS Retention Time 1.066 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 787 [M+H]$^+$.

REFERENCE EXAMPLE 8-1

4-Bromo-N-methylpyridin-2-amine

[Formula 97]

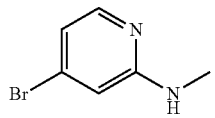

To 4-bromo-2-fluoropyridine (0.50 g), a 2.0 mol/L solution of methylamine in tetrahydrofuran (7.1 mL) was added, and the mixture was stirred for 1 hour under microwave irradiation (Biotage 60, 150° C.). The reaction solution was concentrated, and then, the obtained residue was purified by silica gel column chromatography (MORITEX Purif Pack-NH, hexane:ethyl acetate=99:1→60:40) to obtain the title compound (0.49 g, 93%) as a colorless solid.

$^1$H NMR (300 MHz, CDCl$_3$) δ ppm 2.91 (d, J=5.1 Hz, 3H), 6.56 (d, J=1.6 Hz, 1H), 6.73 (dd, J=5.4, 1.6 Hz, 1H), 7.90 (d, J=5.4 Hz, 1H).

MS (+): 187 [M+H]$^+$.

REFERENCE EXAMPLE 8-2

6-Chloro-N-methylpyrimidin-4-amine

[Formula 98]

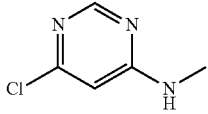

To a solution of 4,6-dichloropyrimidine (0.50 g) in tetrahydrofuran (0.84 mL), triethylamine (0.94 mL) was added, then a 2.0 mol/L solution of methylamine in tetrahydrofuran (1.7 mL) was added dropwise under ice cooling, and the mixture was stirred at room temperature for 23 hours. The reaction solution was concentrated, and then, the obtained residue was purified by silica gel column chromatography (MORITEX Purif Pack-NH, chloroform) to obtain the title compound (0.45 g, 93%) as a colorless solid.

$^1$H NMR (300 MHz, CDCl$_3$) δ ppm 2.96 (d, J=5.0 Hz, 3H), 6.35 (s, 1H), 8.35 (s, 1H).

MS (+): 144 [M+H]$^+$.

REFERENCE EXAMPLE 8-3

N-{2-[2-(2-Aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate

[Formula 99]

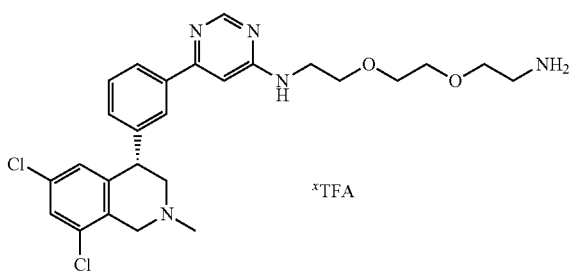

(1) To a solution of 4,6-dichloropyrimidine (0.60 g) in tetrahydrofuran (10 mL), triethylamine (0.56 mL) was added, then a suspension of tert-butyl {2-[2-(2-aminoethoxy)ethoxy]ethyl}carbamate (0.50 g) in tetrahydrofuran (15 mL) was added in small portions, and the mixture was stirred at room temperature for 20 hours. The reaction mixture was further stirred at 60° C. for 5 hours. The reaction solution was allowed to cool and then concentrated under reduced pressure. Water was added to the obtained residue, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, chloroform:methanol=100:0→92:8) to obtain tert-butyl [2-(2-{2-[(6-chloropyrimidin-4-yl)amino]ethoxy}ethoxy)ethyl]carbamate (0.59 g, 41%) as a colorless oil substance.

$^1$H NMR (300 MHz, CDCl$_3$) δ ppm 1.45 (s, 9H), 3.22-3.76 (m, 12H), 6.39 (s, 1H), 8.35 (s, 1H).

MS (+): 361 [M+H]$^+$.

(2) To a suspension of (4S)-6,8-dichloro-2-methyl-4-[3-(4,4,5,5-tetramethyl-1,3,2-dioxaborolan-2-yl)phenyl]-1,2,3,4-tetrahydroisoquinoline hydrochloride (0.25 g) obtained in Reference Example 3-3, tert-butyl [2-(2-{2-[(6-chloropyrimidin-4-yl)amino]ethoxy}ethoxy)ethyl]carbamate (0.20 g), and tetrakis(triphenylphosphine)palladium(0) (32 mg) in 1,4-dioxane (8.0 mL), a saturated aqueous solution of sodium bicarbonate (1.4 mL) was added in an argon gas atmosphere, and the mixture was stirred for 12 hours under heating to reflux. The reaction solution was allowed to cool, and then, the insoluble matter was filtered off. The obtained filtrate was purified by reverse-phase preparative HPLC (column (YMC-Actus Triart 5 m C18 50×30 mm), mobile phase (0.1% trifluoroacetic acid in H$_2$O:0.1% trifluoroacetic acid in MeCN=90:10→20:80→5:95, 40 mL/min.) to obtain tert-butyl [2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]carbamate trifluoroacetate (0.28 g) as a colorless amorphous substance.

$^1$H NMR (300 MHz, CD$_3$OD) δ ppm 1.41 (s, 9H), 3.12-3.25 (m, 5H), 3.44-3.97 (m, 12H), 4.45-4.56 (m, 1H), 4.73-4.84 (m, 2H), 6.85-6.92 (m, 1H), 6.98-7.08 (m, 1H), 7.53-7.61 (m, 2H), 7.65-7.91 (m, 3H), 8.65-8.75 (m, 1H).

MS (+): 616 [M+H]$^+$.

(3) To a solution of tert-butyl [2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]carbamate trifluoroacetate (0.28 g) in 1,2-dichloroethane (15 mL), trifluoroacetic acid (5.0 mL) was added, and the mixture was stirred at room temperature for 2 hours. The reaction solution was concentrated under reduced pressure, followed by azeotropy with methanol. The solvent was distilled off under reduced pressure to obtain the title compound (0.33 g) as a colorless amorphous substance.

$^1$H NMR (600 MHz, CD$_3$OD) δ ppm 3.04-3.15 (m, 5H), 3.57-3.91 (m, 12H), 4.41-4.51 (m, 1H), 4.69-4.78 (m, 2H), 6.80-6.89 (m, 1H), 6.96-7.07 (m, 1H), 7.47-7.57 (m, 2H), 7.62-7.69 (m, 1H), 7.70-7.88 (m, 2H), 8.59-8.71 (m, 1H).

MS (+): 516 [M+H]$^+$.

REFERENCE EXAMPLE 8-4

N-{2-[2-(2-Aminoethoxy)ethoxy]ethyl}-6-{3-[(4S)-6,8-dichloro-2-methyl-1,2,3,4-tetrahydroisoquinolin-4-yl]phenyl}pyrazin-2-amine (1) A solution of 2,6-dichloropyrazine (0.30 g), tert-butyl {2-[2-(2-aminoethoxy)ethoxy]ethyl}carbamate (0.50 g), and triethylamine (0.62 mL) in N,N-dimethylformamide (15 mL) was stirred at 80° C. for 4 hours. The reaction solution was allowed to cool, and then, water was added thereto, followed by extraction with ethyl acetate. The organic layer was washed with saturated saline, then dried over anhydrous magnesium sulfate, and filtered, and then, the filtrate was concentrated under reduced pressure. The obtained residue was purified by silica gel column chromatography (Biotage (registered trademark) SNAP Cartridge HP-Sphere, chloroform:methanol=100:0→80:20) and further purified by silica gel column chromatography (Biotage(registered trademark) SNAP Cartridge HP-Sphere, hexane:ethyl acetate=92:8→34:66) to obtain tert-butyl [2-(2-{2-[(6-chloropyrazin-2-yl)amino]ethoxy}ethoxy)ethyl]carbamate (0.29 g, 40%) as a colorless oil substance.

¹H NMR (300 MHz, CDCl₃) δ ppm 1.45 (s, 9H), 3.20-3.45 (m, 2H), 3.53-3.71 (m, 10H), 5.00-5.10 (m, 1H), 5.34-5.46 (m, 1H), 7.67-7.88 (m, 2H).
MS (+): 361 [M+H]⁺.

(2) To a solution of (4S)-6,8-dichloro-2-methyl-4-[3-(4,4,5,5-tetramethyl-1,3,2-dioxaborolan-2-yl)phenyl]-1,2,3,4-tetrahydroisoquinoline (0.16 g) obtained in Reference Example 3-2 and tert-butyl [2-(2-{2-[(6-chloropyrazin-2-yl)amino]ethoxy}ethoxy)ethyl]carbamate (0.25 g) in 1,4-dioxane (7.5 mL), a solution of sodium bicarbonate (0.16 g) in water (2.5 mL) and tetrakis(triphenylphosphine)palladium (0) (22 mg) were added in a nitrogen gas atmosphere, and the mixture was stirred at 110° C. for 12 hours. The reaction solution was concentrated under reduced pressure, and then, the residue was purified by reverse-phase preparative HPLC (column (YMC-Actus Triart 5 μm C18 50×30 mm), mobile phase (0.1% trifluoroacetic acid in H₂O:0.1% trifluoroacetic acid in MeCN=97:3→30:70→5:95, 40 mL/min.) to obtain tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]carbamate trifluoroacetate (0.25 g) as a yellow oil substance.

¹H NMR (300 MHz, CDCl₃) δ ppm 1.43 (br. s., 9H), 3.06 (s, 3H), 3.21-3.89 (m, 16H), 3.99-4.24 (m, 1H), 4.65-4.89 (m, 2H), 6.79-6.86 (m, 1H), 7.32 (d, J=7.7 Hz, 1H), 7.36-7.39 (m, 1H), 7.53 (t, J=7.7 Hz, 1H), 7.76 (s, 1H), 7.89 (d, J=7.7 Hz, 1H), 8.10 (s, 1H), 8.21 (s, 1H).
MS (+): 616 [M+H]⁺.

(3) To a solution of tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]carbamate trifluoroacetate (0.29 g) in 1,2-dichloroethane (3.0 mL), trifluoroacetic acid (1.0 mL) was added under ice cooling, and the mixture was stirred at room temperature for 1 hour. The reaction solution was concentrated under reduced pressure, and the obtained residue was purified by silica gel column chromatography (Biotage(registered trademark) SNAP Cartridge KP-NH, chloroforn:methanol=100:0→80:20) to obtain the title compound (0.18 g, 78% (2 steps)) as a colorless oil substance.

¹H NMR (600 MHz, CD₃OD) δ ppm 2.50 (s, 3H), 2.66-2.71 (m, 1H), 2.76 (t, J=5.4 Hz, 2H), 3.07-3.12 (m, 1H), 3.50 (t, J=5.4 Hz, 2H), 3.58 (d, J=16.10 Hz, 1H), 3.60-3.71 (m, 8H), 3.88 (d, J=16.10 Hz, 1H), 4.37-4.41 (m, 1H), 6.85 (m, 1H), 7.25 (d, J=7.8 Hz, 1H), 7.30-7.38 (m, 1H), 7.44 (t, J=7.8 Hz, 1H), 7.81 (s, 1H), 7.86 (s, 1H), 7.92 (d, J=7.8 Hz, 1H), 8.13 (s, 1H).
MS (+): 516 [M+H]⁺.

REFERENCE EXAMPLE 8-5

N-{2-[2-(2-Aminoethoxy)ethoxy]ethyl}-5-{3-[(4S)-6,8-dichloro-2-methyl-1,2,3,4-tetrahydroisoquinolin-4-yl]phenyl}pyrimidin-2-amine ditrifluoroacetate (1) To a solution of tert-butyl {2-[2-(2-aminoethoxy)ethoxy]ethyl}carbamate (0.40 g) in dimethyl sulfoxide (5.0 mL), potassium carbonate (0.45 g) and 2,5-dibromopyrimidine (0.38 g) were added, and the mixture was stirred at 100° C. for 2 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge HP-Sphere, hexane:ethyl acetate=100:0→20:80) to obtain tert-butyl [2-(2-{2-[(5-bromopyrimidin-2-yl)amino]ethoxy}ethoxy)ethyl]carbamate (0.51 g, 78%) as a colorless amorphous substance.
LC-MS Retention Time 0.928 min
LC:Agilent 1290
ESI/APCI MS:Agilent 6130
Column: Waters Acquity CSH C18 1.7 um, 2.1×50 mm
Solvent: H₂O:CH3CN(0.1% Formic acid)
Gradient: 0.8 mL/min, 0 min(80:20)→1.2-1.4 min(1:99)
MS (+): 405 [M+H]⁺.

(2) The title compound (0.10 g) was obtained as a colorless amorphous substance through substantially the same reaction as in Reference Example 8-3(2)(3) except that tert-butyl [2-(2-{2-[(5-bromopyrimidin-2-yl)amino]ethoxy}ethoxy)ethyl]carbamate was used instead of tert-butyl [2-(2-{2-[(6-chloropyrimidin-4-yl)amino]ethoxy}ethoxy)ethyl]carbamate obtained in Reference Example 8-3(1).
LC-MS Retention Time 0.294 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(80:20) 1.2-1.4 min(1:99)
MS (+): 516 [M+H]⁺.

REFERENCE EXAMPLE 8-6

N-{2-[2-(2-Aminoethoxy)ethoxy]ethyl}-4-[3-(6,8-dichloro-2-methyl-1,2,3,4-tetrahydroisoquinolin-4-yl)phenyl]pyridin-2-amine trifluoroacetate The title compound (40 mg) was obtained as a colorless amorphous substance through substantially the same reaction as in Reference Example 8-3(1)(2)(3) except that 4-bromo-2-fluoropyridine was used instead of 4,6-dichloropyrimidine, and 6,8-dichloro-2-methyl-4-[3-(4,4,5,5-tetramethyl-1,3,2-dioxaborolan-2-yl)phenyl]-1,2,3,4-tetrahydroisoquinoline obtained in Reference Example 3-1 was used instead of (4S)-6,8-dichloro-2-methyl-4-[3-(4,4,5,5-tetramethyl-1,3,2-dioxaborolan-2-yl)phenyl]-1,2,3,4-tetrahydroisoquinoline hydrochloride obtained in Reference Example 3-3.

¹H NMR (300 MHz, CD₃OD) δ ppm 3.06-3.13 (m, 2H), 3.17 (s, 3H), 3.60-3.83 (m, 11H), 3.85-3.95 (m, 1H), 4.46-4.58 (m, 1H), 4.73-4.87 (m, 2H), 6.82-6.89 (m, 1H), 7.18-7.25 (m, 1H), 7.32-7.38 (m, 1H), 7.43-7.49 (m, 1H), 7.50-7.54 (m, 1H), 7.59-7.67 (m, 1H), 7.71-7.76 (m, 1H), 7.78-7.85 (m, 1H), 7.88-7.94 (m, 1H).
MS (+): 515 [M+H]⁺.

REFERENCE EXAMPLE 8-7

N-{2-[2-(2-Aminoethoxy)ethoxy]ethyl}-4-{3-[(4S)-6,8-dichloro-2-methyl-1,2,3,4-tetrahydroisoquinolin-4-yl]phenyl}pyridin-2-amine trifluoroacetate The title compound (0.34 g) was obtained as a colorless oil substance through substantially the sane reaction as in Reference Example 8-3(1)(2)(3) except that 4-bromo-2-fluoropyridine was used instead of 4,6-dichloropyrimidine.

¹H NMR (300 MHz, CD₃OD) δ ppm 3.06-3.13 (m, 2H), 3.16 (s, 3H), 3.60-3.75 (m, 9H), 3.75-3.82 (m, 2H), 3.85-3.96 (m, 1H), 4.46-4.57 (m, 1H), 4.72-4.83 (m, 2H), 6.84-6.90 (m, 1H), 7.18-7.24 (m, 1H), 7.31-7.35 (m, 1H), 7.43-7.49 (m, 1H), 7.53-7.56 (m, 1H), 7.59-7.67 (m, 1H), 7.70-7.74 (m, 1H), 7.79-7.85 (m, 1H), 7.88-7.93 (m, 2H).
MS (+): 515 [M+H]⁺.

REFERENCE EXAMPLE 8-8

N-{2-[2-(2-Aminoethoxy)ethoxy]ethyl}-6-{3-[(4S)-6,8-dichloro-2-methyl-1,2,3,4-tetrahydroisoquinolin-4-yl]phenyl}pyridazin-4-amine trifluoroacetate The title compound (0.18 g) was obtained as a brown oil substance through substantially the same reaction as in Reference Example 8-5(1)(2) except that 3,5-dibromopyridazine was used instead of 2,5-dibromopyrimidine.

$^1$H NMR (300 MHz, CDCl$_3$) δ ppm 1.45 (br. s., 9H), 2.49 (s, 3H), 2.61-2.71 (m, 1H), 2.87-3.20 (m, 1H), 3.25-3.90 (m, 14H), 4.27-4.41 (m, 1H), 4.95 (br. s., 1H), 5.06 (br. s., 1H), 6.67-7.01 (m, 2H), 7.12-7.26 (m, 2H), 7.42 (t, J=7.7 Hz, 1H), 7.81 (d, J=7.7 Hz, 1H), 7.88-7.96 (m, 1H), 8.53-8.70 (m, 1H).

MS (+): 616 [M+H]$^+$.

(2) The title compound (0.18 g, quant.) was obtained as a brown oil substance through substantially the same reaction as in Reference Example 8-3(3) except that tert-butyl [2-(2-{2-[(6-{3-[(4S)-6,8-dichloro-2-methyl-1,2,3,4-tetrahydroisoquinolin-4-yl]phenyl}pyridazin-4-yl)amino]ethoxy}ethoxy)ethyl]carbamate was used instead of tert-butyl [2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]carbamate obtained in Reference Example 8-3(2).

$^1$H NMR (600 MHz, CD$_3$OD) δ ppm 3.07-3.14 (m, 2H), 3.19 (s, 3H), 3.63-3.75 (m, 10H), 3.75-3.83 (m, 4H), 3.86-3.98 (m, 1H), 4.44-4.58 (m, 1H), 4.76-4.90 (m, 3H), 6.89 (s, 1H), 7.33-7.40 (m, 1H), 7.49-7.57 (m, 1H), 7.59 (d, J=7.8Hz, 1H), 7.72 (t, J=7.8Hz, 1H), 7.85 (s, 1H), 7.88 (d, J=7.8Hz, 1H), 8.49-8.82 (m, 1H).

MS (+): 516 [M+H]$^+$

REFERENCE EXAMPLE 8-9

N-(2-{2-[2-(2-Aminoethoxy)ethoxy]ethoxy}ethyl)-6-{3-[(4S)-6,8-dichloro-2-methyl-1,2,3,4-tetrahydroisoquinolin-4-yl]phenyl}pyrimidin-4-amine (1) To a solution of 2-{2-[2-(2-azidoethoxy)ethoxy]ethoxy}ethanamine (2.8 g) in N,N-dimethylformamide (24 mL), di-tert-butyl dicarbonate (2.8 g) was added, and the mixture was stirred at room temperature for 2 hours. The reaction solution was concentrated under reduced pressure, and the obtained residue was purified by silica gel column chromatography (Biotage(registered trademark) SNAP Cartridge HP-Sphere, hexane:ethyl acetate=98:2→30:70) to obtain tert-butyl (2-{2-[2-(2-azidoethoxy)ethoxy]ethoxy}ethyl)carbamate (4.2 g) as a colorless oil substance.

$^1$H NMR (300 MHz, CDCl$_3$) δ ppm 1.45 (s, 9H), 3.26-3.37 (m, 2H), 3.36-3.44 (m, 2H), 3.50-3.59 (m, 2H), 3.59-3.73 (m, 10H), 5.02 (br. s, 1H).

MS (+): 341 [M+Na]$^+$.

(2) To a solution of tert-butyl (2-{2-[2-(2-azidoethoxy)ethoxy]ethoxy}ethyl)carbamate (4.2 g) in tetrahydrofuran (35 mL), triphenylphosphine (3.7 g) was added, and the mixture was stirred at room temperature for 2 hours. Water (10 mL) was added to the reaction solution, and the mixture was stirred at room temperature for 45 minutes and at 60° C. for 2 hours. The reaction solution was allowed to cool and then concentrated under reduced pressure, and the obtained residue was purified by silica gel column chromatography (Biotage(registered trademark) SNAP Cartridge KP-NH, chloroform:ethyl acetate=100:0→0:100). The solvent was distilled off under reduced pressure. Then, water was added to the obtained residue, and the mixture was washed with toluene. The aqueous layer was concentrated under reduced pressure to obtain tert-butyl (2-{2-[2-(2-aminoethoxy)ethoxy]ethoxy}ethyl)carbamate (3.1 g, 84% (2 steps)) as a colorless oil substance.

$^1$H NMR (300 MHz, CDCl$_3$) δ ppm 1.45 (s, 9H), 2.84-2.91 (m, 2H), 3.25-3.37 (m, 2H), 3.48-3.58 (m, 4H), 3.59-3.70 (m, 8H), 5.25 (br. s, 1H).

MS (+): 293 [M+H]$^+$.

(3) To a solution of 4,6-dichloropyrimidine (0.20 g) and tert-butyl (2-{2-[2-(2-aminoethoxy)ethoxy]ethoxy}ethyl)carbamate (0.36 g) in acetonitrile (7.4 mL), potassium carbonate (0.20 g) was added, and the mixture was stirred at 80° C. for 17 hours. The reaction solution was allowed to cool and then concentrated under reduced pressure, and the obtained residue was purified by silica gel column chromatography (Biotage(registered trademark) SNAP Cartridge HP-Sphere, chloroform:methanol=100:0→88:12) to obtain tert-butyl {2-[2-(2-{2-[(6-chloropyrimidin-4-yl)amino]ethoxy}ethoxy)ethoxy]ethyl}carbamate (0.51 g, quant.) as a yellow oil substance.

$^1$H NMR (300 MHz, CDCl$_3$) δ ppm 1.44 (s, 9H), 3.20-3.40 (m, 2H), 3.44-3.75 (m, 14H), 6.42 (s, 1H), 8.34 (s, 1H).

MS (+): 405 [M+H]$^+$.

(4) tert-Butyl {2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}carbamate trifluoroacetate (0.17 g) was obtained as a colorless oil substance through substantially the same reaction as in Reference Example 8-3(2) except that tert-butyl {2-[2-(2-{2-[(6-chloropyrimidin-4-yl)amino]ethoxy}ethoxy)ethoxy]ethyl}carbamate was used instead of tert-butyl [2-(2-{2-[(6-chloropyrimidin-4-yl)amino]ethoxy}ethoxy)ethyl]carbamate obtained in Reference Example 8-3(1).

LC-MS Retention Time 0.547 min

LC:Agilent 1290

ESI/APCI MS:Agilent 6130

Column: Waters Acquity CSH C18 1.7 um, 2.1×50 mm

Solvent: H$_2$O:CH$_3$CN(0.1% Formic acid)

Gradient: 0.8 mL/min, 0 min(80:20)→1.2-1.4 min(1:99)

MS (+): 660 [M+H]$^+$.

(5) The title compound (0.11 g, 40% (2 steps)) was obtained as a colorless oil substance through substantially the same reaction as in Reference Example 8-4(3) except that tert-butyl {2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}carbamate was used instead of tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]carbamate trifluoroacetate obtained in Reference Example 8-4(2).

$^1$H NMR (300 MHz, CDCl$_3$) δ ppm 2.46 (s, 3H), 2.56-2.67 (m, 1H), 2.81-2.90 (m, 2H), 2.94-3.06 (m, 1H), 3.47-3.57 (m, 3H), 3.58-3.73 (m, 12H), 3.76-3.86 (m, 1H), 4.25-4.36 (m, 1H), 6.28 (br. s, 1H), 6.70-6.77 (m, 1H), 6.78-6.83 (m, 1H), 7.16-7.24 (m, 2H), 7.39 (t, J=7.6 Hz, 1H), 7.78-7.87 (m, 2H), 8.64 (d, J=1.1 Hz, 1H).

MS (+): 560 [M+H]$^+$.

REFERENCE EXAMPLE 8-10

N-(2-{2-[2-(2-Aminoethoxy)ethoxy]ethoxy}ethyl)-6-{3-[(4S)-6,8-dichloro-2-methyl-1,2,3,4-tetrahydroisoquinolin-4-yl]phenyl}pyridazin-4-amine (1) tert-Butyl {2-[2-(2-{2-[(6-bromopyridazin-4-yl)amino]ethoxy}ethoxy)ethoxy]ethyl}carbamate (0.28 g, 50%) was obtained as a brown oil substance through substantially the same reaction as in Reference Example 8-5(1) except that 3,5-dibromopyridazine was used instead of 2,5-dibromopyrimidine, and tert-butyl (2-{2-[2-(2-aminoethoxy)ethoxy]ethoxy}ethyl)carbamate obtained in Reference Example 8-9(2) was used instead of tert-butyl {2-[2-(2-aminoethoxy)ethoxy]ethyl}carbamate.

$^1$H NMR (300 MHz, CDCl$_3$) δ ppm 1.45 (s, 9H), 3.21-3.70 (m, 16H), 5.26 (br. s., 1H), 5.44 (br. s., 1H), 6.59-6.75 (m, 1H), 8.50-8.62 (m, 1H).

MS (+): 449, 451 [M+H]$^+$.
MS (−): 447, 449 [M−H]$^+$.

(2) The title compound (34 mg, 13% (2 steps)) was obtained as a colorless oil substance through substantially the same reaction as in Reference Example 8-4(2)(3) except that tert-butyl {2-[2-(2-{2-[(6-bromopyridazin-4-yl)amino]ethoxy}ethoxy)ethoxy]ethyl}carbamate was used instead of tert-butyl [2-(2-{2-[(6-chloropyrazin-2-yl)amino]ethoxy}ethoxy)ethyl]carbamate obtained in Reference Example 8-4(1).

$^1$H NMR (300 MHz, CD$_3$OD) δ ppm 2.50 (s, 3H), 2.63-2.86 (m, 3H), 3.05-3.17 (m, 1H), 3.44-3.74 (m, 15H), 3.86-3.94 (m, 1H), 4.35-4.46 (m, 1H), 6.85 (s, 1H), 7.05 (d, J=3.4 Hz, 1H), 7.25-7.35 (m, 2H), 7.44-7.53 (m, 1H), 7.74-7.85 (m, 2H), 8.53 (d, J=3.4 Hz, 1H).

MS (+): 560 [M+H]$^+$.

REFERENCE EXAMPLE 8-11

N-(2-{2-[2-(2-Aminoethoxy)ethoxy]ethoxy}ethyl)-6-{3-[(4S)-6,8-dichloro-2-methyl-1,2,3,4-tetrahydroisoquinolin-4-yl]phenyl}pyrazin-2-amine The title compound (0.14 g, 27% (3 steps)) was obtained as a colorless oil substance through substantially the same reaction as in Reference Example 8-4(1)(2)(3) except that 2,6-dichloropyrazine was used instead of 4,6-dichloropyrimidine, and tert-butyl 2-{2-[2-(2-aminoethoxy)ethoxy]ethoxy}ethyl)carbamate obtained in Reference Example 8-9(2) was used instead of tert-butyl 2-[2-(2-aminoethoxy)ethoxy]ethyl}carbamate.

$^1$H NMR (300 MHz, CDCl$_3$) δ ppm 2.46-2.51 (m, 3H), 2.55-2.75 (m, 1H), 2.84-2.92 (m, 2H), 2.98-3.08 (m, 1H), 3.50-3.60 (m, 3H), 3.61-3.77 (m, 12H), 3.77-3.85 (m, 1H), 4.25-4.37 (m, 1H), 5.68 (m, 1H), 6.83-6.87 (m, 1H), 7.14-7.21 (m, 1H), 7.21-7.26 (m, 1H), 7.32-7.52 (m, 1H), 7.78-7.83 (m, 1H), 7.83-7.93 (m, 2H), 8.22 (s, 1H).

MS (+): 560 [M+H]$^+$.

The structures of Reference Examples 8-4 to 8-11 are shown in Table 1-1 below.

TABLE 1-1

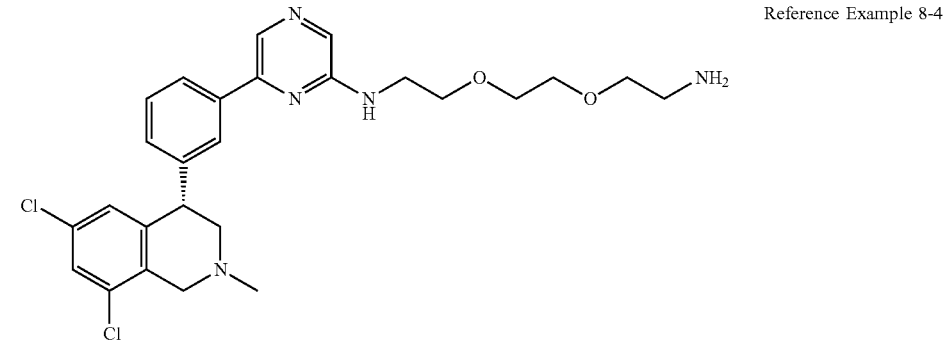

Reference Example 8-4

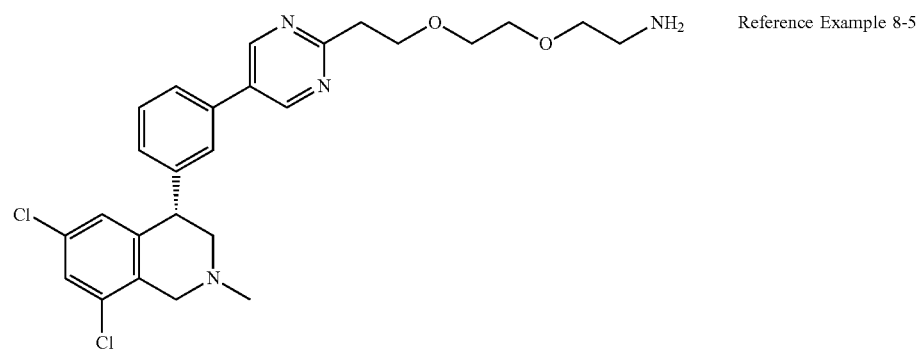

Reference Example 8-5

TABLE 1-1-continued
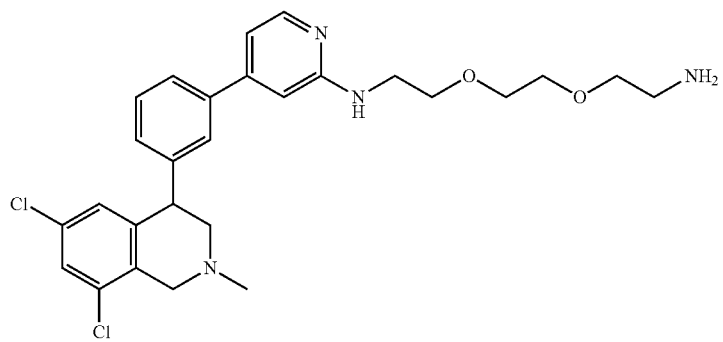 [SMILES: CN1Cc2c(Cl)cc(Cl)cc2C(c2cccc(-c3ccnc(NCCOCCOCCN)c3)c2)C1]
Reference Example 8-6
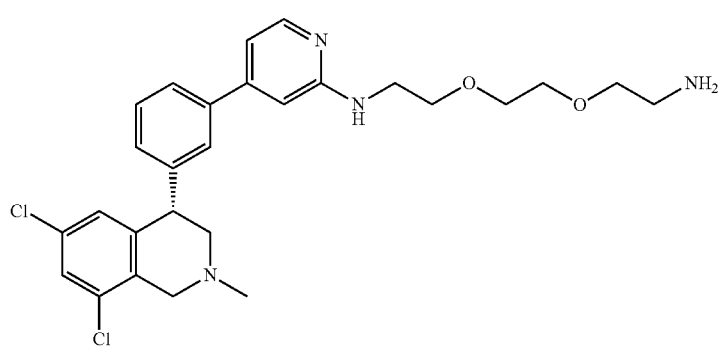 [SMILES: CN1Cc2c(Cl)cc(Cl)cc2[C@H](c2cccc(-c3ccnc(NCCOCCOCCN)c3)c2)C1]
Reference Example 8-7
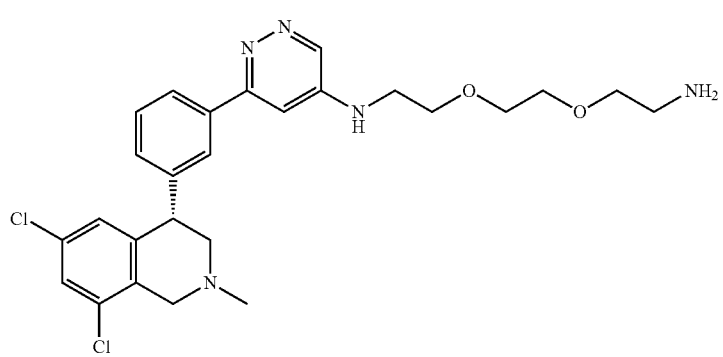 [SMILES: CN1Cc2c(Cl)cc(Cl)cc2[C@H](c2cccc(-c3cc(NCCOCCOCCN)cnn3)c2)C1]
Reference Example 8-8
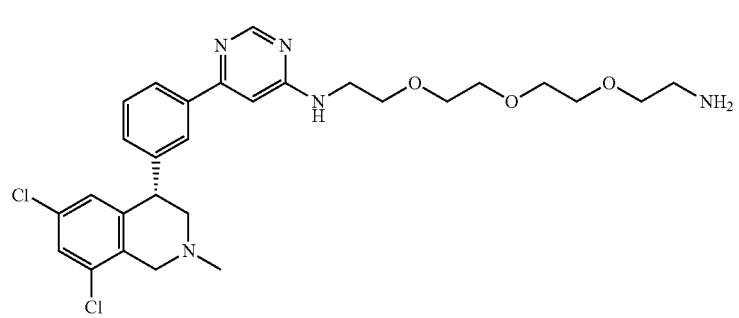 [SMILES: CN1Cc2c(Cl)cc(Cl)cc2[C@H](c2cccc(-c3cc(NCCOCCOCCOCCN)ncn3)c2)C1]
Reference Example 8-9
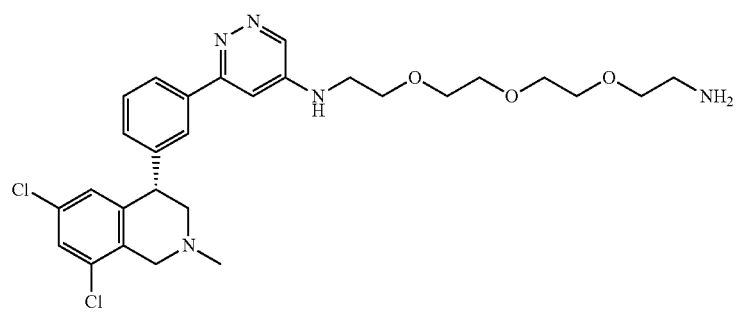 [SMILES: CN1Cc2c(Cl)cc(Cl)cc2[C@H](c2cccc(-c3cc(NCCOCCOCCOCCN)cnn3)c2)C1]
Reference Example 8-10

| | |
|---|---|
| TABLE 1-1-continued | |
| 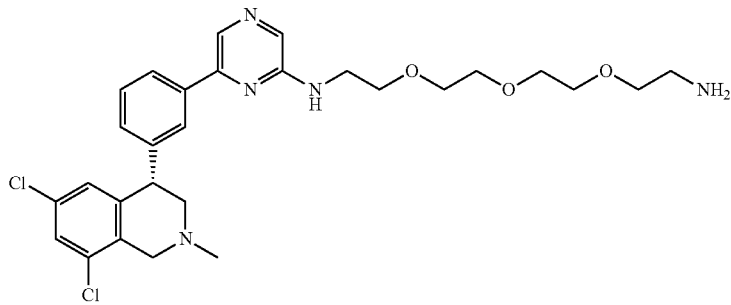 [SMILES: CN1Cc2c(Cl)cc(Cl)cc2[C@H](c2cccc(-c3cncc(NCCOCCOCCOCCN)n3)c2)C1] | Reference Example 8-11 |

REFERENCE EXAMPLE 9-1

N-(2-{2-[2-(2-Aminoethoxy)ethoxy]ethoxy}ethyl)-5-{3-[(4S)-6,8-dichloro-2-methyl-1,2,3,4-tetrahydroisoquinolin-4-yl]phenyl}pyrimidin-2-amine

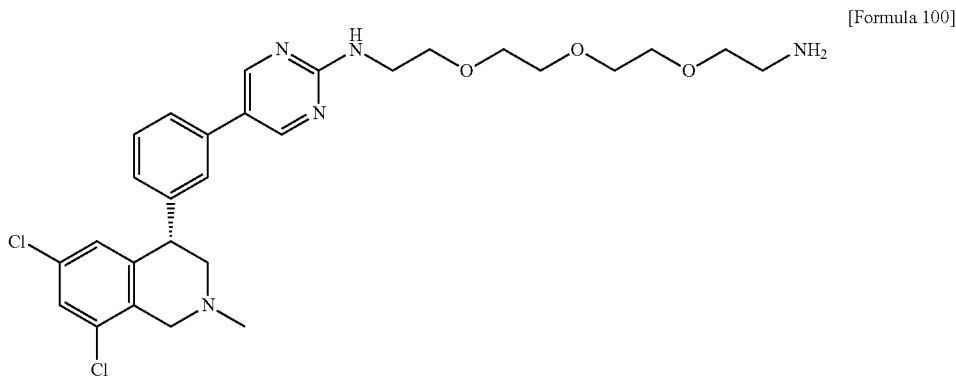 [SMILES: CN1Cc2c(Cl)cc(Cl)cc2[C@H](c2cccc(-c3cnc(NCCOCCOCCOCCN)nc3)c2)C1]

[Formula 100]

(1) To a solution of 2-{2-[2-(2-azidoethoxy)ethoxy]ethoxy}ethanamine (1.5 g) in dimethyl sulfoxide (80 mL), 2,5-dibromopyrimidine (1.7 g) and potassium carbonate (1.9 g) were added, and the mixture was stirred at 100° C. for 3 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→0:100) to obtain N-(2-{2-[2-(2-azidoethoxy)ethoxy]ethoxy}ethyl)-5-bromopyrimidin-2-amine (2.1 g, 81%).

LC-MS Retention Time 0.849 min
LC:Agilent 1290
ESI/APCI MS:Agilent 6130
Column: Waters Acquity CSH C18 1.7 um, 2.1×50 mm
Solvent: $H_2O$:CH3CN(0.1% Formic acid)
Gradient: 0.8 mL/min, 0 min(80:20)→1.2-1.4 min(1:99)
MS (+): 375, 377 $[M+H]^+$.

(2) To a solution of (N-(2-{2-[2-(2-azidoethoxy)ethoxy]ethoxy}ethyl)-5-bromopyrimidin-2-amine (1.8 g) in a tetrahydrofuran (42 mL)-water (8.3 mL) mixed solvent, triphenylphosphine (1.2 g) was added, and the mixture was stirred at room temperature for 6 hours. di-tert-Butyl dicarbonate (1.9 g) was added to the reaction solution, and the mixture was stirred overnight at room temperature. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→0:100) to obtain N-(2-{2-[2-(2-azidoethoxy)ethoxy]ethoxy}ethyl)-5-bromopyrimidin-2-amine (1.1 g, 57%).

LC-MS Retention Time 0.929 min
LC:Agilent 1290
ESI/APCI MS:Agilent 6130
Column: Waters Acquity CSH C18 1.7 um, 2.1×50 mm
Solvent: $H_2O$:CH3CN(0.1% Formic acid)
Gradient: 0.8 mL/min, 0 min(80:20) 1.2-1.4 min(1:99)
MS (+): 449, 451 $[M+H]^+$.

(3) The title compound (0.27 g, 33% (2 steps)) was obtained as a pale yellow oil substance through the same reaction as in Reference Example 8-4(2)(3) except that tert-butyl ({2-[2-(2-{2-[(5-bromopyrimidin-2-yl)amino]ethoxy}ethoxy)ethoxy]ethyl}carbamate was used instead of tert-butyl [2-(2-{2-[(6-chloropyrazin-2-yl)amino]ethoxy}ethoxy)ethyl]carbamate obtained in Reference Example 8-4(1).

LC-MS Retention Time 0.358 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(80:20)→1.2-1.4 min(1:99)
MS (+): 560 $[M+H]^+$.

REFERENCE EXAMPLE 10-1

N-{2-[2-(2-Aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate

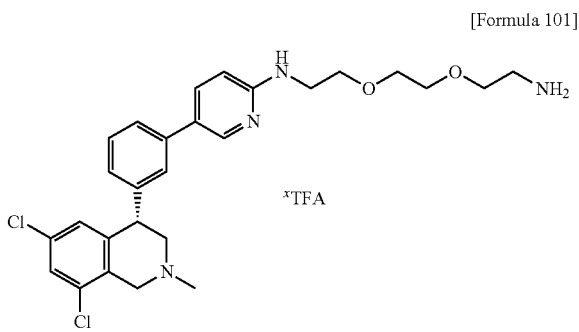 [SMILES: CN1Cc2c(Cl)cc(Cl)cc2[C@H](c2cccc(-c3ccc(NCCOCCOCCN)nc3)c2)C1]

[Formula 101]

(1) To a suspension of (4S)-4-(3-bromophenyl)-6,8-dichloro-2-methyl-1,2,3,4-tetrahydroisoquinoline (0.15 g) obtained in Reference Example 1-1, (6-fluoropyridin-3-yl)boronic acid (0.12 g), and tetrakis(triphenylphosphine)palladium(0) (46 mg) in 1,4-dioxane (20 mL), a saturated aqueous solution of sodium bicarbonate (1.0 mL) was added, and the mixture was stirred at 100° C. for 2 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=88:12→0:100) to obtain (4S)-6,8-dichloro-4-[3-(6-fluoropyridin-3-yl)phenyl]-2-methyl-1,2,3,4-tetrahydroisoquinoline (0.14 g, 88%) as a brown oil substance.

LC-MS Retention Time 0.661 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(80:20)→1.2-1.4 min(1:99)
MS (+): 387 [M+H]$^+$.

(2) A mixture of (4S)-6,8-dichloro-4-[3-(6-fluoropyridin-3-yl)phenyl]-2-methyl-1,2,3,4-tetrahydroisoquinoline (0.14 g) and tert-butyl {2-[2-(2-aminoethoxy)ethoxy]ethyl}carbamate (0.90 g) was stirred for 4 hours under microwave irradiation (Biotage 60, 130° C.). Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge HP-Sphere, chloroform:methanol=98:2→80:20) to obtain tert-butyl [2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]carbamate (0.17 g, 75%) as a light brown oil substance.

LC-MS Retention Time 0.520 min
LC:Agilent 1290
ESI/APCI MS:Agilent 6130
Column: Waters Acquity CSH C18 1.7 um, 2.1×50 mm
Solvent: $H_2O$:$CH3CN$(0.1% Formic acid)
Gradient: 0.8 mL/min, 0 min(80:20) 1.2-1.4 min(1:99)
MS (+): 615 [M+H]$^+$.

(3) The title compound (0.27 g) was obtained as a brown oil substance through substantially the same reaction as in Reference Example 8-3(3) except that tert-butyl [2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]carbamate was used instead of tert-butyl [2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]carbamate trifluoroacetate obtained in Reference Example 8-3(2).

LC-MS Retention Time 0.568 min
LC:Agilent 1290
ESI/APCI MS:Agilent 6130
Column: Waters Acquity CSH C18 1.7 um, 2.1×50 mm
Solvent: $H_2O$:$CH3CN$(0.1% Formic acid)
Gradient: 0.8 mL/min, 0 min(95:5)→1.2 min(50:50)
1.0 mL/min, →1.38 min(3:97)
MS (+): 515 [M+H]$^+$.

REFERENCE EXAMPLE 10-2

N-(2-{2-[2-(2-Aminoethoxy)ethoxy]ethoxy}ethyl)-5-{3-[(4S)-6,8-dichloro-2-methyl-1,2,3,4-tetrahydroisoquinolin-4-yl]phenyl}pyridin-2-amine

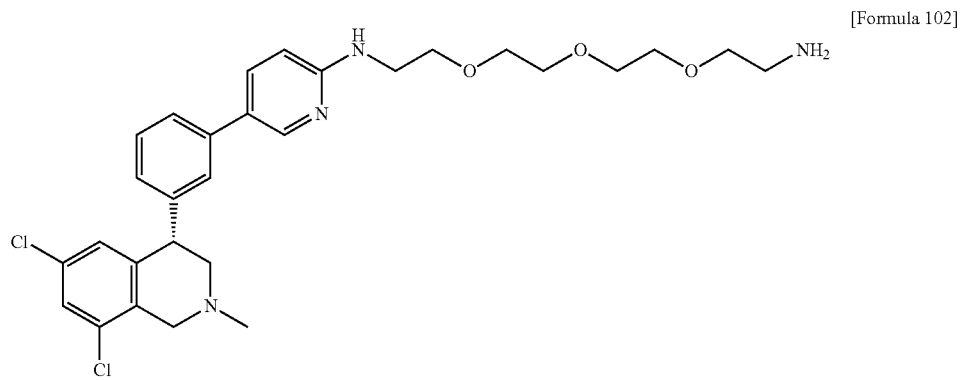 [SMILES: CN1Cc2c(Cl)cc(Cl)cc2[C@H](c2cccc(-c3ccc(NCCOCCOCCOCCN)nc3)c2)C1]

[Formula 102]

Substantially the same reaction as in Reference Example 10-1(2)(3) was carried out except that tert-butyl (2-{2-[2-(2-aminoethoxy)ethoxy]ethoxy}ethyl)carbamate obtained in Reference Example 8-9(2) was used instead of tert-butyl {2-[2-(2-aminoethoxy)ethoxy]ethyl}carbamate. The reaction product was purified by silica gel column chromatography (Biotage(registered trademark) SNAP Cartridge SNAP Cartridge KP-NH, chloroform:methanol=100:0→95:5) to obtain the title compound (60 mg, 60% (2 steps)) as a yellow oil substance.

LC-MS Retention Time 0.594 min
LC:Agilent 1290
ESI/APCI MS:Agilent 6130
Column: Waters Acquity CSH C18 1.7 um, 2.1×50 mm
Solvent: H₂O:CH3CN(0.1% Formic acid)
Gradient: 0.8 mL/min, 0 min(95:5)→1.2 min(50:50) 1.0 mL/min, →1.38 min(3:97)
MS (+): 559 [M+H]⁺.

REFERENCE EXAMPLE 10-3

N-{2-[2-(2-Aminoethoxy)ethoxy]ethyl}-5-{3-[(4S)-6,8-dichloro-2-methyl-1,2,3,4-tetrahydroisoquinolin-4-yl]phenyl}pyridazin-3-amine

[Formula 103]

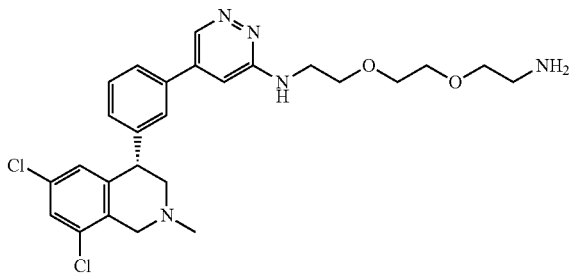

(1) To a solution of (4S)-6,8-dichloro-2-methyl-4-[3-(4,4,5,5-tetramethyl-1,3,2-dioxaborolan-2-yl)phenyl]-1,2,3,4-tetrahydroisoquinoline (0.48 g) obtained in ReferenceExample 3-2 and 3,5-dichloropyridazine (0.22 g) in 1,4-dioxane (18 mL), a solution of sodium carbonate (0.46 g) in water (6.0 mL) and tetrakis(triphenylphosphine)palladium (0) (63 mg) were added in an argon gas atmosphere, and the mixture was stirred for 15 hours under heating to reflux. The reaction solution was concentrated under reduced pressure. Then, ethyl acetate was added to the obtained residue, and the mixture was filtered through Celite (registered trademark). The filtrate was concentrated under reduced pressure. The obtained residue was purified by reverse-phase preparative HPLC (column (YMC-Actus Triart 5 µm C18 50×30 mm), mobile phase (0.1% trifluoroacetic acid in H₂O:0.1% trifluoroacetic acid in MeCN=97:3→30:70→5:95, 40 mL/min.) and further purified by silica gel column chromatography (Biotage(registered trademark) SNAP Cartridge KP-NH, hexane:ethyl acetate=100:0→80:20) to obtain (4S)-6,8-dichloro-4-[3-(6-chloropyridazin-4-yl)phenyl]-2-methyl-1,2,3,4-tetrahydroisoquinoline (0.37 g, 83%) as a pale yellow oil substance.

¹H NMR (600 MHz, CDCl₃) δ ppm 2.49 (s, 3H), 2.65-2.70 (m, 1H), 2.97-3.09 (m, 1H), 3.59 (d, J=16.1 Hz, 1H), 3.81 (d, J=16.1 Hz, 1H), 4.27-4.41 (m, 1H), 6.80-6.84 (m, 1H), 7.24-7.26 (m, 1H), 7.33 (d, J=7.7 Hz, 1H), 7.49 (t, J=7.7 Hz, 1H), 7.86 (d, J=2.3 Hz, 1H), 7.91 (d, J=7.7 Hz, 1H), 7.97 (s, 1H), 9.16 (d, J=2.3 Hz, 1H).

MS (+): 404 [M+H]⁺.

(2) A solution of (4S)-6,8-dichloro-4-[3-(6-chloropyridazin-4-yl)phenyl]-2-methyl-1,2,3,4-tetrahydroisoquinoline (0.14 g) and 2,2'-[ethane-1,2-diylbis(oxy)]diethanamine (0.52 mL) in 1,4-dioxane (4.0 mL) was stirred at an outside temperature of 150° C. for 4 hours and at 120° C. for 19 hours. The reaction solution was concentrated under reduced pressure, and then, the obtained residue was purified by reverse-phase preparative HPLC (column (YMC-Actus Triart 5 µm C18 50×30 mm), mobile phase (0.1% formic acid in H₂O:0.1% formic acid in MeCN=95:5→80:20→50:50→5:95, 40 mL/min.) and further purified by silica gel column chromatography (MORITEX Purif Pack-NH, chloroform:methanol=100:0→80:20) to obtain the title compound (0.12 g, 64%) as a colorless oil substance.

LC-MS Retention Time 0.477 min

LC:Agilent 1290

ESI/APCI MS:Agilent 6130

Column: Waters Acquity CSH C18 1.7 um, 2.1×50 mm

Solvent: H₂O:CH₃CN(0.1% Formic acid)

Gradient: 0.8 mL/min, 0 min(95:5)→1.2 min(50:50)

1.0 mL/min, →1.38 min(3:97)

MS (+): 516 [M+H]⁺.

REFERENCE EXAMPLE 10-4

N-(2-{2-[2-(2-Aminoethoxy)ethoxy]ethoxy}ethyl)-5-{3-[(4S)-6,8-dichloro-2-methyl-1,2,3,4-tetrahydroisoquinolin-4-yl]phenyl}pyridazin-3-amine

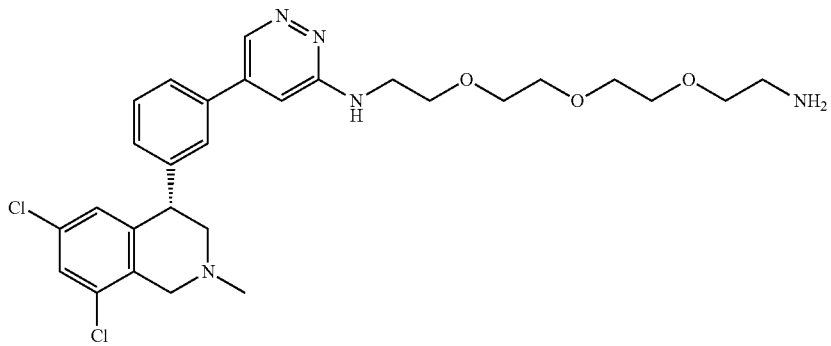

[Formula 104]

The title compound (71 mg, 59%) was obtained as a colorless oil substance through substantially the same reaction as in Reference Example 10-3(2) except that 2,2'-[oxybis(ethane-2,1-diyloxy)]diethanamine was used instead of 2,2'-[ethane-1,2-diylbis(oxy)]diethanamine.

$^1$H NMR (300 MHz, CDCl$_3$) δ ppm 2.48 (s, 3H), 2.60-2.70 (m, 1H), 2.86-2.92 (m, 2H), 2.99-3.08 (m, 1H), 3.37-3.57 (m, 5H), 3.61-3.79 (m, 10H), 3.79-3.88 (m, 1H), 4.29-4.37 (m, 1H), 6.22 (br. s., 1H), 6.78 (d, J=2.7 Hz, 1H), 6.81-6.85 (m, 1H), 7.18-7.25 (m, 2H), 7.41 (t, J=7.6 Hz, 1H), 7.80 (d, J=7.6 Hz, 1H). 7.88-7.92 (m, 1H), 8.61 (d, J=2.7 Hz, 1H).

MS (+): 560 [M+H]$^+$.

REFERENCE EXAMPLE 11-1

2-(2-{2-[(6-{3-[(4S)-6,8-Dichloro-2-methyl-1,2,3,4-tetrahydroisoquinolin-4-yl]phenyl}pyrimidin-4-yl)oxy]ethoxy}ethoxy)ethanamine

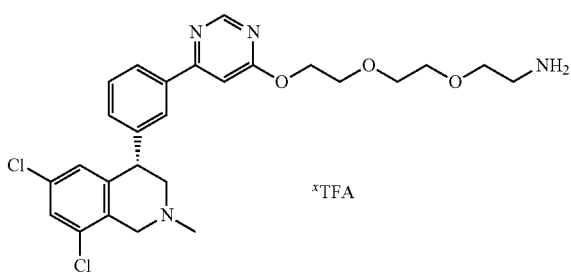

[Formula 105]

(1) To a solution of 2-[2-(2-chloroethoxy)ethoxy]ethanol (1.0 g) in N,N-dimethylformamide (35 mL), potassium phthalimide (6.0 g) was added, and the mixture was stirred at 100° C. for 18 hours. The reaction solution was allowed to cool, and then, the insoluble matter was filtered off and washed with ethyl acetate. The filtrates were concentrated under reduced pressure. Water was added to the obtained residue, followed by extraction with chloroform. The organic layer was dried over anhydrous magnesium sulfate and filtered, and then, the filtrate was concentrated under reduced pressure to obtain 2-{2-[2-(2-hydroxyethoxy)ethoxy]ethyl}-1H-isoindole-1,3(2H)-dione (8.3 g) as a pale yellow oil substance.

$^1$H NMR (300 MHz, CDCl$_3$) δ ppm 3.51-3.57 (m, 2H), 3.59-3.71 (m, 6H), 3.73-3.80 (m, 2H), 3.89-3.95 (m, 2H), 7.70-7.74 (m, 2H), 7.84-7.88 (m, 2H).

MS (+): 280 [M+H]$^+$.

(2) To a solution of 2-{2-[2-(2-hydroxyethoxy)ethoxy]ethyl}-1H-isoindole-1,3(2H)-dione (0.16 g) in 1,4-dioxane (3.0 mL), sodium hydride (purity: 55%, 28 mg) was added under ice cooling, and the mixture was stirred at room temperature for 25 minutes. 4,6-Dichloropyrimidine (0.10 g) was added in small portions to the reaction solution, and the mixture was stirred at 80° C. for 10 hours. Sodium sulfate decahydrate was added thereto under ice cooling. The insoluble matter was filtered off, and the filtrate was concentrated under reduced pressure. The obtained residue was purified by silica gel column chromatography (Biotage (registered trademark) SNAP Cartridge HP-Sphere, chloroform:methanol=100:0→94:6) and further purified by silica gel column chromatography (Biotage(registered trademark) SNAP Cartridge HP-Sphere, hexane:ethyl acetate=99:1→50:50→25:75) to obtain 2-[2-(2-{2-[(6-chloropyrimidin-4-yl)oxy]ethoxy}ethoxy)ethyl]-1H-isoindole-1,3(2H)-dione (75 mg, 33%) as a colorless solid.

$^1$H NMR (600 MHz, CDCl$_3$) δ ppm 3.54-3.59 (m, 4H), 3.66 (t, J=5.8 Hz, 2H), 3.68-3.71 (m, 2H), 3.82 (t, J=5.8 Hz, 2H), 4.35-4.41 (m, 2H), 6.69 (d, J=0.8 Hz, 1H), 7.59-7.66 (m, 2H), 7.71-7.77 (m, 2H), 8.45 (s, 1H).

MS (+): 392 [M+H]$^+$.

(3) {2-[2-(2-{2-[(6-{3-[(4S)-6,8-Dichloro-2-methyl-1,2,3,4-tetrahydroisoquinolin-4-yl]phenyl}pyrimidin-4-yl)oxy]ethoxy}ethoxy)ethyl]-1H-isoindole-1,3(2H)-dione (0.57 g, 60%) was obtained as a pale yellow amorphous substance through substantially the same reaction as in Reference Example 8-3(2) except that 2-[2-(2-{2-[(6-chloropyrimidin-4-yl)oxy]ethoxy}ethoxy)ethyl]-1H-isoindole-1,3(2H)-dione was used instead of tert-butyl [2-(2-{2-[(6-chloropyrimidin-4-yl)amino]ethoxy}ethoxy)ethyl]carbamate obtained in Reference Example 8-3(1).

$^1$H NMR (300 MHz, CDCl$_3$) δ ppm 2.48 (s, 3H), 2.58-2.69 (m, 1H), 2.98-3.08 (m, 1H), 3.49-3.71 (m, 5H), 3.72-3.87 (m, 5H), 3.87-3.94 (m, 2H), 4.28-4.37 (m, 1H), 4.46-4.53 (m, 2H), 6.78-6.81 (m, 1H), 7.12 (d, J=1.1 Hz, 1H), 7.21-7.29 (m, 2H), 7.40-7.47 (m, 1H), 7.65-7.69 (m, 2H), 7.79-7.83 (m, 2H), 7.86-7.93 (m, 2H), 8.80 (d, J=1.1 Hz, 1H).

MS (+): 647 [M+H]$^+$.

(4) To a solution of {2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethyl]-1H-isoindole-1,3(2H)-dione (0.57 g) in ethanol (21 mL), hydrazine monohydrate (2.1 mL) was added, and the mixture was stirred at 80° C. for 2 hours. The reaction solution was allowed to cool, and then, the insoluble matter was filtered off and washed with diethyl ether. The filtrates were concentrated under reduced pressure, and the residual aqueous layer was subjected to extraction with chloroform. The organic layer was dried over anhydrous magnesium sulfate and filtered, and then, the filtrate was concentrated under reduced pressure. The obtained residue was purified by silica gel column chromatography (MORITEX Purif Pack-NH, ethyl acetate:methanol=100:0→95:5) and further purified by silica gel column chromatography (Biotage(registered trademark) SNAP Cartridge HP-Sphere, chloroform:methanol=99:1→91:9→80:20→50:50→75:25) to obtain the title compound (0.34 g, 74%) as a light brown oil substance.

$^1$H NMR (300 MHz, CDCl$_3$) δ ppm 2.48 (s, 3H), 2.58-2.68 (m, 1H), 2.84-2.92 (m, 2H), 2.97-3.07 (m, 1H), 3.48-3.61 (m, 3H), 3.63-3.69 (m, 2H), 3.70-3.76 (m, 2H), 3.77-3.86 (m, 1H), 3.86-3.92 (m, 2H), 4.27-4.36 (m, 1H), 4.55-4.63 (m, 2H), 6.77-6.82 (m, 1H), 7.14 (d, J=1.1 Hz, 1H), 7.21-7.29 (m, 2H), 7.39-7.48 (m, 2H), 7.85-7.93 (m, 2H), 8.81 (d, J=1.1 Hz, 1H).

MS (+): 517 [M+H]$^+$.

REFERENCE EXAMPLE 11-2

2-[2-(2-{2-[(6-{3-[(4S)-6,8-Dichloro-2-methyl-1,2,3,4-tetrahydroisoquinolin-4-yl]phenyl}pyrimidin-4-yl)oxy]ethoxy}ethoxy)ethoxy]ethanamine obtain 4-(2-{2-[2-(2-azidoethoxy)ethoxy]ethoxy}ethoxy)-6-chloropyrimidine (0.39 g, 86%) as a colorless oil substance.

$^1$H NMR (300 MHz, CDCl$_3$) δ ppm 3.33-3.45 (m, 2H), 3.59-3.76 (m, 10H), 3.79-3.90 (m, 2H), 4.51-4.60 (m, 2H), 6.79-6.85 (m, 1H), 8.56 (d, J=0.8 Hz, 1H).

MS (+): 332 [M+H]$^+$.

(2) tert-Butyl {2-[2-(2-{2-[(6-chloropyrimidin-4-yl)oxy]ethoxy}ethoxy)ethoxy]ethyl}carbamate (1.6 g, 92%) was obtained as a colorless oil substance through substantially the same reaction as in Reference Example 9-1(2) except that 4-(2-{2-[2-(2-azidoethoxy)ethoxy]ethoxy}ethoxy)-6-chloropyrimidine was used instead of (N-(2-{2-[2-(2-azidoethoxy)ethoxy]ethoxy}ethyl)-5-bromopyrimidin-2-amine.

$^1$H NMR (300 MHz, CDCl$_3$) δ ppm 1.44 (s, 9H), 3.31 (q, J=5.2 Hz, 2H), 3.50-3.57 (m, 2H), 3.58-3.74 (m, 8H), 3.82-3.88 (m, 2H), 4.51-4.62 (m, 2H), 5.06 (br. s., 1H), 6.82 (d, J=0.9 Hz, 1H), 8.56 (d, J=0.9 Hz, 1H).

MS (+): 406 [M+H]$^+$.

(3) To a solution of (4S)-6,8-dichloro-2-methyl-4-[3-(4,4,5,5-tetramethyl-1,3,2-dioxaborolan-2-yl)phenyl]-1,2,3,4-tetrahydroisoquinoline hydrochloride (1.2 g) obtained in Reference Example 3-3 in a 1,4-dioxane (16 mL)-water (4.0 mL) mixed solvent, potassium carbonate (2.1 g) was added in a nitrogen gas atmosphere, and the mixture was stirred at room temperature for 10 minutes. Then, tert-butyl {2-[2-(2-{2-[(6-chloropyrimidin-4-yl)oxy]ethoxy}ethoxy)ethoxy]ethyl}carbamate (1.6 g) and tetrakis(triphenylphosphine)palladium(0) (0.31 g) were added thereto, and the mixture was stirred at 95° C. for 16 hours. The reaction solution was concentrated under reduced pressure, and then, the obtained residue was purified by silica gel column chromatography (Biotage(registered trademark) SNAP Cartridge HP-Sphere,

[Formula 106]

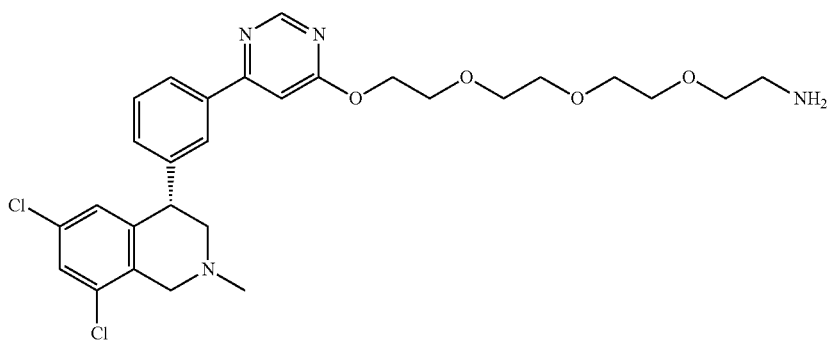

(1) To a solution of 4,6-dichloropyrimidine (0.20 g) in tetrahydrofuran (3.9 mL), a solution of 2-{2-[2-(2-azidoethoxy)ethoxy]ethoxy}ethanol (0.29 g) in tetrahydrofuran (1.5 mL) was added, then potassium tert-butoxide (0.14 g) was added in small portions under ice cooling, and the mixture was stirred at the same temperature as above for 1 hour and 15 minutes. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→50:50) to hexane:ethyl acetate=85:15→0:100) and further purified by silica gel column chromatography (Biotage(registered trademark) SNAP Cartridge KP-NH, hexane:ethyl acetate=92:8→65:35) to obtain tert-butyl ({2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}carbamate (1.2 g, 69%) as a colorless oil substance.

$^1$H NMR (300 MHz, CDCl$_3$) δ ppm 1.43 (s, 9H), 2.48 (s, 3H), 2.63 (dd, J=11.8, 8.1 Hz, 1H), 3.01 (dd, J=11.8, 5.4 Hz, 1H), 3.31 (m, 2H), 3.50-3.56 (m, 2H), 3.57-3.85 (m, 10H), 3.85-3.93 (m, 2H), 4.26-4.36 (m, 1H), 4.55-4.63 (m, 2H), 5.06 (br. s., 1H), 6.80 (s, 1H), 7.13 (d, J=0.6 Hz, 1H), 7.24 (m, J=2.2 Hz, 2H), 7.43 (t, J=7.6 Hz, 1H), 7.85-7.92 (m, 2H), 8.81 (d, J=0.6 Hz, 1H).

MS (+): 661 [M+H]$^+$.

(4) The title compound (1.0 g, 97%) was obtained as a colorless oil substance through substantially the same reaction as in Reference Example 8-4(3) except that tert-butyl ({2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}carbamate was used instead of tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethyl]carbamate trifluoroacetate obtained in Reference Example 8-4(2).

$^1$H NMR (300 MHz, CDCl$_3$) δ ppm 2.48 (s, 3H), 2.63 (dd, J=11.5, 8.1 Hz, 1H), 2.86 (t, J=5.2 Hz, 2H), 3.01 (dd, J=11.5, 5.4 Hz, 1H), 3.45-3.76 (m, 11H), 3.81 (d, J=16.3 Hz, 1H), 3.85-3.92 (m, 2H), 4.23-4.38 (m, 1H), 4.53-4.66 (m, 2H), 6.80 (d, J=1.2 Hz, 1H), 7.14 (d, J=1.1 Hz, 1H), 7.21-7.26 (m, 2H), 7.43 (t, J=7.6 Hz, 1H), 7.84-7.94 (m, 2H), 8.81 (d J=1.1 Hz, 1H).

MS (+): 561 [M+H]$^+$.

REFERENCE EXAMPLE 12-1

2-{2-[2-(4-{3-[(4S)-6,8-Dichloro-2-methyl-1,2,3,4-tetrahydroisoquinolin-4-yl]phenyl}-1H-pyrazol-1-yl)ethoxy]ethoxy}ethanamine

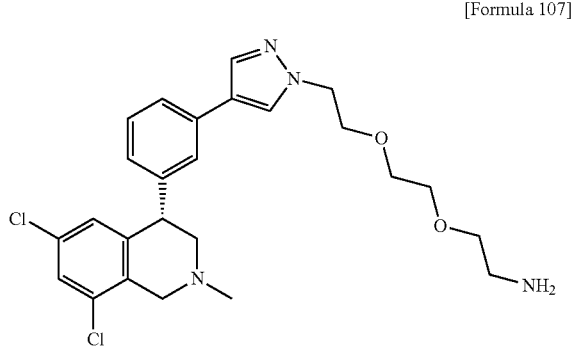 [SMILES: CN1Cc2c(Cl)cc(Cl)cc2[C@H](c2cccc(-c3cnn(CCOCCOCCN)c3)c2)C1]

[Formula 107]

(1) To a solution of tert-butyl {2-[2-(2-hydroxyethoxy)ethoxy]ethyl}carbamate (1.0 g) in tetrahydrofuran (20 mL), triphenylphosphine (2.1 g) and carbon tetrabromide (2.7 g) were added, and the mixture was stirred at room temperature for 1 day. The reaction solution was filtered through Celite (registered trademark) and then washed with diethyl ether, and then, the filtrates were concentrated under reduced pressure. The obtained residue was purified by silica gel column chromatography (Biotage (registered trademark) SNAP Cartridge HP-Sphere, hexane:ethyl acetate=100:0→50:50) to obtain tert-butyl {2-[2-(2-bromoethoxy)ethoxy]ethyl}carbamate (1.0 g, 80%) as a colorless oil substance.

$^1$H NMR (300 MHz, CDCl$_3$) δ ppm 1.45 (s, 9H), 3.28-3.36 (m, 2H), 3.45-3.51 (m, 2H), 3.53-3.58 (m, 2H), 3.62-3.69 (m, 4H), 3.78-3.86 (m, 2H), 5.01 (br. s., 1H).

(2) A solution of (4S)-6,8-dichloro-2-methyl-4-[3-(1H-pyrazol-4-yl)phenyl]-1,2,3,4-tetrahydroisoquinoline (0.11 g) obtained in Example 1-4 mentioned later, tert-butyl {2-[2-(2-bromoethoxy)ethoxy]ethyl}carbamate (0.15 g), potassium carbonate (76 mg), and tetrabutylammonium iodide (11 mg) in 1,4-dioxane (1.1 mL) was stirred at 60° C. for 1 day. The reaction solution was allowed to cool, and then, water was added thereto, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge KP-NH, hexane:ethyl acetate=100:0→70:30) to obtain tert-butyl (2-{2-[2-(4-{3-[(4S)-6,8-dichloro-2-methyl-1,2,3,4-tetrahydroisoquinolin-4-yl]phenyl}-1H-pyrazol-1-yl)ethoxy]ethoxy}ethyl)carbamate (85 mg, 47%) as a colorless oil substance.

$^1$H NMR (300 MHz, CDCl$_3$) δ ppm 1.43 (s, 9H), 2.49 (s, 3H), 2.60 (dd, J=11.5, 8.7 Hz, 1H), 3.02 (dd, J=11.5, 5.9 Hz, 1H), 3.24-3.77 (m, 9H), 3.81-3.92 (m, 3H), 4.20-4.27 (m, 1H), 4.33 (t, J=5.4 Hz, 2H), 5.02 (br. s., 1H), 6.81-6.83 (m, 1H), 6.99 (d, J=7.6 Hz, 1H), 7.22-7.41 (m, 4H), 7.74 (s, 1H), 7.76 (s, 1H).

MS (+): 589 [M+H]$^+$.

(3) The title compound (52 mg, 74%) was obtained as a brown oil substance through substantially the same reaction as in Reference Example 8-4(3) except that tert-butyl (2-{2-[2-(4-{3-[(4S)-6,8-dichloro-2-methyl-1,2,3,4-tetrahydroisoquinolin-4-yl]phenyl}-1H-pyrazol-1-yl)ethoxy]ethoxy}ethyl)carbamate was used instead of tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethyl]carbamate trifluoroacetate obtained in Reference Example 8-4(2).

LC-MS Retention Time 0.736 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 489 [M+H]$^+$.

REFERENCE EXAMPLE 12-2

2-{2-[2-(5-{3-[(4S)-6,8-Dichloro-2-methyl-1,2,3,4-tetrahydroisoquinolin-4-yl]phenyl}-2H-tetrazol-2-yl)ethoxy]ethoxy}ethanamine trifluoroacetate

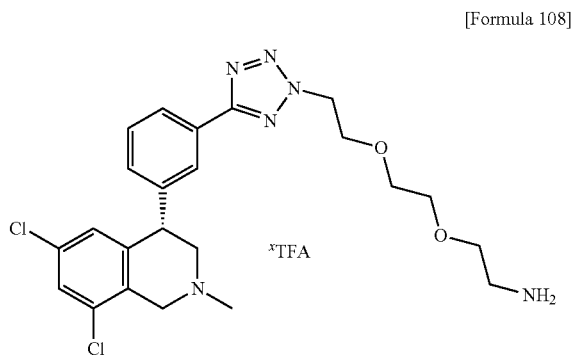 [SMILES: CN1Cc2c(Cl)cc(Cl)cc2[C@H](c2cccc(-c3nnn(CCOCCOCCN)n3)c2)C1]

[Formula 108]

(1) tert-Butyl (2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethyl)carbamate (0.24 g, 70%) was obtained as a pale yellow oil substance through substantially the same reaction as in Reference Example 12-1(2) except that (4S)-6,8-dichloro-2-methyl-4-[3-(2H-tetrazol-5-yl)phenyl]-1,2,3,4-tetrahydroisoquinoline obtained in Example 2-1 was used instead of (4S)-6,8-dichloro-2-methyl-4-[3-(1H-pyrazol-4-yl)phenyl]-1,2,3,4-tetrahydroisoquinoline obtained in Example 1-4 mentioned later.
¹H NMR (300 MHz, CDCl₃) δ ppm 1.42 (s, 9H), 2.49 (s, 3H), 2.65 (dd, J=11.7, 8.4 Hz, 1H), 3.03 (dd, J=11.7, 5.6 Hz, 1H), 3.20-3.34 (m, 2H), 3.43-3.66 (m, 7H), 3.83 (d, J=15.9 Hz, 1H), 4.11 (t, J=5.7 Hz, 2H), 4.26-4.36 (m, 1H), 4.85 (t, J=5.7 Hz, 2H), 6.80 (d, J=1.1 Hz, 1H), 7.22-7.30 (m, 2H), 7.44 (t, J=7.8 Hz, 1H), 7.98 (t, J=1.4 Hz, 1H), 8.06 (dt, J=7.8, 1.4 Hz, 1H).

MS (+): 591 [M+H]⁺.

(2) The title compound (0.34 g) was obtained as a pale yellow oil substance through substantially the same reaction as in Reference Example 8-3(3) except that tert-butyl (2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethyl)carbamate was used instead of tert-butyl [2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]carbamate obtained in Reference Example 8-3(2).

LC-MS Retention Time 0.720 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(95:5)→1.2 min(50:50) 1.0 mL/min, →1.38 min(3:97)
MS (+): 491 [M+H]⁺.

REFERENCE EXAMPLE 12-3

14-(5-{3-[(4S)-6,8-Dichloro-2-methyl-1,2,3,4-tetrahydroisoquinolin-4-yl]phenyl}-2H-tetrazol-2-yl)-3,6,9,12-tetraoxatetradecan-1-amine reduced pressure to obtain 14-azido-3,6,9,12-tetraoxatetradecan-1-ol (5.5 g) as a light red oil substance.
¹H NMR (300 MHz, CDCl₃) δ ppm 3.39 (t, J=5.1 Hz, 2H), 3.56-3.77 (m, 18H).

MS (+): 264 [M+H]⁺.

(2) To a solution of 14-azido-3,6,9,12-tetraoxatetradecan-1-ol (5.5 g) in tetrahydrofuran (60 mL), triphenylphosphine (4.3 g) was added, and the mixture was stirred at room temperature for 5 minutes. Then, water (6.0 mL) was added thereto, and the mixture was stirred at room temperature for 5 hours. di-tert-Butyl dicarbonate (4.3 g) and tetrahydrofuran (1.5 mL) were added to the reaction solution, and the mixture was stirred at room temperature for 66 hours. The solvent was distilled off under reduced pressure, and then, the obtained residue was purified by silica gel column chromatography (Biotage(registered trademark) SNAP Cartridge HP-Sphere, chloroform:methanol=100:0→85:15) to obtain tert-butyl (14-hydroxy-3,6,9,12-tetraoxatetradec-1-yl)carbamate (3.3 g) as a pale yellow oil substance.
¹H NMR (300 MHz, CDCl₃) δ ppm 1.45 (s, 9H), 3.32 (q, J=5.1 Hz, 2H), 3.50-3.57 (m, 2H), 3.59-3.81 (m, 16H).

MS (+): 360 [M+Na]⁺.

(3) tert-Butyl (14-bromo-3,6,9,12-tetraoxatetradec-1-yl)carbamate (1.1 g, 60%) was obtained as a colorless oil substance through substantially the same reaction as in Reference Example 12-1(1) except that tert-butyl (14-hydroxy-3,6,9,12-tetraoxatetradec-1-yl)carbamate was used instead of tert-butyl {2-[2-(2-hydroxyethoxy)ethoxy]ethyl}carbamate.
¹H NMR (300 MHz, CDCl₃) δ ppm 1.45 (s, 9H), 3.31 (q, J=5.3 Hz, 2H), 3.44-3.51 (m, 2H), 3.51-3.57 (m, 2H), 3.59-3.71 (m, 12H), 3.77-3.85 (m, 2H).

MS (+): 422 [M+Na]⁺.

[Formula 109]

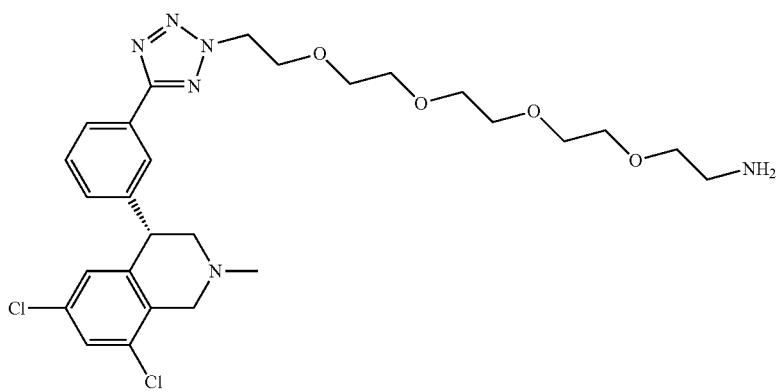

(1) To a solution of 3,6,9,12-tetraoxatetradecane-1,14-diol (15 g) in tetrahydrofuran (50 mL), methanesulfonyl chloride (1.2 mL) was added, then a solution of triethylamine (2.2 mL) in tetrahydrofuran (25 mL) was added dropwise under ice cooling, and the mixture was stirred at room temperature for 12 hours. The solvent was distilled off under reduced pressure. To the obtained residue, ethanol (75 mL) was added, then sodium azide (5.1 g) was added, and the mixture was stirred for 3 hours under heating to reflux. The reaction solution was allowed to cool and then concentrated under reduced pressure. Water was added to the obtained residue, followed by extraction with chloroform. The organic layer was dried over anhydrous magnesium sulfate and filtered, and then, the filtrate was concentrated under (4) The title compound (0.13 g, 36% (2 steps)) was obtained as a colorless oil substance through substantially the same reaction as in Reference Example 12-1(2)(3) except that (4S)-6,8-dichloro-2-methyl-4-[3-(2H-tetrazol-5-yl)phenyl]-1,2,3,4-tetrahydroisoquinoline obtained in Example 2-1 was used instead of (4S)-6,8-dichloro-2-methyl-4-[3-(1H-pyrazol-4-yl)phenyl]-1,2,3,4-tetrahydroisoquinoline obtained in Example 1-4 mentioned later, and tert-butyl (14-bromo-3,6,9,12-tetraoxatetradec-1-yl)carbamate was used instead of tert-butyl {2-[2-(2-bromoethoxy)ethyl}carbamate obtained in Reference Example 12-1().
¹H NMR (300 MHz, CDCl₃) δ ppm 2.48 (s, 3H), 2.64 (dd, J=11.6, 8.3 Hz, 1H), 2.86 (t, J=5.2 Hz, 2H), 2.97-3.08 (m, 1H), 3.47-3.53 (m, 2H), 3.56-3.68 (m, 13H), 3.83 (d, J=16.0 Hz, 1H), 4.06-4.15 (m, 2H), 4.26-4.34 (m, 1H), 4.84 (t, J=5.6 Hz, 2H), 6.80 (dd, J=2.1, 1.0 Hz, 1H), 7.21-7.29 (m, 2H), 7.44 (t, J=7.7 Hz, 1H), 7.98 (t, J=1.7 Hz, 1H), 8.05 (dt, J=7.7, 1.7 Hz, 1H).

MS (+): 579 [M+H]$^+$.

REFERENCE EXAMPLE 12-4

2-(2-{2-[2-(5-{3-[(4S)-6,8-Dichloro-2-methyl-1,2,3,4-tetrahydroisoquinolin-4-yl]phenyl}-2H-tetrazol-2-yl)ethoxy]ethoxy}ethoxy)ethanamine

[Formula 110]

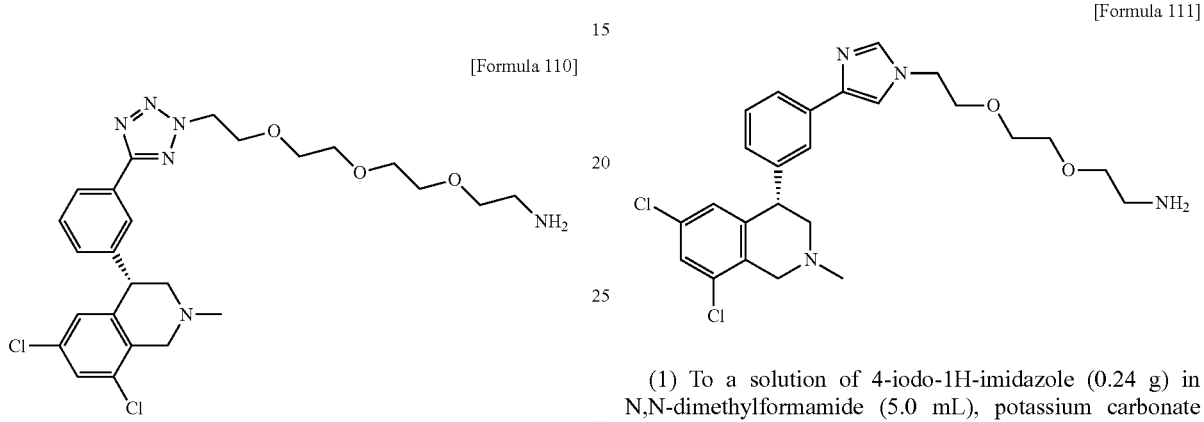

(1) tert-Butyl (2-{2-[2-(2-hydroxyethoxy)ethoxy]ethoxy}ethyl)carbamate (2.4 g, 90%) was obtained as a colorless oil substance through substantially the same reaction as in Reference Example 12-3(2) except that 2-{2-[2-(2-azidoethoxy)ethethoxy]ethoxy}ethanol was used instead of 14-azido-3,6,9,12-tetraoxatetradecan-1-ol obtained in Reference Example 12-3(1).

$^1$H NMR (300 MHz, CDCl$_3$) δ ppm 1.45 (s, 9H), 3.32 (q, J=4.9 Hz, 2H), 3.51-3.57 (m, 2H), 3.59-3.77 (m, 12H).

MS (+): 316 [M+Na]$^+$.

(2) tert-Butyl (2-{2-[2-(2-bromoethoxy)ethoxy]ethoxy}ethyl)carbamate (2.2 g, 74%) was obtained as a colorless oil substance through substantially the same reaction as in Reference Example 12-1(1) except that tert-butyl (2-{2-[2-(2-hydroxyethoxy)ethoxy]ethoxy}ethyl)carbamate was used instead of tert-butyl {2-[2-(2-hydroxyethoxy)ethoxy]ethyl}carbamate.

$^1$H NMR (300 MHz. CDCl$_3$) δ ppm 1.45 (s, 9H), 3.32 (q, J=5.3 Hz, 2H), 3.44-3.51 (m, 2H), 3.52-3.58 (m, 2H), 3.59-3.73 (m, 8H), 3.82 (t, J=6.3 Hz, 2H).

MS (+): 378 [M+Na]$^+$.

(3) The title compound (0.42 g) was obtained as a pale yellow amorphous substance through substantially the same reaction as in Reference Example 12-1(2)(3) except that (4S)-6,8-dichloro-2-methyl-4-[3-(2H-tetrazol-5-yl)phenyl]-1,2,3,4-tetrahydroisoquinoline obtained in Example 2-1 was used instead of (4S)-6,8-dichloro-2-methyl-4-[3-(1H-pyrazol-4-yl)phenyl]-1,2,3,4-tetrahydroisoquinoline obtained in Example 1-4 mentioned later, and tert-butyl (2-{2-[2-(2-bromoethoxy)ethoxy]ethoxy}ethyl)carbamate was used instead of tert-butyl {2-[2-(2-bromoethoxy)ethoxy]ethyl}carbamate obtained in Reference Example 12-1(1).

$^1$H NMR (300 MHz, CDCl$_3$) δ ppm 2.48 (s, 3H), 2.64 (dd, J=11.6, 8.3 Hz, 1H), 2.84 (t, J=5.2 Hz, 2H), 3.02 (dd, J=11.6, 5.7 Hz, 1H), 3.47 (t, J=5.2 Hz, 2H), 3.51-3.68 (m, 9H), 3.83 (d, J=16.2 Hz, 1H), 4.07-4.15 (m, 2H), 4.27-4.35 (m, 1H), 4.84 (t, J=5.7 Hz, 2H), 6.80 (d, J=1.1 Hz, 1H), 7.23-7.28 (m, 2H), 7.44 (t, J=7.7 Hz, 1H), 7.98 (t, J=1.7 Hz, 1H), 8.02-8.09 (m, 1H).

MS (+): 535 [M+H]$^+$.

REFERENCE EXAMPLE 13-1

2-{2-[2-(4-{3-[(4S)-6,8-Dichloro-2-methyl-1,2,3,4-tetrahydroisoquinolin-4-yl]phenyl}-1H-imidazol-1-yl)ethoxy]ethoxy}ethanamine

[Formula 111]

(1) To a solution of 4-iodo-1H-imidazole (0.24 g) in N,N-dimethylformamide (5.0 mL), potassium carbonate (0.34 g) and tert-butyl {2-[2-(2-bromoethoxy)ethoxy]ethyl}carbamate (0.42 g) obtained in Reference Example 12-1(1) were added, and the mixture was stirred at 100° C. for 3 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→0:100) to obtain tert-butyl (2-{2-[2-(4-iodo-1H-imidazol-1-yl)ethoxy]ethoxy}ethyl)carbamate (0.34 g, 65%).

LC-MS Retention Time 1.005 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 426 [M+H]$^+$.

(2) To a solution of (4S)-6,8-dichloro-2-methyl-4-[3-(4,4,5,5-tetramethyl-1,3,2-dioxaborolan-2-yl)phenyl]-1,2,3,4-tetrahydroisoquinoline (60 mg) obtained in Reference Example 3-2 in a 1,4-dioxane (4.2 mL)-water (0.83 mL) mixed solvent, tert-butyl (2-{2-[2-(4-iodo-1H-imidazol-1-yl)ethoxy]ethoxy}ethyl)carbamate (73 mg), tetrakis(triphenylphosphine)palladium(0) (17 mg), and potassium carbonate (59 mg) were added in a nitrogen gas atmosphere, and the mixture was stirred at 100° C. for 2 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge HP-Sphere, chloroform:methanol=100:0→90:10) to obtain tert-butyl ((2-{2-[2-(4-{3-[(4S)-6,8-dichloro-2-methyl-1,2,3,4- tetrahydroisoquinolin-4-yl]phenyl}-1H-imidazol-1-yl)ethoxy]ethoxy}ethyl)carbamate (36 mg, 43%).

LC-MS Retention Time 0.873 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 589 [M+H]$^+$.

(3) The title compound (30 mg, 100%) was obtained as a pale yellow oil substance through substantially the same reaction as in Reference Example 8-4(3) except that tert-butyl {((2-{2-[2-(4-{3-[(4S)-6,8-dichloro-2-methyl-1,2,3,4-tetrahydroisoquinolin-4-yl]phenyl}-1H-imidazol-1-yl)ethoxy]ethoxy}ethyl)carbamate was used instead of tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]carbamate trifluoroacetate obtained in Reference Example 8-4(2).

LC-MS Retention Time 0.357 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 489 [M+H]$^+$.

REFERENCE EXAMPLE 14-1

2-{2-[2-(5-{3-[(4S)-6,8-Dichloro-2-methyl-1,2,3,4-tetrahydroisoquinolin-4-yl]phenyl}-4H-1,2,4-triazol-3-yl)ethoxy]ethoxy}ethanamine

[Formula 112]

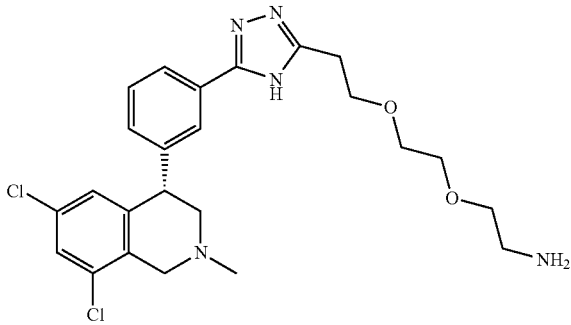

(1) To a solution of tert-butyl [2-(2-hydroxyethoxy)ethyl]carbamate (5.0 g) in 1,4-dioxane (15 mL), tert-butyl acrylate (7.1 mL) was added, then a 60% aqueous potassium hydroxide solution (0.57 mL) was added, and the mixture was stirred at room temperature for 1 day. Water was added to the reaction solution, followed by extraction with chloroform. The organic layer was washed with saturated saline, then dried over anhydrous magnesium sulfate, and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→40:60) to obtain tert-butyl 2,2-dimethyl-4-oxo-3,8,11-trioxa-5-azatetradecan-14-ate (5.0 g, 62%) as a colorless oil substance.

$^1$H NMR (300 MHz, CDCl$_3$) δ ppm 1.42-1.48 (m, 18H), 2.52 (t, J=6.5 Hz, 2H), 3.27-3.35 (m, 2H), 3.51-3.56 (m, 2H), 3.60 (s, 4H), 3.72 (t, J=6.5 Hz, 2H), 4.81-5.17 (m, 1H).

(2) To a solution of tert-butyl 2,2-dimethyl-4-oxo-3,8,11-trioxa-5-azatetradecan-14-ate (5.0 g) in chloroform (25 mL), trifluoroacetic acid (25 mL) was added under ice cooling, and the mixture was stirred at room temperature for 4 hours. The reaction solution was concentrated under reduced pressure, followed by azeotropy with chloroform. The solvent was distilled off under reduced pressure to obtain 3-[2-(2-aminoethoxy)ethoxy]propanoic acid trifluoroacetate (4.3 g) as a brown oil substance.

LC-MS Retention Time 0.208 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 178 [M+H]$^+$.
MS (−): 176 [M−H]$^+$.

(3) To a solution of 3-[2-(2-aminoethoxy)ethoxy]propanoic acid trifluoroacetate (3.3 g) in water (17 mL), a solution of saturated sodium bicarbonate (2.4 g) and benzyl chloroformate (1.6 mL) in 1,4-dioxane (5.0 mL) was added in a water bath, and the mixture was stirred at room temperature for 1 day. The reaction solution was concentrated under reduced pressure, and then, 1 mol/L hydrochloric acid was added to the residue, followed by extraction with ethyl acetate. The organic layer was dried over anhydrous magnesium sulfate and filtered, and then, the filtrate was concentrated under reduced pressure to obtain 3-oxo-1-phenyl-2,7,10-trioxa-4-azatridecan-13-oic acid (3.5 g, 98% (2 steps)) as a pale yellow oil substance.

$^1$H NMR (300 MHz, DMSO-d$_6$) δ ppm 2.44 (t, J=6.4 Hz, 2H), 3.10-3.17 (m, 2H), 3.38-3.43 (m, 2H), 3.46-3.50 (m, 4H), 3.57-3.62 (m, 2H), 5.01 (s, 2H), 7.28-7.37 (m, 5H).
MS (+): 312 [M+H]$^+$.
MS (−): 310 [M−H]$^+$.

(4) A solution of 3-oxo-1-phenyl-2,7,10-trioxa-4-azatridecan-13-oic acid (3.5 g), tert-butyl carbazate (2.2 g), 1-ethyl-3-(3-dimethylaminopropyl)carbodiimide hydrochloride (3.2 g), 1-hydroxybenzotriazole monohydrate (2.6 g), and triethylamine (2.4 mL) in chloroform (35 mL) was stirred at room temperature for 1 day. Water was added to the reaction solution, followed by extraction with chloroform. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, chloroform:methanol=100:0→90:10) to obtain tert-butyl 4,14-dioxo-16-phenyl-7,10,15-trioxa-2,3,13-triazahexadecan-1-oate (2.1 g, 44%) as a colorless oil substance.

LC-MS Retention Time 0.789 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (−): 424 [M−H]$^+$.

(5) To a solution of tert-butyl 4,14-dioxo-16-phenyl-7,10,15-trioxa-2,3,13-triazahexadecan-1-oate (2.1 g) in chloroform (11 mL), trifluoroacetic acid (11 mL) was added under ice cooling, and the mixture was stirred at room temperature for 2 hours. The reaction solution was concentrated under reduced pressure, and then, the obtained residue was purified by silica gel column chromatography (Biotage(registered trademark) SNAP Cartridge KP-NH, chloroform:methanol=100:0→90:10) to obtain benzyl {2-[2-(3-hydrazinyl-3-oxopropoxy)ethoxy]ethyl}carbamate (1.2 g, 72%) as a colorless amorphous substance.

$^1$H NMR (300 MHz, CDCl$_3$) δ ppm 2.47-2.52 (m, 2H), 3.39-3.44 (m, 2H), 3.56-3.70 (m, 8H), 4.99-5.14 (m, 2H), 6.81-7.00 (m, 1H), 7.31-7.41 (m, 5H), 8.22 (br. s., 1H).

MS (+): 326 [M+H]$^+$.

(6) To a solution of 3-[(4S)-6,8-dichloro-2-methyl-1,2,3,4-tetrahydroisoquinolin-4-yl]benzonitrile (0.60 g) obtained in Reference Example 4-1 in ethanol (6.0 mL), acetyl chloride (4.8 mL) was added dropwise under ice cooling in a nitrogen gas atmosphere, and the mixture was stirred at room temperature for 1 day under sealed conditions. A saturated aqueous solution of sodium bicarbonate was slowly added thereto under ice cooling, followed by extraction with ethyl acetate. The organic layer was dried over anhydrous magnesium sulfate and filtered, and then, the filtrate was concentrated under reduced pressure to obtain ethyl 3-[(4S)-6,8-dichloro-2-methyl-1,2,3,4-tetrahydroisoquinolin-4-yl]benzenecarboximidate (0.63 g, 91%) as a yellow oil substance.

LC-MS Retention Time 0.645 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 363 [M+H]$^+$.

(7) A solution of benzyl {2-[2-(3-hydrazinyl-3-oxopropoxy)ethoxy]ethyl}carbamate (0.33 g) and ethyl 3-[(4S)-6,8-dichloro-2-methyl-12,3,4-tetrahydroisoquinolin-4-yl]benzenecarboximidate (0.31 g) in acetic acid (3.1 mL) was stirred for 2 hours under heating to reflux. The reaction solution was concentrated, and then, the obtained residue was purified by silica gel column chromatography (Biotage (registered trademark) SNAP Cartridge HP-Sphere, chloroform:methanol=100:0→90:10) and then further purified by silica gel column chromatography (Biotage(registered trademark) SNAP Cartridge KP-NH, hexane:ethyl acetate=100:0→0:100) to obtain benzyl (2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethyl)carbamate (0.35 g, 66%) as a pale yellow oil substance. Also, benzyl (2-{2-[2-(5-{3-[(4S)-6,8-dichloro-2-methyl-1,2,3,4-tetrahydroisoquinolin-4-yl]phenyl}-1,3,4-oxadiazol-2-yl)ethoxy]ethoxy}ethyl)carbamate (0.16 g, 30%) was obtained as a pale yellow oil substance.

(7)-1: Benzyl (2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethyl)carbamate
LC-MS Retention Time 1.171 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 624 [M+H]$^+$.
MS (−): 622 [M−H]$^+$.

(7)-2: Benzyl (2-{2-[2-(5-{3-[(4S)-6,8-dichloro-2-methyl-1,2,3,4-tetrahydroisoquinolin-4-yl]phenyl}-1,3,4-oxadiazol-2-yl)ethoxy]ethoxy}ethyl)carbamate
LC-MS Retention Time 1.219 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 625 [M+H]$^+$.

(8) To a solution of benzyl (2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethyl)carbamate (0.35 g) in methanol (11 mL), 10% palladium-active carbon (35 mg) was added in a nitrogen gas atmosphere, and the mixture was stirred at room temperature for 1 day in a hydrogen gas atmosphere. 10% palladium-active carbon was filtered off through Celite (registered trademark) and washed with chloroform, and then, the filtrates were concentrated under reduced pressure. The obtained residue was purified by silica gel column chromatography (Biotage(registered trademark) SNAP Cartridge KP-NH, hexane:ethyl acetate=100:0→98:2) to obtain the title compound (0.12 g, 44%) as a colorless amorphous substance.

$^1$H NMR (300 MHz, CDCl$_3$) δ ppm 2.48 (s, 3H), 2.62 (dd, J=11.5, 8.9 Hz, 1H), 3.02-3.19 (m, 5H), 3.45-3.72 (m, 7H), 3.83-3.90 (m, 3H), 4.24-4.34 (m, 1H), 6.78-6.82 (m, 1H), 7.06-7.14 (m, 1H), 7.18-7.22 (m, 1H), 7.36 (t, J=7.7 Hz, 1H), 7.89-7.95 (m, 1H), 7.97-8.03 (m, 1H).

MS (+): 490 [M+H]$^+$.
MS (−): 488 [M−H]$^+$.

REFERENCE EXAMPLE 14-2

2-{2-[2-(5-{3-[(4S)-6,8-Dichloro-2-methyl-1,2,3,4-tetrahydroisoquinolin-4-yl]phenyl}-1,3,4-oxadiazol-2-yl)ethoxy]ethoxy}ethanamine

[Formula 113]

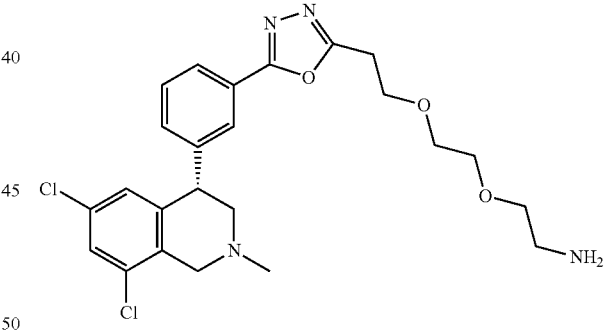

The title compound (47 mg, 38%) was obtained as a pale yellow oil substance through substantially the same reaction as in Reference Example 14-1(8) except that benzyl (2-{2-[2-(5-{3-[(4S)-6,8-dichloro-2-methyl-1,2,3,4-tetrahydroisoquinolin-4-yl]phenyl}-1,3,4-oxadiazol-2-yl)ethoxy]ethoxy}ethyl)carbamate obtained in Reference Example 14-1(7)-2 was used instead of benzyl (2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethyl)carbamate obtained in Reference Example 14-1(7)-1.

LC-MS Retention Time 0.676 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)

1.0 mL/min, →1.38 min(3:97)
MS (+): 491 [M+H]+.

REFERENCE EXAMPLE 14-3

2-(2-{2-[2-(5-{3-[(4S)-6,8-Dichloro-2-methyl-1,2,3,4-tetrahydroisoquinolin-4-yl]phenyl}-4H-1,2,4-triazol-3-yl)ethoxy]ethoxy}ethoxy)ethanamine

[Formula 114]

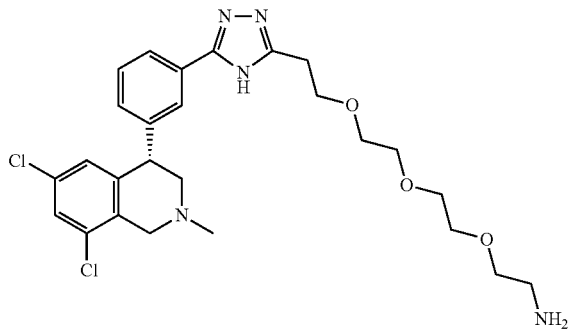

(1) To a suspension of tert-butyl 3-{2-[2-(2-aminoethoxy)ethoxy]ethoxy}propanoate (1.5 g) in water (7.5 mL), a solution of saturated sodium bicarbonate (1.1 g) and benzyl chloroformate (0.76 mL) in 1,4-dioxane (7.5 mL) was added in a water bath, and the mixture was stirred at room temperature for 1 day. The reaction solution was concentrated under reduced pressure, and then, water was added to the residue, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge HP-Sphere, chloroform:methanol=100:0→90:10) to obtain tert-butyl 3-oxo-1-phenyl-2,7,10,13-tetraoxa-4-azahexadecan-16-oate (2.1 g, 92%) as a colorless oil substance.

$^1$H NMR (300 MHz. CDCl$_3$) δ ppm 1.44 (s, 9H), 2.48 (t, J=6.5 Hz, 2H), 3.33-3.42 (m, 2H), 3.51-3.63 (m, 10H), 3.67-3.73 (m, 2H), 5.10 (s, 2H), 5.28-5.39 (m, 1H), 7.31-7.40 (m, 5H).

(2) To a solution of tert-butyl 3-oxo-1-phenyl-2,7,10,13-tetraoxa-4-azahexadecan-16-oate (2.1 g) in 1,4-dioxane (10 mL), a 4 mol/L solution of hydrogen chloride in 1,4-dioxane (10 mL) was added, and the mixture was stirred at room temperature for 1 day. The reaction solution was concentrated under reduced pressure, and then, followed by azeotropy with chloroform. The solvent was distilled off under reduced pressure to obtain 3-oxo-1-phenyl-2,7,10,13-tetraoxa-4-azahexadecan-16-oic acid (1.8 g, 99%) as a colorless oil substance.

$^1$H NMR (300 MHz, CDCl$_3$) δ ppm 2.59 (t, J=5.9 Hz, 2H), 3.36-3.77 (m, 14H), 5.07-5.14 (m, 2H), 7.34-7.38 (m, 5H).
MS (+):356 [M+H]+.
MS (−): 354 [M−H]+.

(3) The title compound (0.11 g, 18% (4 steps)) was obtained as a colorless amorphous substance through substantially the same reaction as in Reference Example 14-1 (4)(5)(7)(8) except that 3-oxo-1-phenyl-2,7,10,13-tetraoxa-4-azahexadecan-16-oic acid was used instead of 3-oxo-1-phenyl-2,7,10-trioxa-4-azatridecan-13-oic acid obtained in Reference Example 14-1(3).

$^1$H NMR (300 MHz, CDCl$_3$) δ ppm 2.46-2.49 (m, 3H), 2.63 (dd, J=11.5, 9.0 Hz, 1H), 2.88-2.94 (m, 2H), 2.98-3.08 (m, 1H), 3.14 (t, J=5.4 Hz, 2H), 3.50-3.85 (m, 14H), 4.27-4.34 (m, 1H), 6.79-6.82 (m, 1H), 7.09-7.15 (m, 1H), 7.21 (dd, J=2.0, 0.8 Hz, 1H), 7.36 (t, J=7.6 Hz, 1H), 7.89-7.94 (m, 1H), 7.98-8.04 (m, 1H).
MS (+): 534 [M+H]+.
MS (−): 532 [M−H]+.

REFERENCE EXAMPLE 15-1

N-{2-[2-(2-Aminoethoxy)ethoxy]ethyl}-5-{3-[(4S)-6,8-dichloro-2-methyl-1,2,3,4-tetrahydroisoquinolin-4-yl]phenyl}pyridine-2-carboxamide

[Formula 115]

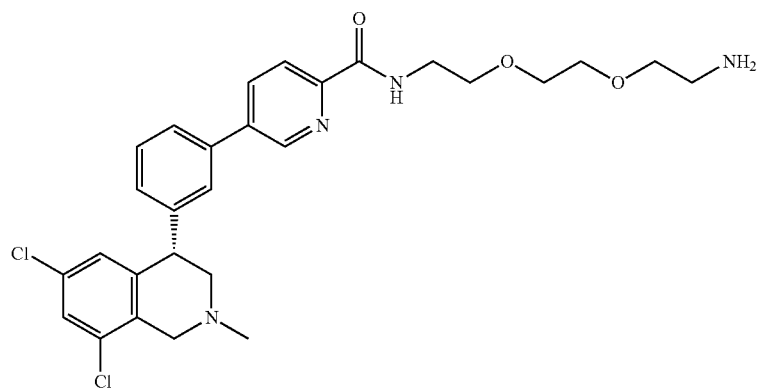

(1) Methyl 5-{3-[(4S)-6,8-dichloro-2-methyl-1,2,3,4-tetrahydroisoquinolin-4-yl]phenyl}pyridine-2-carboxylate (90 mg, 62%) was obtained as a colorless oil substance through substantially the same reaction as in Reference Example 10-1(1) except that [6-(methoxycarbonyl)pyridin-3-yl]boronic acid was used instead of (6-fluoropyridin-3-yl)boronic acid.
LC-MS Retention Time 0.606 min
LC:Agilent 1290
ESI/APCI MS:Agilent 6130

Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 427 [M+H]$^+$.

(2) To a solution of methyl 5-{3-[(4S)-6,8-dichloro-2-methyl-1,2,3,4-tetrahydroisoquinolin-4-yl]phenyl}pyridine-2-carboxylate (90 mg) in a tetrahydrofuran (3.0 mL)-water (1.0 mL) mixed solvent, lithium hydroxide monohydrate (18 mg) was added, and the mixture was stirred at room temperature for 1 hour. The reaction solution was concentrated under reduced pressure to obtain lithium 5-{3-[(4S)-6,8-dichloro-2-methyl-1,2,3,4-tetrahydroisoquinolin-4-yl]phenyl}pyridine-2-carboxylate (88 mg) as a pale yellow solid.

LC-MS Retention Time 0.882 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 413 [M+H]$^+$.

(3) To a solution of lithium 5-{3-[(4S)-6,8-dichloro-2-methyl-1,2,3,4-tetrahydroisoquinolin-4-yl]phenyl}pyridine-2-carboxylate (88 mg) in N,N-dimethylformamide (2.0 mL), tert-butyl {2-[2-(2-aminoethoxy)ethoxy]ethyl}carbamate (80 mg), O-(7-azabenzotriazol-1-yl)-N,N,N',N'-tetramethyluronium hexafluorophosphate (0.13 g), and N,N-diisopropylethylamine (45 mg) were added, and the mixture was stirred overnight at room temperature. The reaction solution was purified by reverse-phase preparative HPLC (column (YMC-Actus Triart 5 μm C18 50×30 mm), mobile phase (0.1% trifluoroacetic acid in $H_2O$:0.1% trifluoroacetic acid in MeCN=90:10→20:80→5:95, 40 mL/min.) to obtain tert-butyl {2-[2-(2-{[(5-{3-[(4S)-6,8-dichloro-2-methyl-1,2,3,4-tetrahydroisoquinolin-4-yl]phenyl}pyridin-2-yl)carbonyl]amino}ethoxy)ethoxy]ethyl}carbamate (0.14 g) as a light brown oil substance.

LC-MS Retention Time 1.275 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 643 [M+H]$^+$.

(4) The title compound (25 mg, 22% (3 steps)) was obtained as a colorless oil substance through substantially the same reaction as in Reference Example 8-4(3) except that tert-butyl {2-[2-(2-{[(5-{3-[(4S)-6,8-dichloro-2-methyl-1,2,3,4-tetrahydroisoquinolin-4-yl]phenyl}pyridin-2-yl)carbonyl]amino}ethoxy)ethoxy]ethyl}carbamate was used instead of tert-butyl [2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]carbamate trifluoroacetate obtained in Reference Example 8-4(2).

LC-MS Retention Time 0.793 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 543 [M+H]$^+$.

REFERENCE EXAMPLE 16-1

4-Nitrophenyl [2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]carbamate

[Formula 116]

To a solution of 4-nitrophenyl chloroformate (0.10 g) in chloroform (2.0 mL), 2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethanamine (0.22 g) obtained in Reference Example 7-1 was added, then triethylamine (86 μL) was added, and the mixture was stirred overnight at room temperature. The reaction solution was purified by silica gel column chromatography (Biotage (registered trademark) SNAP Cartridge HP-Sphere, hexane:ethyl acetate=90:10→0:100→acetone) to obtain the title compound (0.18 g, 63%) as a colorless oil substance.

LC-MS Retention Time 1.235 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 699 [M+H]$^+$.

REFERENCE EXAMPLE 17-1

1,1'-Butane-1,4-diylbis[3-(2-aminoethyl)urea]hydrochloride

[Formula 117]

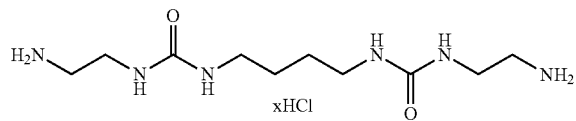

(1) To a solution of tert-butyl (2-aminoethyl)carbamate (0.69 g) in chloroform (10 mL), 1,4-diisocyanatobutane (0.30 g) was added. The mixture was stirred at room temperature for 1 hour, and then, the insoluble matter was collected by filtration and washed with chloroform to obtain di-tert-butyl (4,11-dioxo-3,5,10,12-tetraazatetradecane-1,14-diyl)biscarbamate (0.81 g, 82%) as a colorless solid.

$^1$H NMR (300 MHz, CD$_3$OD) δ ppm 1.33-1.56 (m, 22H) 3.02-3.24 (m, 12H).

(2) To a solution of di-tert-butyl (4,11-dioxo-3,5,10,12-tetraazatetradecane-1,14-diyl)biscarbamate (0.40 g) in methanol (10 mL), a 4 mol/L solution of hydrogen chloride in 1,4-dioxane (0.9 mL) was added, and the mixture was stirred at room temperature for 6 hours. The reaction solution was concentrated under reduced pressure. Then, methanol, chloroform, and tetrahydrofuran were added to the residue, and the mixture was stirred at room temperature. The insoluble matter was collected by filtration to obtain the title compound (0.20 g, 88%) as a colorless solid.

$^1$H NMR (300 MHz, CD$_3$OD) δ ppm 1.41-1.60 (m, 4H) 2.96-3.05 (m, 4H) 3.08-3.19 (m, 4H) 3.33-3.42 (m, 4H).

EXAMPLE 1-1

(4S)-6,8-Dichloro-2-methyl-4-[3-(pyridin-4-yl)phenyl]-1,2,3,4-tetrahydroisoquinoline

[Formula 118]

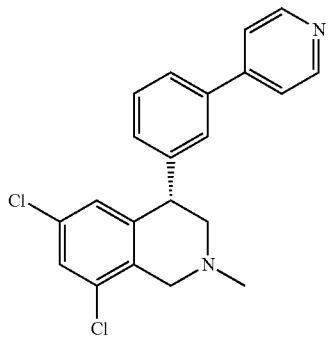

To a suspension of (4S)-4-(3-bromophenyl)-6,8-dichloro-2-methyl-1,2,3,4-tetrahydroisoquinoline (50 mg) obtained in Reference Example 1-1, tetrakis(triphenylphosphine)palladium(0) (7.8 mg), and pyridin-4-ylboronic acid (25 mg) in ethanol (1.5 mL), a saturated aqueous solution of sodium bicarbonate (0.30 mL) was added in an argon gas atmosphere, and the mixture was stirred for 4 hours under heating to reflux. Anhydrous magnesium sulfate was added to the reaction solution, and the mixture was filtered. Then, the filtrate was concentrated under reduced pressure. The obtained residue was purified by silica gel column chromatography (Biotage(registered trademark) SNAP Cartridge HP-Sphere, chloroform:methanol=100:0→90:10) to obtain the title compound (34 mg, 68%) as a yellow amorphous substance).

$^1$H NMR (300 MHz, CDCl$_3$) δ ppm 2.49 (s, 3H), 2.57-2.68 (m, 1H), 2.95-3.06 (m, 1H), 3.52-3.62 (m, 1H), 3.74-3.85 (m, 1H), 4.24-4.35 (m, 1H), 6.83 (d, J=1.2 Hz, 1H), 7.21-7.27 (m, 2H), 7.40-7.51 (m, 4H), 7.51-7.57 (m, 1H), 8.61-8.69 (m, 2H).

MS (+): 369 [M+H]$^+$

EXAMPLE 1-2

(4S)-6,8-Dichloro-2-methyl-4-[3-(pyridin-3-yl)phenyl]-1,2,3,4-tetrahydroisoquinoline trifluoroacetate To a suspension of (4S)-4-(3-bromophenyl)-6,8-dichloro-2-methyl-1,2,3,4-tetrahydroisoquinoline (50 mg) obtained in Reference Example 1-1, tetrakis(triphenylphosphine)palladium(0) (7.8 mg), and pyridin-3-ylboronic acid (25 mg) in ethanol (1.5 mL), a saturated aqueous solution of sodium bicarbonate (0.30 mL) was added in an argon gas atmosphere, and the mixture was stirred for 4 hours under heating to reflux. Anhydrous magnesium sulfate was added to the reaction solution, and the mixture was filtered. Then, the filtrate was concentrated under reduced pressure. The obtained residue was purified by reverse-phase preparative HPLC (column (YMC-Actus Triart 5 μm C18 50×30 mm), mobile phase (0.1% formic acid in H$_2$O:0.1% formic acid in MeCN=95:5→80:20→50:50→5:95, 40 mL/min.) to obtain the title compound (32 mg) as a colorless oil substance.

$^1$H NMR (300 MHz, CD$_3$OD) δ ppm 3.18 (s, 3H), 3.64-3.78 (m, 1H), 3.85-3.99 (m, 1H), 4.46-4.59 (m, 1H), 4.73-4.90 (m, 2H), 6.87-6.92 (m, 1H), 7.42-7.49 (m, 1H), 7.50-7.55 (m, 1H), 7.62-7.70 (m, 1H), 7.74-7.79 (m, 1H), 7.82-7.88 (m, 1H), 8.11 (dd, J=8.2, 5.7 Hz, 1H), 8.79-8.90 (m, 2H), 9.18 (d, J=1.6 Hz, 1H).

MS (+): 369 [M+H]$^+$.

EXAMPLE 1-3

(4S)-6,8-Dichloro-2-methyl-4-[3-(1H-pyrazol-3-yl)phenyl]-1,2,3,4-tetrahydroisoquinoline (1) To a solution of (4S)-4-(3-bromophenyl)-6,8-dichloro-2-methyl-1,2,3,4-tetrahydroisoquinoline (2S,3S)-(+)-dibenzoyl-D-tartrate monoethanol monohydrate (0.10 g) obtained in Reference Example 1-2 in a 1,4-dioxane (8.0 mL)-water (2.0 mL) mixed solvent, 1-(tetrahydro-2H-pyran-2-yl)-5-(4,4,5,5-tetramethyl-1,3,2-dioxaborolan-2-yl)-1H-pyrazole (57 mg), chloro[2-(dicyclohexylphosphino)-3,6-dimethoxy-2'-4'-6'-tri-1-propyl-1,1'-biphenyl][2-(2-aminoethyl)phenyl]palladium(II) (10 mg), and sodium tert-butoxide (60 mg) were added in a nitrogen gas atmosphere, and the mixture was stirred at 100° C. for 1 hour. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→0:100) to obtain (4S)-6,8-dichloro-2- methyl-4-{3-[1-(tetrahydro-2H-pyran-2-yl)-1H-pyrazol-5-yl]phenyl}-1,2,3,4-tetrahydroisoquinoline (10 mg, 16%) as a colorless oil substance.

LC-MS Retention Time 0.661 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 442 $[M+H]^+$.

(2) To a solution of (4S)-6,8-dichloro-2-methyl-4-{3-[1-(tetrahydro-2H-pyran-2-yl)-1H-pyrazol-5-yl]phenyl}-1,2,3,4-tetrahydroisoquinoline (10 mg) in a methanol (1.6 mL)-water (0.40 mL) mixed solvent, trifluoroacetic acid (1.0 mL) was added, and the mixture was stirred at room temperature for 1 hour. The reaction solution was concentrated under reduced pressure, and the obtained residue was purified by silica gel column chromatography (Biotage(registered trademark) SNAP Cartridge KP-NH, hexane:ethyl acetate=100:0→0:100) to obtain the title compound (0.30 mg, 4.0%) as a colorless amorphous substance.

LC-MS Retention Time 0.541 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 358 $[M+H]^+$.

EXAMPLE 1-4

(4S)-6,8-Dichloro-2-methyl-4-[3-(1H-pyrazol-4-yl)phenyl]-1,2,3,4-tetrahydroisoquinoline trifluoroacetate (1) To a solution of (4S)-4-(3-bromophenyl)-6,8-dichloro-2-methyl-1,2,3,4-tetrahydroisoquinoline (0.50 g) obtained in Reference Example 1-1 in a 1,4-dioxane (10 mL)-water (2.5 mL) mixed solvent, tert-butyl 4-(4,4,5,5-tetramethyl-1,3,2-dioxaborolan-2-yl)-1H-pyrazole-1-carboxylate (0.59 g), tris(dibenzylideneacetone)dipalladium(0) (0.12 g), tri(2-furyl)phosphine (0.19 g), and cesium carbonate (0.88 g) were added in a nitrogen gas atmosphere, and the mixture was stirred at 90° C. for 5 hours. Water was added to the reaction solution, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→5:95) to obtain tert-butyl 4-{3-[(4S)-6,8-dichloro-2-methyl-1,2,3,4-tetrahydroisoquinolin-4-yl]phenyl}-1H-pyrazole-1-carboxylate (0.42 g, 68%) as a colorless oil substance.

LC-MS Retention Time 0.740 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 458 $[M+H]^+$.

(2) To a solution of tert-butyl 4-{3-[(4S)-6,8-dichloro-2-methyl-1,2,3,4-tetrahydroisoquinolin-4-yl]phenyl}-1H-pyrazole-1-carboxylate (0.42 g) in chloroform (2.1 mL), trifluoroacetic acid (2.1 mL) was added under ice cooling, and the mixture was stirred at room temperature for 2 hours. The reaction solution was concentrated under reduced pressure, followed by azeotropy with chloroform. The solvent was distilled off under reduced pressure to obtain the title compound (0.42 g) as a black oil substance.

LC-MS Retention Time 0.514 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 358 $[M+H]^+$.

EXAMPLE 1-5

(4S)-6,8-Dichloro-2-methyl-4-[3-(6-methyl-pyridazin-4-yl)phenyl]-1,2,3,4-tetrahydroisoquinoline trifluoroacetate The title compound (28 mg) was obtained as a yellow amorphous substance through substantially the same reaction as in Example 1-2 except that 3-methyl-5-(4,4,5,5-tetramethyl-1,3,2-dioxaborolan-2-yl)pyridazine was used instead of pyridin-3-ylboronic acid.

$^1$H NMR (300 MHz, $CD_3OD$) δ ppm 2.85 (s, 3H), 3.17 (s, 3H), 3.65-3.79 (m, 1H), 3.87-3.99 (m, 1H), 4.45-4.59 (m, 1H), 4.74-4.89 (m, 2H), 6.85-6.92 (m, 1H), 7.49-7.58 (m, 2H), 7.65-7.75 (m, 1H), 7.90-7.96 (m, 1H), 7.97-8.05 (m, 1H), 8.36-8.42 (m, 1H), 9.56-9.63 (m, 1H).
MS (+): 384 $[M+H]^+$.

EXAMPLE 1-6

(4S)-6,8-Dichloro-2-methyl-4-[3-(pyridin-2-yl)phenyl]-1,2,3,4-tetrahydroisoquinoline trifluoroacetate A solution of (4S)-4-(3-bromophenyl)-6,8-dichloro-2-methyl-1,2,3,4-tetrahydroisoquinoline (50 mg) obtained in Reference Example 1-1, tetrakis(triphenylphosphine)palladium(0) (7.8 mg), and 2-(tributylstannanyl)pyridine (74 mg) in 1,4-dioxane (1.5 mL) was stirred at 100° C. for 15 hours in an argon gas atmosphere. The reaction solution was allowed to cool and then purified by reverse-phase preparative HPLC (column (YMC-Actus Triart 5 μm C18 50×30 mm), mobile phase (0.1% trifluoroacetic acid in $H_2O:0.1\%$ trifluoroacetic acid in MeCN=90:10→20:80→5:95, 40 mL/min.) to obtain the title compound (65 mg) as a pale yellow oil substance.

$^1$H NMR (300 MHz, $CD_3OD$) δ ppm 3.17 (s, 3H), 3.63-3.76 (m, 1H), 3.87-3.97 (m, 1H), 4.47-4.58 (m, 1H), 4.72-4.86 (m, 2H), 6.90-6.95 (m, 1H), 7.46-7.51 (m, 1H), 7.53-7.57 (m, 1H), 7.63-7.70 (m, 1H), 7.70-7.76 (m, 1H), 7.86-7.91 (m, 1H), 7.94-8.00 (m, 1H), 8.11-8.17 (m, 1H), 8.26-8.35 (m, 1H), 8.72-8.78 (m, 1H).
MS (+): 369 $[M+H]^+$.

EXAMPLE 1-7

4-{3-[(4S)-6,8-Dichloro-2-methyl-1,2,3,4-tetrahydroisoquinolin-4-yl]phenyl}pyridine-2-carbonitrile The title compound (8.5 mg, 16%) was obtained as a pale yellow amorphous substance through substantially the same reaction as in Example 1-1 except that 4-(4,4,5,5-tetramethyl-1,3,2-dioxaborolan-2-yl)pyridine-2-carbonitrile was used instead of pyridin-4-ylboronic acid.

$^1$H NMR (300 MHz, $CDCl_3$) δ ppm 2.49 (s, 3H), 2.61-2.70 (m, 1H), 2.95-3.04 (m, 1H), 3.58-3.68 (m, 1H), 3.70-

3.80 (m, 1H), 4.25-4.33 (m, 1H), 6.78-6.82 (m, 1H), 7.25-7.27 (m, 1H), 7.30-7.35 (m, 1H), 7.42-7.56 (m, 3H), 7.65-7.71 (m, 1H), 7.85-7.90 (m, 1H), 8.74 (dd, J=5.1, 0.8 Hz, 1H).

MS (+): 394 [M+H]$^+$.

EXAMPLE 1-8

6,8-Dichloro-2-methyl-4-[3-(1-methyl-1H-1,2, 3-triazol-4-yl)phenyl]-1,2,3,4-tetrahydroisoquinoline To a solution of 6,8-dichloro-2-methyl-4-[3-(4,4,5,5-tetramethyl-1,3,2-dioxaborolan-2-yl)phenyl]-1,2,3,4-tetrahydroisoquinoline (50 mg) obtained in Reference Example 3-1 in a dioxane (1.0 mL)-water (0.25 mL) mixed solvent, 4-bromo-1-methyltriazole (23 mg), tri(2-furyl)phosphine (17 mg), cesium carbonate (78 mg), and tris(dibenzylideneacetone)dipalladium(0) (11 mg) were added in a nitrogen gas atmosphere, and the mixture was stirred at 90° C. for 5 hours. The reaction solution was allowed to cool, and then, water was added thereto, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge HP-Sphere, hexane: ethyl acetate=100:0→5:95) to obtain the title compound (12 mg, yield: 23%) as a light brown amorphous substance.

$^1$H NMR (300 MHz, CDCl$_3$) δ ppm 2.48 (s, 3H), 2.63 (dd, J=11.0, 8.5 Hz, 1H), 3.03 (dd, J=11.0, 4.9 Hz, 1H), 3.52 (d, J=15.7 Hz, 1H), 3.84 (d, J=15.7 Hz, 1H), 4.15 (s, 3H), 4.25-4.32 (m, 1H), 6.80-6.83 (m, 1H), 7.08-7.15 (m, 1H), 7.23 (d, J=2.0 Hz, 1H), 7.33-7.40 (m, 1H), 7.60-7.80 (m, 3H).

MS (+): 373 [M+H]$^+$.

EXAMPLE 1-9

4-{3-[(4S)-6,8-Dichloro-2-methyl-1,2,3,4-tetrahydroisoquinolin-4-yl]phenyl}-N-methylpyridin-2-amine trifluoroacetate A suspension of (4S)-6,8-dichloro-2-methyl-4-[3-(4,4,5,5-tetramethyl-1,3,2-dioxaborolan-2-yl)phenyl]-1,2,3,4-tetrahydroisoquinoline (40 mg) obtained in Reference Example 3-2, 4-bromo-N-methylpyridin-2-amine (36 mg) obtained in Reference Example 8-1, tetrakis(triphenylphosphine)palladium(0) (5.6 mg), and a saturated aqueous solution of sodium bicarbonate (0.96 mL) in 1,4-dioxane (4.8 mL) was stirred for 3.5 hours under heating to reflux in a nitrogen gas atmosphere. The reaction solution was purified by reverse-phase preparative HPLC (column (YMC-Actus Triart 5 μm C18 50×30 mm), mobile phase (0.1% trifluoroacetic acid in H$_2$O:0.1% trifluoroacetic acid in MeCN=90:10→20:80→5:95, 40 mL/min.) to obtain the title compound (39 mg) as a colorless amorphous substance.

$^1$H NMR (300 MHz, CD$_3$OD) δ ppm 3.08 (s, 3H), 3.17 (s, 3H), 3.63-3.76 (m, 1H), 3.85-3.96 (m, 1H), 4.46-4.58 (m, 1H), 4.73-4.87 (m, 2H), 6.83-6.90 (m, 1H), 7.17-7.23 (m, 1H), 7.24-7.28 (m, 1H), 7.43-7.49 (m, 1H), 7.50-7.55 (m, 1H), 7.59-7.67 (m, 1H), 7.71-7.76 (m, 1H), 7.79-7.85 (m, 1H), 7.87-7.92 (m, 1H).

MS (+): 398 [M+H]$^+$.

EXAMPLE 1-10

(4S)-6,8-Dichloro-2-methyl-4-[3-(pyrimidin-5-yl)phenyl]-1,2,3,4-tetrahydroisoquinoline trifluoroacetate The title compound (45 mg) was obtained as a colorless amorphous substance through substantially the same reaction as in Example 1-9 except that (4S)-4-(3-bromophenyl)-6,8-dichloro-2-methyl-1,2,3,4-tetrahydroisoquinoline obtained in Reference Example 1-1 was used instead of (4S)-6,8-dichloro-2-methyl-4-[3-(4,4,5,5-tetramethyl-1,3,2-dioxaborolan-2-yl)phenyl]-1,2,3,4-tetrahydroisoquinoline obtained in Reference Example 3-2, and pyrimidin-5-ylboronic acid was used instead of 4-bromo-N-methylpyridin-2-amine obtained in Reference Example 8-1.

$^1$H NMR (300 MHz, CD$_3$OD) δ ppm 3.18 (s, 3H), 3.63-3.77 (m, 1H), 3.87-3.98 (m, 1H), 4.45-4.58 (m, 1H), 4.71-4.88 (m, 2H), 6.88-6.94 (m, 1H), 7.36-7.42 (m, 1H), 7.49-7.53 (m, 1H), 7.58-7.66 (m, 1H), 7.67-7.70 (m, 1H), 7.74-7.79 (m, 1H), 9.08 (s, 2H), 9.15 (s, 1H).

MS (+): 370 [M+H]$^+$.

EXAMPLE 1-11

(4S)-6,8-Dichloro-4-[3-(2-methoxypyridin-4-yl)phenyl]-2-methyl-1,2,3,4-tetrahydroisoquinoline trifluoroacetate The title compound (41 mg) was obtained as a colorless amorphous substance through substantially the same reaction as in Example 1-9 except that (4S)-4-(3-bromophenyl)-6,8-dichloro-2-methyl-1,2,3,4-tetrahydroisoquinoline obtained in Reference Example 1-1 was used instead of (4S)-6,8-dichloro-2-methyl-4-[3-(4,4,5,5-tetramethyl-1,3,2-dioxaborolan-2-yl)phenyl]-1,2,3,4-tetrahydroisoquinoline obtained in Reference Example 3-2, and (2-methoxypyridin-4-yl)boronic acid was used instead of 4-bromo-N-methylpyridin-2-amine obtained in Reference Example 8-1.

$^1$H NMR (300 MHz, CD$_3$OD) δ ppm 3.17 (s, 3H), 3.63-3.76 (m, 1H), 3.86-3.96 (m, 1H), 4.06 (s, 3H), 4.46-4.58 (m, 1H), 4.72-4.87 (m, 2H), 6.86-6.92 (m, 1H), 7.26-7.31 (m, 1H), 7.35-7.44 (m, 2H), 7.50-7.54 (m, 1H), 7.55-7.64 (m, 1H), 7.70-7.75 (m, 1H), 7.78-7.84 (m, 1H), 8.21-8.26 (m, 1H).

MS (+): 399 [M+H]$^+$.

EXAMPLE 1-12

(4S)-6,8-Dichloro-4-[3-(2-ethylpyridin-4-yl)phenyl]-2-methyl-1,2,3,4-tetrahydroisoquinoline trifluoroacetate The title compound (25 mg) was obtained as a yellow amorphous substance through substantially the same reaction as in Example 1-9 except that (4S)-4-(3-bromophenyl)-6,8-dichloro-2-methyl-1,2,3,4-tetrahydroisoquinoline obtained in Reference Example 1-1 was used instead of (4S)-6,8-dichloro-2-methyl-4-[3-(4,4,5,5-tetramethyl-1,3,2-dioxaborolan-2-yl)phenyl]-1,2,3,4-tetrahydroisoquinoline obtained in Reference Example 3-2, and 2-ethyl-4-(4,4,5,5-tetramethyl-1,3,2-dioxaborolan-2-yl)pyridine was used instead of 4-bromo-N-methylpyridin-2-amine obtained in Reference Example 8-1.

$^1$H NMR (300 MHz, CD$_3$OD) δ ppm 1.47 (t, J=7.6 Hz, 3H), 3.09-3.17 (m, 2H), 3.17 (s, 3H), 3.65-3.79 (m, 1H), 3.88-4.00 (m, 1H), 4.46-4.58 (m, 1H), 4.75-4.89 (m, 2H), 6.84-6.92 (m, 1H), 7.50-7.57 (m, 2H), 7.65-7.74 (m, 1H), 7.90-7.95 (m, 1H), 7.97-8.04 (m, 1H), 8.17-8.23 (m, 1H), 8.24-8.29 (m, 1H), 8.69-8.75 (m, 1H).
MS (+): 397 [M+H]$^+$.

EXAMPLE 1-13

(4S)-6,8-Dichloro-4-[3-(6-methoxypyrimidin-4-yl)phenyl]-2-methyl-1,2,3,4-tetrahydroisoquinoline trifluoroacetate The title compound (2.6 mg) was obtained as a colorless amorphous substance through substantially the same reaction as in Example 1-9 except that 4-chloro-6-methoxypyrimidine was used instead of 4-bromo-N-methylpyridin-2-amine obtained in Reference Example 8-1.
$^1$H NMR (300 MHz, CD$_3$OD) δ ppm 3.16 (s, 3H), 3.60-3.75 (m, 1H), 3.85-3.95 (m, 1H), 4.38 (s, 3H), 4.46-4.59 (m, 1H), 4.65-4.80 (m, 2H), 6.86-6.94 (m, 1H), 7.32-7.36 (m, 1H), 7.39-7.46 (m, 1H), 7.53-7.56 (m, 1H), 7.56-7.63 (m, 1H), 7.96-8.01 (m, 1H), 8.04-8.10 (m, 1H), 8.79 (d, J=1.1 Hz, 1H).
MS (+):400 [M+H]$^+$.

EXAMPLE 1-14

(4S)-6,8-Dichloro-2-methyl-4-[3-(pyrazin-2-yl)phenyl]-1,2,3,4-tetrahydroisoquinoline trifluoroacetate The title compound (11 mg) was obtained as a pale yellow oil substance through substantially the same reaction as in Example 1-6 except that 2-(tributylstannanyl)pyrazine was used instead of 2-(tributylstannanyl)pyridine.
$^1$H NMR (300 MHz, CD$_3$OD) δ ppm 3.17 (s, 3H), 3.62-3.76 (m, 1H), 3.86-3.98 (m, 1H), 4.46-4.59 (m, 1H), 4.70-4.84 (m, 2H), 6.88-6.95 (m, 1H), 7.37-7.45 (m, 1H), 7.51-7.56 (m, 1H), 7.57-7.66 (m, 1H), 8.00-8.05 (m, 1H), 8.08-8.15 (m, 1H), 8.54-8.60 (m, 1H), 8.66-8.71 (m, 1H), 9.11-9.17 (m, 1H).
MS (+): 370 [M+H]$^+$.

EXAMPLE 1-15

6-{3-[(4S)-6,8-Dichloro-2-methyl-1,2,3,4-tetrahydroisoquinolin-4-yl]phenyl}-N-methylpyrimidin-4-amine trifluoroacetate The title compound (49 mg) was obtained as a pale yellow amorphous substance through substantially the same reaction as in Example 1-9 except that 6-chloro-N-methylpyrimidin-4-amine obtained in Reference Example 8-2 was used instead of 4-bromo-N-methylpyridin-2-amine obtained in Reference Example 8-1.
$^1$H NMR (300 MHz, CD$_3$OD) δ ppm 3.09-3.21 (m, 6H), 3.60-3.77 (m, 1H), 3.85-3.98 (m, 1H), 4.43-4.58 (m, 1H), 4.71-4.87 (m, 2H), 6.87 (s, 1H), 6.97-7.12 (m, 1H), 7.50-7.62 (m, 2H), 7.64-8.00 (m, 3H), 8.55-8.77 (m, 1H).
MS (+): 399 [M+H]$^+$.

EXAMPLE 1-16

(4S)-6,8-Dichloro-2-methyl-4-[3-(pyrimidin-2-yl)phenyl]-1,2,3,4-tetrahydroisoquinoline trifluoroacetate The title compound (11 mg) was obtained as a colorless amorphous substance through substantially the same reaction as in Example 1-6 except that 2-(tributylstannanyl)pyrimidine was used instead of 2-(tributylstannanyl)pyridine.
$^1$H NMR (300 MHz, CD$_3$OD) δ ppm 3.16 (s, 3H), 3.61-3.74 (m, 1H), 3.85-3.96 (m, 1H), 4.47-4.59 (m, 1H), 4.68-4.80 (m, 2H), 6.89-6.95 (m, 1H). 7.36-7.41 (m, 1H), 7.41-7.46 (m, 1H), 7.53-7.55 (m, 1H), 7.56-7.63 (m, 1H), 8.28-8.32 (m, 1H), 8.39-8.47 (m, 1H), 8.84 (s, 1H), 8.86 (s, 1H).
MS (+): 370 [M+H]$^+$.

EXAMPLE 1-17

(4S)-6,8-Dichloro-2-methyl-4-[3-(pyridazin-4-yl)phenyl]-1,2,3,4-tetrahydroisoquinoline trifluoroacetate The title compound (22 mg) was obtained as a light brown amorphous substance through substantially the same reaction as in Example 1-6 except that 4-(tributylstannanyl)pyridazine was used instead of 2-(tributylstannanyl)pyridine, and (4S)-4-(3-bromophenyl)-6, 8-dichloro-2-methyl-1,2,3,4-tetrahydroisoquinoline (2S,3S)-(+)-dibenzoyl-D-tartrate monoethanol monohydrate obtained in Reference Example 1-2 was used instead of (4S)-4-(3-bromophenyl)-6,8-dichloro-2-methyl-1,2,3,4-tetrahydroisoquinoline obtained in Reference Example 1-1.
$^1$H NMR (300 MHz, CD$_3$OD) δ ppm 3.18 (s, 3H), 3.64-3.77 (m, 1H), 3.87-3.98 (m, 1H), 4.44-4.59 (m, 1H), 4.75-4.87 (m, 2H), 6.87-6.93 (m, 1H), 7.45-7.51 (m, 1H), 7.52-7.55 (m, 1H), 7.63-7.71 (m, 1H), 7.84-7.89 (m, 1H), 7.92-7.97 (m, 1H), 8.17-8.23 (m, 1H), 9.29-9.35 (m, 1H), 9.62-9.67 (m, 1H).
MS (+): 370 [M+H]$^+$.

EXAMPLE 1-18

(4S)-6,8-Dichloro-2-methyl-4-[3-(1-methyl-1H-imidazol-4-yl)phenyl]-1,2,3,4-tetrahydroisoquinoline To a solution of (4S)-6,8-dichloro-2-methyl-4-[3-(4,4,5,5-tetramethyl-1,3,2-dioxaborolan-2-yl)phenyl]-1,2,3,4-tetrahydroisoquinoline (50 mg) obtained in Reference Example 3-2 in dioxane (1.0 mL) and water (0.25 mL), 4-bromo-1-methyl-1H-imidazole (14 mg), tri(2-furyl)phosphine (17 mg), cesium carbonate (78 mg), and tris(dibenzylideneacetone)dipalladium(0) (11 mg) were added in a nitrogen gas atmosphere, and the mixture was stirred at 90° C. for 1 day. The reaction solution was allowed to cool, and then, water was added thereto, followed by extraction with ethyl acetate. The organic layer was dried over anhydrous magnesium sulfate and filtered, and then, the filtrate was concentrated under reduced pressure. The obtained residue was purified by preparative LC-MS (LC (Agilent 1260), ESIMS (6130 Quadrupole, ESI), column (YMC-Actus Triart 5 μm C18 50×30 mm), mobile phase (0.1% formic acid in H$_2$O:0.1% formic acid in CH$_3$CN=95:5→50:50→5:95), 50 mL/min.) to obtain the title compound (3.6 mg, yield: 6.7%) as a colorless oil substance.
$^1$H NMR (300 MHz, CD$_3$OD) δ ppm 2.60 (s, 3H), 2.80 (dd, J=11.8, 9.8 Hz, 1H), 3.17-3.26 (m, 1H), 3.62-3.71 (m, 1H), 3.76 (s, 3H), 4.01-4.12 (m, 1H), 4.37 (dd, J=9.8, 5.8 Hz, 1H), 6.79-6.83 (m, 1H), 7.07 (d, J=7.6 Hz, 1H), 7.31-7.38 (m, 2H), 7.46 (s, 1H), 7.54-7.69 (m, 3H).
MS (+): 372 [M+H]$^+$.

EXAMPLE 1-19

(4S)-6,8-Dichloro-2-methyl-4-[3-(3-methyl-1,2-thiazol-5-yl)phenyl]-1,2,3,4-tetrahydroisoquinoline hydrochloride To a solution of (4S)-6,8-dichloro-2-methyl-4-[3-(4,4,55-tetramethyl-1,3,2-dioxaborolan-2-yl)phenyl]-1,2,3,4-tetrahydroisoquinoline hydrochloride (50 mg) obtained in Reference Example 3-3 in dioxane (1.0 mL) and water (0.25 mL), 3-bromo-5-methyl-isothiazole (24 mg), tri(2-furyl)phosphine (17 mg), cesium carbonate (78 mg), and tris(dibenzylideneacetone)dipalladium(0) (11 mg) were added in a nitrogen gas atmosphere, and the mixture was stirred at 90° C. for 5 hours. The reaction solution was allowed to cool, and then, water was added thereto, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→10:90). To the obtained yellow oil substance (30 mg), ethyl acetate (1.5 mL) and 4 mol/L hydrogen chloride in ethyl acetate (0.5 mL) were added, and the solvent was distilled off under reduced pressure to obtain the title compound (31 mg, yield: 55%) as a light brown solid.

$^1$H NMR (300 MHz, CD$_3$OD) δ ppm 2.50 (s, 3H), 3.17 (s, 3H), 3.57-3.70 (m, 1H), 3.86-3.96 (m, 1H), 4.40-4.53 (m, 1H), 4.62-4.84 (m, 2H), 6.87 (s., 1H), 7.28-7.37 (m, 1H), 7.45 (s, 1H), 7.50-7.59 (m, 2H), 7.63 (s, 1H), 7.71 (d, J=7.8 Hz, 1H).

MS (+): 389 [M+H]$^+$.

EXAMPLE 1-20

(4S)-6,8-Dichloro-2-methyl-4-[3-(pyridazin-3-yl)phenyl]-1,2,3,4-tetrahydroisoquinoline hydrochloride To a solution of (4S)-6,8-dichloro-2-methyl-4-[3-(4,4,5,5-tetramethyl-1,3,2-dioxaborolan-2-yl)phenyl]-1,2,3,4-tetrahydroisoquinoline (30 mg) obtained in Reference Example 3-2 and 3-bromopyridazine hydrobromide (25 mg) in 1,2-dimethoxyethane (2.0 mL), tetrakis(triphenylphosphine)palladium(0) (12 mg) and a 2 mol/L aqueous sodium bicarbonate solution (0.12 mL) were added in a nitrogen gas atmosphere, and the mixture was stirred for 1 hour under microwave irradiation (Biotage 60, 120° C.). The reaction solution was allowed to cool and then filtered through Celite (registered trademark), and the filtrate was concentrated under reduced pressure. The obtained residue was purified by silica gel column chromatography (Biotage(registered trademark) SNAP Cartridge HP-Sphere, hexane:ethyl acetate=80:20→0:100→chloroform:methanol=100:0→80:20), and the obtained residue was further purified by silica gel column chromatography (Biotage (registered trademark) SNAP Cartridge KP-NH, hexane:ethyl acetate=88:12→0:100). The solvent was distilled off under reduced pressure. To the obtained residue, ethyl acetate (0.1 mL) was added, then 4 mol/L hydrogen chloride in ethyl acetate (0.1 mL) was added dropwise, and the mixture was stirred at room temperature for 15 minutes. Then, the solvent was distilled off under reduced pressure to obtain the title compound (2.4 mg) as a pale yellow solid.

$^1$H NMR (600 MHz, CD$_3$OD) δ ppm 3.19 (br. s., 3H), 3.27-3.34 (m, 2H), 3.68-3.83 (m, 1H), 3.84-4.00 (m, 1H), 4.45-4.61 (m, 1H), 6.88 (br. s., 1H), 7.55 (br. s., 1H), 7.58-7.65 (m, 1H), 7.67-7.79 (m, 1H), 8.08-8.25 (m, 2H), 8.38-8.55 (m, 1H), 8.86-9.02 (m, 1H), 9.54 (br. s., 1H).

MS (+): 370 [M+H]$^+$.

EXAMPLE 1-21

(4S)-6,8-Dichloro-2-methyl-4-[3-(1H-pyrrol-2-yl)phenyl]-1,2,3,4-tetrahydroisoquinoline (1) tert-Butyl 2-{3-[(4S)-6,8-dichloro-2-methyl-1,2,3,4-tetrahydroisoquinolin-4-yl]phenyl}-1H-pyrrole-1-carboxylate (54 mg, 58%) was obtained as a pale yellow amorphous substance through substantially the same reaction as in Example 1-1 except that [1-(tert-butoxycarbonyl)-1H-pyrrol-2-yl]boronic acid was used instead of pyridin-4-ylboronic acid.

$^1$H NMR (300 MHz, CDCl$_3$) δ ppm 1.35 (s, 9H), 2.48 (s, 3H), 2.60 (dd, J=11.5, 8.5 Hz, 1H), 3.02 (dd, J=11.5, 5.4 Hz, 1H), 3.48 (d, J=16.3 Hz, 1H), 3.83 (d, J=16.3 Hz. 1H), 4.23 (br. s., 1H), 6.13-6.19 (m, 1H), 6.19-6.24 (m, 1H), 6.85 (s, 1H), 7.10 (d, J=7.3 Hz, 1H), 7.15 (s, 1H), 7.20-7.26 (m, 2H), 7.28 (d, J=7.5 Hz, 1H), 7.33 (dd, J=3.2, 1.8 Hz, 1H).

MS (+): 457 [M+H]$^+$.

(2) To a solution of tert-butyl 2-{3-[(4S)-6,8-dichloro-2-methyl-1,2,3,4-tetrahydroisoquinolin-4-yl]phenyl}-1H-pyrrole-1-carboxylate (42 mg) in 1,2-dichloroethane (1.8 mL), trifluoroacetic acid (0.9 mL) was added, and the mixture was stirred at room temperature for 30 minutes. To the reaction solution, water was added, and a saturated aqueous solution of sodium carbonate was slowly added, followed by extraction with ethyl acetate. The organic layer was washed with a saturated aqueous solution of sodium carbonate and saturated saline, dried over anhydrous sodium sulfate, and filtered, and then, the filtrate was concentrated under reduced pressure. The obtained residue was purified by silica gel column chromatography (Biotage(registered trademark) SNAP Cartridge HP-Sphere, hexane:ethyl acetate=88:12→9:91) to obtain the title compound (16 mg, 48%) as a colorless amorphous substance.

$^1$H NMR (600 MHz, CDCl$_3$) δ ppm 2.50 (s, 3H), 2.63 (br. s., 1H), 3.02 (br. s., 1H), 3.55 (d, J=15.7 Hz, 1H), 3.84 (d. J=16.1 Hz, 1H), 4.25 (br. s., 1H), 6.25-6.33 (m, 1H). 6.47-6.54 (m, 1H), 6.82 (s, 1H), 6.84-6.89 (m, 1H), 6.99 (d, J=7.8 Hz, 1H), 7.24 (d, J=1.7 Hz, 1H), 7.27 (br. s., 1H), 7.31 (t, J=7.6 Hz, 1H), 7.39 (d, J=7.8 Hz, 1H), 8.46 (br. s., 1H).

MS (+): 357 [M+H]$^+$.

EXAMPLE 1-22

(4S)-6,8-Dichloro-2-methyl-4-[3-(1,3-oxazol-2-yl)phenyl]-1,2,3,4-tetrahydroisoquinoline hydrochloride The title compound (6.6 mg, 13%) was obtained as a colorless solid through substantially the same reaction as in Example 1-6 except that 2-(tributylstannanyl)-1,3-oxazole was used instead of 2-(tributylstannanyl)pyridine.

LC-MS Retention Time 0.581 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(80:20)→1.2-1.4 min(1:99)
MS (+): 359 [M+H]$^+$.

EXAMPLE 1-23

(4S)-6,8-Dichloro-4-[3-(furan-2-yl)phenyl]-2-methyl-1,2,3,4-tetrahydroisoquinoline The title compound (28 mg., 58%) was obtained as a colorless amorphous substance through substantially the same reaction as in Example 1-6 except that tributyl(furan-2-yl)stannane was used instead of 2-(tributylstannanyl)pyridine.

$^1$H NMR (300 MHz, CDCl$_3$) δ ppm 2.37-2.53 (m, 3H), 2.60 (dd, J=11.6, 8.6 Hz, 1H), 2.95-3.10 (m, 1H), 3.44-3.58 (m, 1H), 3.84 (d, J=16.2 Hz, 1H), 4.17-4.34 (m, 1H), 6.47 (dd, J=3.3, 1.8 Hz, 1H), 6.64 (dd, J=3.3, 0.7 Hz, 1H), 6.81 (d, J=0.9 Hz, 1H), 7.03 (dt, J=7.7, 1.4 Hz, 1H), 7.23 (d, J=2.2 Hz, 1H), 7.32 (t, J=7.7 Hz, 1H), 7.43-7.52 (m, 2H), 7.53-7.61 (m, 1H).

MS (+): 358 [M+H]$^+$.

The structures of Examples 1-2 to 1-23 are shown in Tables 2-1 and 2-2 below.

TABLE 2-1

| | |
|---|---|
| 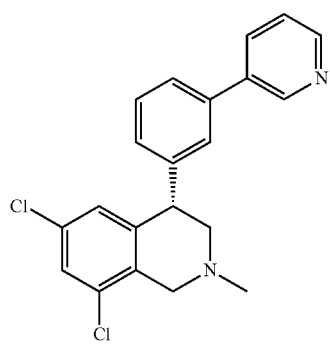 [SMILES: CN1Cc2c(Cl)cc(Cl)cc2[C@H](c2cccc(-c3cccnc3)c2)C1] | Example 1-2 |
| 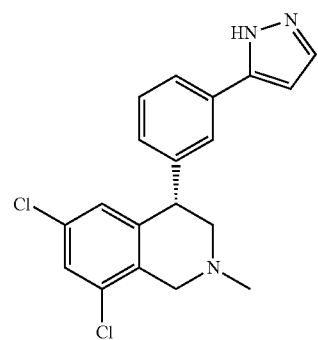 [SMILES: CN1Cc2c(Cl)cc(Cl)cc2[C@H](c2cccc(-c3ccn[nH]3)c2)C1] | Example 1-3 |
| 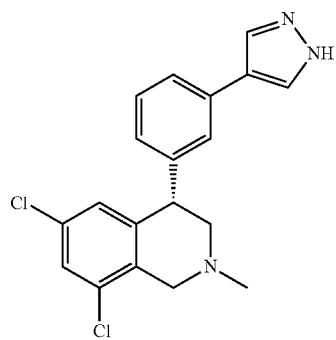 [SMILES: CN1Cc2c(Cl)cc(Cl)cc2[C@H](c2cccc(-c3cn[nH]c3)c2)C1] | Example 1-4 |

TABLE 2-1-continued

| | |
|---|---|
| 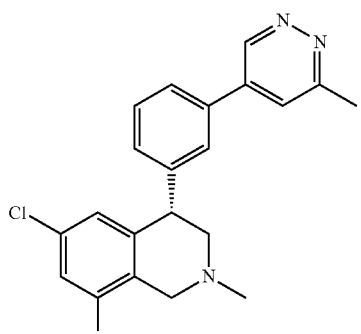 | Example 1-5 |
| 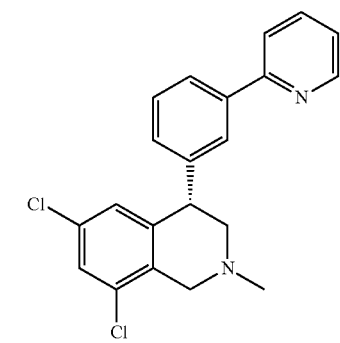 [SMILES: CN1Cc2c(Cl)cc(Cl)cc2[C@H](c2cccc(-c3ccccn3)c2)C1] | Example 1-6 |
| 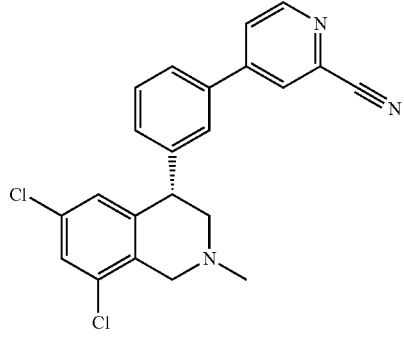 [SMILES: CN1Cc2c(Cl)cc(Cl)cc2[C@H](c2cccc(-c3ccnc(C#N)c3)c2)C1] | Example 1-7 |
| 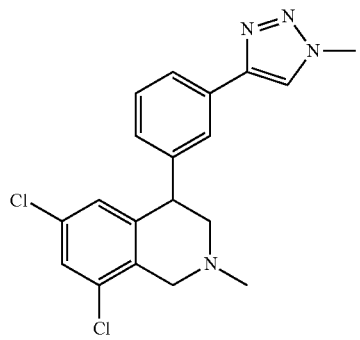 [SMILES: CN1Cc2c(Cl)cc(Cl)cc2C(c2cccc(-c3cn(C)nn3)c2)C1] | Example 1-8 |

TABLE 2-1-continued
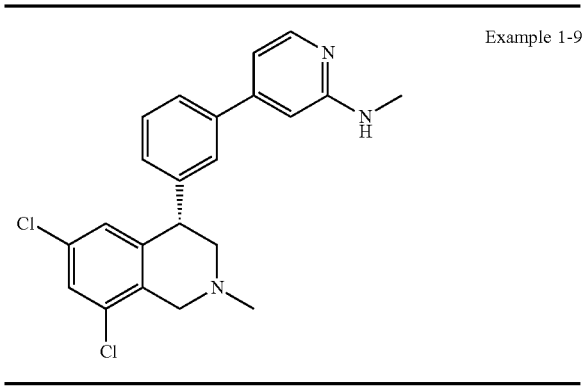
Example 1-9
TABLE 2-2
TABLE 2-2-continued
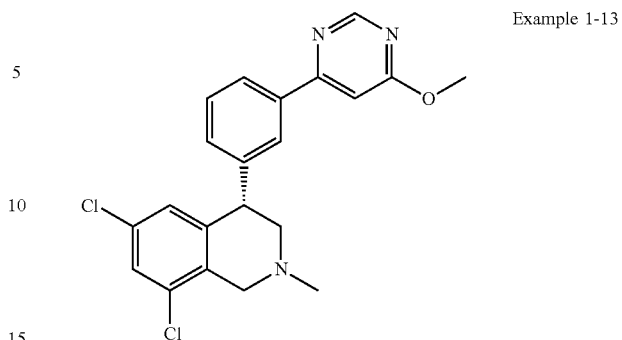
Example 1-13
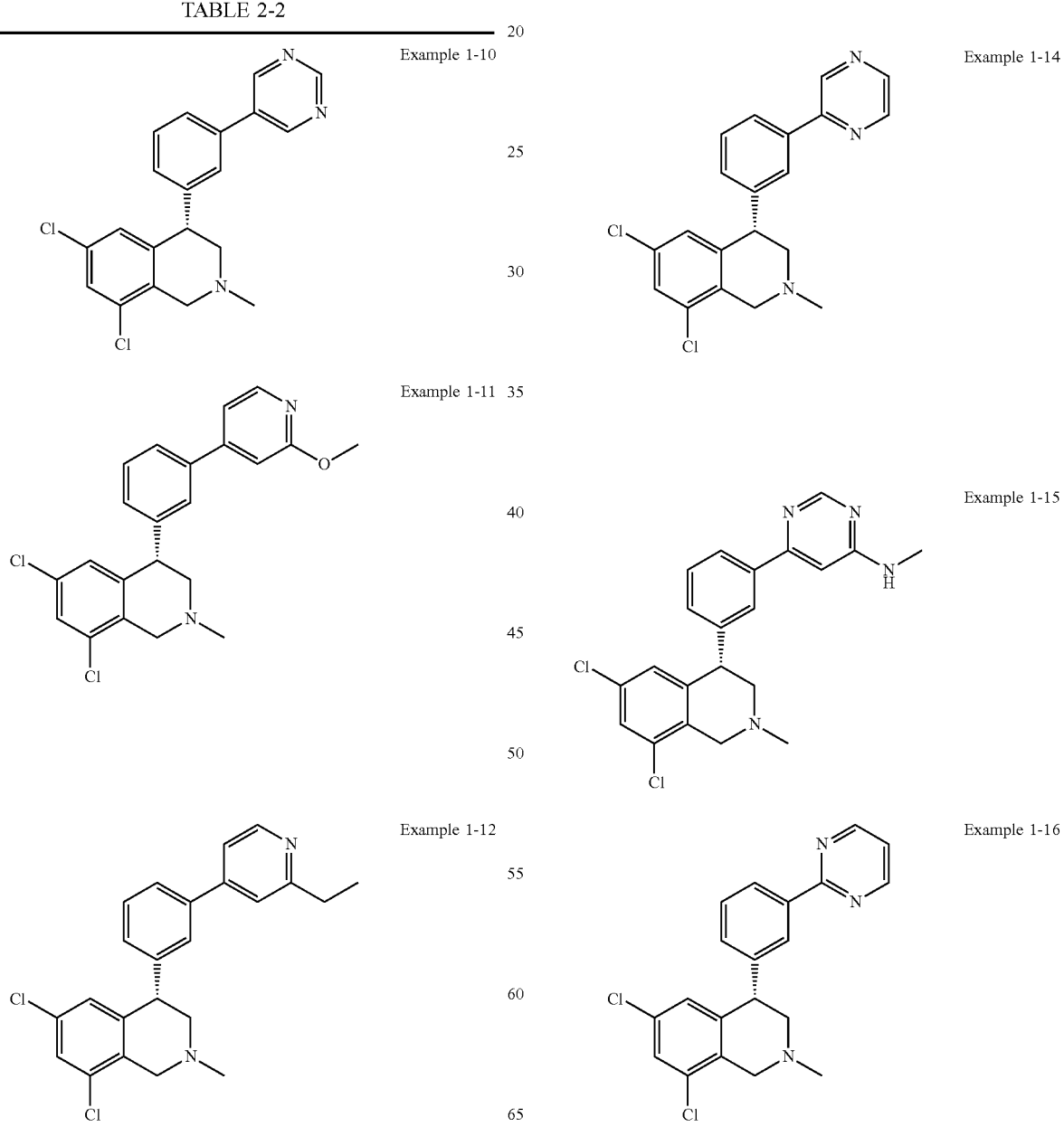
Example 1-10
Example 1-14
Example 1-11
Example 1-15
Example 1-12
Example 1-16

TABLE 2-2-continued
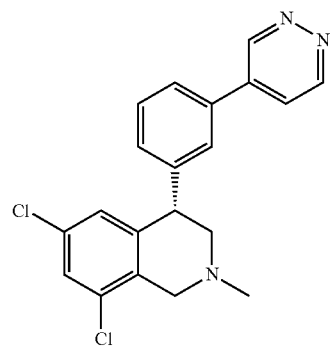 [SMILES: CN1Cc2c(Cl)cc(Cl)cc2[C@H](c2cccc(-c3ccnnc3)c2)C1]
Example 1-17
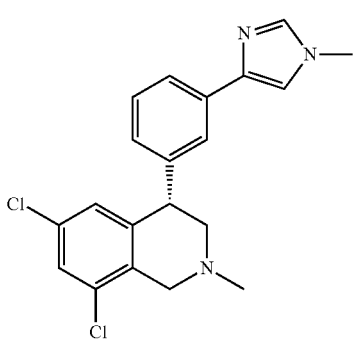 [SMILES: CN1Cc2c(Cl)cc(Cl)cc2[C@H](c2cccc(-c3cn(C)cn3)c2)C1]
Example 1-18
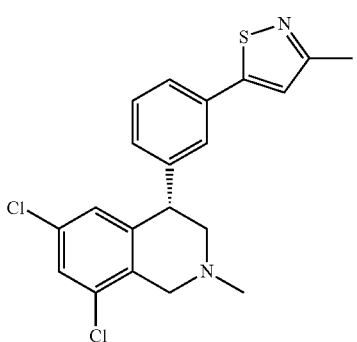 [SMILES: Cc1cc(-c2cccc([C@@H]3CN(C)Cc4c(Cl)cc(Cl)cc43)c2)sn1]
Example 1-19
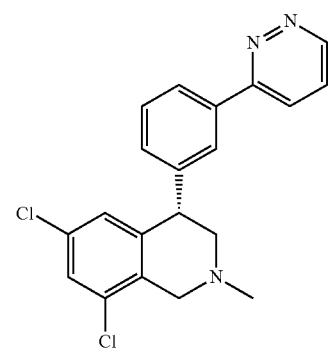 [SMILES: CN1Cc2c(Cl)cc(Cl)cc2[C@H](c2cccc(-c3cccnn3)c2)C1]
Example 1-20
TABLE 2-2-continued
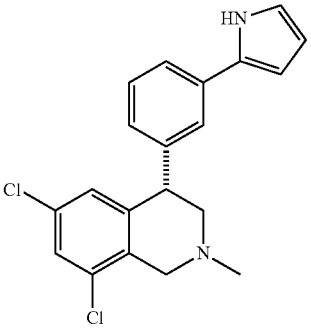 [SMILES: CN1Cc2c(Cl)cc(Cl)cc2[C@H](c2cccc(-c3ccc[nH]3)c2)C1]
Example 1-21
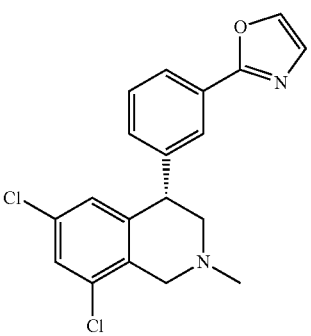 [SMILES: CN1Cc2c(Cl)cc(Cl)cc2[C@H](c2cccc(-c3ncco3)c2)C1]
Example 1-22
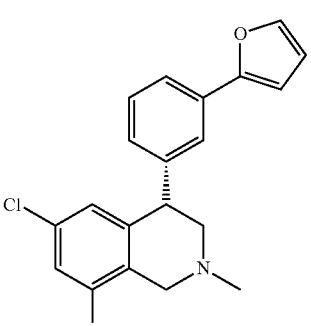
Example 1-23
EXAMPLE 2-1
(4S)-6,8-Dichloro-2-methyl-4-[3-(2H-tetrazol-5-yl)phenyl]-1,2,3,4-tetrahydroisoquinoline
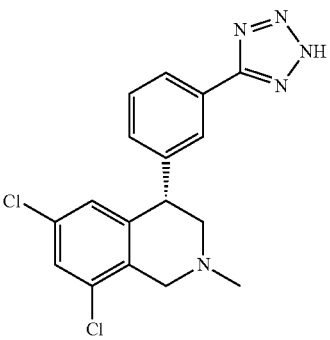
[Formula 119]
To a solution of 3-[(4S)-6,8-dichloro-2-methyl-1,2,3,4-tetrahydroisoquinolin-4-yl]benzonitrile (1.3 g) obtained in Reference Example 4-1 in N,N-dimethylformamide (20 mL), ammonium chloride (0.77 g) and sodium azide (0.93 g) were added, and the mixture was stirred at 100° C. for 17 hours. Water was added to the reaction solution, followed by extraction with chloroform. The organic layer was dried over anhydrous magnesium sulfate and filtered, and then, the filtrate was concentrated under reduced pressure. The obtained residue was purified by silica gel column chromatography (SNAP Cartridge HP-Sphere, Biotage (registered trademark), chloroform:methanol=95:5→40:60) to obtain the title compound (1.1 g, 73%) as a light brown amorphous substance.

$^1$H NMR (300 MHz, CD$_3$OD) δ ppm 2.75 (s, 3H), 2.92-3.05 (m, 1H), 3.38 (dd, J=11.2, 5.1 Hz, 1H), 3.88 (d, J=16.2 Hz, 1H), 4.25 (d, J=16.5 Hz, 1H), 4.83-4.97 (m, 1H), 6.82 (d, J=1.2 Hz, 1H), 7.13-7.30 (m, 2H), 7.44 (t, J=7.8 Hz, 1H), 8.10 (d, J=7.8 Hz, 1H), 8.23 (s, 1H).

MS (+): 360 [M+H]$^+$.

EXAMPLE 3-1

(4S)-6,8-Dichloro-2-methyl-4-[3-(3-methyl-1H-1,2,4-triazol-5-yl)phenyl]-1,2,3,4-tetrahydroisoquinoline hydrochloride

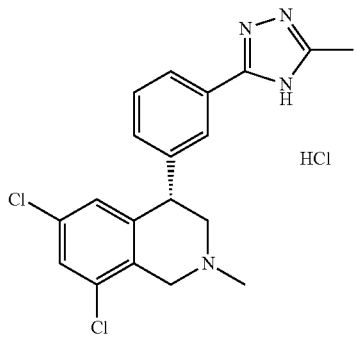

[Formula 120]

To a suspension of 3-[(4S)-6,8-dichloro-2-methyl-1,2,3,4-tetrahydroisoquinolin-4-yl]benzonitrile (50 mg) obtained in Reference Example 4-1 in methanol (0.50 mL), sodium methoxide (28% solution in methanol, 17 mg) was added under ice cooling, and the mixture was stirred at room temperature for 3 days. The reaction solution was concentrated. Acetic acid (0.50 mL) and acetohydrazide (14 mg) were added to the obtained residue, and the mixture was stirred for 2 hours under heating to reflux. The reaction solution was allowed to cool and then concentrated under reduced pressure. A saturated aqueous solution of sodium bicarbonate was added to the obtained residue, followed by extraction with ethyl acetate. The organic layer was dried over anhydrous magnesium sulfate and filtered, and then, the filtrate was concentrated under reduced pressure. The obtained residue was purified by silica gel column chromatography (Biotage (registered trademark) SNAP Cartridge HP-Sphere, chloroform:methanol=100:0→90:10). To the obtained colorless oil substance (4.0 mg), ethyl acetate (1.5 mL) and 4 mol/L hydrogen chloride in ethyl acetate (0.5 mL) were added, and the solvent was distilled off under reduced pressure to obtain the title compound (4.1 mg) as a colorless solid.

$^1$H NMR (300 MHz, CD$_3$OD) δ ppm 2.72 (s, 3H), 3.18 (s, 3H), 3.59-3.79 (m, 1H), 3.93 (dd, J=11.8, 6.1 Hz, 1H), 4.47-4.65 (m, 1H), 4.76-4.86 (m, 2H), 6.88 (br. s., 1H), 7.52-7.60 (m, 2H), 7.68 (t, J=7.8 Hz, 1H), 7.94-8.05 (m, 2H).

MS (+): 373 [M+H]$^+$.
MS (−): 371 [M−H]$^+$.

EXAMPLE 4-1

(4S)-6,8-Dichloro-2-methyl-4-[3-(5-methyl-1,2,4-oxadiazol-3-yl)phenyl]-1,2,3,4-tetrahydroisoquinoline hydrochloride

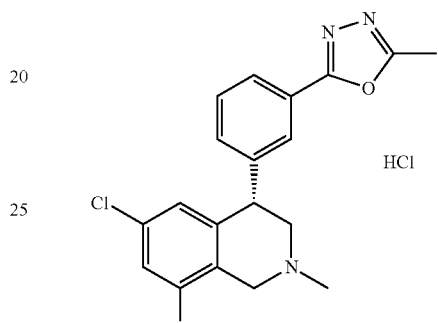

[Formula 121]

To a suspension of 3-[(4S)-6,8-dichloro-2-methyl-1,2,3,4-tetrahydroisoquinolin-4-yl]benzonitrile (50 mg) obtained in Reference Example 4-1 in methanol (0.50 mL), hydroxylamine (50% aqueous solution, 34 mg) was added under ice cooling, and the mixture was stirred at room temperature for 3 days. The reaction solution was concentrated. Chloroform (0.50 mL) was added to the obtained residue, then triethylamine (33 μL) and acetyl chloride (13 μL) were added under ice cooling, and the mixture was stirred at room temperature for 2 hours and at 60° C. for 4 hours. The solvent was distilled off under reduced pressure. N,N-Dimethylformamide (0.50 mL) was added to the residue, and the mixture was stirred at 100° C. for 5 hours. The reaction solution was allowed to cool, and then, water was added thereto, followed by extraction with ethyl acetate. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=100:0→30:70). To the obtained yellow oil substance (9.1 mg), ethyl acetate (1.5 mL) and 4 mol/L hydrogen chloride in ethyl acetate (0.5 mL) were added, and the solvent was distilled off under reduced pressure to obtain the title compound (9.3 mg) as a yellow solid.

$^1$H NMR (300 MHz, CD$_3$OD) δ ppm 2.65 (s, 3H), 3.16 (s, 3H), 3.55-3.72 (m, 1H), 3.86-3.96 (m, 1H), 4.43-4.55 (m, 1H), 4.68-4.85 (m, 2H), 6.84-6.92 (m, 1H), 7.44-7.64 (m, 3H), 7.96 (s, 1H), 8.04-8.12 (m, 1H).

MS (+): 374 [M+H]$^+$.

EXAMPLE 5-1

(4S)-6,8-Dichloro-2-methyl-4-[3-(3-methyl-1,2-oxazol-5-yl)phenyl]-1,2,3,4-tetrahydroisoquinoline hydrochloride

[Formula 122]

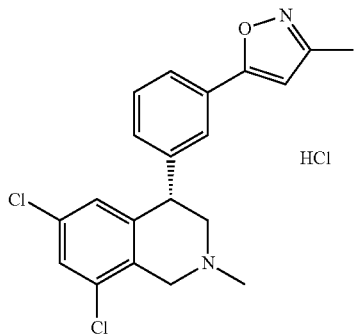

To a solution of (4S)-6,8-dichloro-4-(3-ethynylphenyl)-2-methyl-1,2,3,4-tetrahydroisoquinoline (90 mg) obtained in Reference Example 2-1, isocyanatobenzene (0.19 mL), and nitroethane (20 µL) in toluene (2.0 mL), triethylamine (2.6 µL) was added, and the mixture was stirred at 80° C. for 12 hours. The reaction solution was allowed to cool. Then, water was added thereto, and the mixture was stirred for 50 minutes. The insoluble matter was filtered off, and the filtrate was concentrated under reduced pressure. The obtained residue was purified by silica gel column chromatography (Biotage(registered trademark) SNAP Cartridge HP-Sphere, hexane:ethyl acetate=100:0→50:50). The solvent was distilled off under reduced pressure, and the obtained residue was dissolved in ethyl acetate (0.5 mL). To the solution, 4 mol/L hydrogen chloride in ethyl acetate (0.5 mL) was added dropwise under ice cooling, and the mixture was stirred for 15 minutes. Then, the solvent was distilled off under reduced pressure to obtain the title compound (49 mg, 42%) as a light brown amorphous substance.

$^1$H NMR (600 MHz, DMSO-$d_6$) δ ppm 2.28 (s, 3H), 2.98 (br. s., 3H), 3.51-3.69 (m, 1H), 3.69-3.88 (m, 1H), 4.31-4.48 (m, 1H), 4.53-4.70 (m, 1H), 4.70-4.80 (m, 1H), 6.78 (br. s., 1H), 6.91 (s, 1H), 7.39 (d, J=8.0 Hz, 1H), 7.57 (t, J=8.0 Hz, 1H), 7.68 (br. s., 1H), 7.76 (s, 1H), 7.83 (d, J=8.0 Hz, 1H), 11.22 (br. s., 1H).

MS (+): 373 [M+H]+

EXAMPLE 6-1

1,1'-Butane-1,4-diylbis[3-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethyl)urea]

[Formula 123]

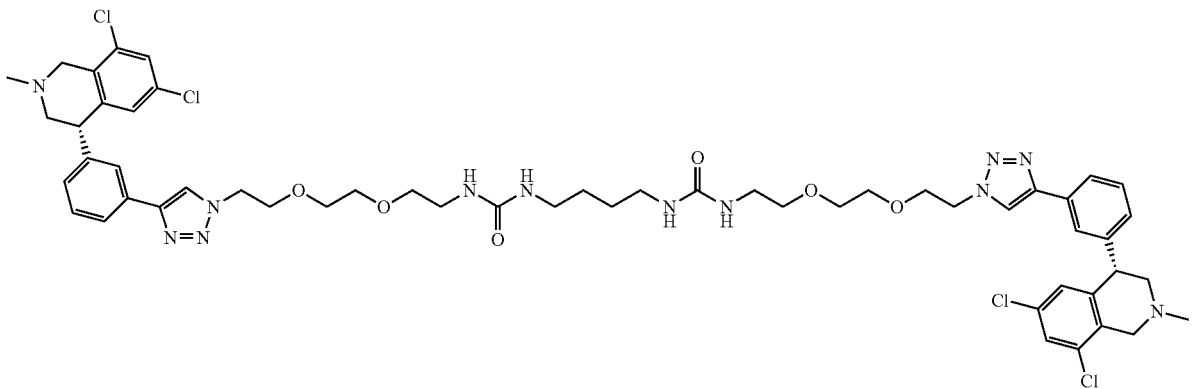

To a solution of (4S)-6,8-dichloro-4-(3-ethynylphenyl)-2-methyl-1,2,3,4-tetrahydroisoquinoline (70 mg) obtained in Reference Example 2-1 in a tert-butanol (3.3 mL)-water (1.7 mL) mixed solvent, 1,1'-butane-1,4-diylbis(3-{2-[2-(2-azidoethoxy)ethoxy]ethyl}urea) (43 mg) obtained in Reference Example 5-1, copper sulfate (1.1 mg), and sodium ascorbate (8.8 mg) were added, and the mixture was stirred at room temperature for 3 hours. The reaction solution was concentrated under reduced pressure, and the obtained residue was purified by silica gel column chromatography (Biotage (registered trademark) SNAP Cartridge KP-NH, chloroform:methanol=100:0→80:20) to obtain the title compound (65 mg, 52%) as a colorless amorphous substance.
LC-MS Retention Time 0.548 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1121 $[M+H]^+$.

EXAMPLE 6-2

1,1'-Butane-1,4-diylbis {3-[2-(2-{2-[2-(4-{3-[(4S)-6, 8-dichloro-2-methyl-1,2,3,4-tetrahydroisoquinolin-4-yl]phenyl}-1H-1,2,3-triazol-1-yl)ethoxy] ethoxy}ethoxy)ethyl]urea}hydrochloride To a solution of (4S)-6,8-dichloro-4-(3-ethynylphenyl)-2-methyl-1,2,3,4-tetrahydroisoquinoline hydrochloride (0.30 g) obtained in Reference Example 2-2 in a tert-butanol (4.0 mL)-water (1.0 mL) mixed solvent, 1,1'-butane-1,4-diylbis [3-(2-{2-[2-(2-azidoethoxy)ethoxy]ethoxy}ethyl)urea] (0.25 g) obtained in Reference Example 5-2, copper sulfate (21 mg), and sodium ascorbate (33 mg) were added, and the mixture was stirred at room temperature for 3 hours. Then, the reaction mixture was stirred for 2 days under heating to reflux. The reaction solution was concentrated under reduced pressure, and the obtained residue was purified by silica gel column chromatography (Biotage(registered trademark) SNAP Cartridge KP-NH, chloroform:methanol=100: 0→70:30). The solvent was distilled off under reduced pressure. The obtained residue was purified by preparative LC-MS (LC (Agilent 1260), ESIMS (6130 Quadrupole, ESI), colunm (YMC-Actus Triart 5 m C18 50×30 mm), mobile phase (0.1% formic acid in $H_2O$:0.1% formic acid in $CH_3CN$=90:10→80:20→5:95), 50 mL/min.). The solvent was distilled off under reduced pressure, and the obtained residue was purified by silica gel column chromatography (Biotage(registered trademark) SNAP Cartridge KP-NH, chloroform:methanol=100:0→70:30). The solvent was distilled off under reduced pressure, and the obtained residue was dissolved in ethanol. To the solution, 4 mol/L hydrogen chloride in 1,4-dioxane (0.20 mL) was added, and the solvent was distilled off under reduced pressure to obtain the title compound (78 mg) as a colorless amorphous substance.
LC-MS Retention Time 0.555 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1209 $[M+H]f$, 1231 $[M+Na]^+$.

EXAMPLE 6-3

N,N'-Bis(2-{2-[2-(4-{3-[(4S)-6,8-dichloro-2-methyl-1,2,3,4-tetrahydroisoquinolin-4-yl]phenyl}-1H-1,2, 3-triazol-1-yl)ethoxy]ethoxy}ethyl)butanediamide hydrochloride The title compound (7.0 mg) was obtained as a colorless amorphous substance through substantially the same reaction as in Example 6-2 except that N,N'-bis {2-[2-(2-azidoethoxy)ethoxy]ethyl}butanediamide obtained in Reference Example 6-1 was used instead of 1,1'-butane-1,4-diylbis[3-(2-{2-[2-(2-azidoethoxy)ethoxy]ethoxy}ethyl) urea] obtained in Reference Example 5-2.
LC-MS Retention Time 0.542 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1063 $[M+H]^+$.

EXAMPLE 6-4

1-(4-{3-[(4S)-6,8-Dichloro-2-methyl-1,2,3,4-tetrahydroisoquinolin-4-yl]phenyl}-1H-1,2,3-triazol-1-yl)-N-(2-{2-[2-(4-{3-[(4S)-6,8-dichloro-2-methyl-1,2,3, 4-tetrahydroisoquinolin-4-yl]phenyl}-1H-1,2,3-triazol-1-yl)ethoxy]ethoxy}ethyl)-10-oxo-3,6,12-trioxa-9-azatetradecan-14-amide hydrochloride The title compound (33 mg) was obtained as a colorless amorphous substance through substantially the same reaction as in Example 6-2 except that 1-azido-N-{2-[2-(2-azidoethoxy)ethoxy]ethyl)-10-oxo-3,6,12-trioxa-9-azatetradecan-14-amide obtained in Reference Example 6-2 was used instead of 1,1'-butane-1,4-diylbis[3-(2-{2-[2-(2-azidoethoxy)ethoxy]ethoxy}ethyl)urea] obtained in Reference Example 5-2.
LC-MS Retention Time 1.027 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1079 $[M+H]^+$.

EXAMPLE 6-5

1,1'-Benzene-1,4-diylbis[3-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy] ethoxy}ethyl)urea]hydrochloride The title compound (41 mg) was obtained as a colorless amorphous substance through substantially the same reaction as in Example 6-2 except that 1,1'-benzene-1,4-diylbis (3-{2-[2-(2-azidoethoxy)ethoxy]ethyl}urea) obtained in Reference Example 5-3 was used instead of 1,1'-butane-1, 4-diylbis[3-(2-{2-[2-(2-azidoethoxy)ethoxy}ethyl) urea] obtained in Reference Example 5-2.
LC-MS Retention Time 1.069 min
LC:Agilent 1290
ESI/APCI MS:Agilent 6130
Column: Waters Acquity CSH C18 1.7 um, 2.1×50 mm
Solvent: $H_2O:CH3CN$(0.1% Formic acid)
Gradient: 0.8 mL/min, 0 min(95:5)→1.2 min(50:50)
1.0 mL/min, →1.38 min(3:97)
MS (+): 1141 $[M+H]^+$.

EXAMPLE 6-6

(2R,3R)—N,N'-Bis(2-{2-[2-(4-{3-[(4S)-6,8-dichloro-2-methyl-1,2,3,4-tetrahydroisoquinolin-4-yl] phenyl}-1H-1,2,3-triazol-1-yl)ethoxy]ethoxy}ethyl)-2, 3-dihydroxybutanediamide hydrochloride The title compound (20 mg) was obtained as a colorless amorphous substance through substantially the same reaction as in Example 6-2 except that (2R,3R)—N,N'-bis {2-

[2-(2-azidoethoxy)ethoxy]ethyl}-2,3-dihydroxybutanediamide obtained in Reference Example 6-3 was used instead of 1,1'-butane-1,4-diylbis[3-(2-{2-[2-(2-azidoethoxy)ethoxy]ethoxy}ethyl)urea] obtained in Reference Example 5-2.

LC-MS Retention Time 1.008 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1095 [M+H]$^+$.

EXAMPLE 6-7

(2R,3S,4R,5S)—N,N'-Bis(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethyl)-2,3,4,5-tetrahydroxyhexanediamide hydrochloride To a solution of (2R,3S,4R,5S)—N,N'-bis {2-[2-(2-azidoethoxy)ethoxy]ethyl}-2,3,4,5-tetrahydroxyhexanediamide (74 mg) obtained in Reference Example 6-4 in a tert-butanol (8.0 mL)-water (2.0 mL) mixed solvent, (4S)-6,8-dichloro-4-(3-ethynylphenyl)-2-methyl-1,2,3,4-tetrahydroisoquinoline hydrochloride (0.10 g) obtained in Reference Example 2-2, copper sulfate (7.1 mg), sodium ascorbate (11 mg), and triethylamine (0.40 mL) were added, and the mixture was stirred at room temperature for 3 hours. The reaction solution was concentrated under reduced pressure, and the obtained residue was purified by silica gel column chromatography (Biotage(registered trademark) SNAP Cartridge KP-NH, chloroform:methanol=100:0→70:30). The solvent was distilled off under reduced pressure. The obtained residue was dissolved in ethanol. To the solution, 4 mol/L hydrogen chloride in 1,4-dioxane (0.20 mL) was added, and the solvent was distilled off under reduced pressure to obtain the title compound (0.15 g) as a pale green amorphous substance.

LC-MS Retention Time 0.976 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1155 [M+H]$^+$.

EXAMPLE 6-8

(2R,3S,4R,5S)—N,N'-Bis[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]-2,3,4,5-tetrahydroxyhexanediamide hydrochloride To a solution of (2R,3S,4R,5S)—N,N'-bis(2-{2-[2-(2-azidoethoxy)ethoxy]ethoxy}ethyl)-2,3,4,5-tetrahydroxyhexanediamide (87 mg) obtained in Reference Example 6-5 in a tert-butanol (8.0 mL)-water (2.0 mL) mixed solvent, (4S)-6, 8-dichloro-4-(3-ethynylphenyl)-2-methyl-1,2,3,4-tetrahydroisoquinoline hydrochloride (0.10 g) obtained in Reference Example 2-2, copper sulfate (7.1 mg), sodium ascorbate (11 mg), and triethylamine (0.40 mL) were added, and the mixture was stirred at room temperature for 3 hours. The reaction solution was concentrated under reduced pressure, and the obtained residue was purified by silica gel column chromatography (Biotage (registered trademark) SNAP Cartridge KP-NH, chloroform:methanol=100:0→70:30). The solvent was distilled off under reduced pressure. The obtained residue was dissolved in ethanol. To the solution, 4 mol/L hydrogen chloride in 1,4-dioxane (0.20 mL) was added, and the solvent was distilled off under reduced pressure to obtain the title compound (0.14 g) as a pale green amorphous substance.

LC-MS Retention Time 1.016 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1243 [M+H]$^+$.

EXAMPLE 6-9

(2R,3R)—N,N'-Bis[14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradec-1-yl]-2,3-dihydroxybutanediamide hydrochloride To a solution of (4S)-6,8-dichloro-4-(3-ethynylphenyl)-2-methyl-1,2,3,4-tetrahydroisoquinoline hydrochloride (0.13 g) obtained in Reference Example 2-2, copper sulfate (2.8 mg), sodium ascorbate (7.1 mg), and N,N-diisopropylethylamine (0.18 mL) in an ethanol (6.4 mL)-water (1.6 mL) mixed solvent, a solution of (2R,3R)—N,N'-bis(14-azido-3,6,9,12-tetraoxatetradec-1-yl)-2,3-dihydroxybutanediamide (0.11 g) obtained in Reference Example 7-4 in an ethanol (1.6 mL)-water (0.4 mL) mixed solvent was added, and the mixture was stirred at room temperature for 22 hours. Then, copper sulfate (2.8 mg) and sodium ascorbate (7.1 mg) were added thereto, and the mixture was stirred at room temperature for 24 hours. The reaction solution was concentrated under reduced pressure, and the obtained residue was purified by reverse-phase preparative HPLC (column (YMC-Actus Triart 5 μm C18 50×30 mm), mobile phase (0.1% formic acid in $H_2O$:0.1% formic acid in MeCN=95:5→80:20→50:50→5:95, 40 mL/min.). The solvent was distilled off under reduced pressure, and the obtained residue was purified by silica gel column chromatography (Biotage (registered trademark) SNAP Cartridge KP-NH, chloroform:methanol=98:2→85:15). The solvent was distilled off under reduced pressure. Ethanol (3.0 mL) and 4 mol/L hydrogen chloride in ethyl acetate (24 μL) were added to the obtained residue (30 mg), and the mixture was stirred at room temperature for 15 minutes. The solvent was distilled off under reduced pressure. Diethyl ether was added to the obtained residue. After pulverization, the supernatant was removed. The obtained residue was concentrated under reduced pressure to obtain the title compound (33 mg, 14%) as a colorless amorphous substance.

LC-MS Retention Time 1.041 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)

1.0 mL/min, →1.38 min(3:97)
MS (+): 1271 [M+H]+.

EXAMPLE 6-10

(2R,3R)—N,N'-Bis[17-(4-{3-[(4S)-6,8-dichloro-2-methyl-1,2,3,4-tetrahydroisoquinolin-4-yl]phenyl}-1H-1,2,3-triazol-1-yl)-3,6,9,12,15-pentaoxaheptadec-1-yl]-2,3-dihydroxybutanediamide hydrochloride The title compound (37 mg, 9.9%) was obtained as a colorless amorphous substance through substantially the same reaction as in Example 6-9 except that (2R,3R)—N,N'-bis(17-azido-3,6,9,12,15-pentaoxaheptadec-1-yl)-2,3-dihydroxybutanediamide obtained in Reference Example 7-5 was used instead of (2R,3R)—N,N'-bis(14-azido-3,6,9,12-tetraoxatetradec-1-yl)-2,3-dihydroxybutanediamide obtained in Reference Example 7-4.

LC-MS Retention Time 1.059 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1360 [M+H]+.

EXAMPLE 6-11

(2R,3S,4R,5S)—N,N'-Bis[14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradec-1-yl]-2,3,4,5-tetrahydroxyhexanediamide hydrochloride The title compound (72 mg, 19%) was obtained as a colorless amorphous substance through substantially the same reaction as in Example 6-9 except that (2R,3S,4R,5S)—N,N'-bis(1,4-azido-3,6,9,12-tetraoxatetradec-1-yl)-2,3,4,5-tetrahydroxyhexanediamide obtained in Reference Example 7-6 was used instead of (2R,3R)—N,N'-bis(14-azido-3,6,9,12-tetraoxatetradec-1-yl)-2,3-dihydroxybutanediamide obtained in Reference Example 7-4.

LC-MS Retention Time 1.022 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (−): 1329 [M−H]+.

EXAMPLE 6-12

(2R,3S,4R,5S)—N-[17-(4-{3-[(4R)-6,8-Dichloro-2-methyl-1,2,3,4-tetrahydroisoquinolin-4-yl]phenyl}-1H-1,2,3-triazol-1-yl)-3,6,9,12,15-pentaoxaheptadec-1-yl]-N'-[17-(4-{3-[(4S)-6,8-dichloro-2-methyl-1,2,3,4-tetrahydroisoquinolin-4-yl]phenyl}-1H-1,2,3-triazol-1-yl)-3,6,9,12,15-pentaoxaheptadec-1-yl]2,3,4,5-tetrahydroxyhexanediamide hydrochloride The title compound (85 mg, 19%) was obtained as a colorless amorphous substance through substantially the same reaction as in Example 6-9 except that (2R,3 S,4R,5 S)—N,N'-bis(17-azido-3,6,9,12,15-pentaoxaheptadec-1-yl)-2,3,4,5-tetrahydroxyhexanediamide obtained in Reference Example 7-7 was used instead of (2R,3R)—N,N'-bis(14-azido-3,6,9,12-tetraoxatetradec-1-yl)-2,3-dihydroxybutanediamide obtained in Reference Example 7-4.

LC-MS Retention Time 1.037 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1420 [M+H]+.

EXAMPLE 6-13

1,1'-[Carbonylbis(iminoethane-2,1-diyl)]bis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl] urea}hydrochloride To a solution of (4S)-6,8-dichloro-4-(3-ethynylphenyl)-2-methyl-1,2,3,4-tetrahydroisoquinoline hydrochloride (0.12 g) obtained in Reference Example 2-2 in an ethanol (6.0 mL)-water (1.5 mL) mixed solvent, sodium bicarbonate (30 mg) was added, and the mixture was stirred for 10 minutes in a nitrogen gas atmosphere. Then, 1,1'-[carbonylbis(iminoethane-2,1-diyl)]bis[3-(2-{2-[2-(2-azidoethoxy)ethoxy]ethoxy}ethyl)urea] (0.10 g) obtained in Reference Example 5-4, copper sulfate (2.6 mg), and sodium ascorbate (7.0 mg) were added, and the mixture was stirred at 50° C. for 3 hours. The reaction solution was concentrated under reduced pressure, and the obtained residue was purified by silica gel column chromatography (Biotage(registered trademark) SNAP Cartridge KP-NH, chloroform:methanol=100:0→60:40). The solvent was distilled off under reduced pressure. To the obtained residue, 1,4-dioxane (2.0 mL) was added, then 4 mol/L hydrogen chloride in 1,4-dioxane (0.88 mL) was added, and the mixture was stirred. The solvent was distilled off under reduced pressure, and the obtained residue was dissolved in a small amount of methanol. To the solution, ethyl acetate was then added. The obtained suspension was concentrated under reduced pressure to obtain the title compound (0.10 g, 49%) as a colorless amorphous substance.

LC-MS Retention Time 0.561 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1267 [M+H]+.

The structures of Examples 6-2 to 6-13 are shown in Tables 3-1 and 3-2 below.
EXAMPLES 6-2 to 6-13
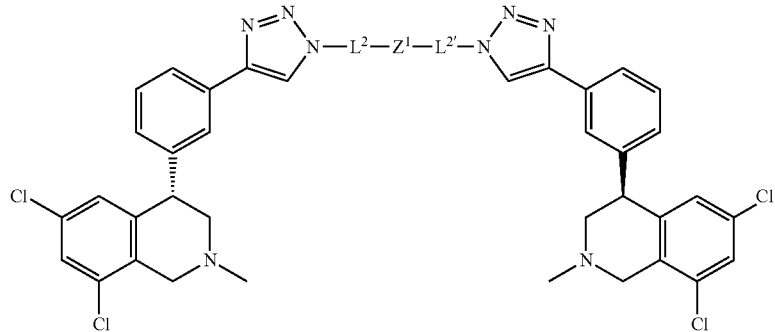
[Formula 124]
TABLE 3-1
| Example | $L^2, L^{2'}$ | $Z^1$ |
|---|---|---|
| 6-2 | ~~~O~~O~~O~~~ | ~~NH-C(O)-NH-(CH2)4-NH-C(O)-NH~~ |
| 6-3 | ~~~O~~O~~~ | ~~NH-C(O)-CH2-CH2-C(O)-NH~~ |
| 6-4 | ~~~O~~O~~~ | ~~NH-C(O)-CH2-O-CH2-C(O)-NH~~ |
| 6-5 | ~~~O~~O~~~ | ~~NH-C(O)-NH-C6H4-NH-C(O)-NH~~ |
| 6-6 | ~~~O~~O~~~ | ~~NH-C(O)-CH(OH)-CH(OH)-C(O)-NH~~ |
| 6-7 | ~~~O~~O~~~ | ~~NH-C(O)-CH(OH)-CH(OH)-CH(OH)-CH(OH)-C(O)-NH~~ |

TABLE 3-1-continued

| Example | L², L²' | Z¹ |
|---|---|---|
| 6-8 | (PEG-type linker with three ether oxygens) | (diamide with OH, OH, OH, OH substituents) |

TABLE 3-2

| Example | L², L²' | Z¹ |
|---|---|---|
| 6-9 | (PEG-type linker with four ether oxygens) | (diamide with OH, OH substituents) |
| 6-10 | (PEG-type linker with five ether oxygens) | (diamide with OH, OH substituents) |
| 6-11 | (PEG-type linker with four ether oxygens) | (diamide with OH, OH, OH, OH substituents) |
| 6-12 | (PEG-type linker with five ether oxygens) | (diamide with OH, OH, OH, OH substituents) |
| 6-13 | (PEG-type linker with three ether oxygens) | (bis-urea linker with ethylene bridge and ketone) |

EXAMPLE 7-1

1,1'-Butane-1,4-diylbis {3-[14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradec-1-yl]urea}hydrochloride nolin-4-yl]phenyl}pyrimidin-4-amine trifluoroacetate (0.12 g) obtained in Reference Example 8-3 in 1,2-dichloroethane (10 mL), triethylamine (0.17 mL) was added, then a solution of 1,4-diisocyanatobutane (8.0 mg) in 1,2-dichloroethane (4.0 mL) was added dropwise, and the mixture was stirred at room temperature for 15 minutes. The reaction solution was concentrated under reduced pressure, and then, the

[Formula 125]

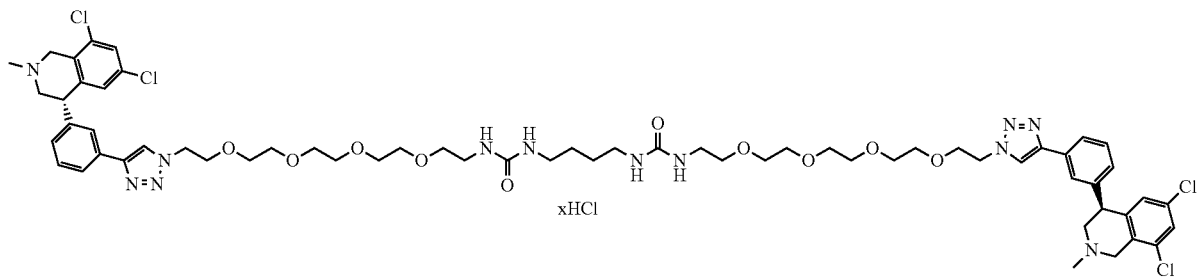
xHCl

To a solution of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine (98 mg) obtained in Reference Example 7-2 in 1,2-dichloroethane (8.0 mL), a solution of 1,4-diisocyanatobutane in 1,2-dichloroethane (0.05 mol/L, 1.5 mL) was added, and the mixture was stirred at room temperature for 10 minutes. Then, a solution of 1,4-diisocyanatobutane in 1,2-dichloroethane (0.05 mol/L, 0.20 mL) was further added thereto, and the mixture was stirred at room temperature for 10 minutes. The reaction solution was concentrated, and then, the obtained residue was purified by reverse-phase preparative HPLC (column (YMC-Actus Triart 5 μm C18 50×30 mm), mobile phase (0.1% formic acid in $H_2O$:0.1% formic acid in MeCN=95:5→80:20→50:50→5:95, 40 mL/min.). The solvent was distilled off under reduced pressure, and the obtained residue was purified by silica gel column chromatography (Biotage (registered trademark) SNAP Cartridge KP-NH, chloroform:methanol=99:1→85:15). The solvent was distilled off under reduced pressure. Ethanol (3.0 mL) and 4 mol/L hydrogen chloride in ethyl acetate (62 μL) were added to the obtained residue (80 mg), and the mixture was stirred at room temperature for 15 minutes. The solvent was distilled off under reduced pressure, and diethyl ether was added to the obtained residue. After pulverization, the supernatant was removed. The obtained residue was concentrated under reduced pressure to obtain the title compound (80 mg) as a colorless amorphous substance.
LC-MS Retention Time 1.078 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1297 [M+H]$^+$.

EXAMPLE 7-2

1,1'-Butane-1,4-diylbis {3-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]urea} tetrahydrochloride To a solution of N-{2-[2-(2-aminoethoxy)ethoxy]ethyl}-6-{3-[(4S)-6,8-dichloro-2-methyl-1,2,3,4-tetrahydroisoquiresidue was purified by reverse-phase preparative HPLC (column (YMC-Actus Triart 5 m C18 50×30 mm), mobile phase (0.1% trifluoroacetic acid in $H_2O$:0.1% trifluoroacetic acid in MeCN=97:3→30:70→5:95, 40 mL/min.) and further purified by silica gel column chromatography (MORITEX Purif Pack-NH). The solvent was distilled off under reduced pressure. Ethanol (1.5 mL) and 2 mol/L hydrochloric acid (0.13 mL) were added to the obtained residue (49 mg), and then, the solvent was distilled off under reduced pressure to obtain the title compound (55 mg, 61%) as a pale yellow amorphous substance.
LC-MS Retention Time 0.851 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1173 [M+H]$^+$.

EXAMPLE 7-3

1,1'-Butane-1,4-diylbis {3-[2-(2-{2-[(5-{3-[(4S)-6,8-dichloro-2-methyl-1,2,3,4-tetrahydroisoquinolin-4-yl]phenyl}pyrimidin-2-yl)amino]ethoxy}ethoxy)ethyl]urea}hydrochloride The title compound (32 mg) was obtained as a pale yellow amorphous substance through substantially the same reaction as in Example 7-2 except that N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyrimidin-2-amine trifluoroacetate obtained in Reference Example 8-5 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3.
LC-MS Retention Time 1.103 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1173 [M+H]$^+$.

EXAMPLE 7-4

1,1'-Butane-1,4-diylbis {3-[2-(2-{2-[(4-{3-[(4S)-6,8-dichloro-2-methyl-1,2,3,4-tetrahydroisoquinolin-4-yl]phenyl}pyridin-2-yl)amino]ethoxy}ethoxy)ethyl]urea}pentahydrochloride The title compound (62 mg) was obtained as a colorless amorphous substance through substantially the same reaction as in Example 7-2 except that N-{2-[2-(2-aminoethoxy)ethoxy]ethyl}-4-{3-[(4S)-6,8-dichloro-2-methyl-1,2,3,4-tetrahydroisoquinolin-4-yl]phenyl}pyridin-2-amine trifluoroacetate obtained in Reference Example 8-7 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3.

LC-MS Retention Time 0.806 min
LC:Agilent 1290
ESI/APCI MS:Agilent 6130
Column: Waters Acquity CSH C18 1.7 um, 2.1×50 mm
Solvent: $H_2O$:CH3CN(0.1% Formic acid)
Gradient: 0.8 mL/min, 0 min(95:5)→1.2 min(50:50)
1.0 mL/min, →1.38 min(3:97)
MS (+): 1171 [M+H]$^+$.

EXAMPLE 7-5

1,1'-Butane-1,4-diylbis[3-(2-{2-[2-(4-{3-[(4S)-6,8-dichloro-2-methyl-1,2,3,4-tetrahydroisoquinolin-4-yl]phenyl}-1H-pyrazol-1-yl)ethoxy]ethoxy}ethyl)urea]diformate The title compound (3.1 mg, 5.1%) was obtained as a colorless oil substance through substantially the same reaction as in Example 7-1 (without carrying out the operation of forming hydrochloride) except that 2-{2-[2-(4-{3-[(4S)-6,8-dichloro-2-methyl-1,2,3,4-tetrahydroisoquinolin-4-yl]phenyl}-1H-pyrazol-1-yl)ethoxy]ethoxy}ethanamine obtained in Reference Example 12-1 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.

LC-MS Retention Time 1.083 min
LC:Agilent 1290
ESI/APCI MS:Agilent 6130
Column: Waters Acquity CSH C18 1.7 um, 2.1×50 mm
Solvent: $H_2O$:CH3CN(0.1% Formic acid)
Gradient: 0.8 mL/min, 0 min(95:5)→1.2 min(50:50)
1.0 mL/min, →1.38 min(3:97)
MS (+): 1119 [M+H]$^+$.

EXAMPLE 7-6

1,1'-Butane-1,4-diylbis {3-[2-(2-{2-[(6-{3-[(4S)-6,8-dichloro-2-methyl-1,2,3,4-tetrahydroisoquinolin-4-yl]phenyl}pyridazin-4-yl)amino]ethoxy}ethoxy)ethyl]urea}pentahydrochloride The title compound (34 mg, 22%) was obtained as a pale yellow amorphous substance through substantially the same reaction as in Example 7-2 except that N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyridazin-4-amine trifluoroacetate obtained in Reference Example 8-8 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3.

LC-MS Retention Time 0.748 min
LC:Agilent 1290
ESI/APCI MS:Agilent 6130
Column: Waters Acquity CSH C18 1.7 um, 2.1×5 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1173 [M+H]$^+$.

EXAMPLE 7-7

1,1'-Butane-1,4-diylbis {3-[2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]urea}

The title compound (4.0 mg, 13%) was obtained as a light brown solid through substantially the same reaction as in Example 7-2 (without carrying out the operation of forming hydrochloride) except that N-{2-[2-(2-aminoethoxy)ethoxy]ethyl}-5-{3-[(4S)-6, 8-dichloro-2-methyl-1, 2,34-tetrahydroisoquinolin-4-yl]phenyl}pyridin-2-amine trifluoroacetate obtained in Reference Example 10-1 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3.

LC-MS Retention Time 0.829 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1171 [M+H]$^+$.

EXAMPLE 7-8

1,1'-Benzene-1,4-diylbis{3-[2-(2-{2-[(5-{3-[(4S)-6, 8-dichloro-2-methyl-1,2,3,4-tetrahydroisoquinolin-4-yl]phenyl}pyridin-2-yl)amino]ethoxy}ethoxy)ethyl]urea}

The title compound (4.0 mg, 13%) was obtained as a light brown solid through substantially the same reaction as in Example 7-2 (without carrying out the operation of forming hydrochloride) except that N-{2-[2-(2-aminoethoxy)ethoxy)ethoxy]ethyl}-5-{3-[(4S)-6, 8-dichloro-2-methyl-1,2,3,4-tetrahydroisoquinolin-4-yl]phenyl}pyridin-2-amine trifluoroacetate obtained in Reference Example 10-1 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3, and 1,4-diisocyanatobenzene was used instead of 1,4-diisocyanatobutane.

LC-MS Retention Time 0.845 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1191 [M+H]$^+$.

EXAMPLE 7-9

1,1'-Butane-1,4-diylbis[3-(2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethyl)urea]hydrochloride The title compound (62 mg) was obtained as a colorless solid through substantially the same reaction as in Example 7-2 except that 2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethanamine trifluoroacetate obtained in Reference Example 12-2 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3.
LC-MS Retention Time 1.099 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1123 $[M+H]^+$.

EXAMPLE 7-10

1,1'-Benzene-1,4-diylbis[3-(2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethyl)urea]hydrochloride The title compound (17 mg) was obtained as a colorless solid through substantially the same reaction as in Example 7-2 except that 2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethanamine trifluoroacetate obtained in Reference Example 12-2 was used instead of N-{²-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3, and 1,4-diisocyanatobenzene was used instead of 1,4-diisocyanatobutane.
LC-MS Retention Time 1.135 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1143 $[M+H]^+$.

EXAMPLE 7-11

1,1'-Benzene-1,4-diylbis {3-[2-(2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethyl]urea} trifluoroacetate The title compound (2.2 mg) was obtained as a pale yellow amorphous substance through substantially the same reaction as in Example 7-2 (without carrying out the operation of forming hydrochloride) except that trifluoroacetate of 2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethanamine obtained in Reference Example 11-1 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3, and 1,4-diisocyanatobenzene was used instead of 1,4-diisocyanatobutane.
LC-MS Retention Time 0.642 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1195 $[M+H]^+$.

EXAMPLE 7-12

1,1'-Butane-1,4-diylbis {3-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethyl]urea} tetrahydrochloride The title compound (15 mg, 60%) was obtained as a colorless amorphous substance through substantially the same reaction as in Example 7-2 except that trifluoroacetate of 2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethanamine obtained in Reference Example 11-1 was used instead of N-{2-[2-(2-aminoethoxy)ethoxy]ethyl}-6-{3-[(4S)-6, 8-dichloro-2-methyl-1,2,3,4-tetrahydroisoquinolin-4-yl]phenyl}pyrimidin-4-amine trifluoroacetate obtained in Reference Example 8-3.
LC-MS Retention Time 1.143 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1175 $[M+H]^+$.

EXAMPLE 7-13

1,1'-Butane-1,4-diylbis {3-[2-(2-(2-{2-[(5-{3-[(4S)-6,8-dichloro-2-methyl-1,2,3,4-tetrahydroisoquinolin-4-yl]phenyl}pyridazin-3-yl)amino]ethoxy}ethoxy)ethyl]urea} tetrahydrochloride The title compound (25 mg, 46%) was obtained as a colorless amorphous substance through substantially the same reaction as in Example 7-1 except that N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridazin-3-amine obtained in Reference Example 10-3 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
LC-MS Retention Time 0.744 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1173 $[M+H]^+$.

EXAMPLE 7-14

1,1'-Benzene-1,4-diylbis {3-[2-(2-{2-[(6-{3-[(4S)-6, 8-dichloro-2-methyl-1,2,3,4-tetrahydroisoquinolin-4-yl]phenyl}pyrimidin-4-yl)amino]ethoxy}ethoxy) ethyl]urea} trifluoroacetate The title compound (11 mg) was obtained as a pale yellow amorphous substance through substantially the same reaction as in Example 7-2 (without carrying out the operation of forming hydrochloride) except that 1,4-diisocyanatobenzene was used instead of 1,4-diisocyanatobutane.
LC-MS Retention Time 0.870 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1193 [M+H]$^+$.

EXAMPLE 7-15

1,1'-Butane-1,4-diylbis[3-(2-{2-[2-(4-{3-[(4S)-6,8-dichloro-2-methyl-1,2,3,4-tetrahydroisoquinolin-4-yl]phenyl}-1H-imidazol-1-yl)ethoxy]ethoxy}ethyl) urea]hydrochloride The title compound (15 mg) was obtained as a colorless amorphous substance through substantially the same reaction as in Example 7-1 except that 2-{2-[2-(4-{3-[(4S)-6,8-dichloro-2-methyl-1,2,3,4-tetrahydroisoquinolin-4-yl]phenyl}-1H-imidazol-1-yl)ethoxy]ethoxy}ethanamine obtained in Reference Example 13-1 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
LC-MS Retention Time 0.717 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1119 [M+H]$^+$.

EXAMPLE 7-16

1,1'-Benzene-1,4-diylbis(3-{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy) ethoxy]ethyl}urea) hydrochloride The title compound (42 mg) was obtained as a pale yellow amorphous substance through substantially the same reaction as in Example 7-1 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrimidin-4-amine obtained in Reference Example 8-9 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2, and 1,4-diisocyanatobenzene was used instead of 1,4-diisocyanatobutane.
LC-MS Retention Time 0.890 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1281 [M+H]$^+$.

EXAMPLE 7-17

1,1'-Butane-1,4-diylbis(3-{2-[2-(2-{2-[(5-{3-[(4S)-6, 8-dichloro-2-methyl-1,2,3,4-tetrahydroisoquinolin-4-yl]phenyl}pyridin-2-yl)amino]ethoxy}ethoxy) ethoxy]ethyl}urea) hydrochloride The title compound (14 mg) was obtained as a colorless solid through substantially the same reaction as in Example 7-1 except that N-(2-{2-[2-(2-aminoethoxy)ethoxy]ethoxy}ethyl)-5-{3-[(4S)-6,8-dichloro-2-methyl-1,2,3,4-tetrahydroisoquinolin-4-yl]phenyl}pyridin-2-amine obtained in Reference Example 10-2 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
LC-MS Retention Time 0.845 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1260 [M+H]$^+$.

EXAMPLE 7-18

N,N'-(10,17-Dioxo-3,6,21,24-tetraoxa-9,11,16,18-tetraazahexacosane-1,26-diyl)bis(5-{3-[(4S)-6,8-dichloro-2-methyl-1,2,3,4-tetrahydroisoquinolin-4-yl]phenyl}pyridine-2-carboxamide) hydrochloride The title compound (26 mg) was obtained as a colorless solid through substantially the same reaction as in Example 7-1 except that N-{2-[2-(2-aminoethoxy)ethoxy]ethyl}-5-{3-[(4S)-6, 8-dichloro-2-methyl-1,2,3,4-tetrahydroisoquinolin-4-yl]phenyl}pyridine-2-carboxamide obtained in Reference Example 15-1 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
LC-MS Retention Time 1.132 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1227 [M+H]$^+$.

EXAMPLE 7-19

1,1'-Butane-1,4-diylbis(3-{2-[2-(2-{2-[(6-{3-[(4S)-6, 8-dichloro-2-methyl-1,2,3,4-tetrahydroisoquinolin-4-yl]phenyl}pyridazin-4-yl)amino]ethoxy}ethoxy) ethoxy]ethyl}urea) hexahydrochloride The title compound (34 mg, 76%) was obtained as a colorless amorphous substance through substantially the same reaction as in Example 7-1 except that N-(2-{2-[2-(2- aminoethoxy)ethoxy]ethoxy}ethyl)-6-{3-[(4S)-6,8-dichloro-2-methyl-1,2,3,4-tetrahydroisoquinolin-4-yl]phenyl}pyridazin-4-amine obtained in Reference Example 8-10 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
  LC-MS Retention Time 0.771 min
  LC:Agilent 1290
  ESI/APCI MS:Agilent 6130
  Column: Waters Acquity CSH C18 1.7 um, 2.1×50 mm
  Solvent: $H_2O$:CH3CN(0.1% Formic acid)
  Gradient: 0.8 mL/min, 0 min(95:5)→1.2 min(50:50)
  1.0 mL/min, →1.38 min(3:97)
  MS (+): 1262 $[M+H]^+$.

EXAMPLE 7-20

1,1'-Butane-1,4-diylbis{3-[2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]urea}pentahydrochloride The title compound (48 mg, 69%) was obtained as a yellow amorphous substance through substantially the same reaction as in Example 7-1 except that N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrazin-2-amine obtained in Reference Example 8-4 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
  LC-MS Retention Time 1.114 min
  LC:Agilent 1290
  ESI/APCI MS:Agilent 6130
  Column: Waters Acquity CSH C18 1.7 um, 2.1×50 mm
  Solvent: $H_2O$:$CH_3CN$(0.1% Formic acid)
  Gradient: 0.8 mL/min, 0 min(95:5)→1.2 min(50:50)
  1.0 mL/min, →1.38 min(3:97)
  MS (+): 1173 $[M+H]^+$.

EXAMPLE 7-21

1,1'-Butane-1,4-diylbis[3-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethyl)urea]diformate To a solution of 2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethanamine (30 mg) obtained in Reference Example 14-1 in chloroform (0.6 mL), a solution of 1,4-diisocyanatobutane (3.9 μL) in chloroform (0.6 mL) was slowly added dropwise, and the mixture was stirred at room temperature for 2 hours. The reaction solution was concentrated under reduced pressure, and then, the obtained residue was purified by preparative LC-MS (LC (Agilent 1260), ESIMS (6130 Quadrupole, ESI), column (YMC-Actus Triart 5 μm C18 50×30 mm), mobile phase (0.1% formic acid in $H_2O$:0.1% formic acid in $CH_3CN$=95:5→50:50→5:95), 50 mL/min.) to obtain the title compound (4.5 mg, 13%) as a colorless amorphous substance.
  LC-MS Retention Time 0.973 min
  LC:Agilent 1290
  ESI/APCI MS:Agilent 6130
  Column: Waters Acquity CSH C18 1.7 um, 2.1×50 mm
  Solvent: $H_2O$:$CH_3CN$(0.1% Formic acid)
  Gradient: 0.8 mL/min, 0 min(95:5)→1.2 min(50:50)
  1.0 mL/min, →1.38 min(3:97)
  MS (+): 1121 $[M+H]^+$.

EXAMPLE 7-22

1,1'-Butane-1,4-diylbis {3-[2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethyl]urea} diformate The title compound (16 mg, 44%) was obtained as a colorless amorphous substance through substantially the same reaction as in Example 7-21 except that 2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethanamine obtained in Reference Example 14-3 was used instead of 2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethanamine obtained in Reference Example 14-1.
  LC-MS Retention Time 0.989 min
  LC:Agilent 1290
  ESI/APCI MS:Agilent 6130
  Column: Waters Acquity CSH C18 1.7 um, 2.1×50 mm
  Solvent: $H_2O$:$CH_3CN$(0.1% Formic acid)
  Gradient: 0.8 mL/min, 0 min(95:5)→1.2 min(50:50)
  1.0 mL/min, →1.38 min(3:97)
  MS (+): 1209 $[M+H]^+$.
  MS (−): 1207 $[M–H]^+$.

EXAMPLE 7-23

1,1'-Butane-1,4-diylbis[3-(2-{2-[2-(5-{3-[(4S)-6,8-dichloro-2-methyl-1,2,3,4-tetrahydroisoquinolin-4-yl]phenyl}-1,3,4-oxadiazol-2-yl)ethoxy]ethoxy}ethyl)urea]tetraformate The title compound (9.3 mg, 15%) was obtained as a colorless amorphous substance through substantially the same reaction as in Example 7-21 except that 2-{2-[2-(5-{3-[(4S)-6, 8-dichloro-2-methyl-1,2,3,4-tetrahydroisoquinolin-4-yl]phenyl}-1,3,4-oxadiazol-2-yl)ethoxy]ethoxy}ethanamine obtained in Reference Example 14-2 was used instead of 2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethanamine obtained in Reference Example 14-1.
  LC-MS Retention Time 1.030 min
  LC:Agilent 1290
  ESI/APCI MS:Agilent 6130
  Column: Waters Acquity CSH C18 1.7 um, 2.1×50 mm
  Solvent: $H_2O$:$CH_3CN$(0.1% Formic acid)
  Gradient: 0.8 mL/min, 0 min(95:5)→1.2 min(50:50)
  1.0 mL/min, →1.38 min(3:97)
  MS (+): 1123 $[M+H]^+$.

EXAMPLE 7-24

1,1'-Benzene-1,4-diylbis{3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethyl]urea}hydrochloride To a solution of 2-(2-{2-[2-(4-{3-[(4S)-6,8-dichloro-2-methyl-1,2,3,4-tetrahydroisoquinolin-4-yl]phenyl}-1H-1,2, 3-triazol-1-yl)ethoxy]ethoxy}ethoxy)ethanamine (40 mg) obtained in Reference Example 7-1 in chloroform (1.0 mL), 1,4-diisocyanatobenzene (4.8 mg) was added, and the mixture was stirred overnight at room temperature. The reaction solution was concentrated, and then, the obtained residue was purified by preparative TLC (Fuji Silysia Chemical Ltd. "CHROMATOREX TLC Plates NH 0.25 mm", chloroform:methanol=40:1). The solvent was distilled off under reduced pressure, and then, the obtained residue was dissolved in methanol. To the solution, a 4 mol/L solution of hydrogen chloride in 1,4-dioxane was added, and then, the solvent was distilled off under reduced pressure to obtain the title compound (25 mg) as a colorless solid.

LC-MS Retention Time 1.066 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1229 [M+H]$^+$.

EXAMPLE 7-25

1,1'-Benzene-1,4-diylbis(3-{2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}urea) hydrochloride The title compound (32 mg) was obtained as a pale yellow amorphous substance through substantially the same reaction as in Example 7-1 except that 2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethanamine obtained in Reference Example 11-2 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2, and 1,4-diisocyanatobenzene was used instead of 1,4-diisocyanatobutane.

LC-MS Retention Time 0.680 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1283 [M+H]$^+$.

EXAMPLE 7-26

1,1'-[Ethane-1,2-diylbis(oxyethane-2,1-diyl)]bis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl] urea}hydrochloride To a solution of 4-nitrophenyl [2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]carbamate (42 mg) obtained in Reference Example 16-1 in a chloroform (1.2 mL)-triethylamine (7.8 μL) mixed solvent, triethylamine (17 μL) and a solution of 2,2'-[ethane-1,2-diylbis(oxy)]diethanamine in chloroform (0.5 mol/L, 48 μL) were added, and the mixture was stirred at 80° C. for 3 hours. The reaction solution was concentrated under reduced pressure, and the obtained residue was purified by preparative TLC (Fuji Silysia Chemical Ltd. "CHROMATOREX TLC Plates NH 0.25 mm", chloroform:methanol=40:1). The solvent was distilled off under reduced pressure, and then, the obtained residue was dissolved in methanol. To the solution, a 4 mol/L solution of hydrogen chloride in 1,4-dioxane was added, and then, the solvent was distilled off under reduced pressure to obtain the title compound (15 mg) as a colorless amorphous substance.

LC-MS Retention Time 1.036 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1291 [M+Na]$^+$.

EXAMPLE 7-27

1,1'-Hexane-1,6-diylbis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea}hydrochloride The title compound (11 mg) was obtained as a colorless amorphous substance through substantially the same reaction as in Example 7-1 except that 1,6-diisocyanatohexane was used instead of 1,4-diisocyanatobutane.

LC-MS Retention Time 1.088 min
LC:Agilent 1290
ESI/APCI MS:Agilent 6130
Column: Waters Acquity CSH C18 1.7 um, 2.1×50 mm
Solvent: $H_2O:CH3CN$(0.1% Formic acid)
Gradient: 0.8 mL/min, 0 min(95:5)→1.2 min(50:50) 1.0 mL/min, →1.38 min(3:97)
MS (+): 1237 [M+H]$^+$.

EXAMPLE 7-28

1,1'-Octane-1,8-diylbis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea}hydrochloride The title compound (20 mg) was obtained as a colorless amorphous substance through substantially the same reaction as in Example 7-1 except that 1,8-diisocyanatooctane was used instead of 1,4-diisocyanatobutane.

LC-MS Retention Time 1.139 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1265 [M+H]$^+$.

EXAMPLE 7-29

1,1'-Butane-1,4-diylbis {3-[14-(5-{3-[(4S)-6,8-dichloro-2-methyl-1,2,3,4-tetrahydroisoquinolin-4-yl]phenyl}-2H-tetrazol-2-yl)-3,6,9,12-tetraoxatetradec-1-yl]urea}hydrochloride The title compound (60 mg) was obtained as a colorless amorphous substance through substantially the same reaction as in Example 7-1 except that 14-(5-{3-[(4S)-6, 8-dichloro-2-methyl-1,2,3,4-tetrahydroisoquinolin-4-yl]phenyl}-2H-tetrazol-2-yl)-3,6,9,12-tetraoxatetradecan-1-amine obtained in Reference Example 12-3 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.

LC-MS Retention Time 1.153 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1299 $[M+H]^+$.

EXAMPLE 7-30

1,1'-Butane-1,4-diylbis {3-[2-(2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethoxy)ethyl]urea}hydrochloride The title compound (0.22 g) was obtained as a colorless oil substance through substantially the same reaction as in Example 7-1 except that 2-(2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethoxy)ethanamine obtained in Reference Example 12-4 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.

LC-MS Retention Time 1.138 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1211 $[M+H]^+$.

EXAMPLE 7-31

1,1'-Butane-1,4-diylbis(3-{2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}urea) hydrochloride The title compound (76 mg) was obtained as a colorless oil substance through substantially the same reaction as in Example 7-1 except that 2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethanamine obtained in Reference Example 11-2 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.

LC-MS Retention Time 0.654 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20) 1.2-1.4 min(1:99)
MS (+): 1263 $[M+H]^+$.

EXAMPLE 7-32

1,1'-Butane-1,4-diylbis(3-{2-[2-(2-{2-[(5-{3-[(4S)-6,8-dichloro-2-methyl-1,2,3,4-tetrahydroisoquinolin-4-yl]phenyl}pyridazin-3-yl)amino]ethoxy}ethoxy)ethoxy]ethyl}urea) tetrahydrochloride The title compound (29 mg, 77%) was obtained as a colorless amorphous substance through substantially the same reaction as in Example 7-1 except that N-(2-{2-[2-(2-aminoethoxy)ethoxy]ethoxy}ethyl)-5-{3-[(4S)-6,8-dichloro-2-methyl-1,2,3,4-tetrahydroisoquinolin-4-yl]phenyl}pyridazin-3-amine obtained in Reference Example 10-4 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.

LC-MS Retention Time 0.788 min
LC:Agilent 1290
ESI/APCI MS:Agilent 6130
Column: Waters Acquity CSH C18 1.7 um, 2.1×50 mm
Solvent: $H_2O:CH3CN$(0.1% Formic acid)
Gradient: 0.8 mL/min, 0 min(95:5)→1.2 min(50:50) 1.0 mL/min, →1.38 min(3:97)
MS (+): 1262 $[M+H]^+$.

EXAMPLE 7-33

1,1'-Butane-1,4-diylbis(3-{2-[2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethoxy]ethyl}urea) hexahydrochloride The title compound (78 mg, 76%) was obtained as a yellow amorphous substance through substantially the same reaction as in Example 7-1 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrazin-2-amine obtained in Reference Example 8-11 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.

LC-MS Retention Time 1.154 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1262 $[M+H]^+$.

EXAMPLE 7-34

1,1'-Ethane-1,2-diylbis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea}hydrochloride The title compound (30 mg) was obtained as a colorless amorphous substance through substantially the same reaction as in Example 7-26 except that ethane-1,2-diamine was used instead of 2,2'-[ethane-1,2-diylbis(oxy)]diethanamine.

LC-MS Retention Time 1.045 min
LC:Agilent 1290
ESI/APCI MS:Agilent 6130
Column: Waters Acquity CSH C18 1.7 um, 2.1×50 mm Solvent: H₂O:CH₃CN(0.1% Formic acid)
Gradient: 0.8 mL/min, 0 min(95:5)→1.2 min(50:50)
1.0 mL/min, →1.38 min(3:97)
MS (+): 1181 [M+H]⁺.

EXAMPLE 7-35

1,1'-Propane-1,3-diylbis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea}hydrochloride

EXAMPLE 7-36

1,3-Bis[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl] urea hydrochloride 1,1'-Propane-1,3-diylbis {3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea}hydrochloride (25 mg) was obtained as a colorless amorphous substance through substantially the same reaction as in Example 7-26 except that propane-1,3-diamine was used instead of 2,2'-[ethane-1,2-diylbis(oxy)]diethanamine. Also, 1,3-bis[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea hydrochloride (13 mg) was obtained as a colorless amorphous substance.

EXAMPLE 7-35

LC-MS Retention Time 1.053 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(95:5)→1.2 min(50:50)
1.0 mL/min, →1.38 min(3:97)
MS (+): 1195 [M+H]⁺.

EXAMPLE 7-36

LC-MS Retention Time 1.068 min
LC:Agilent 1290
ESI/APCI MS:Agilent 6130
Column: Waters Acquity CSH C18 1.7 um, 2.1×50 mm
Solvent: H₂O:CH3CN(0.1% Formic acid)
Gradient: 0.8 mL/min, 0 min(95:5)→1.2 min(50:50)
1.0 mL/min, →1.38 min(3:97)
MS (+): 1095 [M+H]⁺.

EXAMPLE 7-37

1,1'-(Oxydiethane-2,1-diyl)bis{3-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]urea}hydrochloride The title compound (30 mg) was obtained as a colorless solid through substantially the same reaction as in Example 7-26 except that 2,2'-oxydiethanamine was used instead of 2,2'-[ethane-1,2-diylbis(oxy)]diethanamine.
LC-MS Retention Time 1.052 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(95:5)→1.2 min(50:50)
1.0 mL/min, →1.38 min(3:97)
MS (+): 1225 [M+H]⁺.

EXAMPLE 7-38

1,1'-Butane-1,4-diylbis(3-{2-[2-(2-{2-[(5-{3-[(4S)-6,8-dichloro-2-methyl-1,2,3,4-tetrahydroisoquinolin-4-yl]phenyl}pyrimidin-2-yl)amino]ethoxy}ethoxy)ethoxy]ethyl}urea) hydrochloride The title compound (30 mg) was obtained as a colorless amorphous substance through substantially the same reaction as in Example 7-1 except that N-(2-{2-[2-(2-aminoethoxy)ethoxy]ethoxy}ethyl)-5-{3-[(4S)-6,8-dichloro-2-methyl-1,2,3,4-tetrahydroisoquinolin-4-yl]phenyl}pyrimidin-2-amine obtained in Reference Example 9-1 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
LC-MS Retention Time 1.134 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(95:5)→1.2 min(50:50)
1.0 mL/min, →1.38 min(3:97)
MS (+): 1283 [M+Na]⁺.

EXAMPLE 7-39

1,1'-Butane-1,4-diylbis {3-[17-(4-{3-[(4S)-6,8-dichloro-2-methyl-1,2,3,4-tetrahydroisoquinolin-4-yl]phenyl}-1H-1,2,3-triazol-1-yl)-3,6,9,12,15-pentaoxaheptadec-1-yl]urea}hydrochloride To a solution of 17-(4-{3-[(4S)-6,8-dichloro-2-methyl-1,2,3,4-tetrahydroisoquinolin-4-yl]phenyl}-1H-1,2,3-triazol-1-yl)-3,6,9,12,15-pentaoxaheptadecan-1-amine (0.13 g) obtained in Reference Example 7-3 in 1,2-dichloroethane (4.0 mL), a solution of 1,4-diisocyanatobutane in 1,2-dichloroethane (0.05 mol/L, 1.6 mL) was added, and the mixture was stirred at room temperature for 10 minutes. Then, a solution of 1,4-diisocyanatobutane in 1,2-dichloroethane (0.05 mol/L, 0.20 mL) was further added thereto, and the mixture was stirred at room temperature for 10 minutes. The reaction solution was concentrated, and then, the obtained residue was purified by reverse-phase preparative HPLC (column (YMC-Actus Triart 5 μm C18 50×30 mm), mobile phase (0.1% formic acid in H₂O:0.1% formic acid in MeCN=95:5→80:20→50:50→5:95, 40 mL/min.). The solvent was distilled off under reduced pressure, and the obtained residue was purified by silica gel column chromatography (Biotage(registered trademark) SNAP Cartridge KP-NH, chloroform:methanol=99:1→85:15). The solvent was distilled off under reduced pressure. Ethanol (3.0 mL) and 4 mol/L hydrogen chloride in ethyl acetate (74 μL) were added to the obtained residue (0.10 g), and the mixture was stirred at room temperature for 15 minutes. The solvent was distilled off under reduced pressure, and diethyl ether was added to the obtained residue. After pulverization, the supernatant was removed. The obtained residue was concentrated under reduced pressure to obtain the title compound (83 mg) as a colorless amorphous substance.

LC-MS Retention Time 1.091 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1283 $[M+Na]^+$.

EXAMPLE 7-40

1,1'-Butane-1,4-diylbis(3-{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}urea) trifluoroacetate (1) To a solution of 1,1'-butane-1,4-diylbis[3-(2-{2-[2-(2-azidoethoxy)ethoxy]ethoxy}ethyl)urea] (0.5 g) obtained in Reference Example 5-2 in methanol (10 mL), 10% palladium-active carbon (25 mg) was added in a nitrogen gas atmosphere, and the mixture was stirred at room temperature for 3 hours in a hydrogen gas atmosphere. 10% palladium-active carbon was filtered off through Celite (registered trademark) and washed with chloroform, and then, the filtrates were concentrated under reduced pressure to obtain 1,1'-butane-1,4-diylbis[3-(2-{2-[2-(2-aminoethoxy)ethoxy]ethoxy}ethyl)urea] (0.45 g, 99%) as a colorless solid.

$^1$H NMR (300 MHz, DMSO-$d_6$) δ ppm 1.31-1.36 (m, 4H), 2.63 (t, J=5.8 Hz, 4H), 2.92-3.00 (m, 4H), 3.12 (q, J=5.8 Hz, 4H), 3.31-3.40 (m, 8H), 3.43-3.59 (m, 16H), 5.81 (t, J=5.7 Hz, 2H), 5.93 (t, J=5.7 Hz, 2H).

MS (+):525 $[M+H]^+$.

(2) To a suspension of 4,6-dichloropyrimidine (43 mg) and 1,1'-butane-1,4-diylbis[3-(2-{2-[2-(2-aminoethoxy)ethoxy]ethoxy}ethyl)urea] (30 mg) in tetrahydrofuran (1.0 mL), triethylamine (40 μL) was added, and the mixture was stirred at 70° C. for 19 hours. The reaction solution was allowed to cool and then concentrated under reduced pressure. Water was added to the obtained residue, followed by extraction with chloroform. The organic layer was dried over anhydrous magnesium sulfate and filtered, and then, the filtrate was concentrated under reduced pressure. The obtained residue was purified by silica gel column chromatography (Biotage(registered trademark) SNAP Cartridge HP-Sphere, hexane:ethyl acetate=99:1→0:100→chloroform:methanol=100:0→80:20) to obtain 1,1'-butane-1,4-diylbis(3-{2-[2-(2-{2-[(6-chloropyrimidin-4-yl)amino]ethoxy}ethoxy)ethoxy]ethyl}urea) (28 mg, 65%) as a colorless oil substance.

$^1$H NMR (300 MHz, CDCl$_3$) δ ppm 1.40-1.58 (m, 4H), 3.07-3.25 (m, 4H), 3.29-3.43 (m, 4H), 3.48-3.75 (m, 28H), 5.32-5.58 (m, 4H), 6.34-6.65 (m, 4H), 8.32 (s, 2H).

MS (+): 749 $[M+H]^+$.

(3) To a suspension of (4S)-6,8-dichloro-2-methyl-4-[3-(4,4,55-tetramethyl-1,3,2-dioxaborolan-2-yl)phenyl]-1,2,3,4-tetrahydroisoquinoline hydrochloride (41 mg) obtained in Reference Example 3-3, 1,1'-butane-1, 4-diylbis(3-{2-[2-(2-{2-[(6-chloropyrimidin-4-yl)amino]ethoxy}ethoxy)ethoxy]ethyl}urea) (28 mg), and tetrakis(triphenylphosphine)palladium(0) (6.5 mg) in 1,4-dioxane (1.8 mL), a saturated aqueous solution of sodium bicarbonate (0.45 mL) was added in an argon gas atmosphere, and the mixture was stirred for 12 hours under heating to reflux. (4S)-6,8-Dichloro-2-methyl-4-[3-(4,4,5,5-tetramethyl-1,3,2-dioxaborolan-2-yl)phenyl]-1,2,3,4-tetrahydroisoquinoline hydrochloride (42 mg), tetrakis(triphenylphosphine)palladium(0) (13 mg), and a saturated aqueous solution of sodium bicarbonate (0.23 mL) were further added thereto, and the mixture was stirred for 6 hours under heating to reflux. The reaction solution was allowed to cool, and then, the insoluble matter was filtered off. The obtained filtrate was purified by reverse-phase preparative HPLC (column (YMC-Actus Triart 5 m C18 50×30 mm), mobile phase (0.1% trifluoroacetic acid in $H_2O$:0.1% trifluoroacetic acid in MeCN=97:3→30:70→5:95, 40 mL/min.) to obtain the title compound (30 mg) as a pale yellow oil substance.

LC-MS Retention Time 0.872 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50) 1.0 mL/min, →1.38 min(3:97)
MS (+): 1262 $[M+H]^+$.

The structures of Examples 7-2 to 7-40 are shown in Tables 4-1 to 4-3 below.

EXAMPLES 7-2 to 7-40

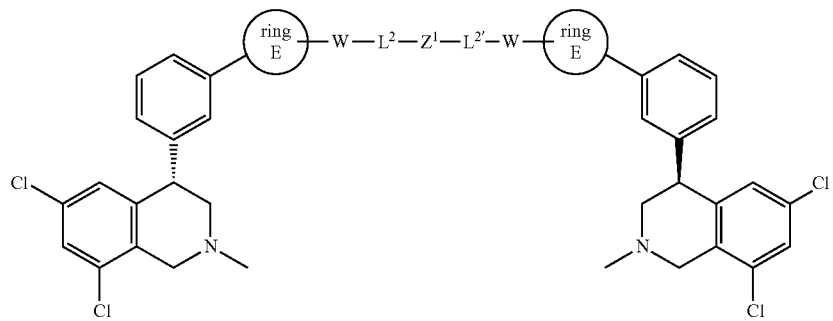

[Formula 126]

TABLE 4-1
| Example | Ring E | W | L², L²' | Z¹ |
|---|---|---|---|---|
| 7-2 | 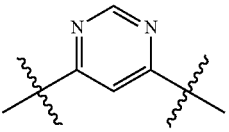 [SMILES: *c1cc(*)ncn1] | —NH— | 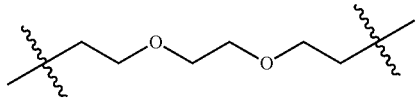 [SMILES: *CCOCCOCC*] | 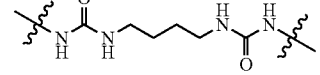 |
| 7-3 | 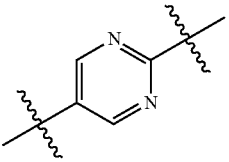 [SMILES: *c1cnc(*)nc1] | —NH— | 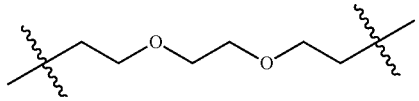 [SMILES: *CCOCCOCC*] | 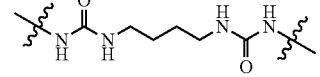 |
| 7-4 | 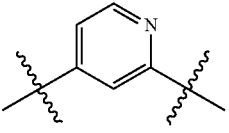 [SMILES: *c1ccnc(*)c1] | —NH— | 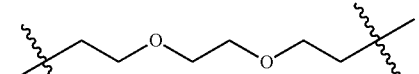 | 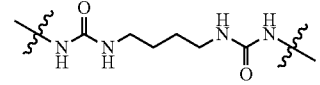 [SMILES: *NC(=O)NCCCCNC(=O)N*] |
| 7-5 | 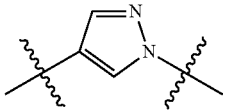 [SMILES: *c1cnn(*)c1] | Single bond | 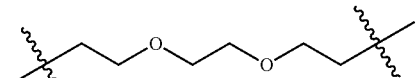 | 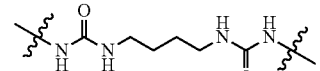 |
| 7-6 | 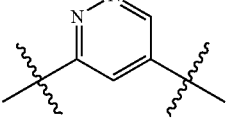 | —NH— | 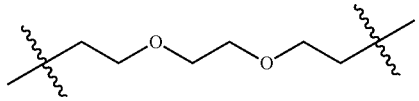 [SMILES: *CCOCCOCC*] | 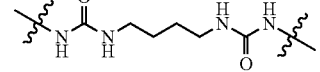 |
| 7-7 | 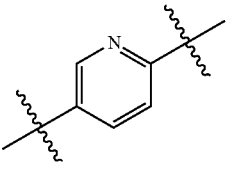 [SMILES: *c1ccc(*)nc1] | —NH— | 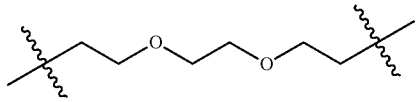 | 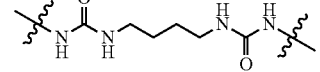 |
| 7-8 | 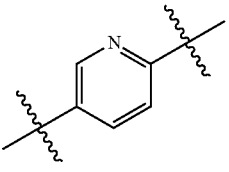 [SMILES: *c1ccc(*)nc1] | —NH— | 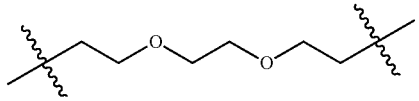 [SMILES: *CCOCCOCC*] | 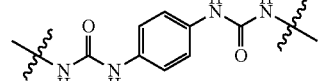 |
| 7-9 | 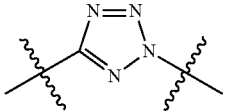 [SMILES: *c1nnn(*)n1] | Single bond | 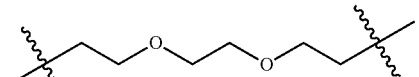 | 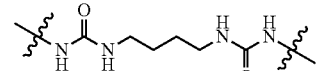 |
| 7-10 | 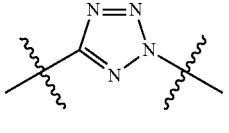 [SMILES: *c1nnn(*)n1] | Single bond | 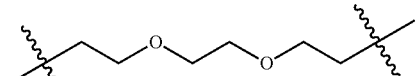 | 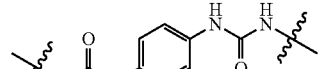 |
| 7-11 | 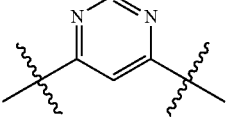 | —O— | 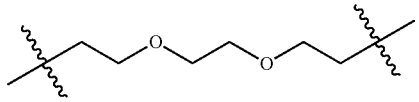 [SMILES: *CCOCCOCC*] | 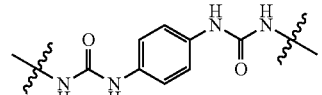 |

TABLE 4-1-continued
| Example | Ring E | W | L², L²' | Z¹ |
|---|---|---|---|---|
| 7-12 | 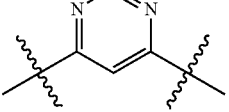 | —O— | 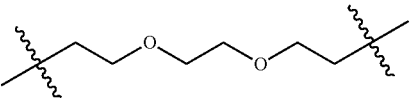 [SMILES: *CCOCCOCC*] | 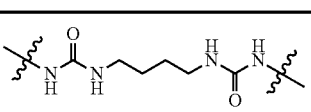 |
| 7-13 | 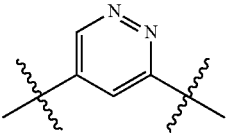 [SMILES: *c1cnnc(*)c1] | —NH— | 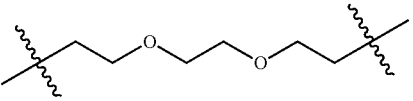 [SMILES: *CCOCCOCC*] | 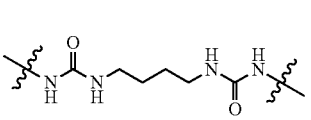 [SMILES: *NC(=O)NCCCCNC(=O)N*] |
| 7-14 | 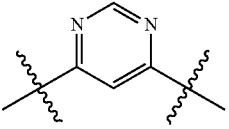 [SMILES: *c1cc(*)ncn1] | —NH— | 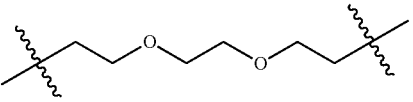 [SMILES: *CCOCCOCC*] | 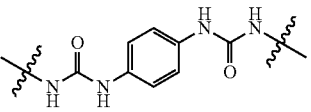 [SMILES: *NC(=O)Nc1ccc(NC(=O)N*)cc1] |
| 7-15 | 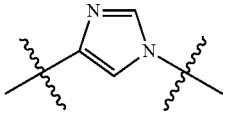 [SMILES: *c1cn(*)cn1] | Single bond | 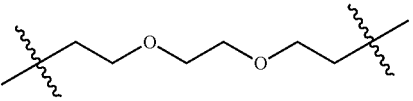 [SMILES: *CCOCCOCC*] | 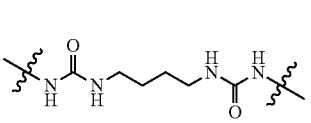 [SMILES: *NC(=O)NCCCCNC(=O)N*] |
TABLE 4-2
| Example | Ring E | W | L², L²' | Z¹ |
|---|---|---|---|---|
| 7-16 | 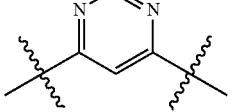 | —NH— | 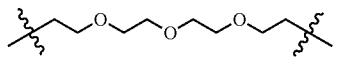 | 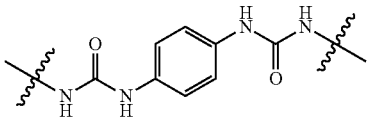 [SMILES: *NC(=O)Nc1ccc(NC(=O)N*)cc1] |
| 7-17 | 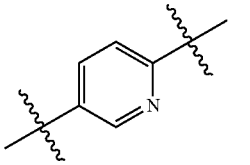 [SMILES: *c1ccc(*)nc1] | —NH— |  | 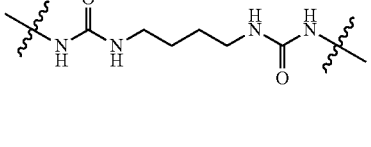 |
| 7-18 | 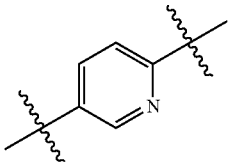 [SMILES: *c1ccc(*)nc1] | —CONH— | 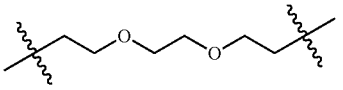 [SMILES: *CCOCCOCC*] | 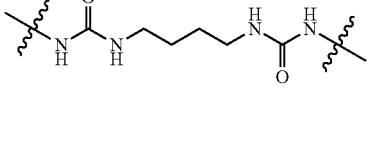 |
| 7-19 | 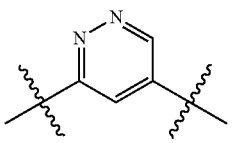 [SMILES: *c1cnnc(*)c1] | —NH— | 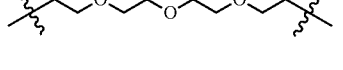 | 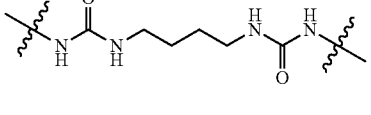 |
| 7-20 | 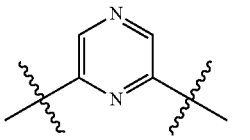 [SMILES: *c1cncc(*)n1] | —NH— | 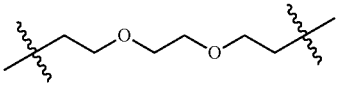 [SMILES: *CCOCCOCC*] | 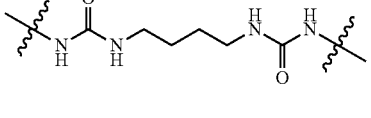 |

TABLE 4-2-continued
| Example | Ring E | W | L², L²' | Z¹ |
|---|---|---|---|---|
| 7-21 | 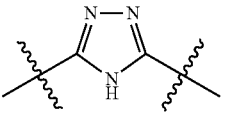 [SMILES: *c1nnc(*)[nH]1] | Single bond | 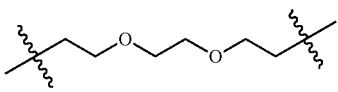 [SMILES: *CCOCCOCC*] | 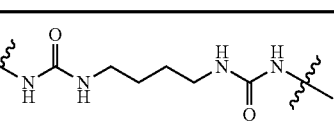 |
| 7-22 | 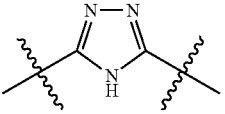 [SMILES: *c1nnc(*)[nH]1] | Single bond | 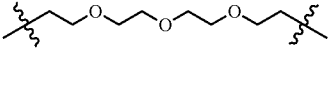 [SMILES: *CCOCCOCCOCC*] | 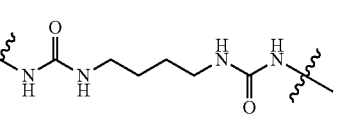 |
| 7-23 | 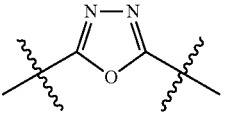 [SMILES: *c1nnc(*)o1] | Single bond | 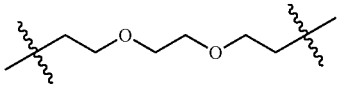 [SMILES: *CCOCCOCC*] | 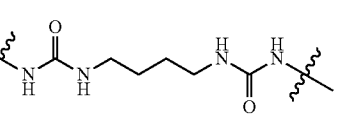 |
| 7-24 | 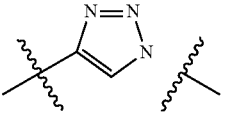 | Single bond | 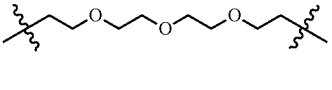 | 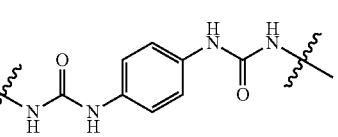 |
| 7-25 | 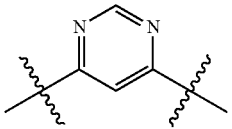 [SMILES: *c1cc(*)ncn1] | —O— | 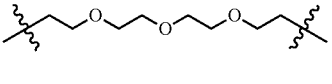 | 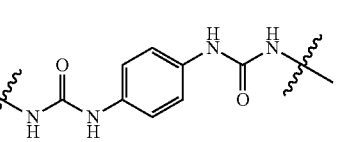 |
| 7-26 | 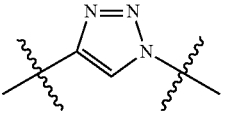 [SMILES: *c1cn(*)nn1] | Single bond | 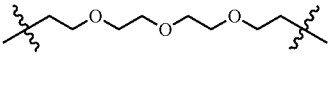 [SMILES: *CCOCCOCCOCC*] | 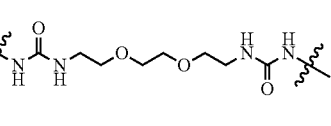 |
| 7-27 | 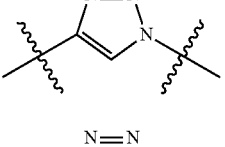 | Single bond |  | 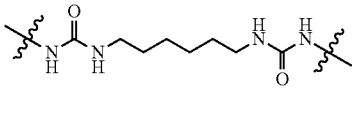 [SMILES: *NC(=O)NCCCCCCNC(=O)N*] |
| 7-28 | 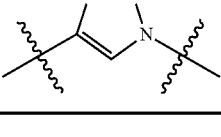 | Single bond |  | 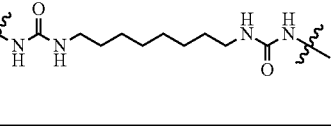 |
TABLE 4-3
| Example | Ring E | W | L², L²' | Z¹ |
|---|---|---|---|---|
| 7-29 | 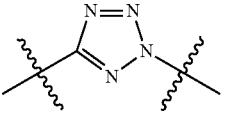 [SMILES: *c1nnn(*)n1] | Single bond | 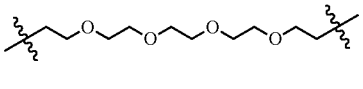 [SMILES: *CCOCCOCCOCCOCC*] | 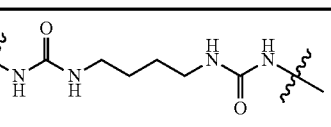 |
| 7-30 | 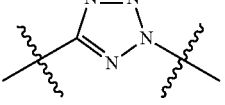 | Single bond | 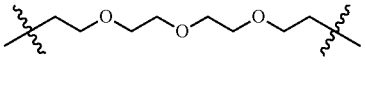 [SMILES: *CCOCCOCCOCC*] | 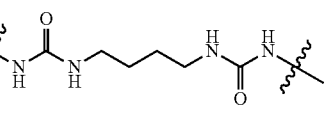 |

TABLE 4-3-continued
| Example | Ring E | W | L², L²' | Z¹ |
|---|---|---|---|---|
| 7-31 | 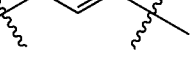 | —O— |  |  |
| 7-32 | 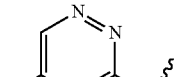 | —NH— | 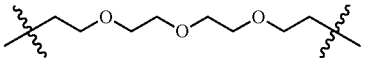 [SMILES: *CCOCCOCCOCC*] | 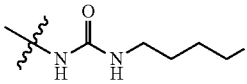 |
| 7-33 | 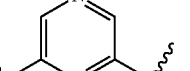 | —NH— | 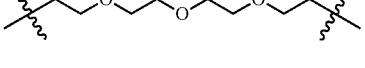 | 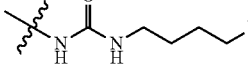 |
| 7-34 | 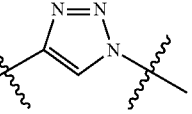 | Single bond | 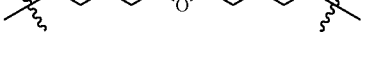 | 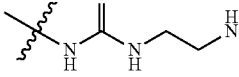 |
| 7-35 | 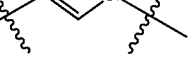 | Single bond |  |  |
| 7-36 | 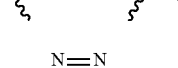 | Single bond |  | 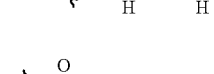 |
| 7-37 | 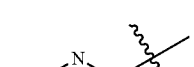 | Single bond | 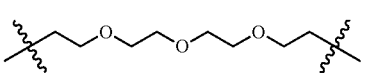 [SMILES: *CCOCCOCCOCC*] | 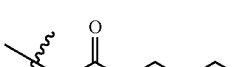 |
| 7-38 | 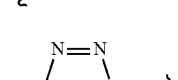 | —NH— | 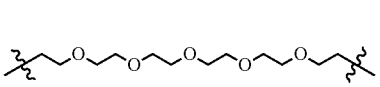 [SMILES: *CCOCCOCCOCCOCCOCC*] |  |
| 7-39 | 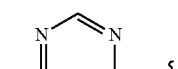 | Single bond | 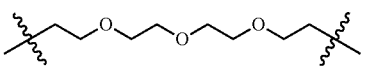 [SMILES: *CCOCCOCCOCC*] | 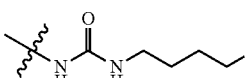 |
| 7-40 |  | —NH— |  |  |

EXAMPLE 7-41

1,1'-Benzene-1,4-diylbis[3-(2-{2-[2-({4-[3-(6,8-dichloro-2-methyl-1,2,3,4-tetrahydroisoquinolin-4-yl)phenyl]pyridin-2-yl}amino)ethoxy]ethoxy}ethyl)urea]trifluoroacetate

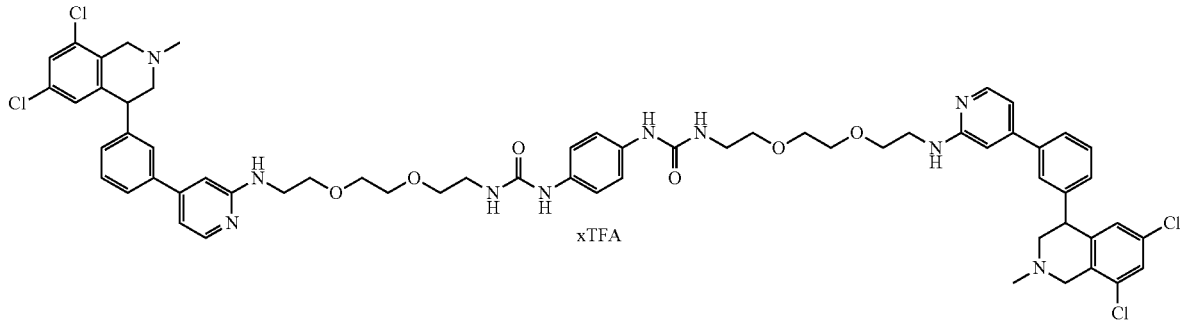

[Formula 127]

The title compound (16 mg) was obtained as a light brown amorphous substance through substantially the same reaction as in Example 7-2 except that N-{2-[2-(2-aminoethoxy)ethoxy]ethyl}-4-[3-(6,8-dichloro-2-methyl-1,2,3,4-tetrahydroisoquinolin-4-yl)phenyl]pyridin-2-amine trifluoroacetate obtained in Reference Example 8-6 was used instead of N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3, and 1,4-diisocyanatobenzene was used instead of 1,4-diisocyanatobutane.

LC-MS Retention Time 0.822 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1191 [M+H]$^+$.

EXAMPLE 7-42

3,3'-Butane-1,4-diylbis {3-[16-(4-{3-[(4S)-6,8-dichloro-2-methyl-1,2,3,4-tetrahydroisoquinolin-4-yl]phenyl}-1H-1,2,3-triazol-1-yl)-4-oxo-8,11,14-trioxa-3,5-diazahexadec-1-yl]urea}formate A solution of 4-nitrophenyl [2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]carbamate (87 mg) obtained in Reference Example 16-1, 1,1'-butane-1,4-diylbis[3-(2-aminoethyl)urea]hydrochloride (20 mg) obtained in Reference Example 17-1, and triethylamine (43 μL) in chloroform (2.0 mL) was stirred at 80° C. for 4 hours. The reaction solution was concentrated under reduced pressure, and the obtained residue was purified by reverse-phase preparative HPLC (column (YMC-Actus Triart 5 μm C18 50×30 mm), mobile phase (0.1% formic acid in $H_2O$: 0.1% formic acid in MeCN=95:5→80:20→50:50→5:95, 40 mL/min.) to obtain the title compound (8.0 mg) as a colorless solid.

LC-MS Retention Time 0.921 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1381 [M+H]$^+$.

EXAMPLE 7-43

1,3-Bis[14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradec-1-yl]urea hydrochloride To a solution of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine (85 mg) obtained in Reference Example 7-2 and triethylamine (45 mg) in chloroform (5.0 mL), bis(trichloromethyl) carbonate (6.5 mg) was added, and the mixture was stirred at room temperature for 30 minutes. The reaction solution was concentrated under reduced pressure, and then, the obtained residue was purified by reverse-phase preparative HPLC (column (YMC-Actus Triart 5 μm C18 50×30 mm), mobile phase (0.1% formic acid in $H_2O$:0.1% formic acid in MeCN=95:5→80:20→50:50→5:95, 40 mL/min.). The solvent was distilled off under reduced pressure, and the obtained residue was purified by silica gel column chromatography (Biotage (registered trademark) SNAP Cartridge KP-NH, chloroform:methanol=98:2→85:15). The solvent was distilled off under reduced pressure. Ethanol (3.0 mL) and 4 mol/L hydrogen chloride in ethyl acetate (69 μL) were added to the obtained residue (82 mg), and the mixture was stirred at room temperature for 15 minutes. The solvent was distilled off under reduced pressure, and diethyl ether was added to the obtained residue. After pulverization, the supernatant was removed. The obtained residue was concentrated under reduced pressure to obtain the title compound (60 mg, 72%) as a colorless amorphous substance.

LC-MS Retention Time 0.984 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)

1.0 mL/min, →1.38 min(3:97)
MS (+): 1183 [M+H]⁺.

EXAMPLE 7-44

1,3-Bis[14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradec-1-yl]urea hydrochloride The title compound (19 mg, 22%) was obtained as a colorless amorphous substance through substantially the same reaction as in Example 7-43 except that 17-(4-{3-[(4S)-6, 8-dichloro-2-methyl-1,2,3,4-tetrahydroisoquinolin-4-yl]phenyl}-1H-1,2,3-triazol-1-yl)-3,6,9,12,15-pentaoxaheptadecan-1-amine obtained in Reference Example 7-3 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2.
LC-MS Retention Time 1.094 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(95:5)→1.2 min(50:50)
1.0 mL/min, →1.38 min(3:97)
MS (+): 1271 [M+H]⁺.

EXAMPLE 7-45

1,1'-Benzene-1,4-diylbis {3-[14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradec-1-yl]urea}hydrochloride The title compound (47 mg, 61%) was obtained as a colorless amorphous substance through substantially the same reaction as in Example 7-1 except that 1,4-diisocyanatobenzene was used instead of 1,4-diisocyanatobutane.
LC-MS Retention Time 1.004 min
LC:Agilent 1290
ESI/APCI MS:Agilent 6130
Column: Waters Acquity CSH C18 1.7 um, 2.1×50 mm
Solvent: H₂O:CH₃CN(0.1% Formic acid)
Gradient: 0.8 mL/min, 0 min(95:5)→1.2 min(50:50)
1.0 mL/min, →1.38 min(3:97)
MS (+): 1317 [M+H]⁺.

EXAMPLE 7-46

1,1'-Benzene-1,4-diylbis {3-[17-(4-{3-[(4S)-6,8-dichloro-2-methyl-1,2,3,4-tetrahydroisoquinolin-4-yl]phenyl}-1H-1,2,3-triazol-1-yl)-3,6,9,12,15-pentaoxaheptadec-1-yl]urea}hydrochloride The title compound (51 mg. 62%) was obtained as a colorless amorphous substance through substantially the same reaction as in Example 7-1 except that 17-(4-{3-[(4S)-6, 8-dichloro-2-methyl-1,2,3,4-tetrahydroisoquinolin-4-yl]phenyl}-1H-1,2,3-triazol-1-yl)-3,6,9,12,15-pentaoxaheptadecan-1-amine obtained in Reference Example 7-3 was used instead of 14-(4-{3-[(4S)-6,8-dichloro-2-methyl-1,2,3,4-tetrahydroisoquinolin-4-yl]phenyl}-1H-1,2,3-triazol-1-yl)-3,6,9,12-tetraoxatetradecan-1-amine obtained in Reference Example 7-2, and 1,4-diisocyanatobenzene was used instead of 1,4-diisocyanatobutane.
LC-MS Retention Time 1.021 min
LC:Agilent 1290
ESI/APCI MS:Agilent 6130
Column: Waters Acquity CSH C18 1.7 um, 2.1×50 mm
Solvent: H₂O:CH3CN(0.1% Formic acid)
Gradient: 0.8 mL/min, 0 min(95:5)→1.2 min(50:50)
1.0 mL/min, →1.38 min(3:97)
MS (+): 1405 [M+H]⁺.

The structures of Examples 7-42 to 7-46 are shown in Table 5-1 below.

EXAMPLES 7-42 to 7-46

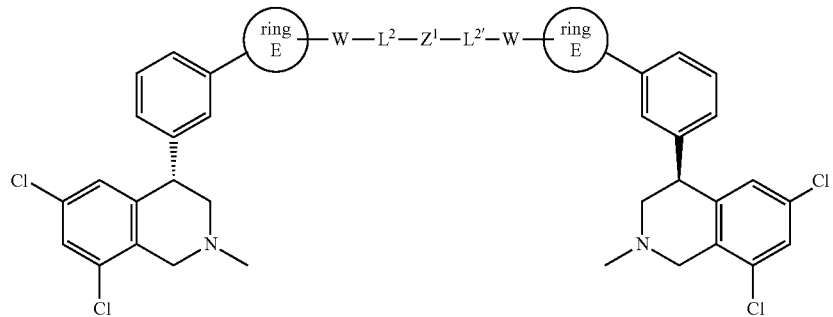

[Formula 128]

TABLE 5-1

| Example | Ring E or E' | W, W' | L², L²' | Z¹ |
|---|---|---|---|---|
| 7-42 | triazole | Single bond | -O-CH₂CH₂-O-CH₂CH₂-O- | -NHC(O)NH-CH₂-NHC(O)NH-(CH₂)₃-NHC(O)NH-CH₂-NHC(O)NH- |
| 7-43 | triazole | Single bond | -O-CH₂CH₂-O-CH₂CH₂-O-CH₂CH₂-O- | -NHC(O)NH- |
| 7-44 | triazole | Single bond | -O-CH₂CH₂-O-CH₂CH₂-O-CH₂CH₂-O-CH₂CH₂-O- | -NHC(O)NH- |
| 7-45 | triazole | Single bond | -O-CH₂CH₂-O-CH₂CH₂-O- | -NHC(O)NH-C₆H₄-NHC(O)NH- |
| 7-46 | triazole | Single bond | -O-CH₂CH₂-O-CH₂CH₂-O-CH₂CH₂-O- | -NHC(O)NH-C₆H₄-NHC(O)NH- |

EXAMPLE 8-1

N,N'-Bis[2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]butanediamide hydrochloride

[Formula 129]

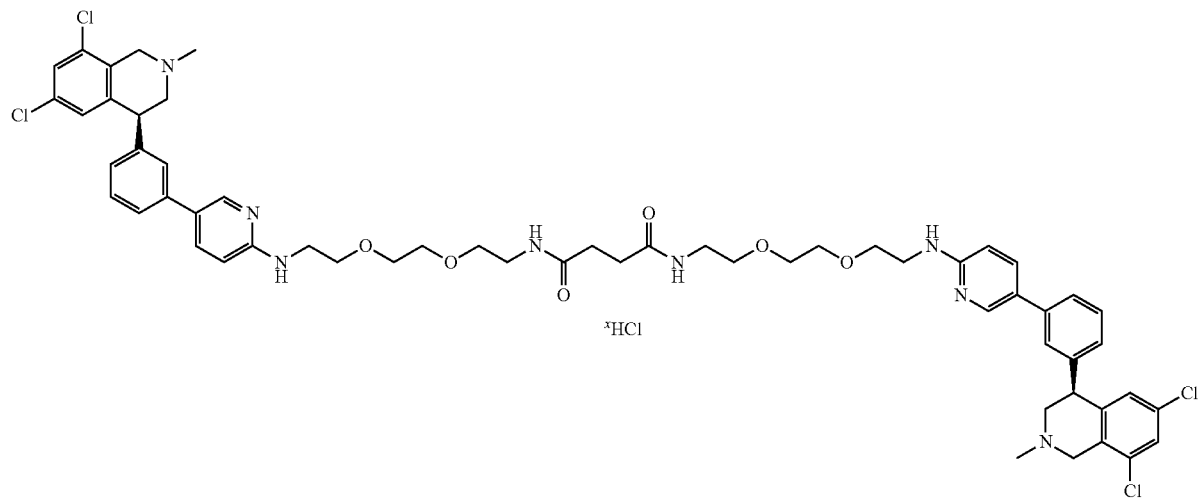

·xHCl

To a solution of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate (30 mg) obtained in Reference Example 10-1 in 1,2-dichloroethane (1.0 mL), triethylamine (17 µL) and a solution of butanedioyl dichloride in 1,2-dichloroethane (0.5 mol/L, 46 µL) were added, and the mixture was stirred overnight at room temperature. The reaction solution was purified by reverse-phase preparative HPLC (column (YMC-Actus Triart 5 µm C18 50×30 mm), mobile phase (0.1% trifluoroacetic acid in H$_2$O:0.1% trifluoroacetic acid in MeCN=90:10→20:80→5:95, 40 mL/min.). The solvent was distilled off under reduced pressure, and then, a saturated aqueous solution of sodium bicarbonate was added to the residue, followed by extraction with chloroform. The organic layer was dried over anhydrous magnesium sulfate and filtered, and then, the filtrate was concentrated under reduced pressure. The obtained residue was dissolved in ethanol. To the solution, a 4 mol/L solution of hydrogen chloride in 1,4-dioxane was added, and then, the solvent was distilled off under reduced pressure to obtain the title compound (14 mg) as a colorless solid.

LC-MS Retention Time 0.823 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 1113 [M+H]$^+$.

EXAMPLE 8-2

(2R,3R)-N,N'-Bis[2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]-2,3-dihydroxybutanediamide hydrochloride To a solution of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate (45 mg) obtained in Reference Example 10-1 in N,N-dimethylformamide (1.0 mL), O-(7-azabenzotriazol-1-yl)-N,N,N',N'-tetramethyluronium hexafluorophosphate (27 mg), N,N-diisopropylethylamine (12 µL), and L-(+)-tartaric acid (5.4 mg) were added, and the mixture was stirred overnight at room temperature. The reaction solution was purified by reverse-phase preparative HPLC (column (YMC-Actus Triart 5 µm C18 50×30 mm), mobile phase (0.1% trifluoroacetic acid in H$_2$O:0.1% trifluoroacetic acid in MeCN=90:10→20:80→5:95, 40 mL/min.) and further purified by preparative TLC (Fuji Silysia Chemical Ltd. "CHROMATOREX TLC Plates NH 0.25 mm", chloroform:methanol=20:1). The solvent was distilled off under reduced pressure, and then, the obtained residue was dissolved in methanol. To the solution, a 4 mol/L solution of hydrogen chloride in 1,4-dioxane was added, and then, the solvent was distilled off under reduced pressure to obtain the title compound (10 mg) as a colorless solid.

LC-MS Retention Time 0.809 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 1145 [M+H]$^+$.

EXAMPLE 8-3

N,N'-Bis[2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]hexanediamide hydrochloride The title compound (21 mg) was obtained as a colorless solid through substantially the same reaction as in Example 8-1 except that hexanedioyl dichloride was used instead of butanedioyl dichloride.

LC-MS Retention Time 0.833 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 1141 [M+H]$^+$.

EXAMPLE 8-4

N,N'-Bis[2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]benzene-1,2-dicarboxamide hydrochloride The title compound (12 mg) was obtained as a colorless solid through substantially the same reaction as in Example 8-1 except that benzene-1,2-dicarbonyl dichloride was used instead of butanedioyl dichloride.

LC-MS Retention Time 0.861 min
LC:Agilent 1290
ESI/APCI MS:Agilent 6130
Column: Waters Acquity CSH C18 1.7 um, 2.1×50 mm
Solvent: H$_2$O:CH$_3$CN(0.1% Formic acid)
Gradient: 0.8 mL/min, 0 min(95:5)→1.2 min(50:50)
1.0 mL/min, →1.38 min(3:97)
MS (+): 1161 [M+H]$^+$.

EXAMPLE 8-5

(2R,3R)-N,N'-Bis[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]-2,3-dihydroxybutanediamide hydrochloride To a solution of 2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethanamine (40 mg) obtained in Reference Example 7-1 in N,N-dimethylformamide (1.0 mL), O-(7-azabenzotriazol-1-yl)-N,N,N',N'-tetramethyluronium hexafluorophosphate (28 mg), N,N-diisopropylethylamine (13 µL), and a solution of L-(+)-tartaric acid in N,N-dimethylformamide (0.5 mol/L, 60 µL) were added, and the mixture was stirred overnight at room temperature. The reaction solution was purified by reverse-phase preparative HPLC (column (YMC-Actus Triart 5 µm C18 50×30 mm), mobile phase (0.1% trifluoroacetic acid in H$_2$O:0.1% trifluoroacetic acid in MeCN=90:10→20:80→5:95, 40 mL/min.) and further purified by preparative TLC (Fuji Silysia Chemical Ltd. "CHROMATOREX TLC Plates NH 0.25 mm", chloroform:methanol=20:1). The solvent was distilled off under reduced pressure, and then, the obtained residue was dissolved in methanol. To the solution, a 4 mol/L solution of hydrogen chloride in 1,4-dioxane was added, and then, the solvent was distilled off under reduced pressure to obtain the title compound (14 mg) as a colorless amorphous substance.

LC-MS Retention Time 1.013 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1183 [M+H]$^+$.

EXAMPLE 8-6

N,N'-Bis[2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethyl]butanediamide pentahydrochloride The title compound (23 mg. 31%) was obtained as a yellow amorphous substance through substantially the same reaction as in Example 8-1 except that N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrazin-2-amine obtained in Reference Example 8-4 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.

LC-MS Retention Time 1.108 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1115 [M+H]$^+$.

EXAMPLE 8-7

1-[(5-{3-[(4S)-6,8-Dichloro-2-methyl-1,2,3,4-tetrahydroisoquinolin-4-yl]phenyl}pyridin-2-yl)amino]-N-[2-(2-{2-[(5-{3-[(4S)-6,8-dichloro-2-methyl-1,2,3,4-tetrahydroisoquinolin-4-yl]phenyl}pyridin-2-yl)amino]ethoxy}ethoxy)ethyl]-10-oxo-3,6,12-trioxa-9-azatetradecan-14-amide hydrochloride The title compound (12 mg) was obtained as a colorless solid through substantially the same reaction as in Example 8-1 except that 2,2'-oxydiacetyl chloride was used instead of butanedioyl dichloride.

LC-MS Retention Time 0.827 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1129 [M+H]$^+$.

EXAMPLE 8-8

(2R,3R)-N,N'-Bis[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethyl]-2,3-dihydroxybutanediamide hydrochloride The title compound (60 mg) was obtained as a pale yellow amorphous substance through substantially the same reaction as in Example 8-2 except that N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine substantially obtained by purifying N-{2-[2-(2-aminoethoxy)ethoxy]ethyl}-6-{3-[(4S)-6,8-dichloro-2-methyl-1,2,3,4-tetrahydroisoquinolin-4-yl]phenyl}pyrimidin-4-amine trifluoroacetate obtained in Reference Example 8-3 by silica gel column chromatography (Biotage(registered trademark) SNAP Cartridge KP-NH, chloroform:methanol=100:0→85:15) was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.

LC-MS Retention Time 0.823 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1147 [M+H]$^+$.

EXAMPLE 8-9

(2S,3S)-N,N'-Bis[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]-2,3-dihydroxybutanediamide hydrochloride To a solution of 2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethanamine (0.10 g) obtained in Reference Example 7-1 in N,N-dimethylformamide (5.0 mL), O-(7-azabenzotriazol-1-yl)-N,N,N',N'-tetramethyluronium hexafluorophosphate (85 mg), N,N-diisopropylethylamine (29 mg), and D-(−)-tartaric acid (13 mg) were added, and the mixture was stirred at room temperature for 3 hours. The reaction solution was concentrated, and then, the obtained residue was purified by silica gel column chromatography (Biotage(registered trademark) SNAP Cartridge KP-NH, chloroform:methanol=100:0→70:30). The solvent was distilled off under reduced pressure, and the obtained residue was dissolved in ethanol (5.0 mL). To the solution, 4 mol/L hydrogen chloride in ethyl acetate (0.20 mL) was added. The solvent was distilled off under reduced pressure to obtain the title compound (15 mg) as a colorless amorphous substance.

LC-MS Retention Time 1.010 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)

Gradient: 0.8 mL/min, 0 min(95:5)→1.2 min(50:50)

1.0 mL/min, →1.38 min(3:97)

MS (+): 1183 [M+H]⁺.

EXAMPLE 8-10

(2R,3R)-N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}-2,3-dihydroxybutanediamide hydrochloride The title compound (60 mg) was obtained as a pale yellow amorphous substance through substantially the same reaction as in Example 8-2 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrimidin-4-amine obtained in Reference Example 8-9 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.

LC-MS Retention Time 0.861 min

LC:Agilent 1290

ESI/APCI MS:Agilent 6130

Column: Waters Acquity CSH C18 1.7 um, 2.1×50 mm

Solvent: $H_2O:CH_3CN$(0.1% Formic acid)

Gradient: 0.8 mL/min, 0 min(95:5)→1.2 min(50:50)

1.0 mL/min, →1.38 min(3:97)

MS (+): 1235 [M+H]⁺.

EXAMPLE 8-11

1-[(6-{3-[(4R)-6,8-Dichloro-2-methyl-1,2,3,4-tetrahydroisoquinolin-4-yl]phenyl}pyrimidin-4-yl)amino]-N-{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}-13-oxo-3,6,9,15-tetraoxa-12-azaheptadecan-17-amide hydrochloride The title compound (30 mg) was obtained as a colorless amorphous substance through substantially the same reaction as in Example 8-1 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrimidin-4-amine obtained in Reference Example 8-9 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1, and 2,2'-oxydiacetyl chloride was used instead of butanedioyl dichloride.

LC-MS Retention Time 0.882 min

LC:Agilent 1290

ESI/APCI MS:Agilent 6130

Column: Waters Acquity CSH C18 1.7 um, 2.1×50 mm

Solvent: $H_2O:CH_3CN$(0.1% Formic acid)

Gradient: 0.8 mL/min, 0 min(95:5)→1.2 min(50:50)

1.0 mL/min, →1.38 min(3:97)

MS (+): 1219 [M+H]⁺.

EXAMPLE 8-12

N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}butanediamide hydrochloride The title compound (47 mg) was obtained as a colorless amorphous substance through substantially the same reaction as in Example 8-1 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrimidin-4-anine obtained in Reference Example 8-9 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.

LC-MS Retention Time 0.884 min

LC:Agilent 1290

ESI/APCI MS:Agilent 6130

Column: Waters Acquity CSH C18 1.7 um, 2.1×50 mm

Solvent: $H_2O:CH_3CN$(0.1% Formic acid)

Gradient: 0.8 mL/min, 0 min(95:5)→1.2 min(50:50)

1.0 mL/min, →1.38 min(3:97)

MS (+): 1203 [M+H]⁺.

EXAMPLE 8-13

N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}hexanediamide hydrochloride The title compound (47 mg) was obtained as a colorless amorphous substance through substantially the same reaction as in Example 8-1 except that N-(2-{2-[2-(2-aminoethoxy)ethoxy]ethoxy}ethyl)-6-{3-[(4S)-6,8-dichloro-2-methyl-1,2,3,4-tetrahydroisoquinolinolin-4-]phenyl}phenylpyrimidin-4-amine obtained in Reference Example 8-9 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1, and hexanedioyl dichloride was used instead of butanedioyl dichloride.

LC-MS Retention Time 0.894 min

LC:Agilent 1290

ESI/APCI MS:Agilent 6130

Column: Waters Acquity CSH C18 1.7 um, 2.1×50 mm

Solvent: $H_2O:CH_3CN$(0.1% Formic acid)

Gradient: 0.8 mL/min, 0 min(95:5)→1.2 min(50:50)

1.0 mL/min, →1.38 min(3:97)

MS (+): 1231 [M+H]⁺.

EXAMPLE 8-14

(2R,3R)-N-[2-(2-{2-[(5-{3-[(4R)-6,8-Dichloro-2-methyl-1,2,3,4-tetrahydroisoquinolin-4-yl]phenyl}pyridazin-3-yl)amino]ethoxy}ethoxy)ethyl]-N'-[2-(2-{2-[(5-{3-[(4S)-6,8-dichloro-2-methyl-1,2,3,4-tetrahydroisoquinolin-4-yl]phenyl}pyridazin-3-yl)amino]ethoxy}ethoxy)ethyl]-2,3-dihydroxybutanamide tetrahydrochloride To a solution of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridazin-3-amine (51 mg) obtained in Reference Example 10-3 and L-(+)-tartaric acid (7.4 mg) in N,N-dimethylformamide (0.3 mL), triethylamine (14 µL), 1-ethyl-3-(3-dimethylaminopropyl)carbodiimide hydrochloride (19 mg), and 1-hydroxybenzotriazole monohydrate (15 mg) were added, and the mixture was stirred at room temperature for 4 hours. The reaction solution was purified by reverse-phase preparative HPLC (column (YMC-Actus Triart 5 µm C18 50×30 mm), mobile phase (0.1% formic acid in $H_2O$:0.1% formic acid in MeCN=95:5→80:20→50: 50→5:95, 40 mL/min.). The solvent was distilled off under reduced pressure, and the obtained residue was purified by silica gel column chromatography (Biotage(registered trademark) SNAP Cartridge KP-NH, chloroform:methanol=100: 0→80:20). The solvent was distilled off under reduced pressure, and the obtained residue (37 mg) was dissolved in ethanol (1.0 mL). To the solution, 2 mol/L hydrochloric acid (0.20 mL) was added, and the mixture was stirred at room temperature for 10 minutes. The solvent was distilled off under reduced pressure to obtain the title compound (35 mg, 55%) as a colorless amorphous substance.

LC-MS Retention Time 0.734 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1147 $[M+H]^+$.

EXAMPLE 8-15

(2R,3R)-N,N'-Bis[2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethyl]-2,3-dihydroxybutanediamide diformate To a solution of 2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethanamine (50 mg) obtained in Reference Example 14-3, 1-ethyl-3-(3-dimethylaminopropyl)carbodiimide hydrochloride (27 mg), 1-hydroxybenzotriazole monohydrate (21 mg), and triethylamine (20 µL) in chloroform (1.0 mL), a solution of L-(+)-tartaric acid (6.3 mg) in N,N-dimethylformamide (1.0 mL) was slowly added dropwise, and the mixture was stirred at room temperature for 5 hours. The reaction solution was concentrated under reduced pressure, and then, the obtained residue was purified by preparative LC-MS (LC (Agilent 1260), ESIMS (6130 Quadrupole, ESI), column (YMC-Actus Triart 5 µm C18 50×30 mm), mobile phase (0.1% formic acid in $H_2O$:0.1% formic acid in $CH_3CN$=95:5→50:50→5:95), 50 mL/min.) to obtain the title compound (7.0 mg, 13%) as a yellow amorphous substance.

LC-MS Retention Time 0.985 min
LC:Agilent 1290
ESI/APCI MS:Agilent 6130
Column: Waters Acquity CSH C18 1.7 um, 2.1×50 mm
Solvent: $H_2O$:CH3CN(0.1% Formic acid)
Gradient: 0.8 mL/min, 0 min(95:5)→1.2 min(50:50)
1.0 mL/min, →1.38 min(3:97)
MS (+): 1183 $[M+H]^+$.

EXAMPLE 8-16

(2R,3R)-N,N'-Bis[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethyl]-2,3-dihydroxybutanediamide hydrochloride The title compound (54 mg) was obtained as a colorless amorphous substance through substantially the same reaction as in Example 8-2 except that 2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethanamine obtained in Reference Example 11-1 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.

LC-MS Retention Time 1.133 min
LC:Agilent 1290
ESI/APCI MS:Agilent 6130
Column: Waters Acquity CSH C18 1.7 um, 2.1×50 mm
Solvent: $H_2O$:$CH_3CN$(0.1% Formic acid)
Gradient: 0.8 mL/min, 0 min(95:5)→1.2 min(50:50)
1.0 mL/min, →1.38 min(3:97)
MS (+): 1149 $[M+H]^+$.

EXAMPLE 8-17

(2R,3R)-N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}-2,3-dihydroxybutanediamide hydrochloride The title compound (60 mg) was obtained as a colorless amorphous substance through substantially the same reaction as in Example 8-2 except that 2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethanamine obtained in Reference Example 11-2 was used instead of N-{2-[2-(2-aminoethoxy)ethoxy]ethyl}-5-{3-[(4S)-6, 8-dichloro-2-methyl-1,2,3,4-tetrahydroisoquinolin-4-yl]phenyl}pyridin-2-amine trifluoroacetate obtained in Reference Example 10-1.

LC-MS Retention Time 1.161 min
LC:Agilent 1290
ESI/APCI MS:Agilent 6130
Column: Waters Acquity CSH C18 1.7 um, 2.1×50 mm
Solvent: $H_2O$:CH3CN(0.1% Formic acid)
Gradient: 0.8 mL/min, 0 min(95:5)→1.2 min(50:50)
1.0 mL/min, →1.38 min(3:97)
MS (+): 1237 $[M+H]^+$.

EXAMPLE 8-18

1-[(6-{3-[(4R)-6,8-Dichloro-2-methyl-1,2,3,4-tetrahydroisoquinolin-4-yl]phenyl}pyrimidin-4-yl)oxy]-N-{2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}-13-oxo-3,6,9,15-tetraoxa-12-azaheptadecan-17-amide hydrochloride The title compound (75 mg) was obtained as a colorless amorphous substance through substantially the same reaction as in Example 8-2 except that 2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethanamine obtained in Reference Example 11-2 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1, and diglycolic acid was used instead of L-(+)-tartaric acid.
LC-MS Retention Time 1.189 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1221 $[M+H]^+$.

EXAMPLE 8-19

(2R,3R)-N,N'-Bis{2-[2-(2-{2-[(5-{3-[(4S)-6,8-dichloro-2-methyl-1,2,3,4-tetrahydroisoquinolin-4-yl]phenyl}pyridazin-3-yl)amino]ethoxy}ethoxy)ethoxy]ethyl}-2,3-dihydroxybutanediamide tetrahydrochloride The title compound (18 mg, 41%) was obtained as a colorless amorphous substance through substantially the same reaction as in Example 8-14 except that N-(2-{2-[2-(2-aminoethoxy)ethoxy]ethoxy}ethyl)-5-{3-[(4S)-6,8-dichloro-2-methyl-1,2,3,4-tetrahydroisoquinolin-4-yl]phenyl}pyridazin-3-amine obtained in Reference Example 10-4 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridazin-3-amine obtained in Reference Example 10-3.
LC-MS Retention Time 0.758 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1235 $[M+H]^+$.

EXAMPLE 8-20

(2R,3R)-N,N'-Bis{2-[2-(2-{2-[(6-{3-[(4S)-6,8-dichloro-2-methyl-1,2,3,4-tetrahydroisoquinolin-4-yl]phenyl}pyrazin-2-yl)amino]ethoxy}ethoxy)ethoxy]ethyl}-2,3-dihydroxybutanediamide tetrahydrochloride The title compound (25 mg, 35%) was obtained as a yellow amorphous substance through substantially the same reaction as in Example 8-14 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrazin-2-amine obtained in Reference Example 8-11 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridazin-3-amine obtained in Reference Example 10-3.
LC-MS Retention Time 1.131 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1235 $[M+H]^+$.

EXAMPLE 8-21

(2R,3R)-N,N'-Bis{2-[2-(2-{2-[(5-{3-[(4S)-6,8-dichloro-2-methyl-1,2,3,4-tetrahydroisoquinolin-4-yl]phenyl}pyrimidin-2-yl)amino]ethoxy}ethoxy)ethoxy]ethyl}-2,3-dihydroxybutanediamide formate The title compound (8.0 mg, 6.0%) was obtained as a colorless amorphous substance through substantially the same reaction as in Example 8-2 (without carrying out the operation of forming hydrochloride) except that N-(2-{2-[2-(2-aminoethoxy)ethoxy]ethoxy}ethyl)-5-{3-[(4S)-6,8-dichloro-2-methyl-1,2,3,4-tetrahydroisoquinolin-4-yl]phenyl}pyrimidin-2-amine obtained in Reference Example 9-1 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.
LC-MS Retention Time 1.119 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1235 $[M+H]^+$.

EXAMPLE 8-22

N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}butanediamide hydrochloride The title compound (40 mg) was obtained as a colorless amorphous substance through substantially the same reaction as in Example 8-1 except that 2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethanamine obtained in Reference Example 11-2 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1.
LC-MS Retention Time 0.657 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20)→1.2-1.4 min(1:99)
MS (+): 1205 $[M+H]^+$, 1227 $[M+Na]^+$.

EXAMPLE 8-23

N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)oxy]ethoxy}ethoxy)ethoxy]ethyl}hexanediamide hydrochloride The title compound (14 mg) was obtained as a colorless amorphous substance through substantially the same reaction as in Example 8-1 except that 2-[2-(2-{2-[(6-{3-[(4S)-

6,8-dichloro-2-methyl-1,2,3,4-tetrahydroisoquinolin-4-yl]phenyl}pyrimidin-4-yl)oxy]ethoxy}ethoxy)ethoxy]ethanamine obtained in Reference Example 11-2 was used instead of N-{2-[2-(2-aminoethoxy)ethoxy]ethyl}-5-{3-[(4S)-6,8-dichloro-2-methyl-1,2,3,4-tetrahydroisoquinolin-4-yl]phenyl}pyridin-2-amine trifluoroacetate obtained in Reference Example 10-1, and hexanedioyl dichloride was used instead of butanedioyl dichloride.

LC-MS Retention Time 0.662 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(80:20) 1.2-1.4 min(1:99)
MS (+): 1233 [M+H]$^+$, 1255 [M+Na]$^+$.

EXAMPLE 8-24

(2R,3S,4R,5S)-N,N'-Bis[2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethyl]-2,3,4,5-tetrahydroxyhexanediamide hydrochloride To a solution of 2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethanamine (58 mg) obtained in Reference Example 14-3 and (4R,4'S,5S,5'R)-2,2,2',2'-tetramethyl-4,4'-bi-1,3-dioxolane-5,5'-dicarboxylic acid (16 mg, described in the pamphlet of WO2006/091894) in N,N-dimethylformamide (1.1 mL), O-(7-azabenzotriazol-1-yl)-N,N,N',N'-tetramethyluronium hexafluorophosphate (45 mg) and N,N-diisopropylethylamine (38 μL) were added, and the mixture was stirred at room temperature for 75 minutes. The reaction solution was purified by reverse-phase preparative HPLC (column (YMC-Actus Triart 5 μm C18 50×30 mm), mobile phase (0.1% formic acid in $H_2O$: 0.1% formic acid in MeCN=97:3→30:70→5:95, 40 mL/min.). The solvent was distilled off under reduced pressure. Water (1.0 mL) and trifluoroacetic acid (2.0 mL) were added to the obtained residue, and the mixture was stirred overnight at room temperature. The solvent was distilled off under reduced pressure, and the obtained residue was purified by reverse-phase preparative HPLC (column (YMC-Actus Triart 5 μm C18 50×30 mm), mobile phase (0.1% formic acid in $H_2O$:0.1% formic acid in MeCN=97:3→30:70→5:95, 40 mL/min.). The obtained purified solution was neutralized using PL-HCO$_3$ MP-SPE (registered trademark) (0.20 g), and the solution was concentrated under reduced pressure. The obtained residue was dissolved in ethanol (1.0 mL). To the solution, 2 mol/L hydrochloric acid (3.0 μL) was added, and then, the mixture was concentrated under reduced pressure to obtain the title compound (2.4 mg) as a pale yellow amorphous substance.

LC-MS Retention Time 0.960 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1243 [M+H]T

EXAMPLE 8-25

(2R,3S,4R,5S)-N,N'-Bis[2-(2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethoxy)ethyl]-2,3,4,5-tetrahydroxyhexanediamide hydrochloride The title compound (20 mg, 28%) was obtained as a pale yellow amorphous substance through substantially the same reaction as in Example 8-24 except that 2-(2-{2-[2-(5-{3-[(4S)-6,8-dichloro-2-methyl-1,2,3,4-tetrahydroisoquinolin-4-yl]phenyl}-2H-tetrazol-2-yl)ethoxy]ethoxy}ethoxy)ethanamine obtained in Reference Example 12-4 was used instead of 2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethanamine obtained in Reference Example 14-3.

LC-MS Retention Time 0.984 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1245 [M+H]

EXAMPLE 8-26

(2R,3S,4R,5S)-N,N'-Bis{2-[2-(2-{2-[(6-{3-[(4S)-6,8-dichloro-2-methyl-1,2,3,4-tetrahydroisoquinolin-4-yl]phenyl}pyrimidin-4-yl)amino]ethoxy}ethoxy)ethoxy]ethyl}-2,3,4,5-tetrahydroxyhexanediamide hydrochloride The title compound (25 mg, 31%) was obtained as a pale yellow amorphous substance through substantially the same reaction as in Example 8-24 except that N-(2-{2-[2-(2-aminoethoxy)ethoxy]ethoxy}ethyl)-6-{3-[(4S)-6,8-dichloro-2-methyl-1,2,3,4-tetrahydroisoquinolin-4-yl]phenyl}pyrimidin-4-amine obtained in Reference Example 8-9 was used instead of 2-(2-{2-[2-(5-{3-[(4S)-6,8-dichloro-2-methyl-1,2,3,4-tetrahydroisoquinolin-4-yl]phenyl}-4H-1,2,4-triazol-3-yl)ethoxy]ethoxy}ethoxy)ethanamine obtained in Reference Example 14-3.

LC-MS Retention Time 0.738 min
LC:Agilent 1290
ESI/APCI MS:Agilent 6130
Column: Waters Acquity CSH C18 1.7 um, 2.1×50 mm
Solvent: $H_2O:CH_3CN$(0.1% Formic acid)
Gradient: 0.8 mL/min, 0 min(95:5)→1.2 min(50:50)
1.0 mL/min, →1.38 min(3:97)
MS (+): 1295 [M+H]$^+$ The structures of Examples 8-2 to 8-26 are shown in Tables 6-1 to 6-3 below.

EXAMPLES 8-2 to 8-26

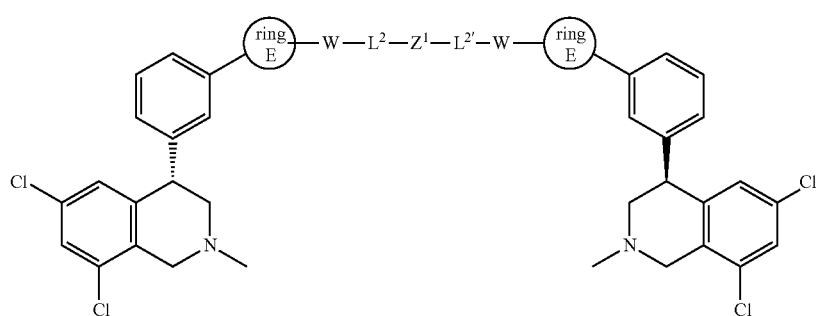

[Formula 130]

TABLE 6-1

| Example | Ring E | W | L², L²' | Z¹ |
|---|---|---|---|---|
| 8-2 | pyridine (2,5) | —NH— | —CH₂CH₂OCH₂CH₂OCH₂CH₂— | —NHC(O)CH(OH)CH(OH)C(O)NH— |
| 8-3 | pyridine (2,5) | —NH— | —CH₂CH₂OCH₂CH₂OCH₂CH₂— | —NHC(O)(CH₂)₃C(O)NH— |
| 8-4 | pyridine (2,5) | —NH— | —CH₂CH₂OCH₂CH₂OCH₂CH₂— | phthalamide (1,2-benzenedicarboxamide) |
| 8-5 | triazole | Single bond | —CH₂CH₂OCH₂CH₂OCH₂CH₂OCH₂CH₂— | —NHC(O)CH(OH)CH(OH)C(O)NH— |
| 8-6 | pyrazine (2,6) | —NH— | —CH₂CH₂OCH₂CH₂OCH₂CH₂— | —NHC(O)CH₂CH₂C(O)NH— |

TABLE 6-1-continued
| Example | Ring E | W | L², L²' | Z¹ |
|---|---|---|---|---|
| 8-7 | 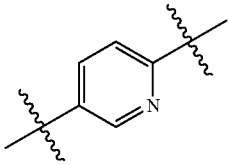 [SMILES: *c1ccc(*)nc1] | —NH— | 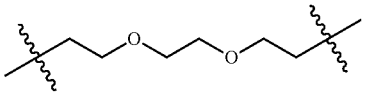 [SMILES: *CCOCCOCC*] | 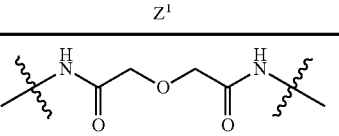 |
| 8-8 | 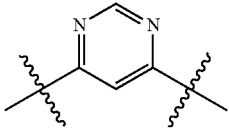 [SMILES: *c1cc(*)ncn1] | —NH— | 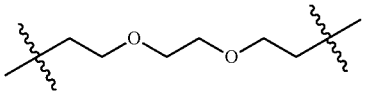 [SMILES: *CCOCCOCC*] | 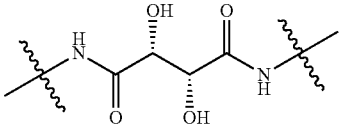 |
| 8-9 | 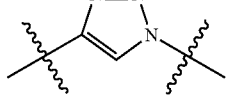 | Single bond | 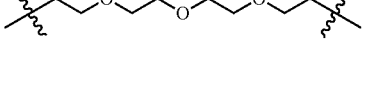 | 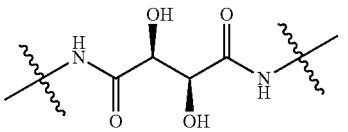 [SMILES: *NC(=O)[C@@H](O)[C@H](O)C(=O)N*] |
| 8-10 | 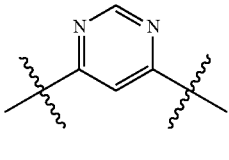 [SMILES: *c1cc(*)ncn1] | —NH— | 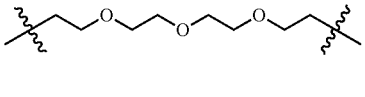 | 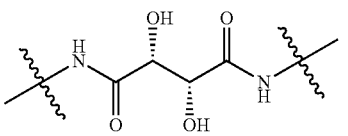 [SMILES: *NC(=O)[C@H](O)[C@@H](O)C(=O)N*] |
| 8-11 | 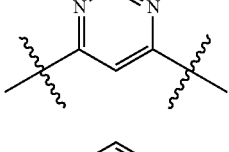 | —NH— | 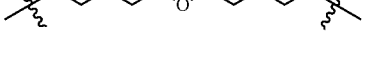 | 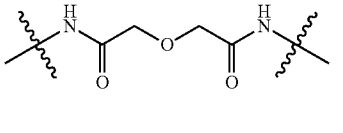 [SMILES: *NC(=O)COCC(=O)N*] |
| 8-12 | 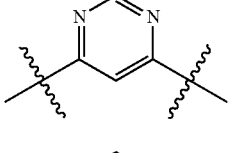 | —NH— | 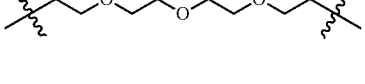 | 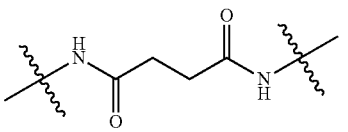 [SMILES: *NC(=O)CCC(=O)N*] |
| 8-13 | 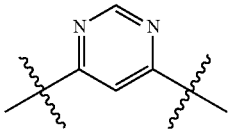 [SMILES: *c1cc(*)ncn1] | —NH— | 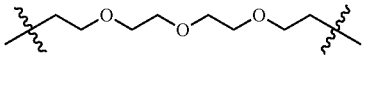 | 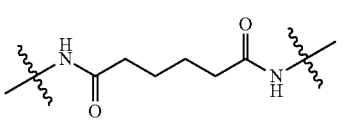 [SMILES: *NC(=O)CCCCC(=O)N*] |
TABLE 6-2
| Example | Ring E | W | L², L²' | Z¹ |
|---|---|---|---|---|
| 8-14 | 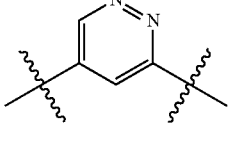 | —NH— | 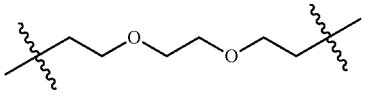 [SMILES: *CCOCCOCC*] | 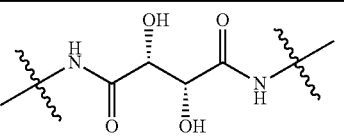 |
| 8-15 | 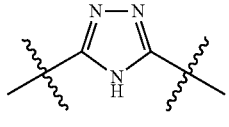 [SMILES: *c1nnc(*)[nH]1] | Single bond | 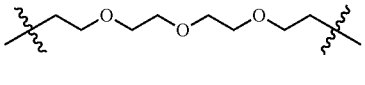 [SMILES: *CCOCCOCCOCC*] | 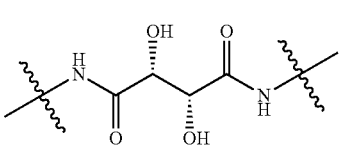 |

TABLE 6-2-continued
| Example | Ring E | W | L², L²' | Z¹ |
|---|---|---|---|---|
| 8-16 | 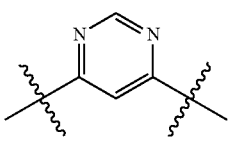 [SMILES: *c1cc(*)ncn1] | —O— | 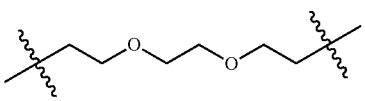 [SMILES: *CCOCCOCC*] | 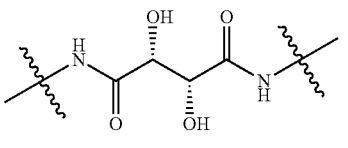 [SMILES: *NC(=O)[C@H](O)[C@@H](O)C(=O)N*] |
| 8-17 | 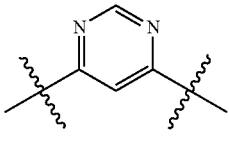 [SMILES: *c1cc(*)ncn1] | —O— | 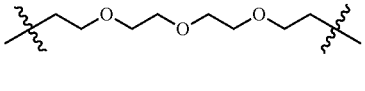 [SMILES: *CCOCCOCCOCC*] | 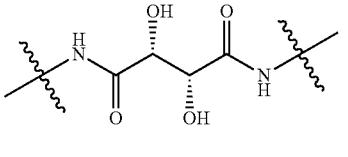 [SMILES: *NC(=O)[C@H](O)[C@@H](O)C(=O)N*] |
| 8-18 | 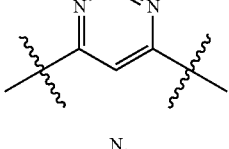 | —O— | 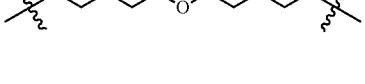 | 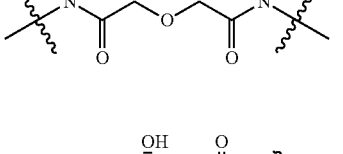 |
| 8-19 | 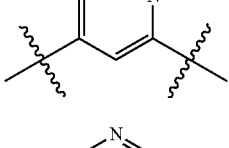 | —NH— |  | 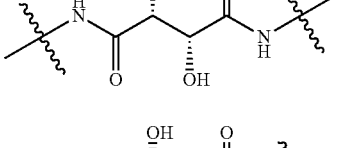 |
| 8-20 | 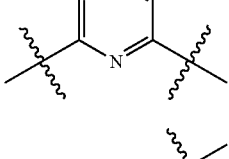 | —NH— |  | 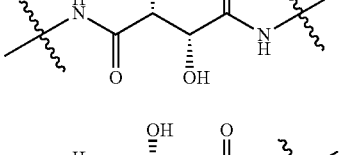 |
| 8-21 | 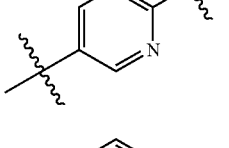 | —NH— |  | 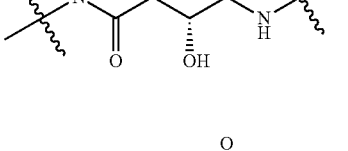 |
| 8-22 | 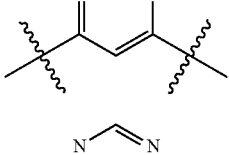 | —O— |  | 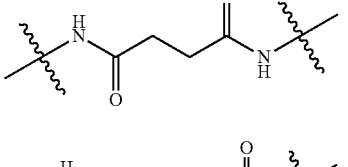 |
| 8-23 | 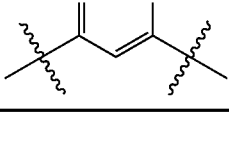 | —O— |  | 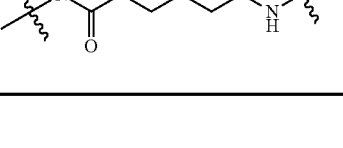 |
TABLE 6-3
| | | | | |
|---|---|---|---|---|
| 8-24 | 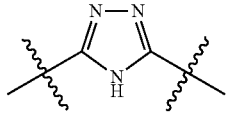 [SMILES: *c1nnc(*)[nH]1] | Single bond | 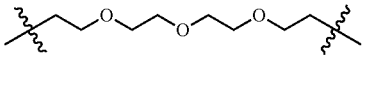 [SMILES: *CCOCCOCCOCC*] | 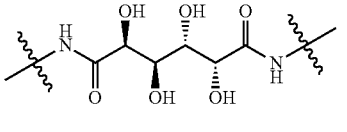 [SMILES: *NC(=O)[C@@H](O)[C@H](O)[C@H](O)[C@@H](O)C(=O)N*] |
| 8-25 | 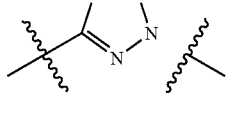 | Single bond | 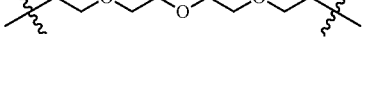 | 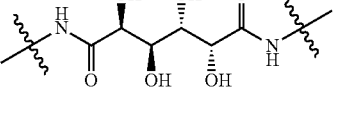 |

TABLE 6-3-continued

| 8-26 | 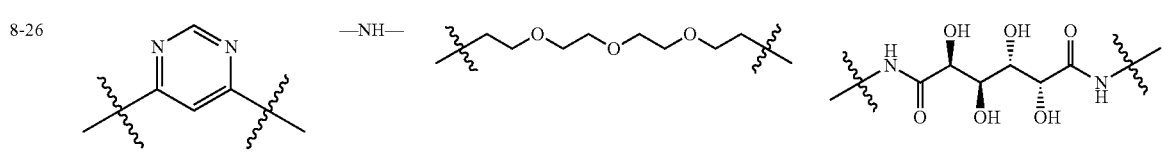 | —NH— | | | |

EXAMPLE 9-1

1-(4-{3-[(4S)-6,8-Dichloro-2-methyl-1,2,3,4-tetrahydroisoquinolin-4-yl]phenyl}-1H-1,2,3-triazol-1-yl)-N-[2-(2-{2-[2-(4-{3-[(4S)-6,8-dichloro-2-methyl-1,2,3,4-tetrahydroisoquinolin-4-yl]phenyl}-1H-1,2,3-triazol-1-yl)ethoxy]ethoxy}ethoxy)ethyl]-15,18-bis[1-(4-{3-[(4S)-6, 8-dichloro-2-methyl-1,2,3,4-tetrahydroisoquinolin-4-yl]phenyl}-1H-1,2,3-triazol-1-yl)-13-oxo-3,6,9-trioxa-12-azatetradecan-14-yl]-13-oxo-3,6,9-trioxa-12,15,18-triazaicosan-20-amide hydrochloride methanol. To the solution, a 4 mol/L solution of hydrogen chloride in 1,4-dioxane was added, and then, the solvent was distilled off under reduced pressure to obtain the title compound (10 mg, 14%) as a pale yellow amorphous substance.

LC-MS Retention Time 1.073 min
LC:Agilent 1290
ESI/APCI MS:Agilent 6130
Column: Waters Acquity CSH C18 1.7 um, 2.1×50 mm
Solvent: $H_2O:CH_3CN(0.1\%$ Formic acid)
Gradient: 0.8 mL/min, 0 min(95:5)→1.2 min(50:50) 1.0 mL/min, →1.38 min(3:97)
MS (+): 2359 $[M+H]^+$.

[Formula 131]

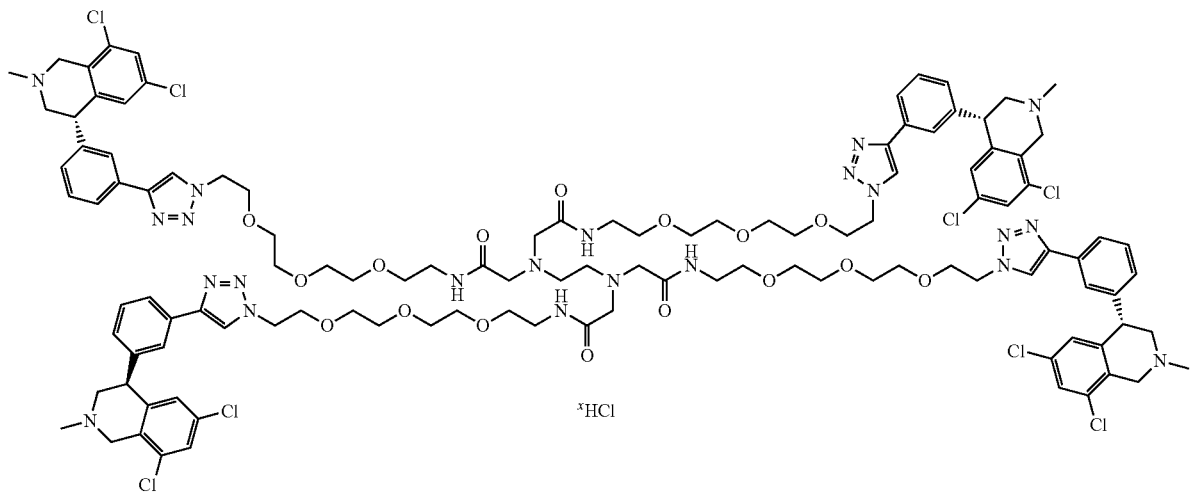

A solution of 1-azido-N-(2-{2-[2-(2-azidoethoxy)ethoxy]ethoxy}ethyl)-15,18-bis(1-azido-13-oxo-3,6,9-trioxa-12-azatetradecan-14-yl)-13-oxo-3,6,9-trioxa-12,15,18-triazaicosan-20-amide (62 mg) obtained in Reference Example 6-6, (4S)-6,8-dichloro-4-(3-ethynylphenyl)-2-methyl-1,2,3,4-tetrahydroisoquinoline (0.10 g) obtained in Reference Example 2-1, copper sulfate (4.5 mg), and sodium ascorbate (12 mg) in an ethanol (2.0 mL)-water (0.5 mL) mixed solvent was stirred at 85° C. for 3 hours. Ethanol was distilled off under reduced pressure. Then, the residue was filtered through a filter, and the filtrate was concentrated under reduced pressure. The obtained residue was purified by reverse-phase preparative HPLC (column (YMC-Actus Triart 5 μm C18 50×30 mm), mobile phase (0.1% trifluoroacetic acid in $H_2O$:0.1% trifluoroacetic acid in MeCN=90:10→20:80→5:95, 40 mL/min.) and further purified by preparative TLC (Fuji Silysia Chemical Ltd. "CHROMATOREX TLC Plates NH 0.25 mm", chloroform:methanol=20:1). The solvent was distilled off under reduced pressure, and then, the obtained residue was dissolved in The compound of the present invention can be evaluated for its NHE3 inhibitory effect according to an approach known in the art, for example, the method described in Test Example 1.

The NHE3 inhibitory effect of the compound of the present invention was measured by use of the method described below in Test Example 1.

TEST EXAMPLE 1

(1) Preparation of Cell Line Deficient in Endogenous NHE

The cell line deficient in endogenous NHE was prepared according to the method of Jacques Pouyssegur et al. (Proc. Natl. Acad. Sci. USA. 1984, Vol. 81, 4833-4837) using opossum kidney (OK) cells (ATCC).

(2) Preparation of Expression Plasmid and Cell Line Stably Expressing Human NHE3

The expression plasmid was constructed by inserting a human NHE3 (SLC9A3, Accession No. NM_004174) cDNA sequence (GeneCopoeia, Inc.) into a pcDNA3.2/V5-DEST vector (Life Technologies Corp.).

The OK cells deficient in endogenous NHE were transfected with the constructed human NHE3 expression plasmid to prepare stably expressing cells. The transfection was carried out by electroporation using a Nucleofector 2b device (Lonza Group Ltd.). A stably expressing cell line was selected in medium supplemented with 500 µg/mL Geneticin (Life Technologies Corp.) and isolated.

(3) NHE3 Inhibition Test

NHE3 activity measurement method using cell: The activity was determined by using the NHE3-mediated recovery of intracellular pH occurring after intracellular acidification, as an index. The intracellular pH was measured by a partial modification of the pH-sensitive fluorescent indicator method reported by Tsien et al. (Proc. Natl. Acad. Sci. USA., 1984, 81, 7436-7440).

The cell line stably expressing human NHE3 was inoculated on a poly-D-lysine-coated 96-well plate (Greiner Bio-one) and cultured overnight. The medium was aspirated from each well, and the cells were washed once with Hank's balanced salt buffer solution (137 mM NaCl, 20 mM HEPES, 5.6 mM glucose, 5.3 mM KCl, 1.3 mM $CaCl_2$, 0.5 mM $MgCl_2$, 0.4 mM $MgSO_4$, 0.4 mM $KH_2PO_4$, 0.3 mM $Na_2HPO_4$, pH 7.4). Then, Hank's balanced salt buffer solution containing 0.25 µM BCECF-AM (Dojindo Laboratories) was added to the cells, which were then incubated at 37° C. for 30 minutes. The solution was aspirated from each well, and $NH_4Cl$ buffer solution (20 mM $NH_4Cl$, 115 mM choline chloride, 20 mM HEPES, 5 mM glucose, 4.7 mM KCl, 1.25 mM $CaCl_2$, 1.25 mM $MgCl_2$, pH 7.4) was added to the cells, which were then incubated at 37° C. for 10 minutes. The cells thus incubated in the $NH_4Cl$ buffer solution were washed with $NH_4Cl$-free buffer solution (133.8 mM choline chloride, 10 mPM HEPES, 5 mM glucose, 4.7 mM KCl, 1.25 mM $CaCl_2$, 1.25 mM $MgCl_2$, 0.97 mM $K_2HPO_4$, 0.23 mM $KH_2PO_4$, pH 7.4) to decrease the intracellular pH. After the washing step, 70 µL of a test compound solution prepared with the $NH_4Cl$-free buffer solution was added to the cells, and 70 iµL of sodium ion-containing buffer solution (133.8 mM NaCl, 10 mM HEPES, 5 mM glucose, 4.7 mM KCl, 1.25 mM $CaCl_2$, 1.25 mM $MgCl_2$, 0.97 mM $Na_2HPO_4$, 0.23 mM $NaH_2PO_4$, pH 7.4) was added thereto in a measurement system FDSS6000 (Hamamatsu Photonics K.K.) to start the recovery of pH. The recovery of intracellular pH was monitored using BCECF fluorescence (excitation wavelength: 480 nm, fluorescence wavelength: 520 to 560 nm), and the initial rate of the pH recovery was plotted. The recovery of pH without test compound was defined as the maximum recovery, and the test compound concentration necessary to inhibit 50% of the maximum recovery was calculated as an $IC_{50}$ value.

(4) Results

The human NHE3 inhibitory activity (nM) of each compound is shown in Table 7-1 below.

TABLE 7-1

| Example No. | $IC_{50}$ (nm) |
|---|---|
| 1-1 | 217 |
| 1-2 | 217 |
| 1-3 | 392 |
| 1-4 | 257 |
| 1-5 | 58.1 |
| 1-6 | 373 |
| 1-7 | 626 |
| 1-8 | 126 |
| 1-9 | 561 |
| 1-10 | 169 |
| 1-11 | 1604 |
| 1-12 | 650 |
| 1-13 | 271 |
| 1-14 | 173 |
| 1-15 | 117 |
| 1-16 | 184 |
| 1-17 | 109 |
| 1-18 | 95.7 |
| 1-19 | 856 |
| 1-20 | 208 |
| 1-21 | 1171 |
| 1-22 | 306 |
| 1-23 | 3220 |
| 2-1 | 89.3 |
| 3-1 | 49.1 |
| 4-1 | 554 |
| 5-1 | 760 |
| 6-1 | 2.4 |
| 6-2 | 5.7 |
| 6-3 | 301 |
| 6-4 | 97.6 |
| 6-5 | 9.5 |
| 6-6 | 75.0 |
| 6-7 | 1.1 |
| 6-8 | 0.8 |
| 6-9 | 4.1 |
| 6-10 | 6.2 |
| 6-11 | 1.4 |
| 6-12 | 2.3 |
| 6-13 | 2.1 |
| 7-1 | 2.2 |
| 7-2 | 9.4 |
| 7-3 | 11.0 |
| 7-4 | 8.4 |
| 7-5 | 4.5 |
| 7-6 | 10.0 |
| 7-7 | 6.8 |
| 7-8 | 1084 |
| 7-9 | 7.3 |
| 7-10 | 13.7 |
| 7-11 | 33.5 |
| 7-12 | 7.5 |
| 7-13 | 12.0 |
| 7-14 | 13.9 |
| 7-15 | 8.1 |
| 7-16 | 16.6 |
| 7-17 | 4.4 |
| 7-18 | 5.6 |
| 7-19 | 17.7 |
| 7-20 | 7.5 |
| 7-21 | 3.8 |
| 7-22 | 5.7 |
| 7-23 | 5.5 |
| 7-24 | 5.6 |
| 7-25 | 13.6 |
| 7-26 | 5.2 |
| 7-27 | 11.3 |
| 7-28 | 7.3 |
| 7-29 | 6.9 |
| 7-30 | 2.8 |
| 7-31 | 12.4 |
| 7-32 | 18.1 |
| 7-33 | 8.6 |
| 7-34 | 3.3 |
| 7-35 | 4.4 |
| 7-36 | 21.4 |
| 7-37 | 6.6 |
| 7-38 | 3.8 |
| 7-39 | 3.2 |
| 7-40 | 11.0 |
| 7-41 | 5518 |
| 7-42 | 5.5 |
| 7-43 | 8.5 |
| 7-44 | 7.6 |
| 7-45 | 5.7 |
| 7-46 | 10.9 |

TABLE 7-1-continued

| Example No. | IC$_{50}$ (nm) |
|---|---|
| 8-1 | 14.9 |
| 8-2 | 10.7 |
| 8-3 | 13.2 |
| 8-4 | 115 |
| 8-5 | 2.8 |
| 8-6 | 15.5 |
| 8-7 | 41.7 |
| 8-8 | 6.2 |
| 8-9 | 3.6 |
| 8-10 | 3.2 |
| 8-11 | 7.5 |
| 8-12 | 6.2 |
| 8-13 | 10.6 |
| 8-14 | 9.1 |
| 8-15 | 1.9 |
| 8-16 | 7.6 |
| 8-17 | 2.5 |
| 8-18 | 10.7 |
| 8-19 | 6.8 |
| 8-20 | 3.3 |
| 8-21 | 3.2 |
| 8-22 | 10.5 |
| 8-23 | 4.7 |
| 8-24 | 3.4 |
| 8-25 | 0.2 |
| 8-26 | 2.2 |
| 9-1 | 13.1 |

The compound of the present invention can be evaluated for its phosphorus absorption inhibitory effect according to an approach known in the art, for example, the method described in Test Example 2.

The phosphorus absorption inhibitory effect of the compound of the present invention was measured by use of the method described below in Test Example 2.

TEST EXAMPLE 2

Phosphorus Absorption Inhibitory Effect of the Compound of the Present Invention in $^{32}$P-Phosphate Oral Loading Test Using SD Rat 8-week-old SD male rats (Japan SLC, Inc.) were used as laboratory animals. Each test compound was suspended or dissolved at a concentration of 0.2 mg/mL or 0.6 mg/mL in Japanese Pharmacopoeia water for injection (manufactured by Hikari Pharmaceutical Co., Ltd.) and orally administered to each rat at a dose of 5 ml/kg body weight. Japanese Pharmacopoeia water for injection was administered at the same dose as above to a control group. 5 minutes after the administration of the test compound or water for injection, a phosphate solution (1.3 mM NaH$_2$PO$_4$) containing 32P-phosphate (PerkinElmer Inc.) was administered thereto at a dose of 5 ml/kg. 30 minutes after the administration of the phosphate solution, blood was collected from the tail vein, and the blood sample was immediately mixed with EDTA-2K (manufactured by Dojindo Laboratories). Then, the mixture was centrifuged at 3000 rpm at 4° C. for 10 minutes to recover plasma.

The radioactivity in 100 µL of the plasma was measured using a liquid scintillation counter and used as a phosphate absorption count. The radioactivity in the plasma of the control group was used as a control, and the rate of inhibition of phosphate absorption was determined according to the following expression:

Rate of inhibition of phosphate absorption (%)=(1−Phosphate absorption count of the test compound administration group/Phosphate absorption count of the control group)×100

(2) Results

The rate of inhibition of phosphate absorption (%: dose: 1 mg/kg or 3 mg/kg) of each compound is shown in Table 8-1 below. The minimum effective dose (MED) can also be calculated by measuring the rate of inhibition at a plurality of doses.

TABLE 8-1

| Example No. | Dose (mg/kg) | Rate of inhibition (%) |
|---|---|---|
| 6-2 | 1 | 47 |
| 6-4 | 3 | −5 |
| 6-5 | 3 | 46 |
| 6-8 | 3 | 34 |
| 6-9 | 3 | 53 |
| 6-10 | 3 | 38 |
| 6-11 | 3 | 33 |
| 6-12 | 3 | 37 |
| 7-2 | 3 | 23 |
| 7-4 | 3 | 27 |
| 7-5 | 3 | 23 |
| 7-6 | 3 | 24 |
| 7-9 | 3 | 22 |
| 7-10 | 3 | 35 |
| 7-15 | 3 | 36 |
| 7-16 | 3 | 34 |
| 7-18 | 3 | 49 |
| 7-19 | 3 | 19 |
| 7-24 | 3 | 31 |
| 7-29 | 3 | 10 |
| 7-30 | 3 | 28 |
| 7-33 | 3 | −1 |
| 7-39 | 1 | 38 |
| 7-40 | 3 | 28 |
| 7-42 | 3 | 29 |
| 7-43 | 3 | 37 |
| 7-45 | 3 | 29 |
| 7-46 | 3 | 23 |
| 8-6 | 3 | 26 |
| 8-8 | 3 | 39 |
| 8-12 | 3 | 6 |
| 8-14 | 1 | 46 |
| 8-16 | 3 | 31 |
| 8-17 | 3 | 18 |
| 8-18 | 3 | 27 |
| 8-20 | 3 | 37 |

INDUSTRIAL APPLICABILITY

The compound of the present invention has an excellent NHE3 inhibitory effect and can provide a pharmaceutical product effective for the prevention or treatment of constipation, hypertension, nephropathy, body fluid retention derived from renal failure, and body fluid retention caused by heart failure, liver cirrhosis, or drugs. The compound of the present invention also has an excellent phosphorus absorption inhibitory effect and can provide a pharmaceutical product effective for the prevention or treatment of CKD-MBD typified by hyperphosphatemia. The present invention is expected to mitigate burdens on patients and contribute to the development of pharmaceutical industry.

The invention claimed is:

1. A compound represented by the following formula [1] or a pharmaceutically acceptable salt thereof:

wherein

A represents a structure represented by the following formula [2]:

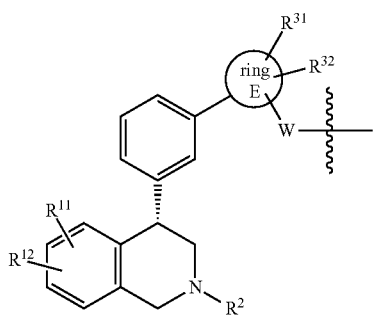

wherein

R$^{11}$ and R$^{12}$ are the same or different and each represents a hydrogen atom or a halogen atom, R$^2$ represents a hydrogen atom or C$_{1-6}$ alkyl, ring E represents pyrrole, furan, pyrazole, imidazole, isoxazole, oxazole, isothiazole, triazole, oxadiazole, tetrazole, pyridine, pyridazine, pyrimidine, or pyrazine, R$^{31}$ and R$^{32}$ are the same or different and each represents a hydrogen atom, cyano, C$_{1-6}$ alkyl, C$_{1-6}$ alkoxy, or mono-C$_{1-6}$ alkylamino, and W represents a single bond, the formula —NH—, the formula —O—, or the formula —CONH—, and Y represents a hydrogen atom or a structure selected from

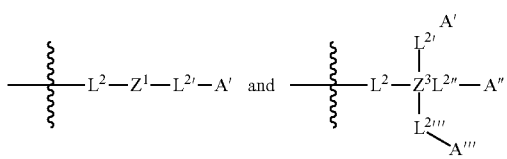

wherein

Z$^1$ represents a structure of the following formula group [4']:

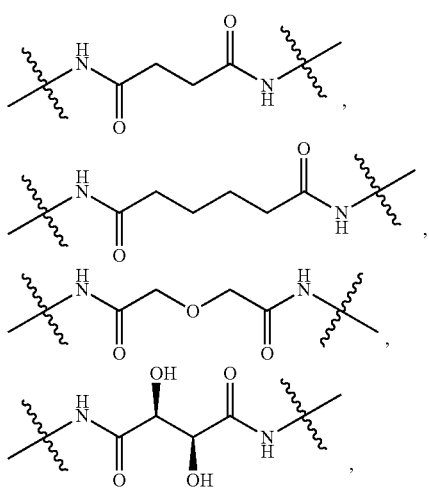

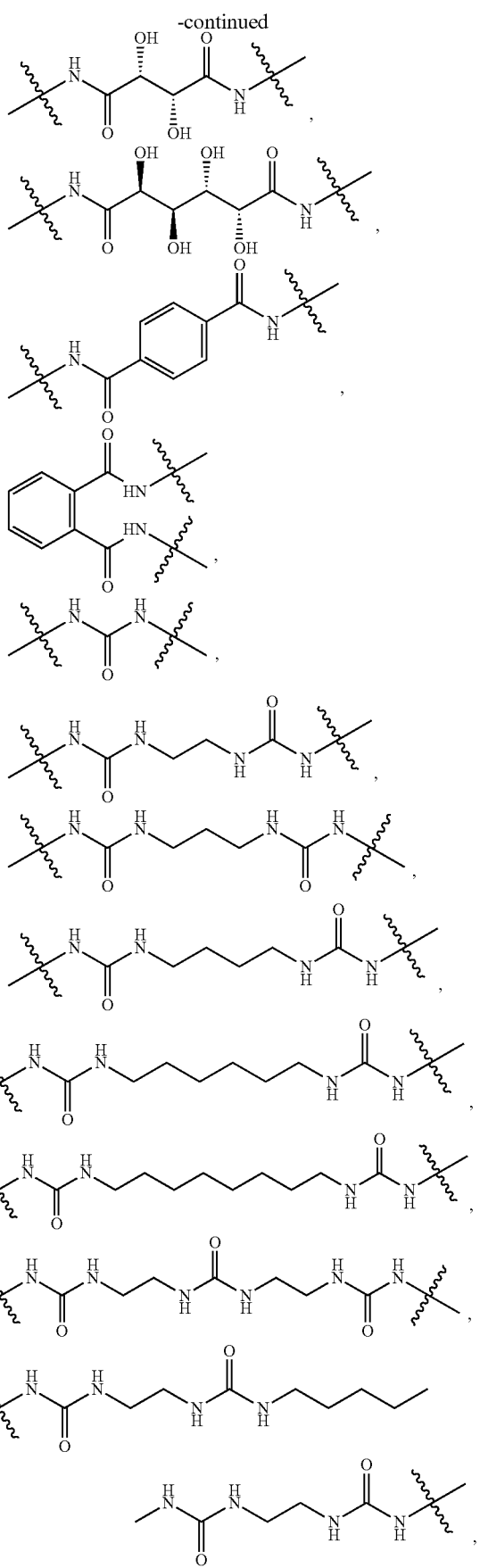

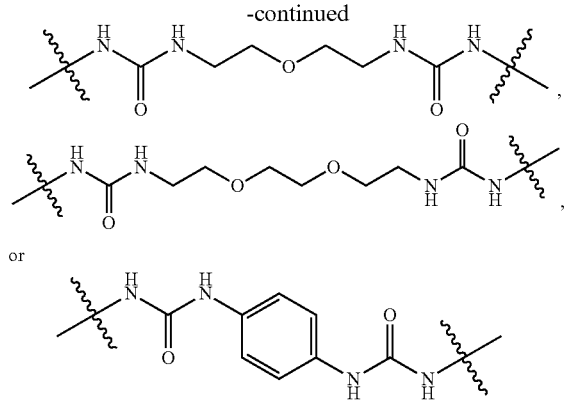

or

Z³ represents a structure of the following formula [4-a]:

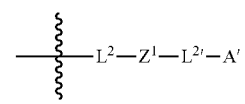
[4-a]

L², L²', L²'', and L²''' are the same or different and each represents a structure of the following formula group [5]:

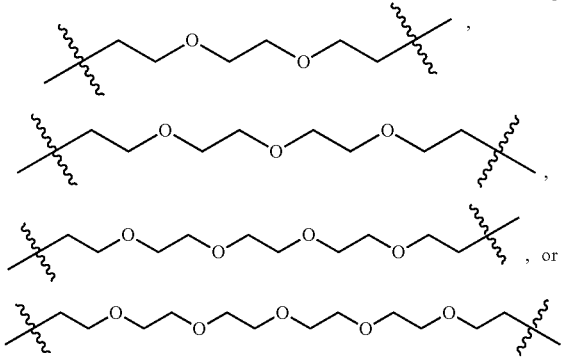

and

A', A'', and A''' each represent the same structure as the structure represented by A.

2. The compound according to claim 1 or a pharmaceutically acceptable salt thereof, wherein Y is a hydrogen atom or a structure represented by the following formula:

$$-L^2-Z^1-L^{2\prime}-A'$$

wherein

Z¹ is a structure of the following formula group [4]:

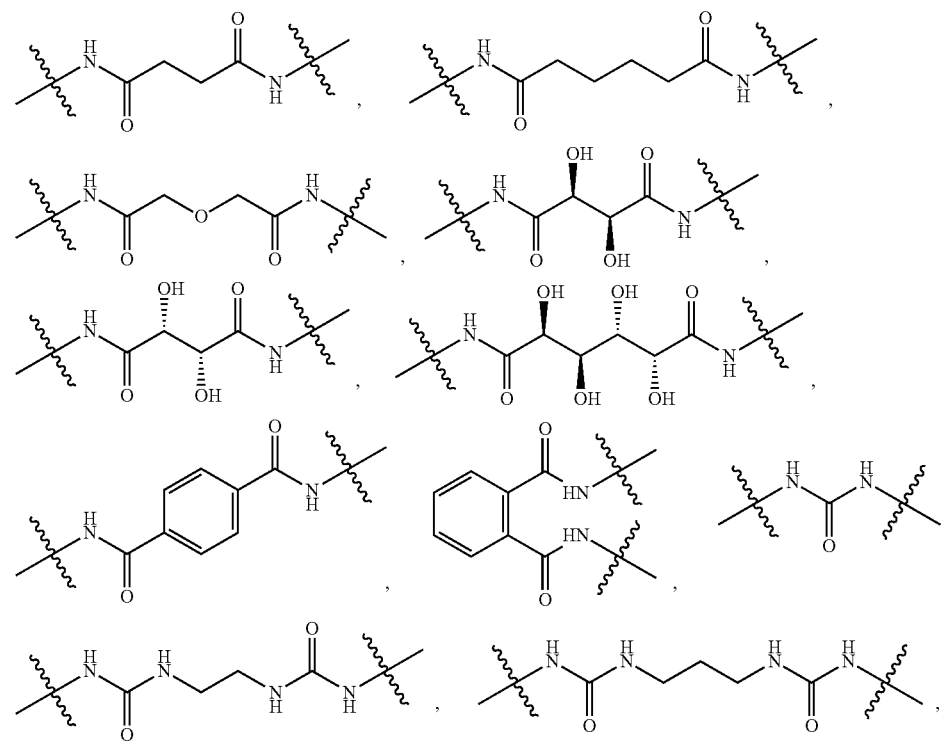
[4]

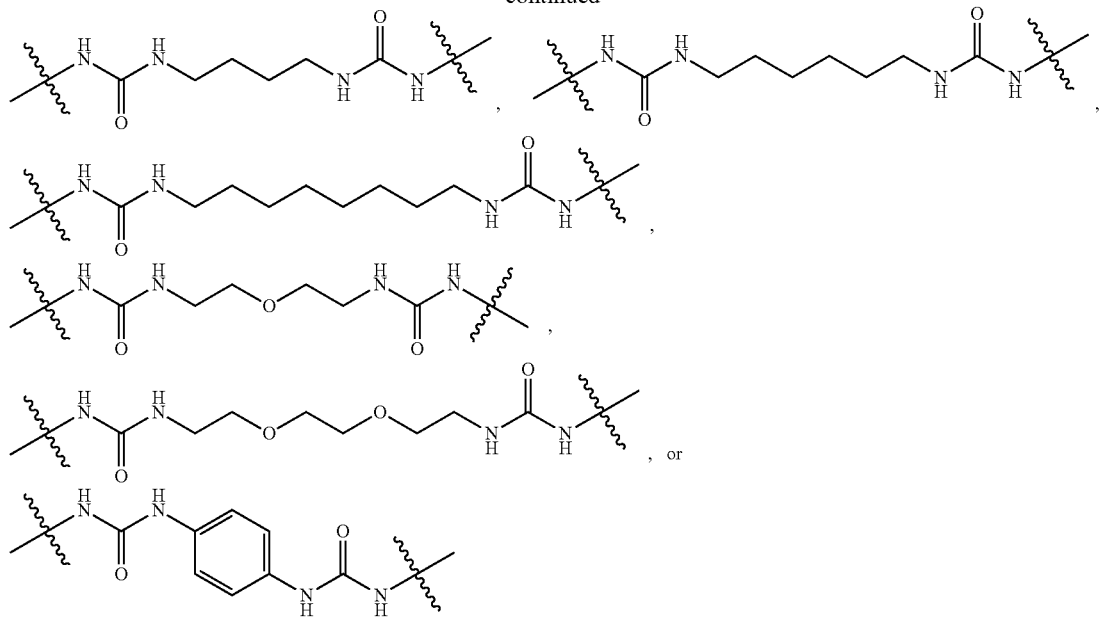

and

L² and L²' are the same,

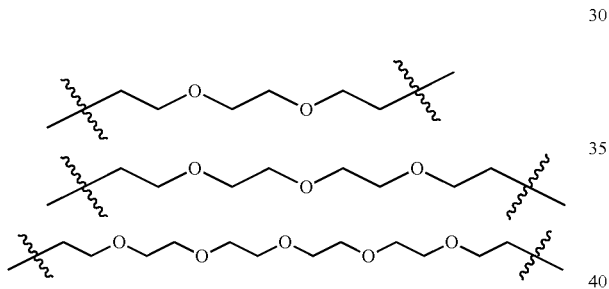

and

A' is the same structure as the structure represented by A.

3. The compound according to claim 1 or a pharmaceutically acceptable salt thereof, wherein Y is a structure represented by the following formula:

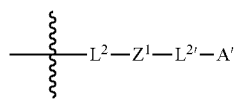

4. The compound according to claim 1 or a pharmaceutically acceptable salt thereof, wherein Z¹ is a structure of the following formula group [6]:

[6]

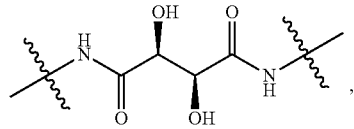

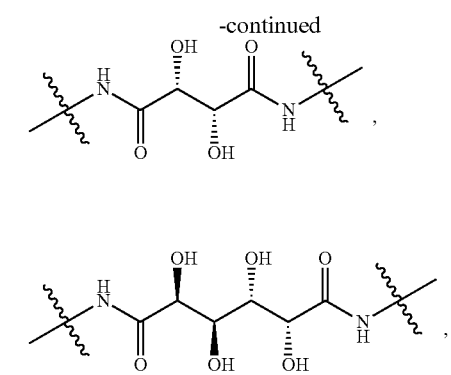

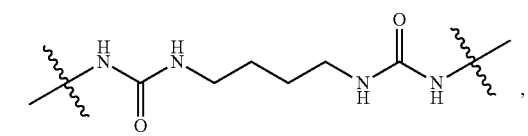

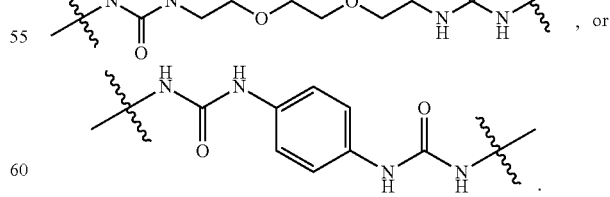

5. The compound according to claim 4 or a pharmaceutically acceptable salt thereof, wherein the structure represented by formula [2] is a structure of the following formula:

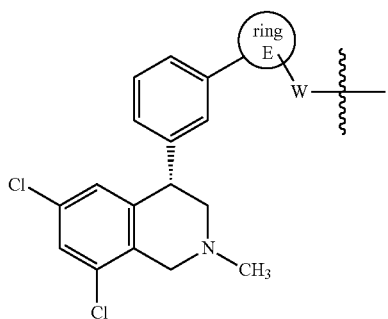

6. The compound according to claim 5 or a pharmaceutically acceptable salt thereof, wherein

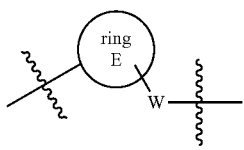

is a structure of the following formula group [9]:

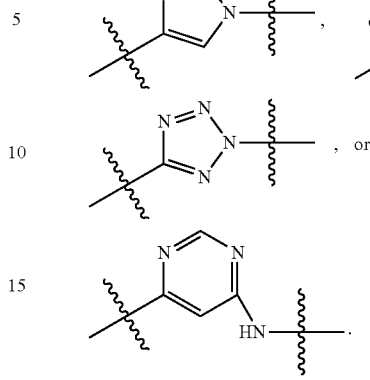

[9]

7. A pharmaceutical composition comprising a compound according to claim 1 or a pharmaceutically acceptable salt thereof and a pharmaceutically acceptable additive.

8. The compound according to claim 1 or a pharmaceutically acceptable salt thereof, wherein the compound is selected from:

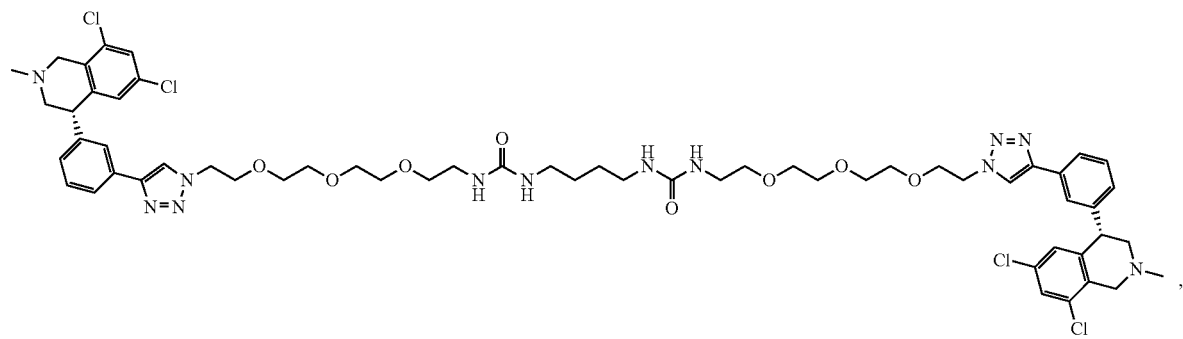

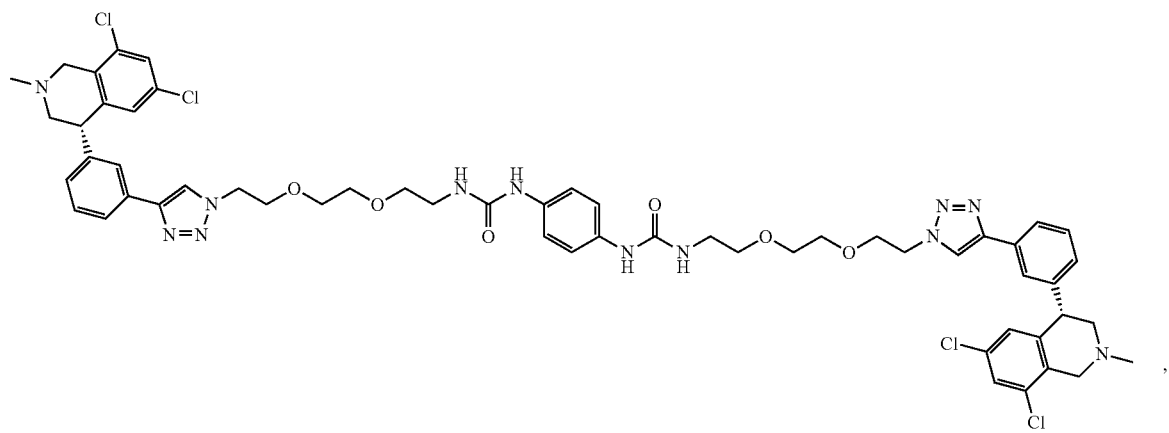

-continued
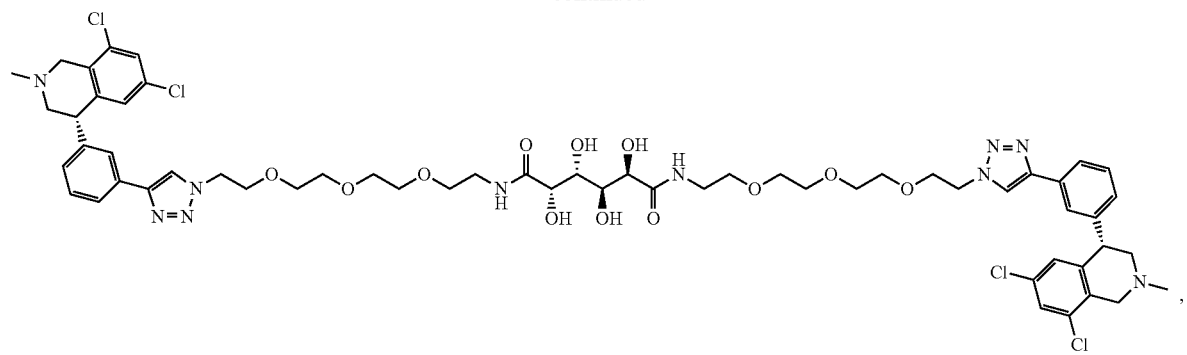
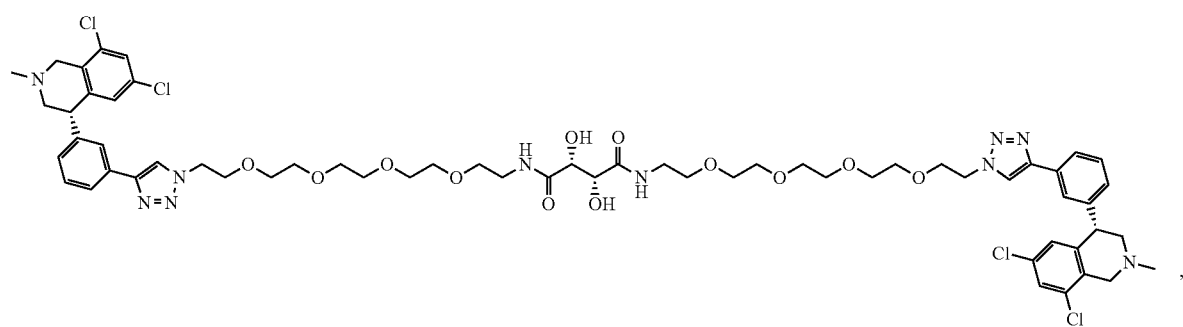
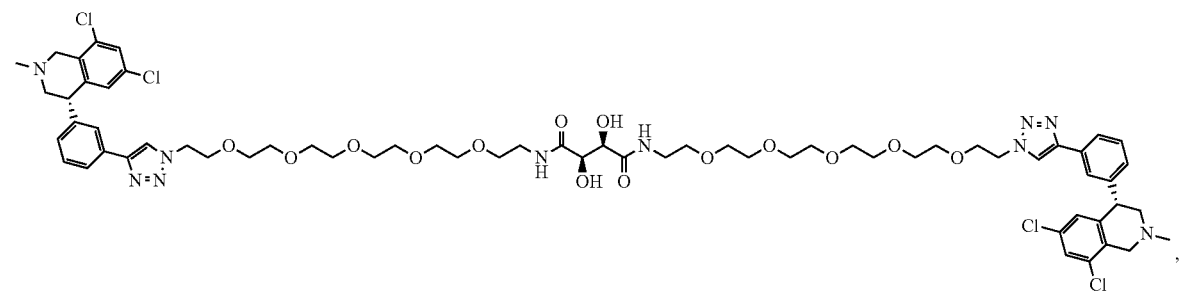
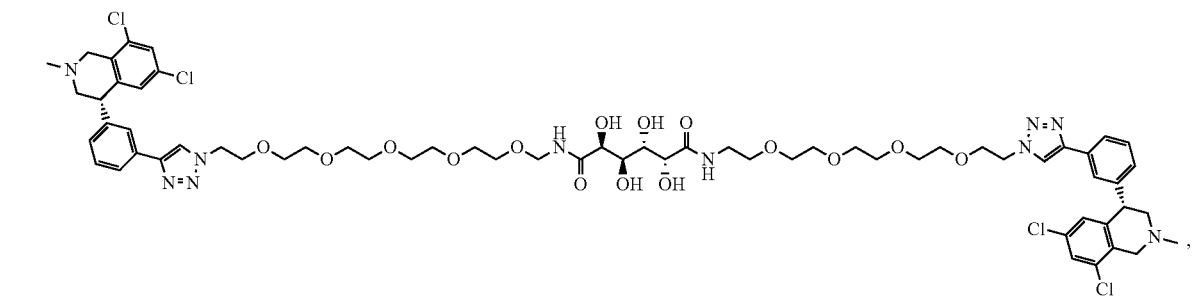
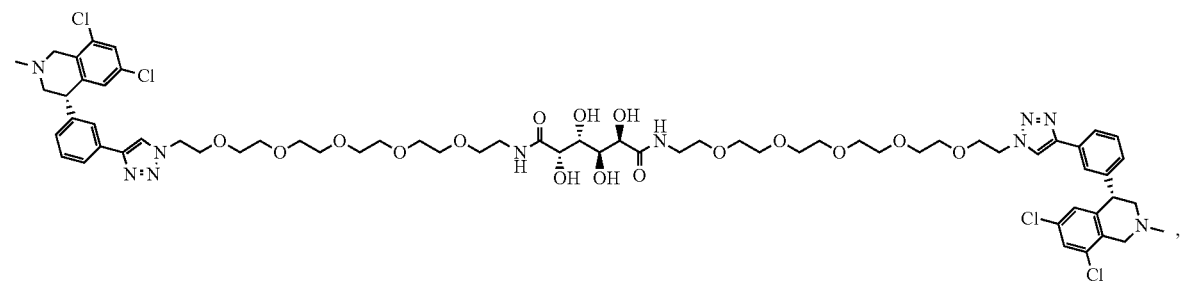

-continued
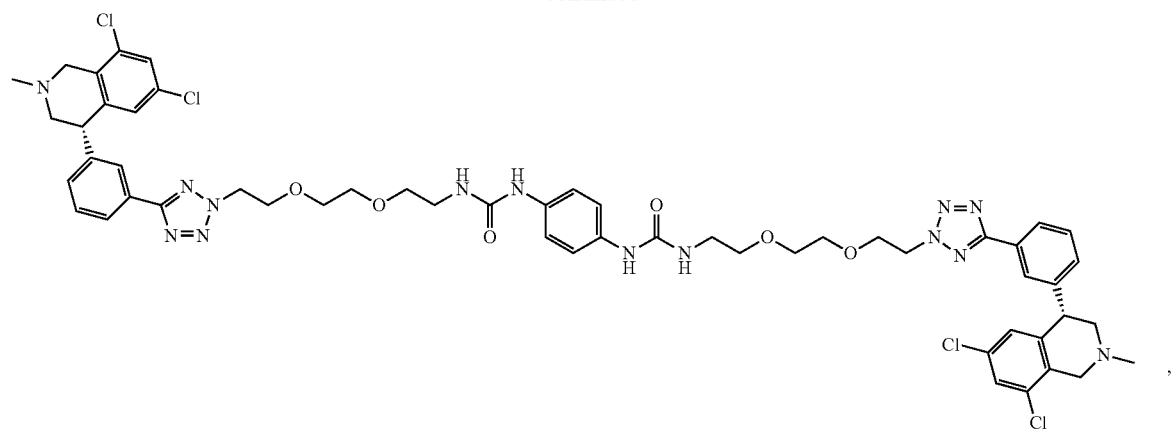
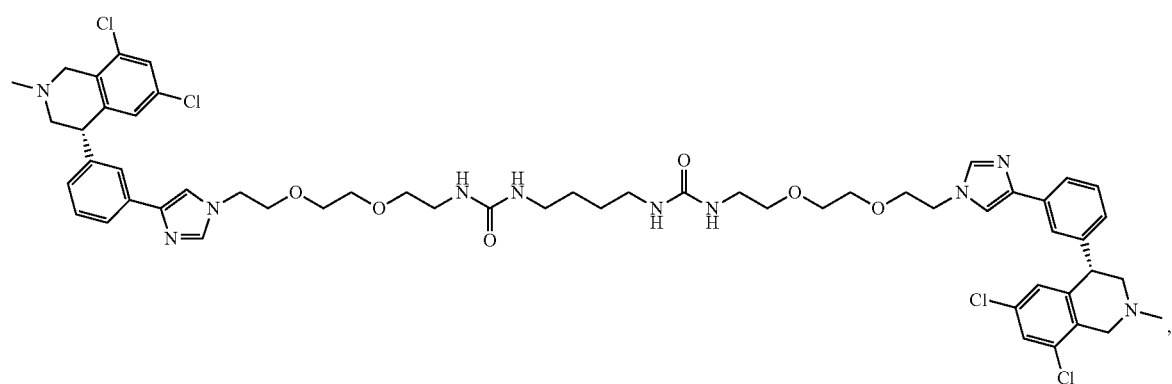
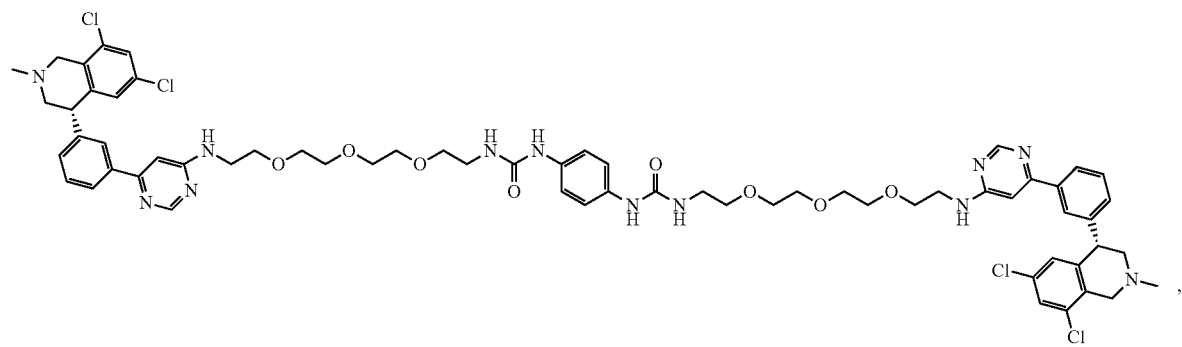
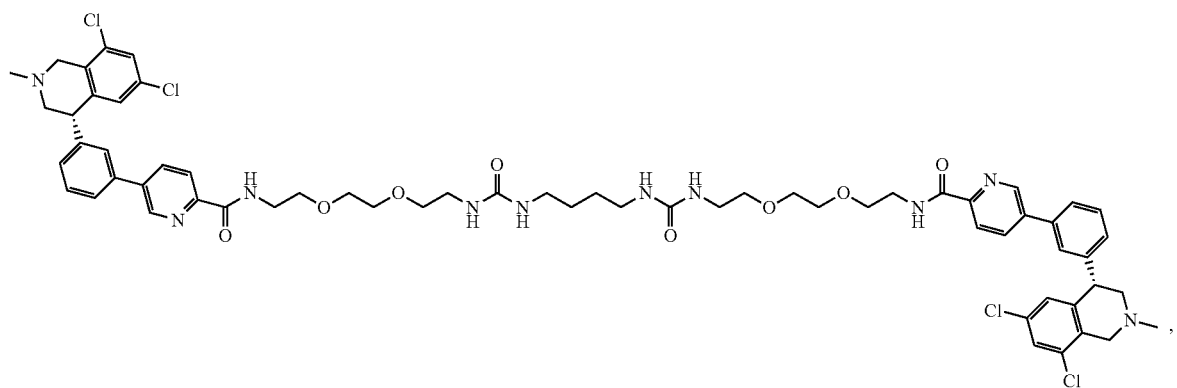

and
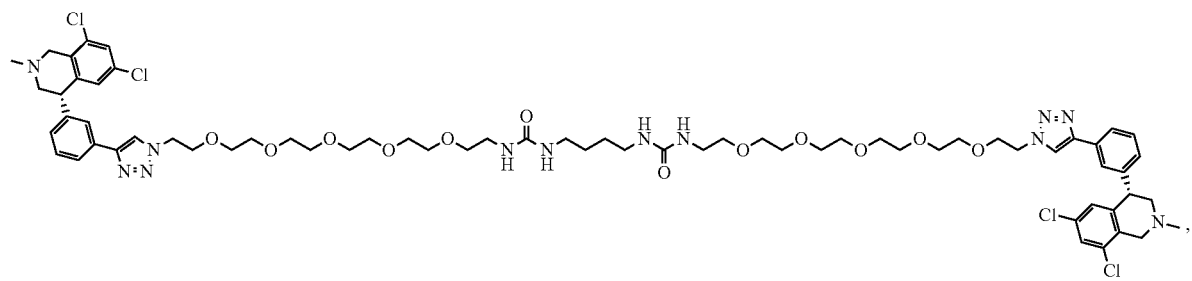
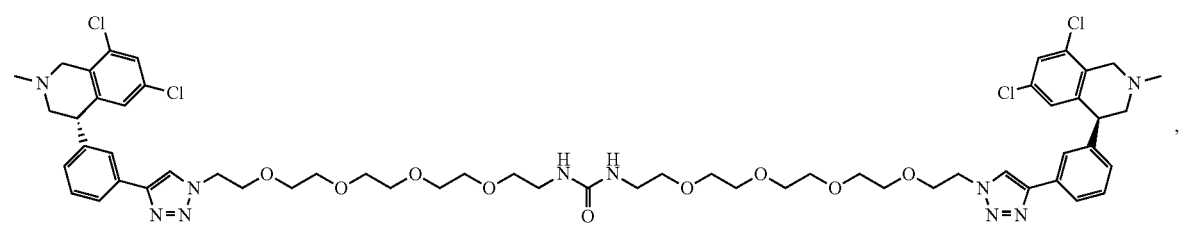,
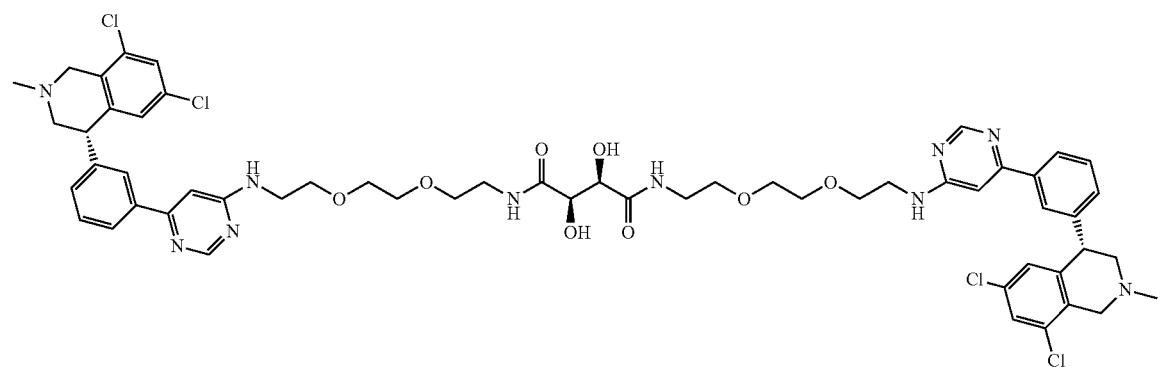,
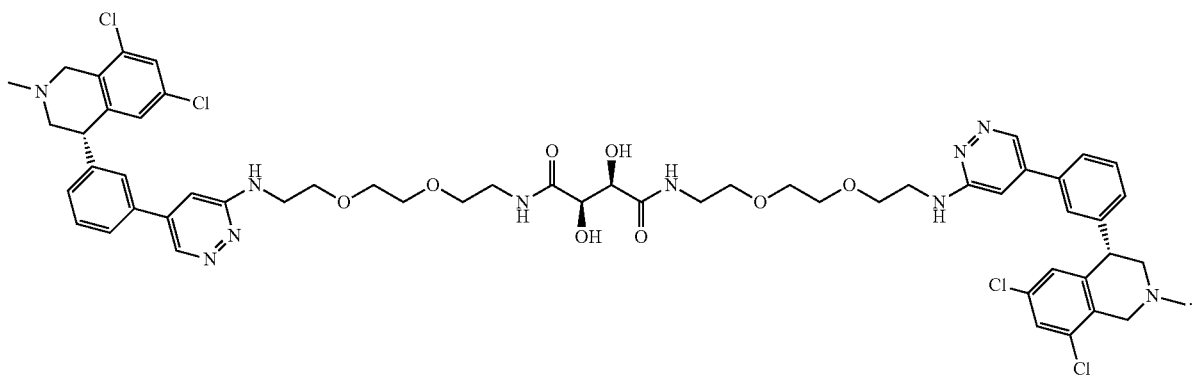.

9. The compound according to claim 1 or a pharmaceutically acceptable salt thereof, wherein the compound is:

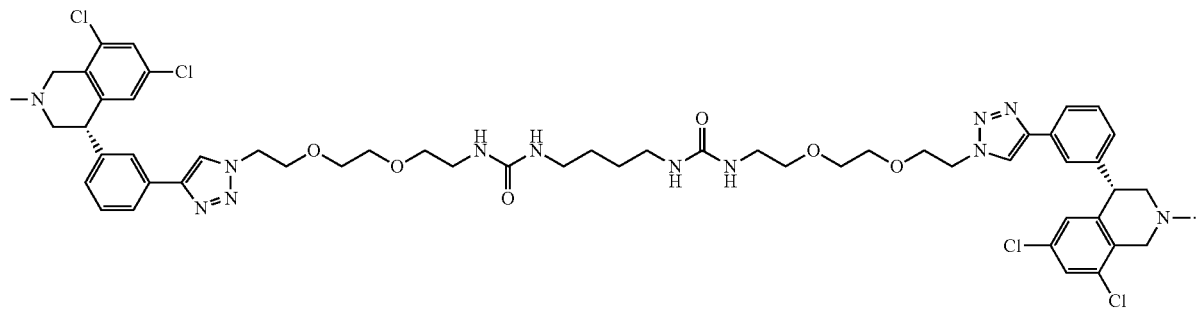

10. The compound according to claim 1 or a pharmaceutically acceptable salt thereof, wherein the compound is:

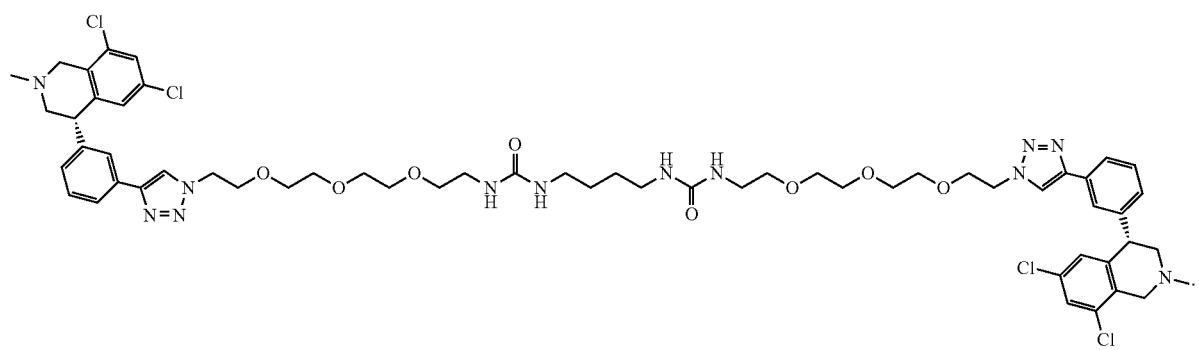

11. The compound according to claim 1 or a pharmaceutically acceptable salt thereof, wherein the compound is:

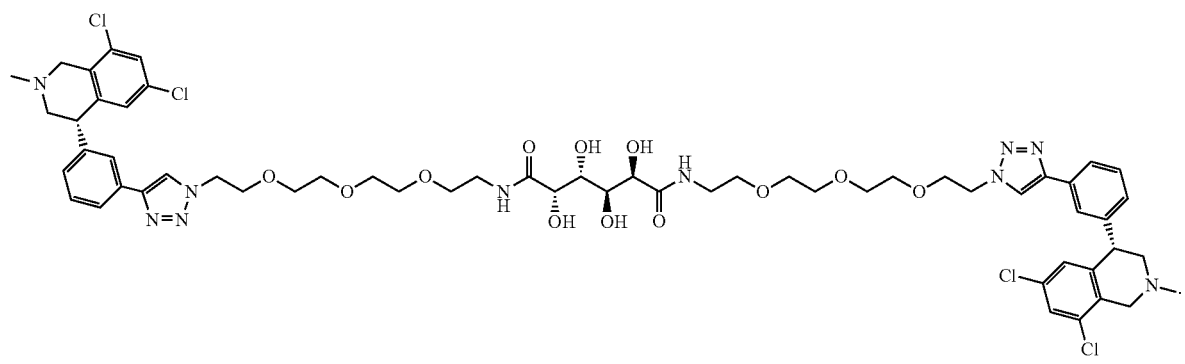

12. A method of inhibiting NHE3 activity in a patient in need thereof comprising administering to said patient a compound according to claim 1 or a pharmaceutically acceptable salt thereof.

13. A method of promoting intestinal water secretion in a patient in need thereof comprising administering to said patient a compound according to claim 1 or a pharmaceutically acceptable salt thereof.

14. A method of treating constipation in a patient in need thereof comprising administering to said patient a compound according to claim 1 or a pharmaceutically acceptable salt thereof.

15. A method of inhibiting sodium absorption in a patient in need thereof comprising administering to said patient a compound according to claim 1 or a pharmaceutically acceptable salt thereof.

16. A method of treating hypertension in a patient in need thereof comprising administering to said patient a compound according to claim 1 or a pharmaceutically acceptable salt thereof.

17. A method of treating nephropathy in a patient in need thereof comprising administering to said patient a compound according to claim 1 or a pharmaceutically acceptable salt thereof.

18. A method of treating body fluid retention in a patient in need thereof comprising administering to said patient a compound according to claim 1 or a pharmaceutically acceptable salt thereof.

19. A method of inhibiting phosphorus absorption in a patient in need thereof comprising administering to said patient a compound according to claim 1 or a pharmaceutically acceptable salt thereof.

20. A method of treating hyperphosphatemia in a patient in need thereof comprising administering to said patient a compound according to claim 1 or a pharmaceutically acceptable salt thereof.

21. A method of treating CKD-MBD in a patient in need thereof comprising administering to said patient a compound according to claim 1 or a pharmaceutically acceptable salt thereof.

* * * * *

UNITED STATES PATENT AND TRADEMARK OFFICE
CERTIFICATE OF CORRECTION

PATENT NO. : 9,932,331 B2  
APPLICATION NO. : 15/328223  
DATED : April 3, 2018  
INVENTOR(S) : Shoichi Kuroda et al.

Page 1 of 1

It is certified that error appears in the above-identified patent and that said Letters Patent is hereby corrected as shown below:

In the Claims

Claim 8, Columns 231-232, fourth formula on page (sixth formula in claim):

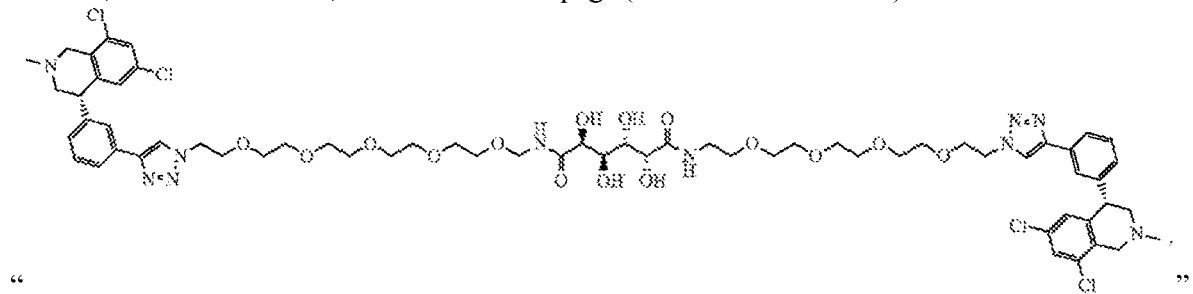

" "

Should read:

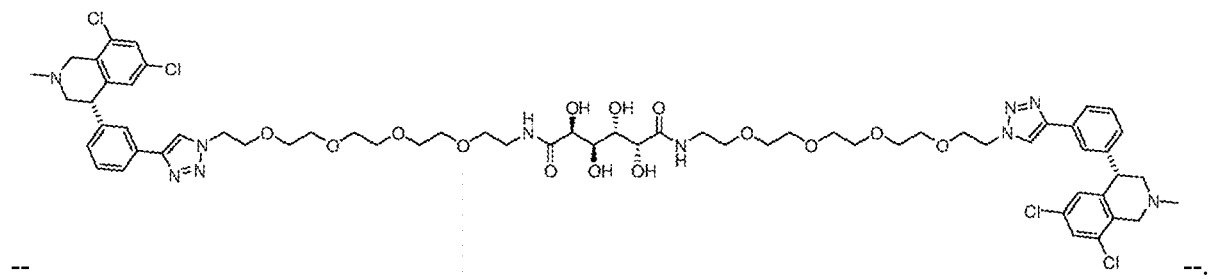

-- --.

Signed and Sealed this  
Fifth Day of June, 2018

Andrei Iancu  
*Director of the United States Patent and Trademark Office*